United States Patent
Wong et al.

(10) Patent No.: US 10,765,681 B2
(45) Date of Patent: Sep. 8, 2020

(54) PURINE COMPOUNDS POSSESSING ANTICANCER ACTIVITY

(71) Applicants: Academia Sinica, Taipei (TW); National Taiwan University, Taipei (TW)

(72) Inventors: Chi-Huey Wong, Rancho Santa Fe, CA (US); Pan-Chyr Yang, Taipei (TW); Jim-Min Fang, Taipei (TW); Szu-Hua Pan, Taipei (TW); Ting-Jen R. Cheng, New Taipei (TW); Ling-Wei Li, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 0 days.

(21) Appl. No.: 16/075,202

(22) PCT Filed: Feb. 3, 2017

(86) PCT No.: PCT/US2017/016453
§ 371 (c)(1),
(2) Date: Aug. 3, 2018

(87) PCT Pub. No.: WO2017/136689
PCT Pub. Date: Aug. 10, 2017

(65) Prior Publication Data
US 2018/0369249 A1 Dec. 27, 2018

Related U.S. Application Data

(60) Provisional application No. 62/291,794, filed on Feb. 5, 2016.

(51) Int. Cl.
| | |
|---|---|
| *C07D 473/00* | (2006.01) |
| *A61K 31/522* | (2006.01) |
| *A61K 45/06* | (2006.01) |
| *A61K 31/337* | (2006.01) |
| *A61K 31/52* | (2006.01) |
| *A61K 31/506* | (2006.01) |
| *A61K 31/502* | (2006.01) |
| *A61K 31/167* | (2006.01) |
| *A61K 31/454* | (2006.01) |
| *A61K 38/05* | (2006.01) |
| *A61K 31/517* | (2006.01) |
| *A61K 31/4025* | (2006.01) |
| *A61K 31/5377* | (2006.01) |
| *A61K 31/69* | (2006.01) |

(Continued)

(52) U.S. Cl.
CPC .......... *A61K 31/522* (2013.01); *A61K 31/167* (2013.01); *A61K 31/337* (2013.01); *A61K 31/4025* (2013.01); *A61K 31/44* (2013.01); *A61K 31/454* (2013.01); *A61K 31/502* (2013.01); *A61K 31/506* (2013.01); *A61K 31/517* (2013.01); *A61K 31/52* (2013.01); *A61K 31/5377* (2013.01); *A61K 31/69* (2013.01); *A61K 35/00* (2013.01); *A61K 38/05* (2013.01); *A61K 45/06* (2013.01); *C07D 473/00* (2013.01); *A61K 2300/00* (2013.01)

(58) Field of Classification Search
CPC .................................................. C07D 473/00
See application file for complete search history.

(56) References Cited

U.S. PATENT DOCUMENTS 9,206,164 B2 * 12/2015 Martyres ............. A61K 31/415
2012/0071476 A1 3/2012 Nakayama et al.
(Continued)

FOREIGN PATENT DOCUMENTS

WO WO-2008051494 A1 * 5/2008 ........... C07D 473/00
WO WO 2015/055071 4/2015

OTHER PUBLICATIONS

M-R Huang et al., 181 European Journal of Medicinal Chemistry (2019) (Year: 2019).*
(Continued)

*Primary Examiner* — Alexander R Pagano
(74) *Attorney, Agent, or Firm* — Polsinelli PC

(57) ABSTRACT

The present disclosure provides compounds of Formulas (I') and (I), and pharmaceutically acceptable salts thereof. The compounds described herein may be useful in treating and/or preventing proliferative diseases (e.g., cancer). Also provided in the present disclosure are pharmaceutical compositions, kits, and uses thereof for treating proliferative diseases.

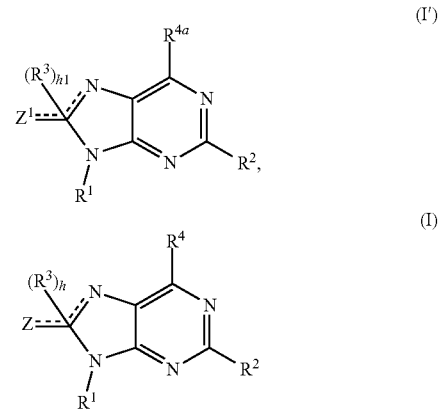

19 Claims, 1 Drawing Sheet

(51) Int. Cl.
*A61K 31/44* (2006.01)
*A61K 35/00* (2006.01)

(56) References Cited

U.S. PATENT DOCUMENTS

2013/0102613 A1  4/2013  Xu et al.
2014/0113917 A1* 4/2014  Martyres ............... A61P 11/00
                                                514/263.2

OTHER PUBLICATIONS

T. Kuo et al., 59 Journal of Medicinal Chemistry (Aug. 18, 2016) (Year: 2016).*
Booth et al., The reactions of diaminomaleonitrile with isocyanates and either aldehydes or ketones revisited. J Org Chem. Dec. 14, 2001;66(25):8436-41.
Chemical Abstract compounds, STN express, RNs 1330159-85-7, 1329838-42-7 (Entered STN: Sep. 8, 2011); RNs 1322288-82-3, 1322284-22-9 (Entered STN: Aug. 24, 2011); RNs 1322029-18-4, 1321709-77-6 (Entered STN: Aug. 23, 2011); RN 1214611-54-7 (Entered STN: Mar. 25, 2010); RN 1004185-02-7 (Entered STN: Feb. 18, 2008); RN 1002295-54-6 (Entered STN: Feb. 8, 2008); RN 932359-23-4 (Entered STN: Apr. 25, 2007); RN 931939-11-6 (Entered STN: Apr. 23, 2007); RN 904268-59-3 (Entered STN: Aug. 24, 2006); RNs 903365-74-2, 903282-88-2, 903257-14-7 (Entered STN: Aug. 22, 2006); RN 899970-93-5 (Entered STN: Aug. 9, 2006); RNs 898446-82-7, 898446-06-5, 898443-26-0 (Entered STN: Aug. 3, 2006); RN 887216-90-2 (Entered STN: Jun. 8, 2006); RN 869069-06-7 (Entered STN: Dec. 1, 2005); RNs 863502-27-6, 863501-47-7, 863501-30-8, 863501-18-2, 863501-82-0 (Entered STN: Sep. 20, 2005).
Kuo et al., Purine-Type Compounds Induce Microtubule Fragmentation and Lung Cancer Cell Death through Interaction with Katanin. J Med Chem. Sep. 22, 2016;59(18):8521-34. doi: 10.1021/acs.jmedchem.6b00797. Epub Aug. 30, 2016.
PCT/US2017/016453, May 22, 2017, International Search Report and Written Opinion.
PCT/US2017/016453, Aug. 16, 2018, International Preliminary Report on Patentability.

* cited by examiner

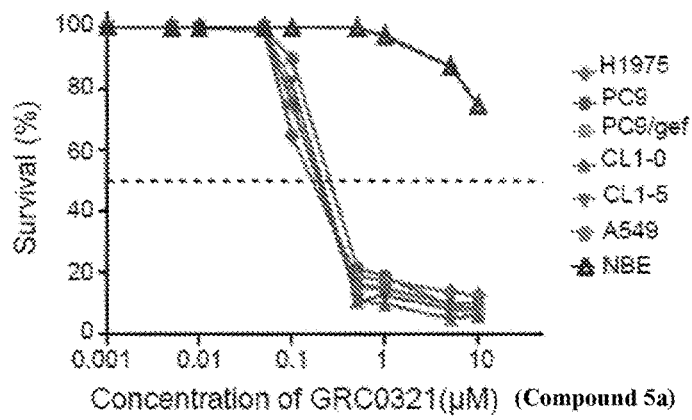
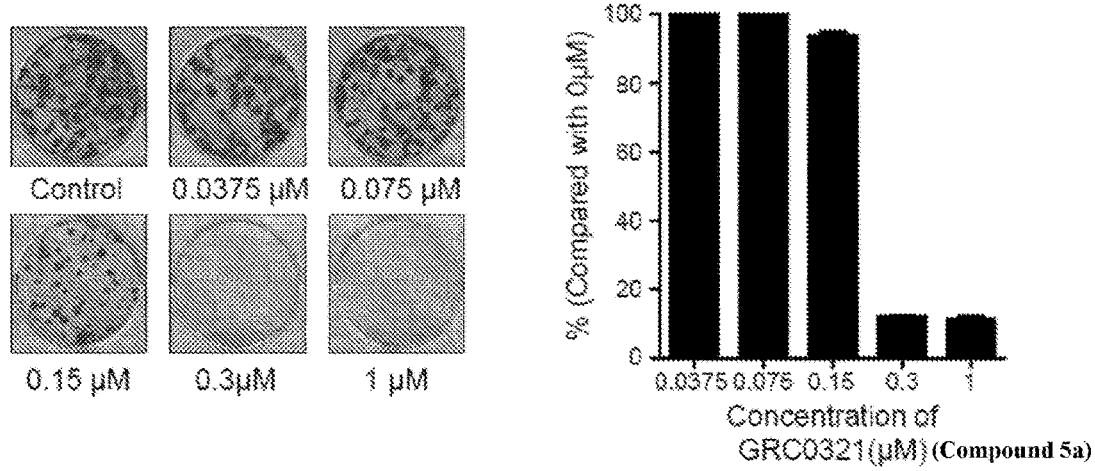
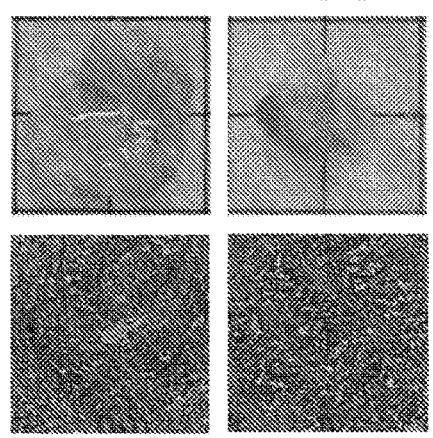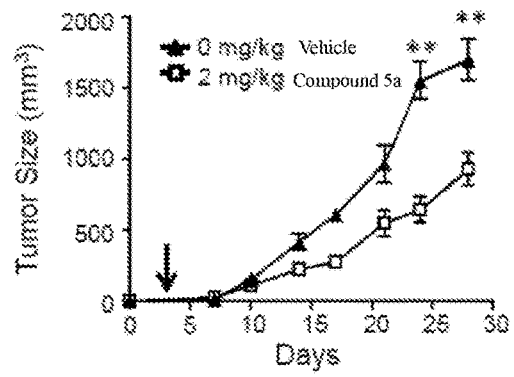

PURINE COMPOUNDS POSSESSING ANTICANCER ACTIVITY

RELATED APPLICATIONS

This Application is a national stage filing under 35 U.S.C. 371 of International Patent Application Serial No. PCT/US2017/016453, filed Feb. 3, 2017, entitled "PURINE COMPOUNDS POSSESSING ANTICANCER ACTIVITY," which The present disclosure claims the benefit of priority to U.S. provisional application No. 62/291,794, filed on Feb. 5, 2016 entitled "PURINE COMPOUNDS POSSESSING ANTICANCER ACTIVITY," the entire contents of each of which are incorporated herein by reference herein.

BACKGROUND OF THE INVENTION

The epidermal growth factor receptors (EGFR) belong to the ErbB family of receptor tyrosine kinases (RTK) and participate in the regulation of cellular homeostasis such as cell proliferation, apoptosis, migration, survival and complex processes including angiogenesis and tumorigenesis (Wheeler, D. L.; et al. *Nat. Rev. Clin. Oncol.* 2010, 7, 493.). It has been established that dysregulated EGFR expression and signaling play a critical role in the etiology of human cancers (Ullrich, A.; et al. *Nature* 1984, 309, 418. Veale, D.; et al. *Brit. J. Cancer* 1987, 55, 513. Weichselbaum, R. R.; et al. *Head Neck* 1989, 11, 437).

Lung cancer is the leading cause of cancer-related mortality worldwide. Despite recent advances in medical and surgical therapies, the improvement in lung cancer mortality due to current treatments remains unsatisfactory. Recently, specific targeted therapies for lung cancer have been developed rapidly. One of these targeted therapies, the use of epidermal growth factor receptor tyrosine kinase inhibitors (EGFR TKIs), was successfully implemented for lung cancer therapy owing to the prevalence of EGFR mutations in non-small cell lung cancer (NSCLC).

However, most patients eventually develop acquired resistance to the therapy after approximately one year on this therapy. Therefore, there is an urgent need to develop new anti-cancer drugs that effectively treat lung cancer.

Breast cancer is a heterogeneous disease that often occurs in the pre- and post-menopause period of women. Most breast cancer cells, such as MCF, are sensitive to estrogen receptor (ER) and progesterone receptor (PR) with overexpression of human epidermal growth factor receptor 2 (HER2). (Subik, K.; et al. *Breast Cancer: Basic Clin. Res.* 2010, 4, 35-41. Holliday D. L. & Speirs, V. *Breast Cancer Res.* 2011, 13, 215. Beelen, K.; et al. *Nat. Rev. Clin. Oncol.* 2012, 9, 529-541.) In contrast, MDA-MB-231 cell is a triple-negative breast cancer (TNBC) cell because it has low expression of HER2 and no expression of ER or PR. Prognosis and treatment of TNBCs are difficult since most drugs only target one of the three receptors. To develop therapeutic agents for treatment of TNBC patients is also especially important.

SUMMARY OF THE INVENTION

The present disclosure provides compounds of Formulas (I') and (I), and pharmaceutically acceptable salts, solvates, hydrates, polymorphs, co-crystals, tautomers, stereoisomers, isotopically labeled derivatives, prodrugs, and compositions thereof. The compounds of Formulas (I') and (I), and pharmaceutically acceptable salts, solvates, hydrates, polymorphs, co-crystals, tautomers, stereoisomers, isotopically labeled derivatives, prodrugs, and compositions thereof, disrupt microtubule organization inside cancer cells, for example, lung cancer cells. The present disclosure further provides methods of using the inventive compounds, and pharmaceutically acceptable salts, solvates, hydrates, polymorphs, co-crystals, tautomers, stereoisomers, isotopically labeled derivatives, prodrugs, and compositions thereof, as therapeutics for the treatment of a proliferative diseases such as cancer (e.g., lung cancer or breast cancer) in a subject in need thereof. In some embodiments, the subject has lung cancer, e.g., non-small cell lung cancer. In some embodiments, the subject has a lung cancer that is resistant to drug treatment, for example, resistant to a tyrosine kinase inhibitor, including those described herein. In some embodiments, the subject has breast cancer, for example, a breast cancer that is negative of estrogen receptor (ER), progesterone receptor (PR) and/or Her2/neu. In some examples, the subject is a human patient having triple-negative breast cancer (negative of estrogen receptor (ER), progesterone receptor (PR) and Her2/neu).

In one aspect, the present disclosure provides compounds of Formula (I'):

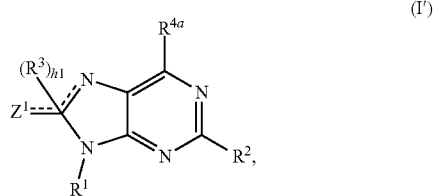

or a pharmaceutically acceptable salt thereof,
wherein:
$Z^1$ is independently Cl, O, S, or N, as valency permits;
h1 is 0, 1, or 2;
$R^1$ and $R^2$ are each independently optionally substituted alkyl, optionally substituted alkenyl, optionally substituted alkynyl, optionally substituted carbocyclyl, optionally substituted aryl, optionally substituted heterocyclyl, or optionally substituted heteroaryl;
$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^A$, —SR$^A$, —NHR$^B$, —N(R$^B$)$_2$, —C(=O)R$^A$, —C(=O)OR$^A$, —C(=O)NHR$^B$, —C(=O)N(R$^B$)$_2$, —SO$_2$R$^A$, or two instances of $R^3$ are taken together with Z to form optionally substituted heterocyclyl;
$R^{4a}$ is optionally substituted alkyl, —C(=O)N(R$^B$)$_2$, —CN, —C(=O)OR$^A$, —C(=O)R$^A$, —C(=O)NR$^B$(OR$^A$), —C(=O)NHN(R$^B$)$_2$, —C(=NH)NH(OR$^A$), —C(=N (OR$^A$)NH$_2$, —C(=NH)NHN(R$^B$)$_2$, —C(=NHN(R$^B$)$_2$) NH$_2$, —C(=NH)N(R$^B$)$_2$, or nitrogen-containing heterocycle; wherein
$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and
$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or OR$^X$;

or two instances of $R^B$ are taken together with the intervening nitrogen to form optionally substituted heterocyclyl;

or $R^A$ and $R^B$ are taken together with the intervening atoms to form optionally substituted heterocyclyl; and $R^X$ is hydrogen, optionally substituted alkyl, or oxygen protecting group.

In certain embodiments, a compound of Formula (I') is of Formula (I):

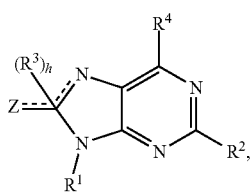
(I)

or a pharmaceutically acceptable salt thereof,
wherein:

Z is independently N, O, or S, as valency permits;

h is 1 or 2;

$R^1$ and $R^2$ are each independently optionally substituted alkyl, optionally substituted alkenyl, optionally substituted alkynyl, optionally substituted carbocyclyl, optionally substituted aryl, optionally substituted heterocyclyl, or optionally substituted heteroaryl;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^A$, —$SR^A$, —$NHR^B$, —$N(R^B)_2$, —C(=O)$R^A$, —C(=O)$OR^A$, —C(=O)$NHR^B$, —C(=O)N($R^B)_2$, —$SO_2R^A$, or two instances of $R^3$ are taken together with Z to form optionally substituted heterocyclyl;

$R^4$ is optionally substituted alkyl, —C(=O)N($R^B)_2$, —CN, —C(=O)$OR^A$, —C(=O)$R^A$, —C(=O)$NR^B(OR^A)$, —C(=O)NHN($R^B)_2$, —C(=NH)NH($OR^A$), —C(=N($OR^A$))$NH_2$, —C(=NH)NHN($R^B)_2$, —C(=NH$R^B)_2$)$NH_2$, —C(=NH)N($R^B)_2$, or tetrazole;

wherein $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or $OR^X$;

or two instances of $R^B$ are taken together with the intervening nitrogen to form optionally substituted heterocyclyl;

or $R^A$ and $R^B$ are taken together with the intervening atoms to form optionally substituted heterocyclyl; and $R^X$ is hydrogen, optionally substituted alkyl, or oxygen protecting group.

In certain embodiments, a compound of Formula (I') is of Formula (I'-A):

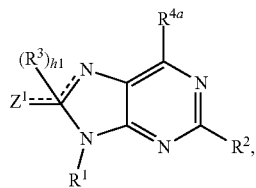
(I'-A)

or a pharmaceutically acceptable salt thereof, wherein:

$R^1$ and $R^2$ are each independently optionally substituted alkyl, optionally substituted alkenyl, optionally substituted alkynyl, optionally substituted carbocyclyl, optionally substituted aryl, optionally substituted heterocyclyl, or optionally substituted heteroaryl;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, CN, $OR^A$, $SR^A$, $NHR^B$, $N(R^B)_2$, C(=O)$R^A$, C(=O)$OR^A$, C(=O)$NHR^B$, C(=O)N($R^B)_2$, $SO_2R^A$, or two instances of $R^3$ are taken together with Z to form optionally substituted heterocyclyl;

$R^{4a}$ is —C(=O)$NR^B(OR^A)$, —C(=O)NHN($R^B)_2$, —C(=NH)NH($OR^A$), —C(=N($OR^A$))$NH_2$, —C(=NH)NHN($R^B)_2$, —C(=NH$R^B)_2$)$NH_2$, —C(=NH)N($R^B)_2$, or nitrogen-containing heterocycle;

when $Z^1$ is independently Cl, S or N, as valency permits, h1 is 0, 1 or 2;

when $Z^1$ is O, h1 is 1; wherein:

$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or $OR^X$;

or two instances of $R^B$ are taken together with the intervening nitrogen to form optionally substituted heterocyclyl;

or $R^A$ and $R^B$ are taken together with the intervening atoms to form optionally substituted heterocyclyl; and $R^X$ is hydrogen, optionally substituted alkyl, or oxygen protecting group.

In certain embodiments, a compound of Formula (I') is of Formula (I'-B):

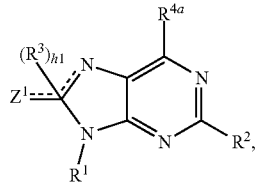
(I'-B)

or a pharmaceutically acceptable salt thereof, wherein:

$R^1$ and $R^2$ are each independently optionally substituted alkyl, optionally substituted alkenyl, optionally substituted alkynyl, optionally substituted carbocyclyl, optionally substituted aryl, optionally substituted heterocyclyl, or optionally substituted heteroaryl;

R³ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, CN, OR^A, SR^A, NHR^B, N(R^B)₂, C(=O)R^A, C(=O)OR^A, C(=O)NHR^B, C(=O)N(R^B)₂, SO₂R^A, or two instances of R³ are taken together with Z to form optionally substituted heterocyclyl;

R^{4a} is —CN, —C(=O)OR^A, —C(=O)NR^B(OR^A), —C(=O)NHN(R^B)₂, —C(=NH)NH(OR^A), —C(=N(OR^A)NH₂, —C(=NH)NHN(R^B)₂, —C(=NHN(R^B)₂)NH₂, —C(=NH)N(R^B)₂, or nitrogen-containing heterocycle;

when Z¹ is independently Cl, S or N, as valency permits, h1 is 0, 1 or 2;

when Z¹ is O, h1 is 1; wherein:

R^A is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and R^B is hydrogen, optionally substituted alkyl, optionally substituted alkenyl, optionally substituted alkynyl, optionally substituted carbocyclyl, optionally substituted aryl, optionally substituted heteroaryl, a nitrogen protecting group, or OR^X;

or two instances of R^B are taken together with the intervening nitrogen to form optionally substituted heterocyclyl;

or R^A and R^B are taken together with the intervening atoms to form optionally substituted heterocyclyl; and R^X is hydrogen, optionally substituted alkyl, or oxygen protecting group.

In certain embodiments, a compound of Formula (I') is of Formula (IA'):

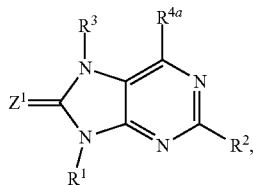
(IA')

or a pharmaceutically acceptable salt thereof, wherein R¹, R², R³, R⁴, and Z¹ are as described herein.

In certain embodiments, a compound of Formula (I) is of Formula (IA):

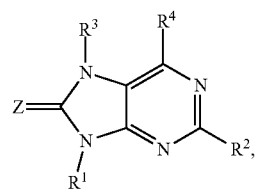
(IA)

or a pharmaceutically acceptable salt thereof, wherein R¹, R², R³, R⁴, and Z are as described herein.

In certain embodiments, a compound of Formula (I') is of Formula (IB'):

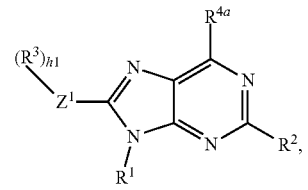
(IB')

or a pharmaceutically acceptable salt thereof, wherein Z, R¹, R², R³, R^{4a} and h1 are as described herein.

In certain embodiments, a compound of Formula (I) is of Formula (IB):

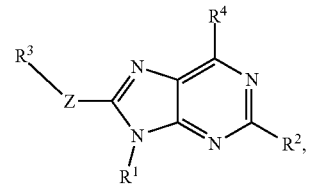
(IB)

or a pharmaceutically acceptable salt thereof, wherein Z, R¹, R², R³, and R⁴ are as described herein.

In certain embodiments, a compound of Formula (IA') is of Formula (IA'-1):

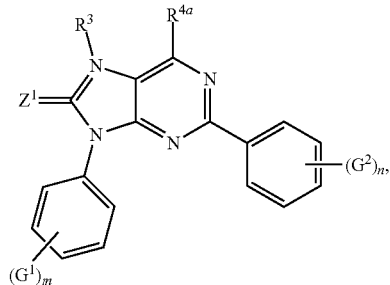
(IA'-1)

or a pharmaceutically acceptable salt thereof, wherein Z¹, R³, R^{4a}, G¹, G², m, and n are defined herein.

In certain embodiments, a compound of Formula (IA') is of Formula (IA'-2):

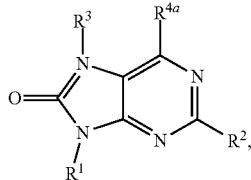
(IA'-2)

In certain embodiments, a compound of Formula (IA) is of Formula (IA-1):

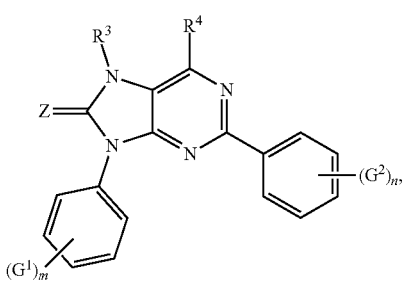
(IA-1)

or a pharmaceutically acceptable salt thereof, wherein Z, $R^3$, $R^4$, $G^1$, $G^2$, m, and n are defined herein.

In certain embodiments, a compound of Formula (IA') is of Formula (I'-a2):

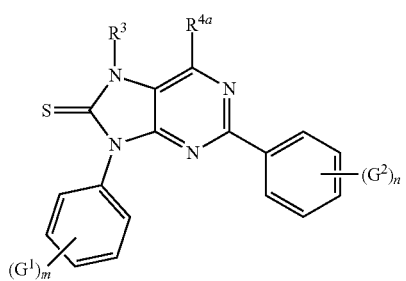
(I'-a2)

or a pharmaceutically acceptable salt thereof, wherein $R^3$, $R^{4a}$, $G^1$, $G^2$, m, and n are defined herein.

In certain embodiments, a compound of Formula (IA') is of Formula (I'-a3):

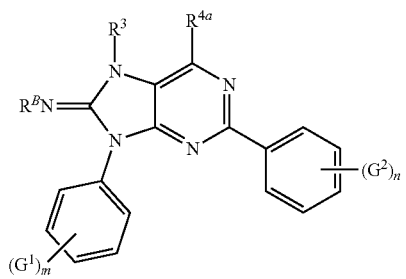
(I'-a3)

or a pharmaceutically acceptable salt thereof, wherein $R^3$, $R^4$, $G^1$, $G^2$, $R^B$, m, and n are defined herein.

In certain embodiments, a compound of Formula (IB) is of Formula (IB-1):

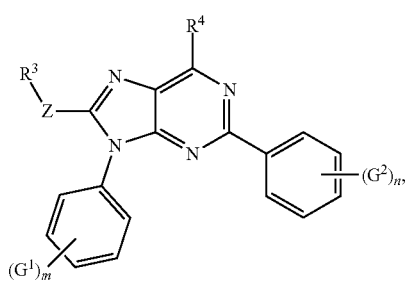
(IB-1)

or a pharmaceutically acceptable salt, solvate, hydrate, polymorph, co-crystal, tautomer, stereoisomer, isotopically labeled derivative, or prodrug thereof, wherein Z, $R^3$, $R^4$, $G^1$, $G^2$, m, and n are defined herein.

In certain embodiments, a compound of Formula (IB') is of Formula (IB'-2):

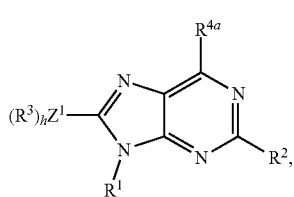
(IB'-2)

or a pharmaceutically acceptable salt, solvate, hydrate, polymorph, co-crystal, tautomer, stereoisomer, isotopically labeled derivative, or prodrug thereof, wherein $Z^1$, h, $R^1$, $R^2$, $R^3$, and $R^{4a}$ are as described herein.

In certain embodiments, a compound of Formula (IB') is of Formula (IB'-3):

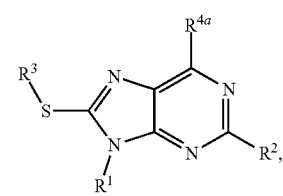
(IB'-3)

or a pharmaceutically acceptable salt, solvate, hydrate, polymorph, co-crystal, tautomer, stereoisomer, isotopically labeled derivative, or prodrug thereof, wherein $R^1$, $R^2$, $R^3$, and $R^{4a}$ are as described herein.

In certain embodiments, a compound of Formula (IB'-3) is of Formula (I'-b2):

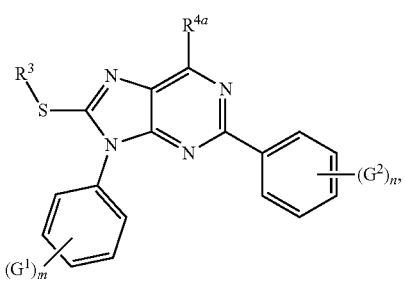
(I'-b2)

or a pharmaceutically acceptable salt, solvate, hydrate, polymorph, co-crystal, tautomer, stereoisomer, isotopically labeled derivative, or prodrug thereof, wherein $R^3$, $R^{4a}$, $G^1$, $G^2$, m, and n are defined herein.

In certain embodiments, a compound of Formula (IB') is of Formula (IB'-4):

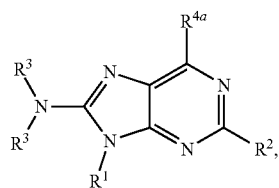
(IB'-4)

or a pharmaceutically acceptable salt, solvate, hydrate, polymorph, co-crystal, tautomer, stereoisomer, isotopically labeled derivative, or prodrug thereof, wherein $R^1$, $R^2$, $R^3$, and $R^{4a}$ are as described herein.

In certain embodiments, a compound of Formula (IB'-4) is of Formula (I'-b3):

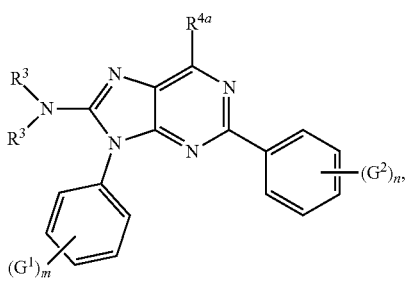
(I'-b3)

or a pharmaceutically acceptable salt, solvate, hydrate, polymorph, co-crystal, tautomer, stereoisomer, isotopically labeled derivative, or prodrug thereof, wherein $R^3$, $R^{4a}$, $G^1$, $G^2$, m, and n are defined herein.

In certain embodiments, a compound of Formula (IB') is of Formula (IB'-5):

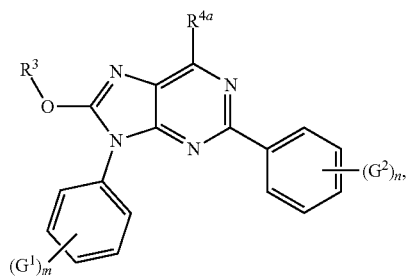
(IB'-5)

or a pharmaceutically acceptable salt, solvate, hydrate, polymorph, co-crystal, tautomer, stereoisomer, isotopically labeled derivative, or prodrug thereof, wherein $R^1$, $R^2$, $R^3$, and $R^4$ are as described herein.

In certain embodiments, the compound of Formula (I) is of the following formulae:

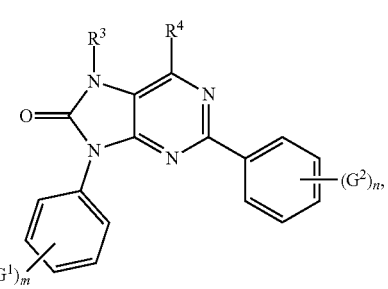
(I-a1)

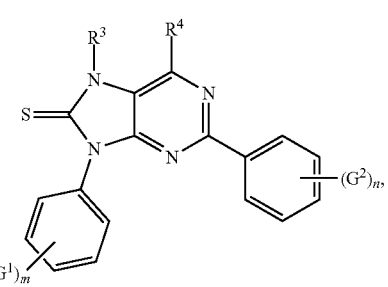
(I-a2)

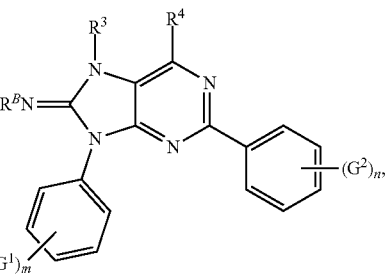
(I-a3)

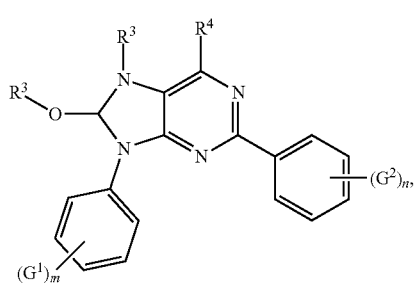
(I-b1)

(I-b2)
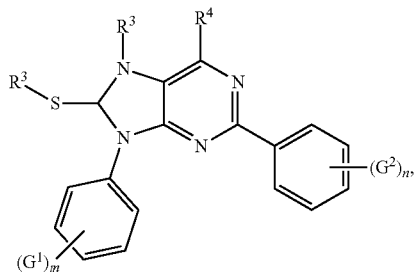
(I-b3)
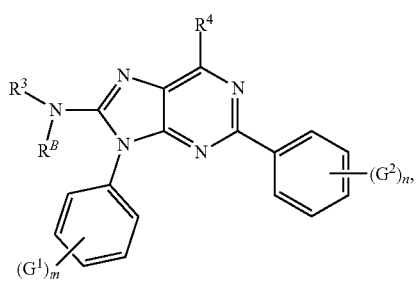
or a pharmaceutically acceptable salt thereof.
In certain embodiments, the compound of Formulas (I') and (I) are of the following formulae:
(I'-a1)
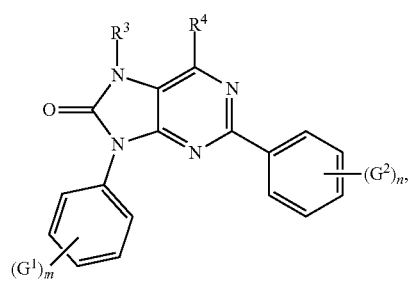
(I'-a2)
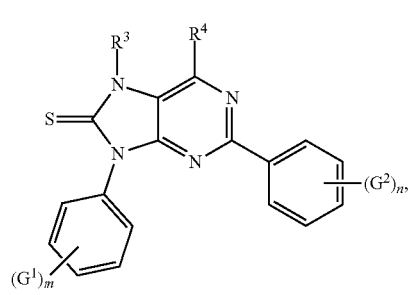
(I'-a3)
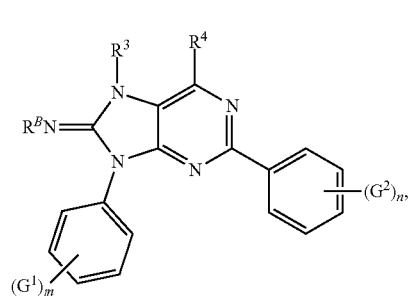
(I'-b1)
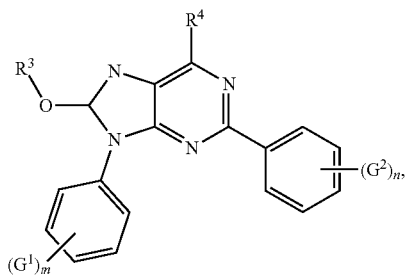
(I'-b2)
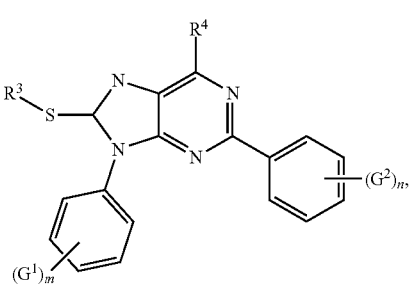
(I'-b3)
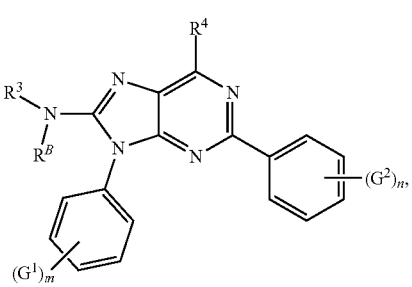
or a pharmaceutically acceptable salt thereof.
Exemplary compounds of Formulas (I') and (I) include, but are not limited to:
(18c)
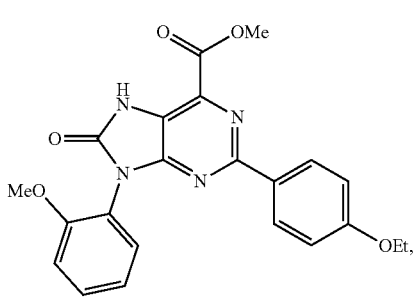
(18d)
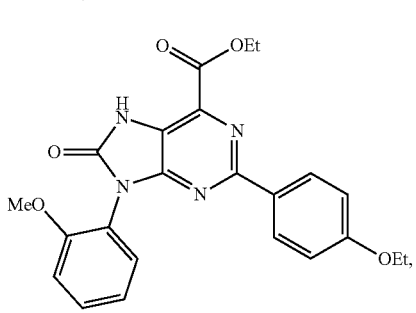

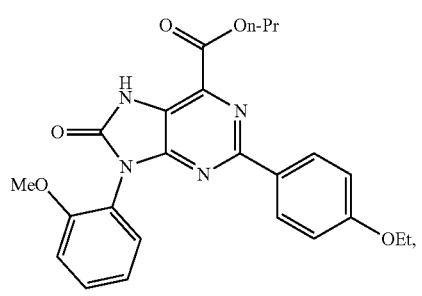
(18e)
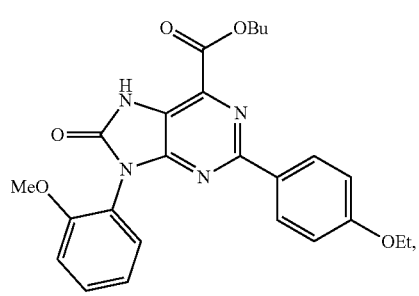
(18f)
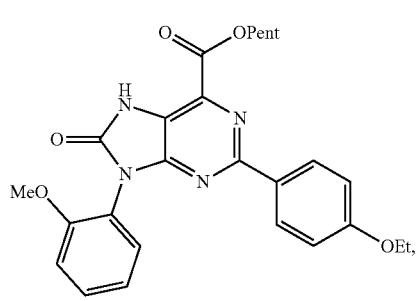
(18g)
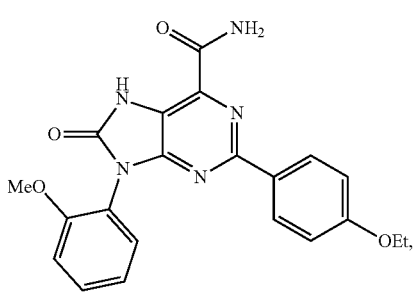
(5a)
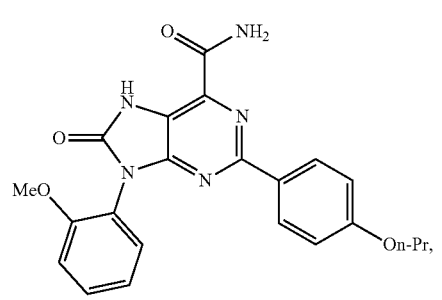
(5a-Pr)
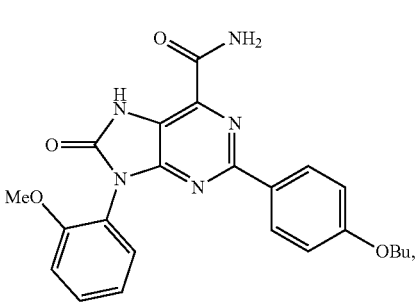
(5c)
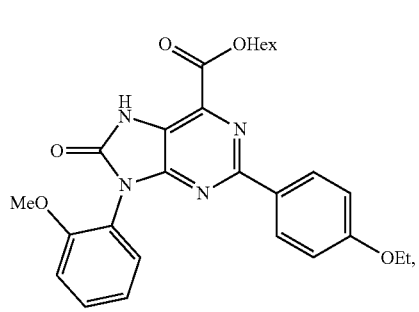
(18h)
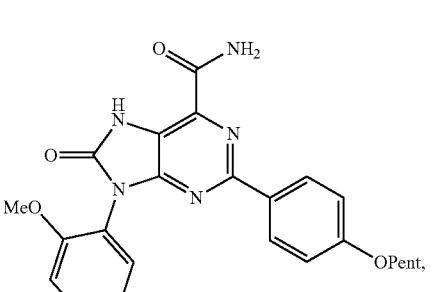
(5a-Pent)
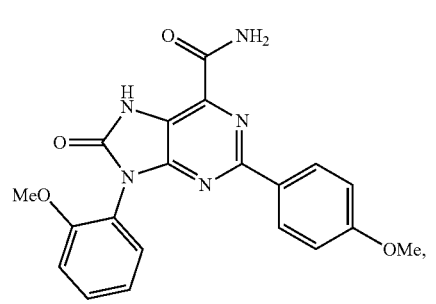
(5a-Me)
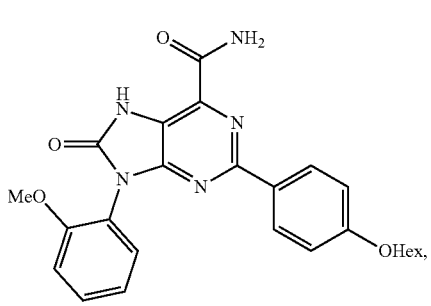
(5d)

-continued
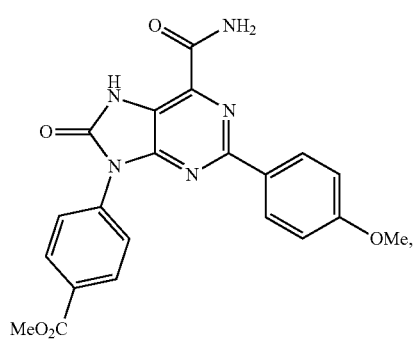
(5f-Me)
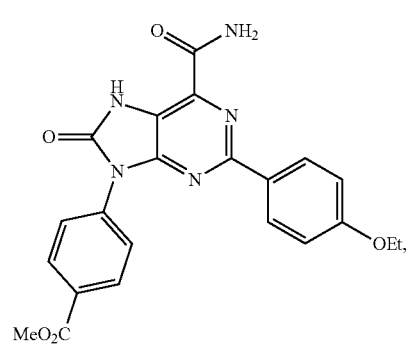
(5f)
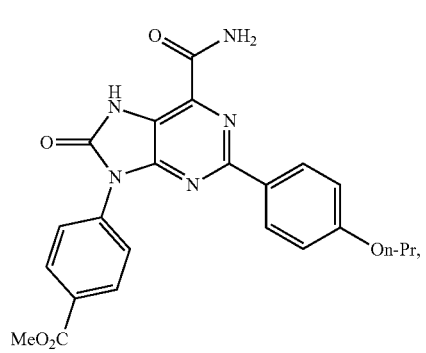
(5f-Pr)
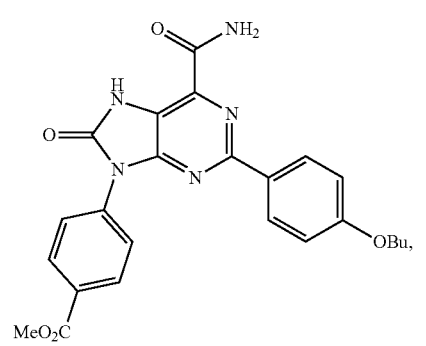
(5f-Bu)
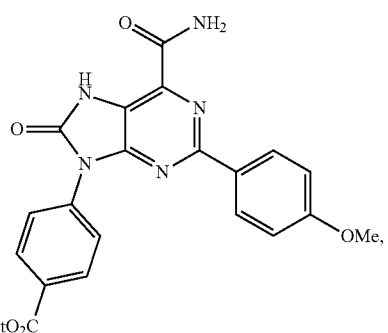
(5f-CO$_2$Et/Me)
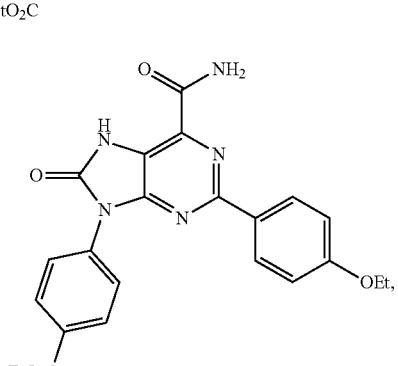
(5f-CO$_2$Et)
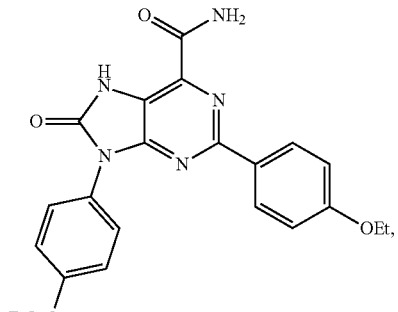
(5f-CO$_2$Et/Pr)
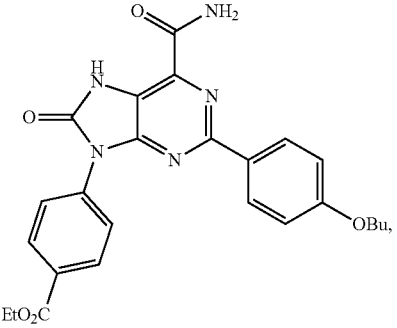
(5f-CO$_2$Et/Bu)

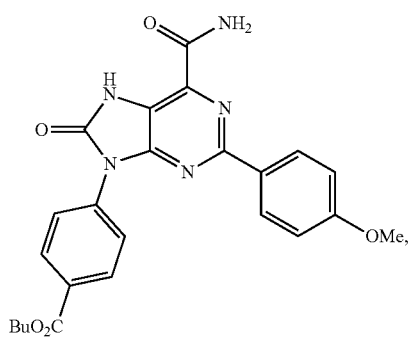
(5f-CO₂Bu/Me)
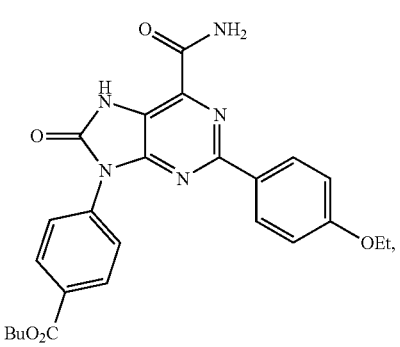
(5f-CO₂Bu)
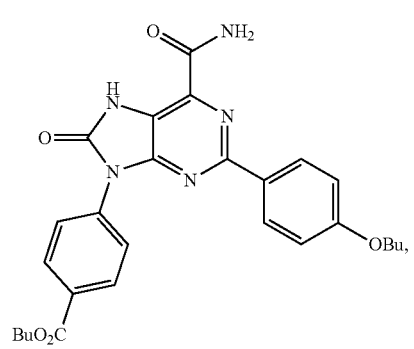
(5f-CO₂Bu/Bu)
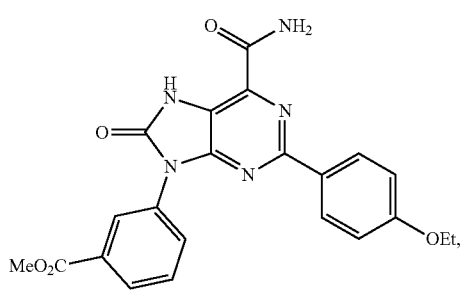
(5e)
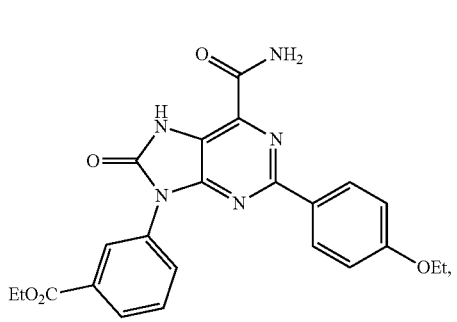
(5e-CO₂Et)
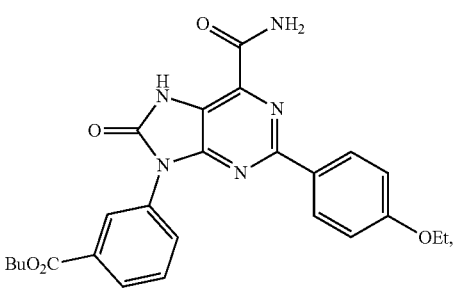
(5e-CO₂Bu)
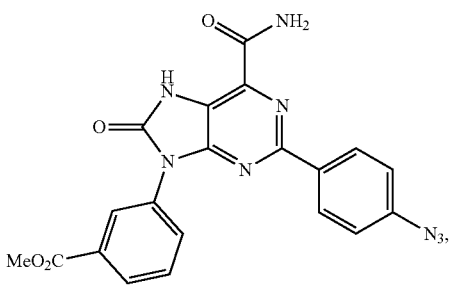
(5g)
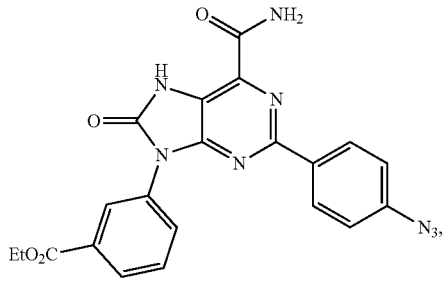
(5g-CO₂Et)
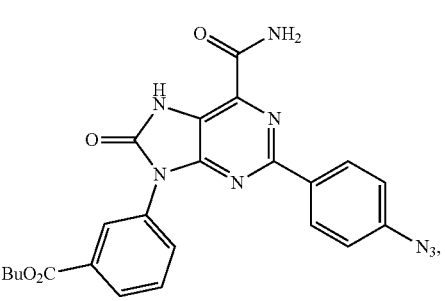
(5g-CO₂Bu)
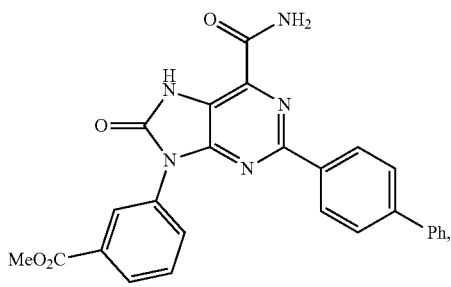
(5i)

(5i-CO2Et)
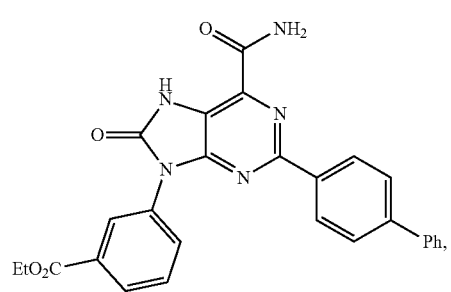
(5i-CO2Pr)
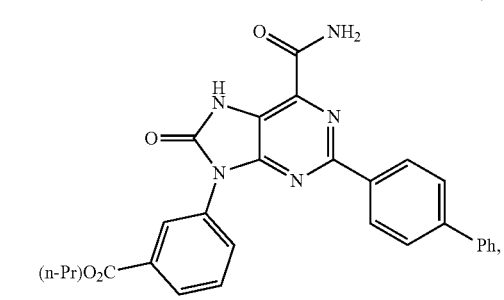
(5i-CO2Bu)
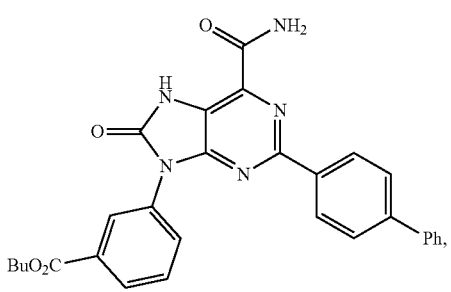
(8a-NH2)
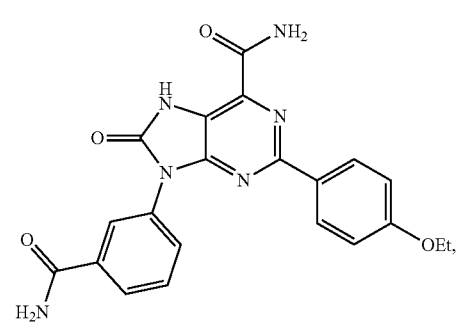
(8a-NHMe)
(8a-NHEt)
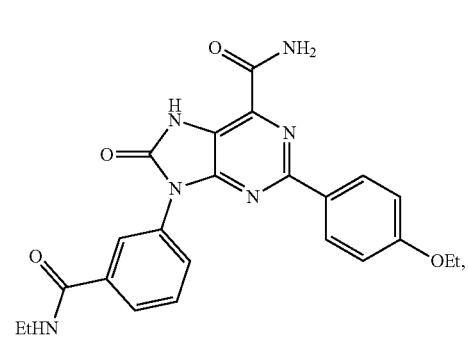
(8a-NHPr)
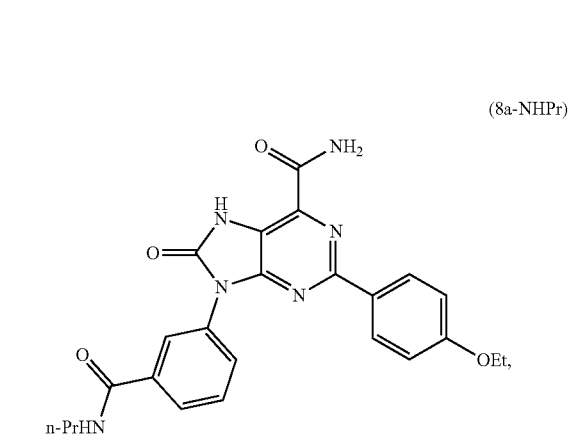
(8a-NHBu)
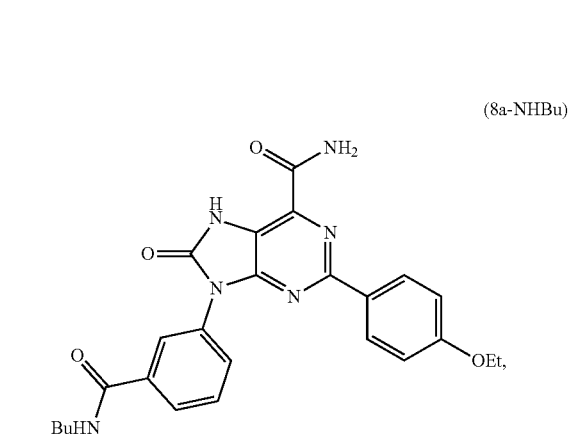
(8c-ethylidene)
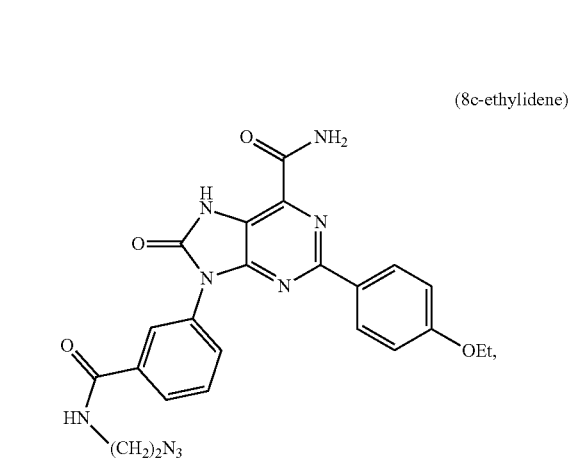

-continued
(8c-propylidene)
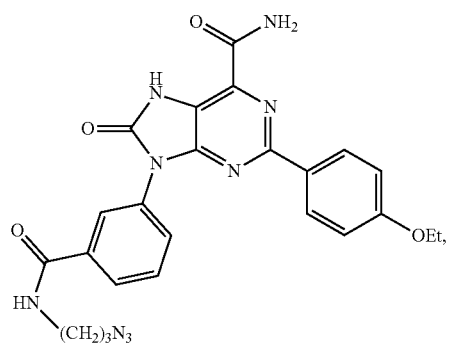
(8c-butylidene)

(8c)
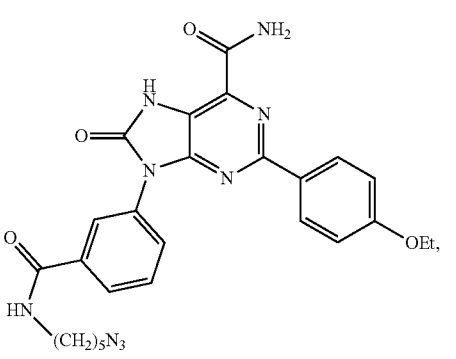
(8c-hexylidene)
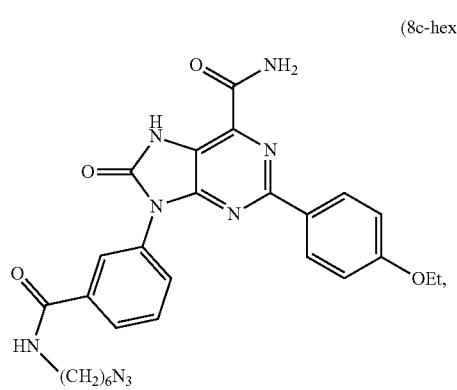
-continued
(8c-ethylidene-NH$_2$)
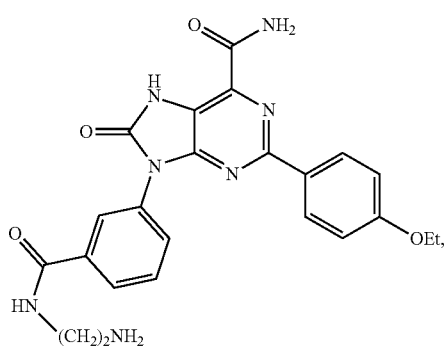
(8c-propylidene-NH$_2$)
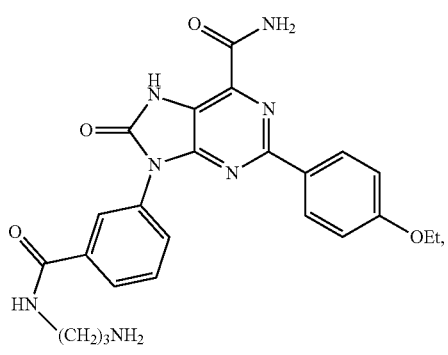
(8c-butylidene-NH$_2$)
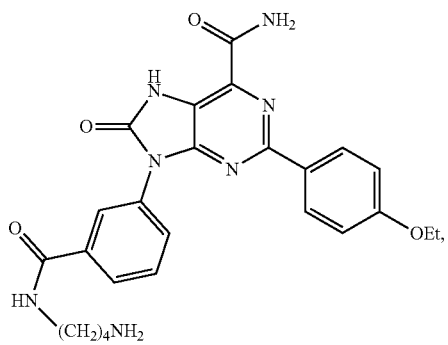
(8c-pentylidene-NH$_2$)
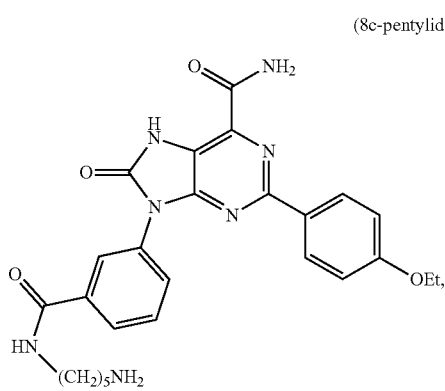

-continued
(8c-hexylidene-NH₂)
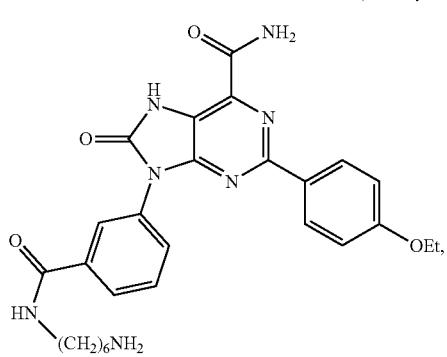
(8d-ethylidene)
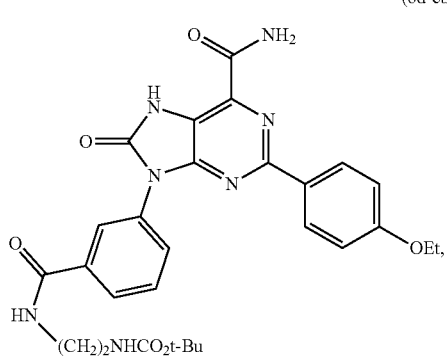
(8d-propylidene)
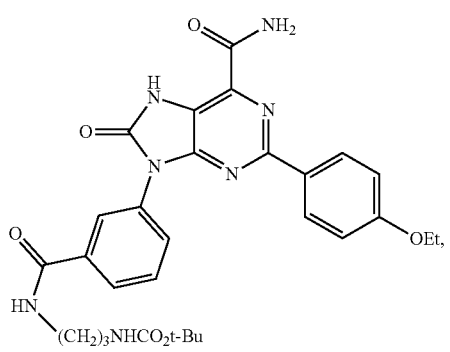
(8d-butylidene)
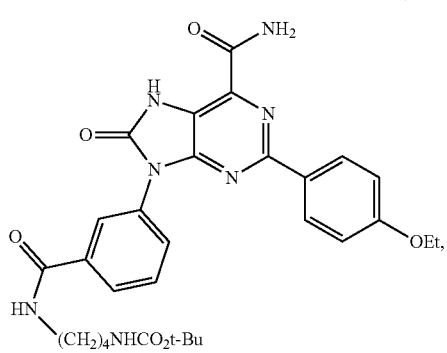
-continued
(8d)
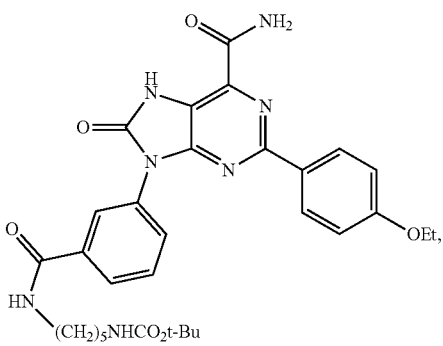
(8d-hexylidene)
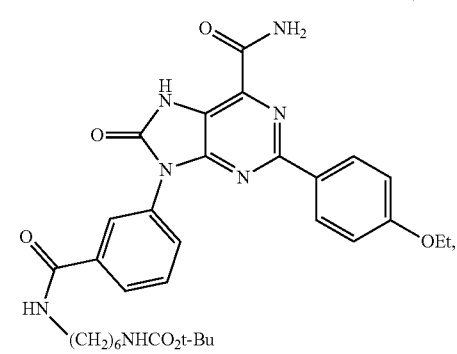
(8f-ethylidene)
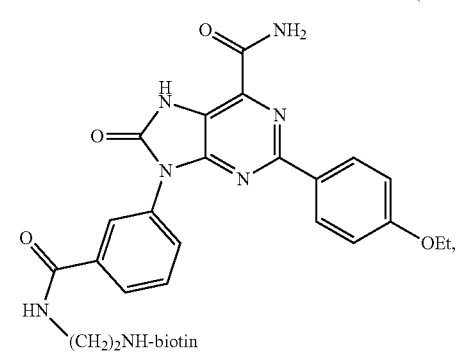
(8f-propylidene)
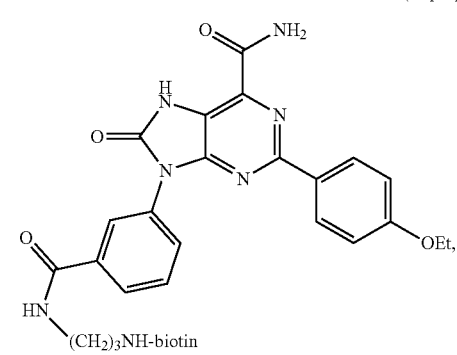

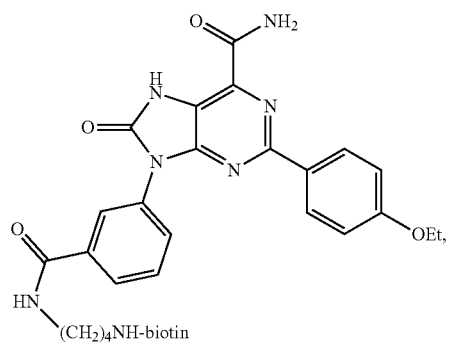
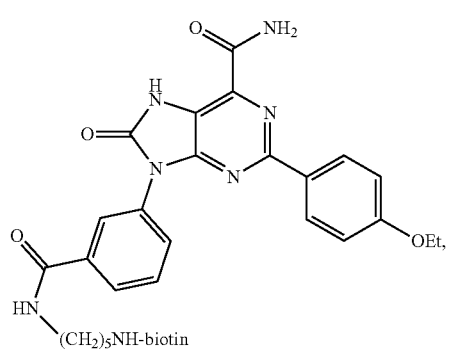
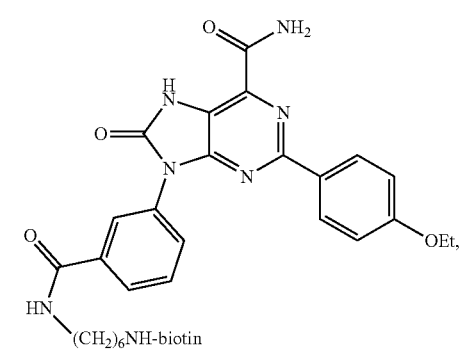
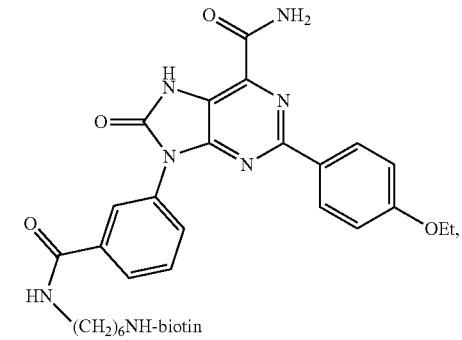

-continued
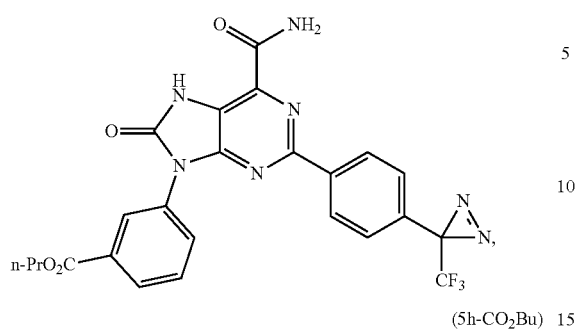
(5h-CO₂Pr)
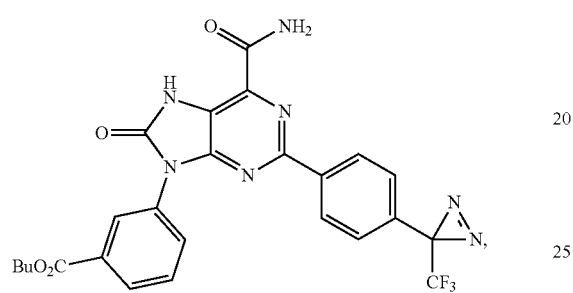
(5h-CO₂Bu)
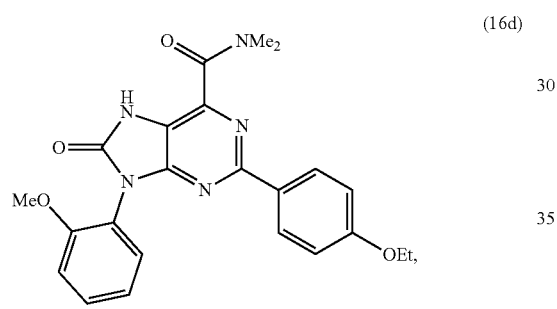
(16d)
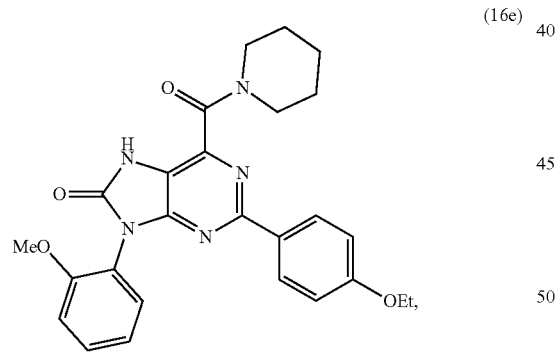
(16e)
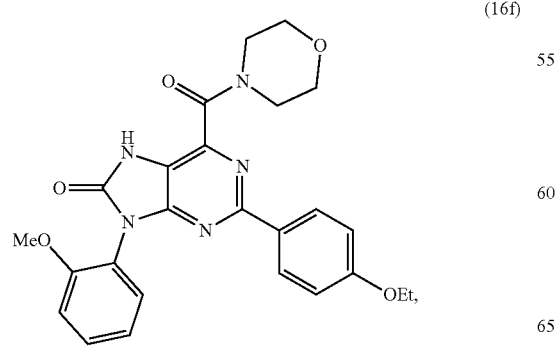
(16f)
-continued
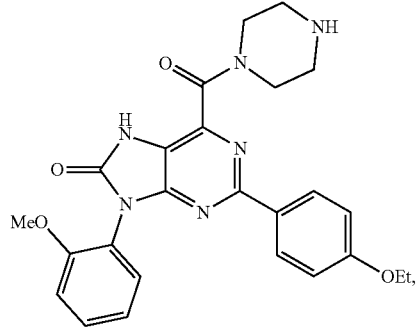
(16g)
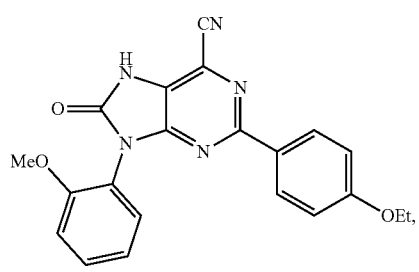
(12a)
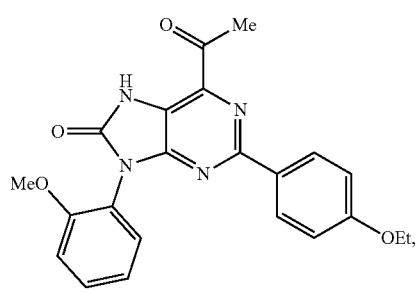
(37a)
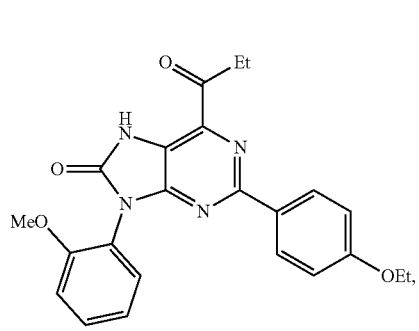
(37b)
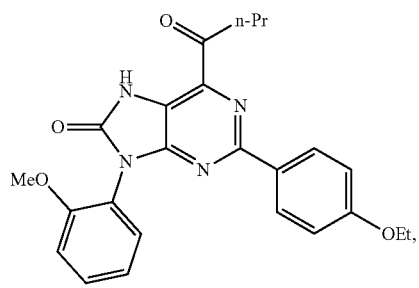
(37c)

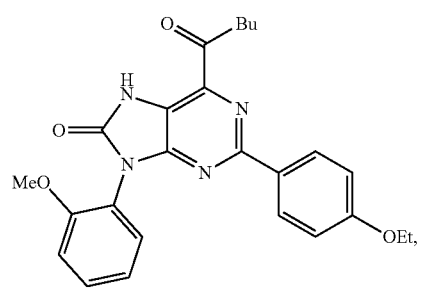
(37d)
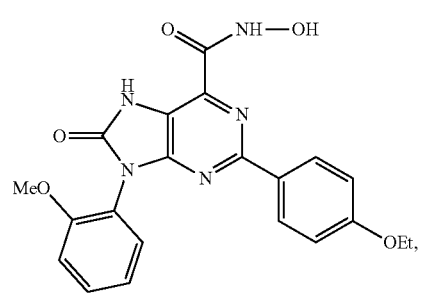
(19a)
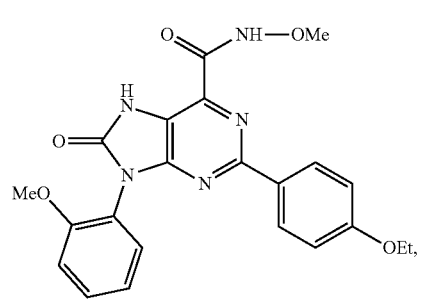
(19b)
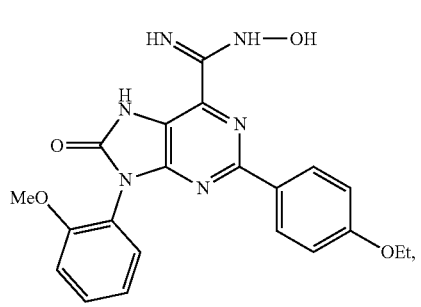
(14a')
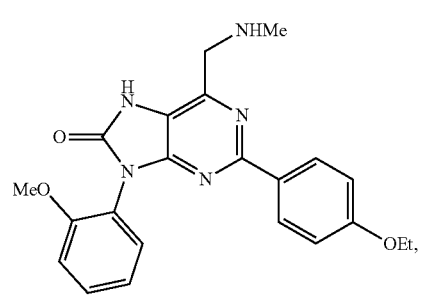
(38a)
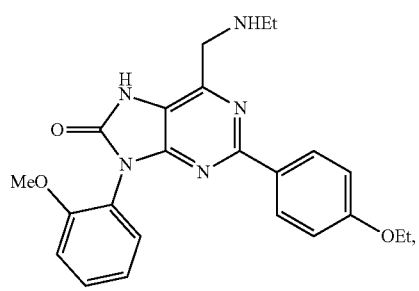
(38b)
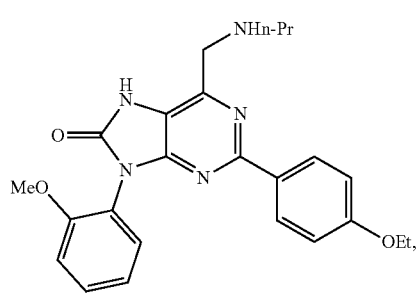
(38c)
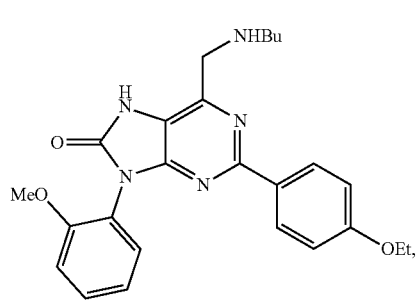
(38d)
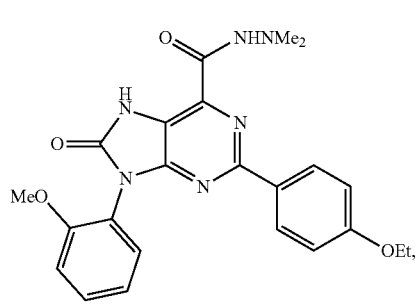
(20b)
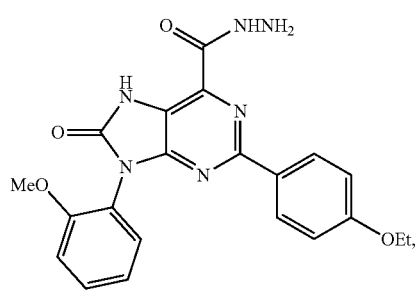
(20a)

-continued
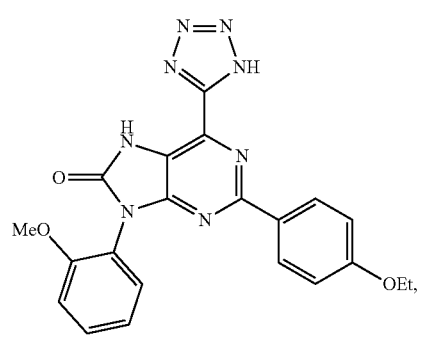
(24b)
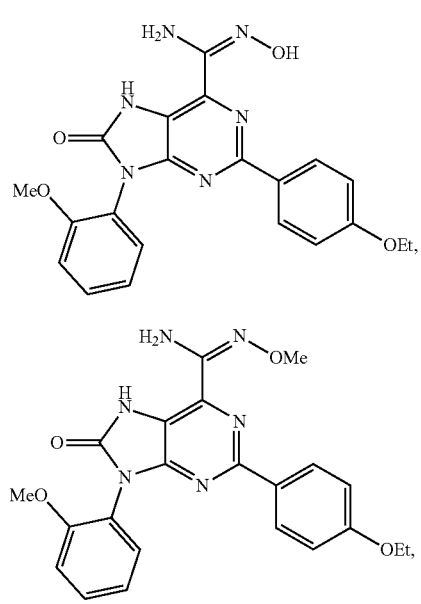
(14a)
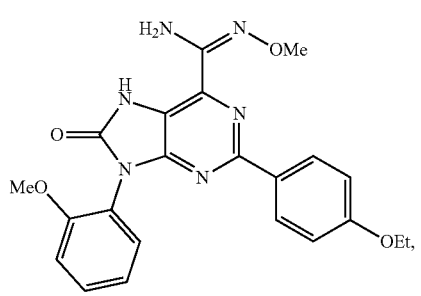
(14h')
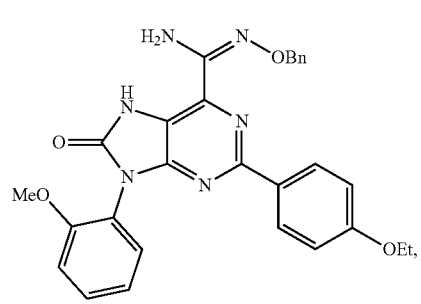
(14i')
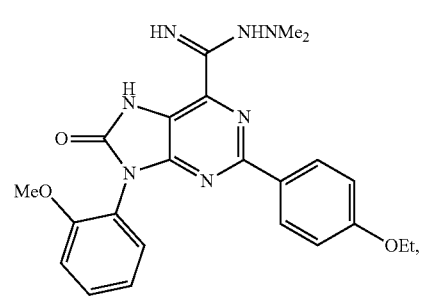
(14j)
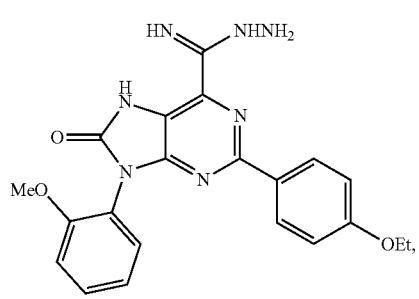
(14k)
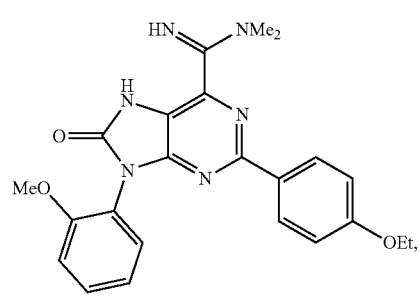
(14l)
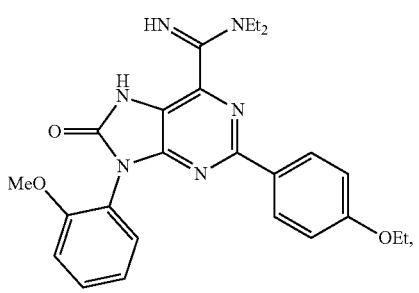
(14m)
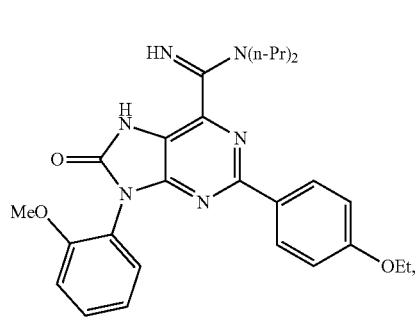
(14n)
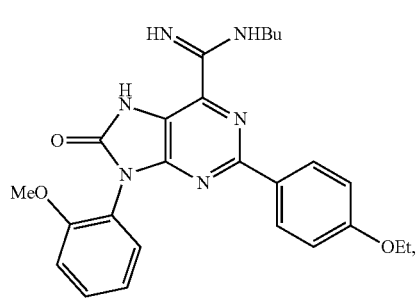
(14o)

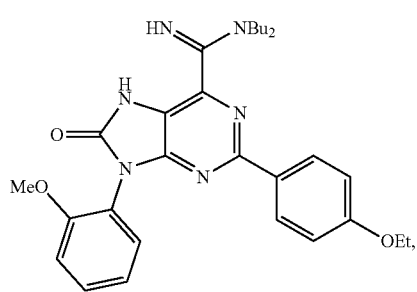 (14p)
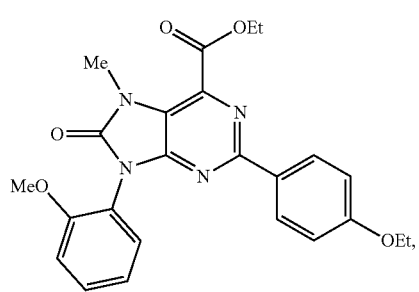 (18j)
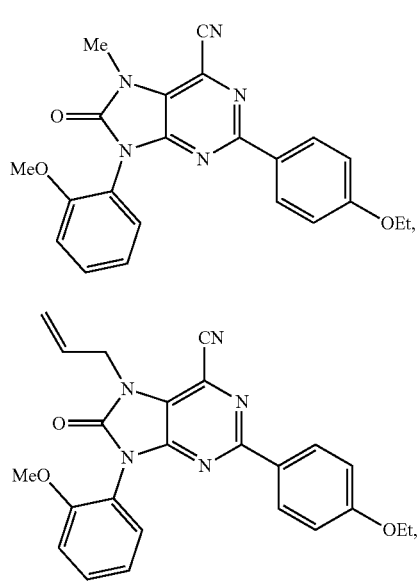 (15a')
(15b)
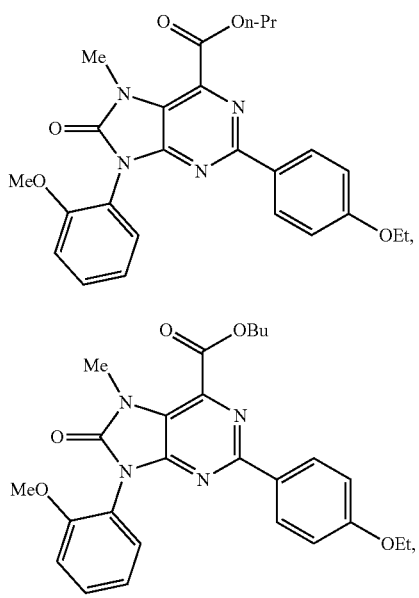 (18k)
(18l)
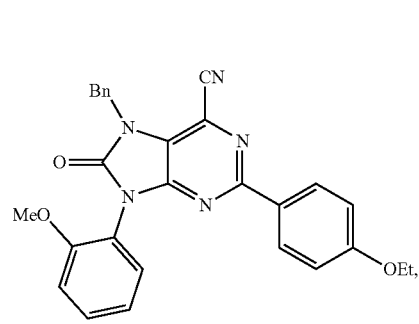 (15c)
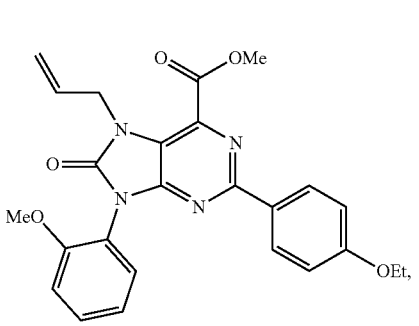 (18m)
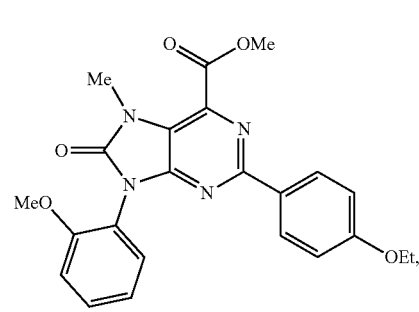 (18i)
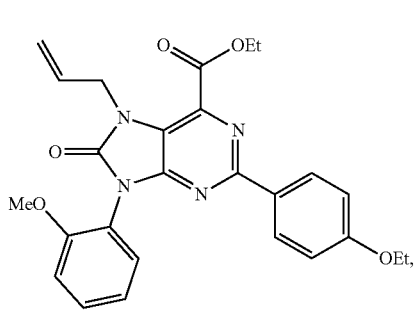 (18n)

-continued
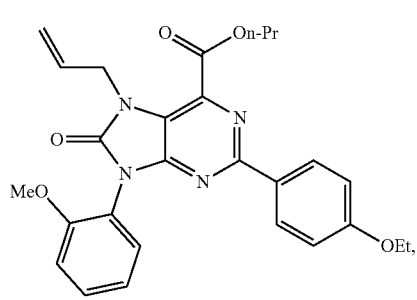
(18o)
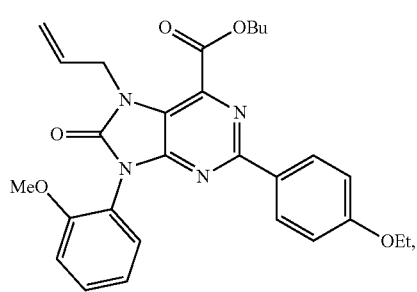
(18p)
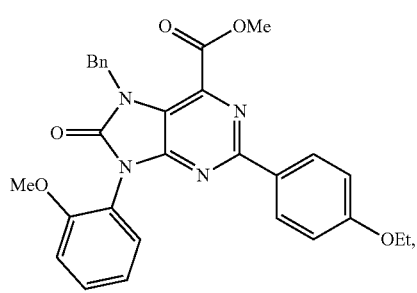
(18q)
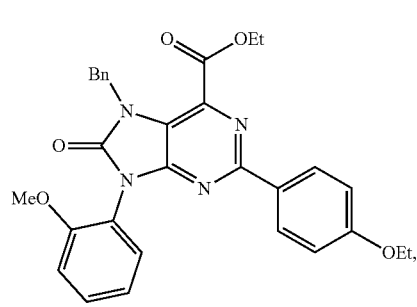
(18r)
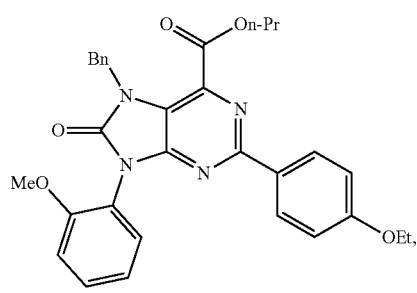
(18s)
-continued
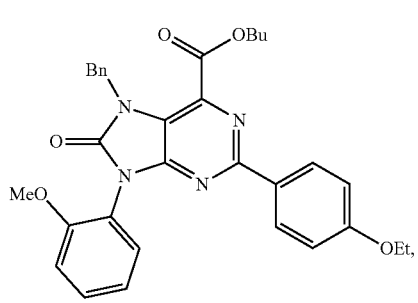
(18t)
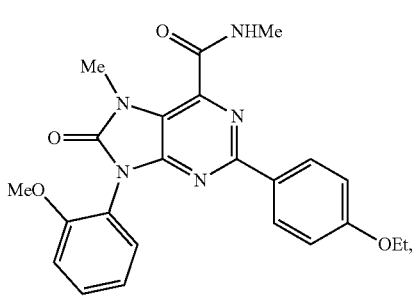
(16h)
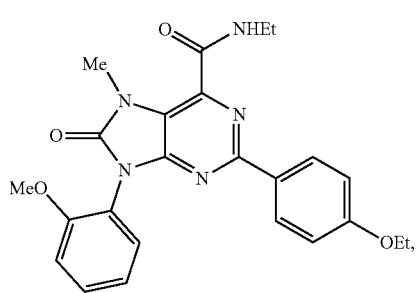
(16i)
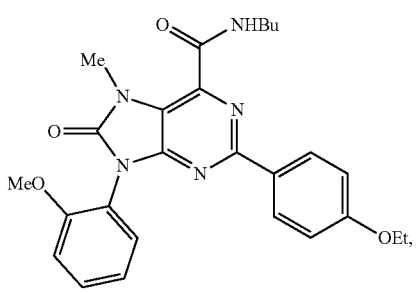
(16j)
(16k)

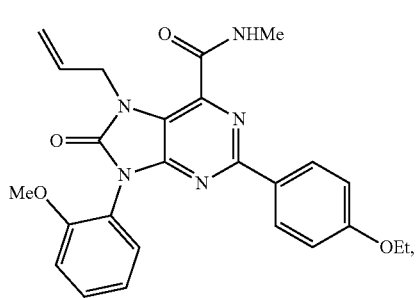
(16l)
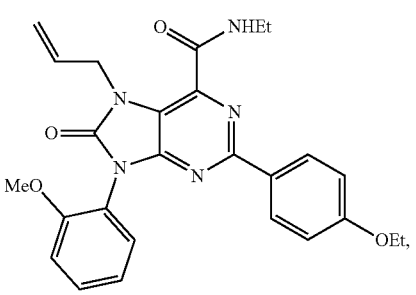
(16m)
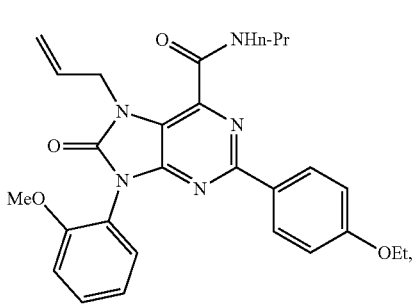
(16n)
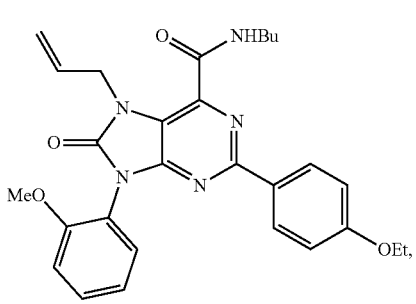
(16o)
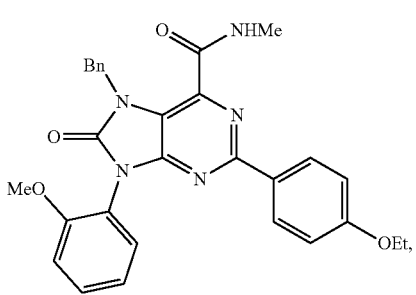
(16p)
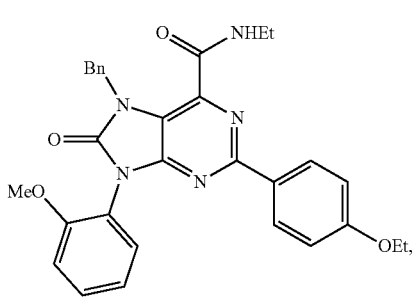
(16q)
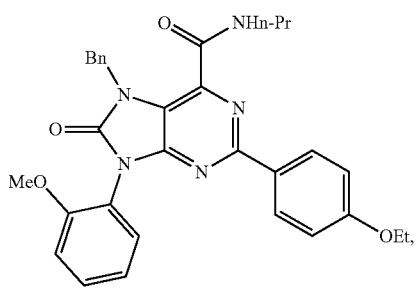
(16r)
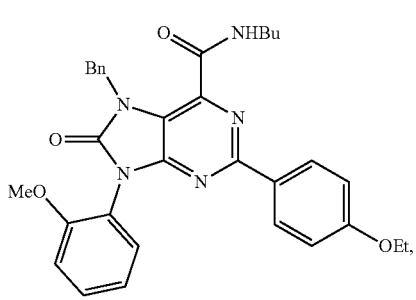
(16s)
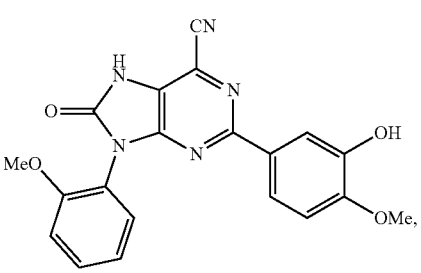
(12f)
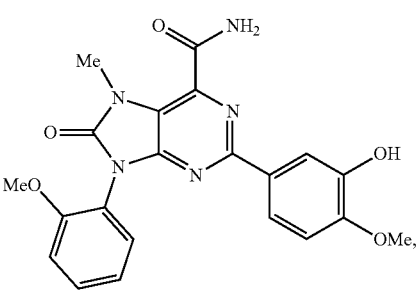
(16b)

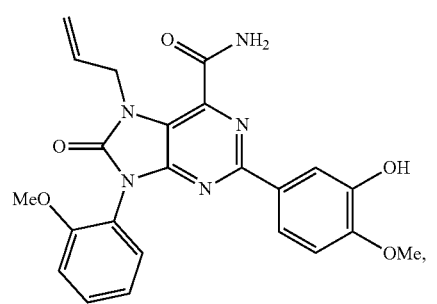
(16b-allyl)
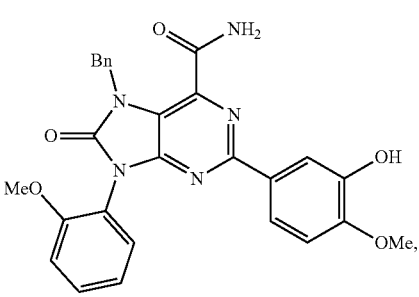
(16b-benzyl)
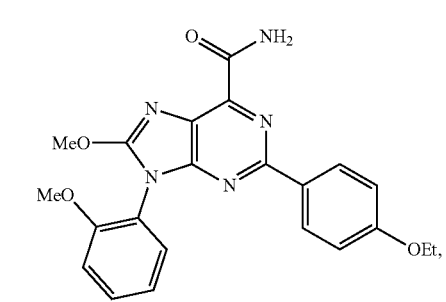
(16a)
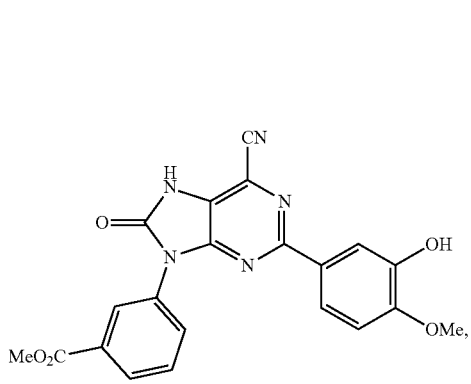
(12h)
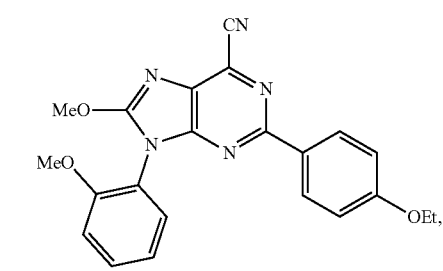
(15a)
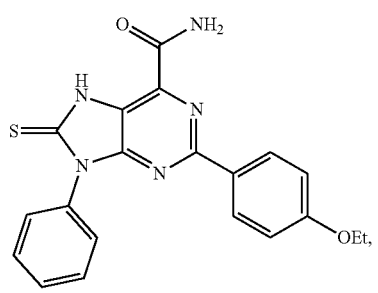
(10g')
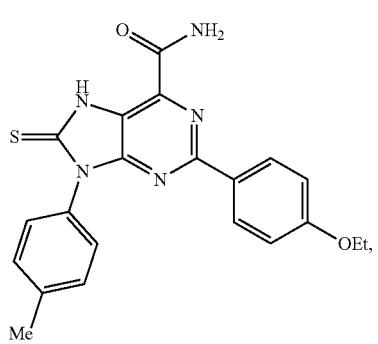
(10h')
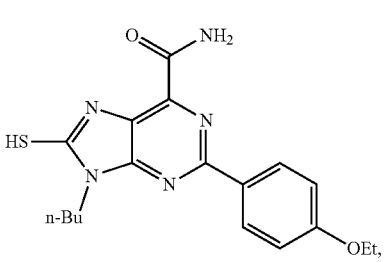
(10f)
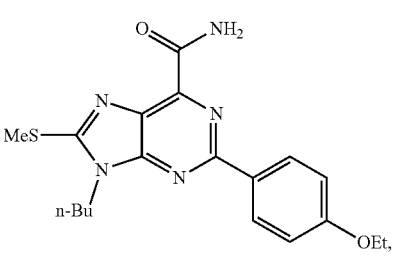
(11h)
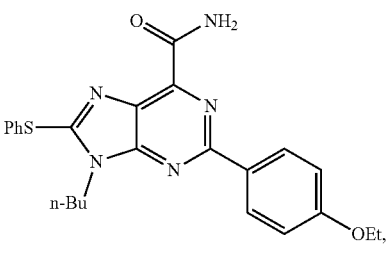
(11i)
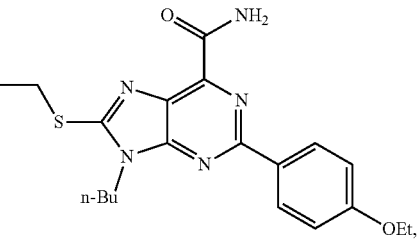
(11j)

-continued
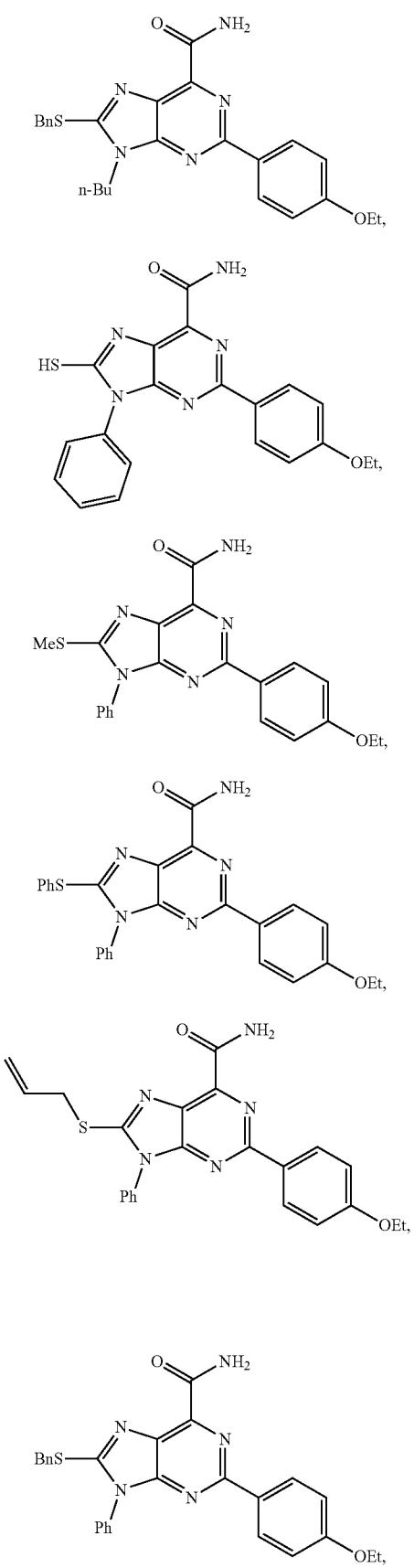
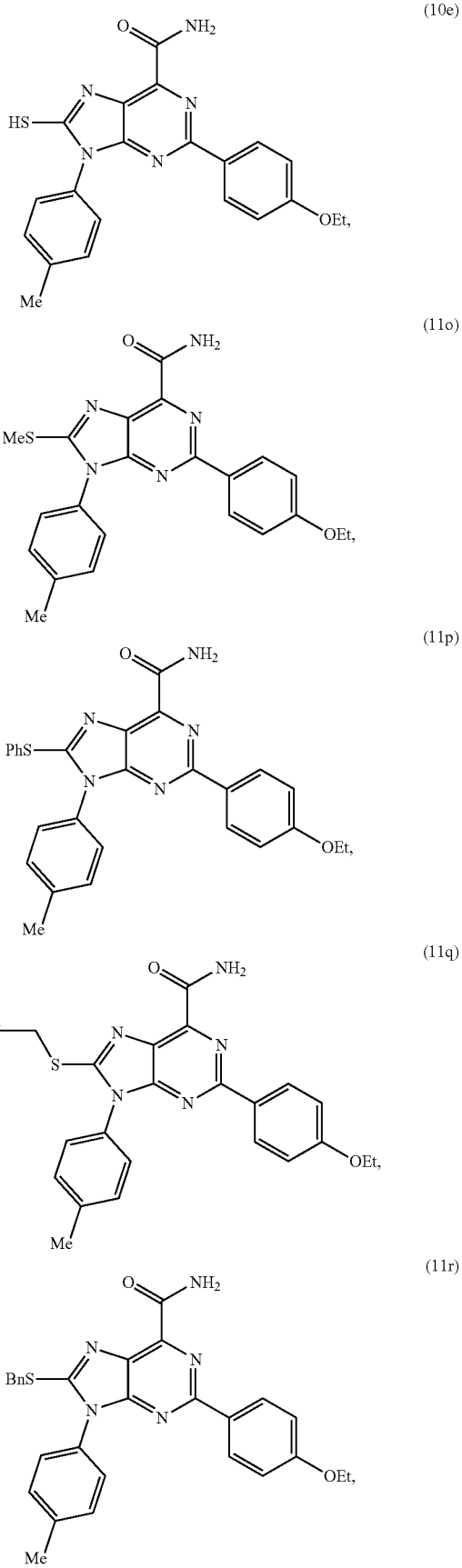

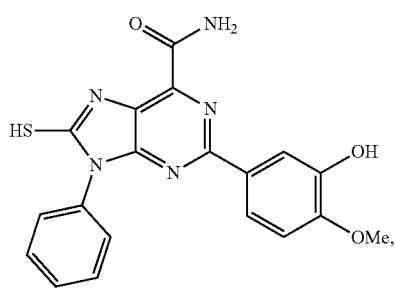
(10d)
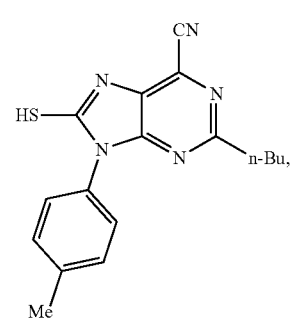
(27b)
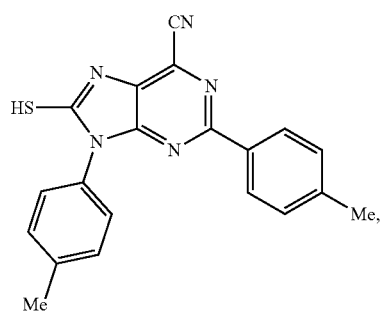
(27c)
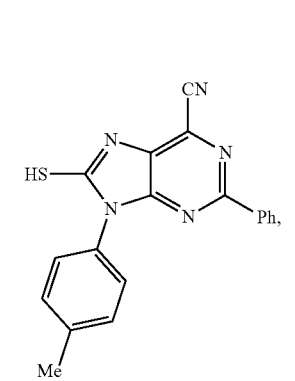
(27d)
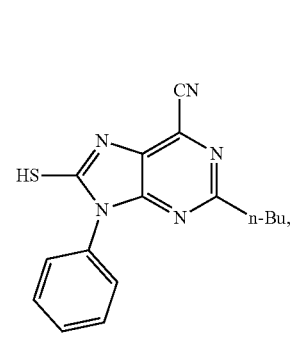
(27e)
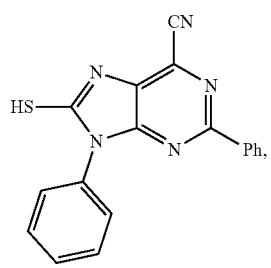
(27f)
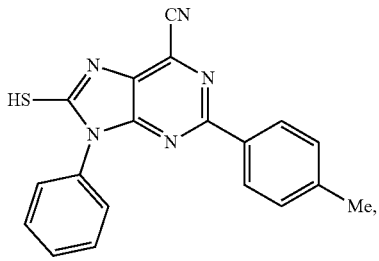
(27g)
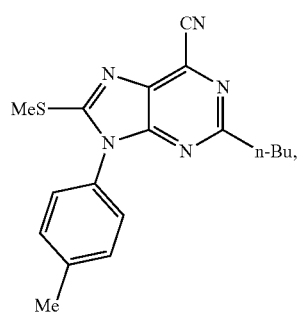
(28b)
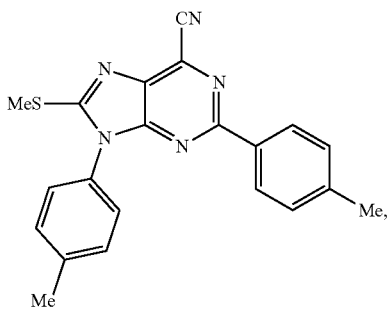
(28c)
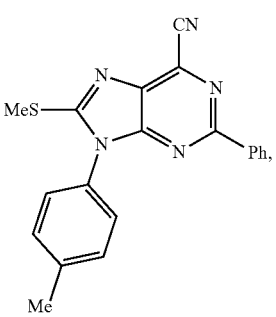
(28d)

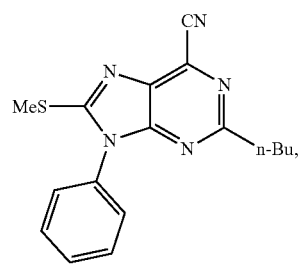
(28e)
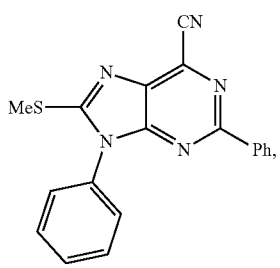
(28f)
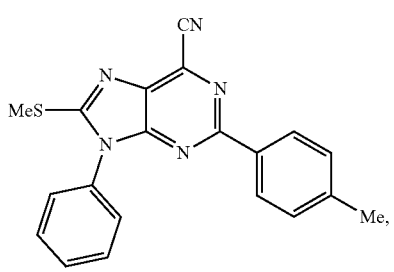
(28g)
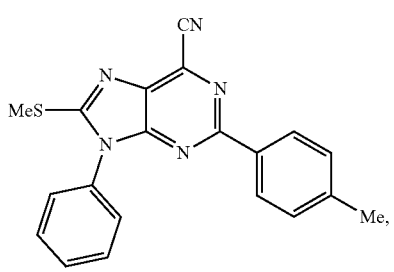
(28h)
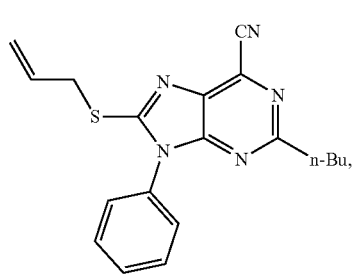
(28i)
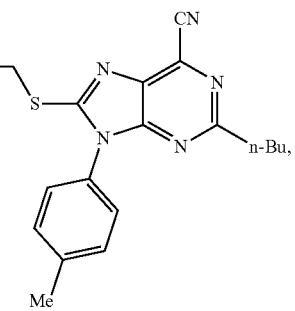
(28j)
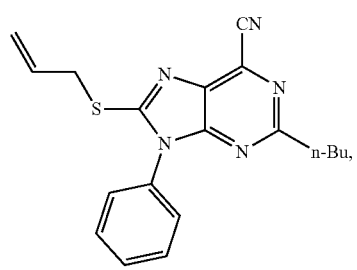
(28k)
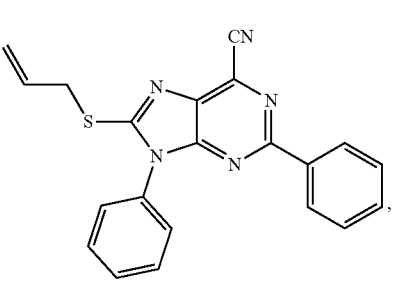
(28l)
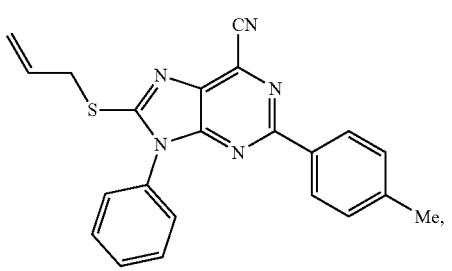
(28m)
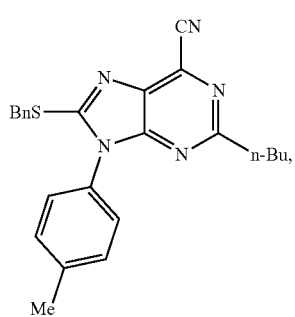
(28n)

-continued
(28o)
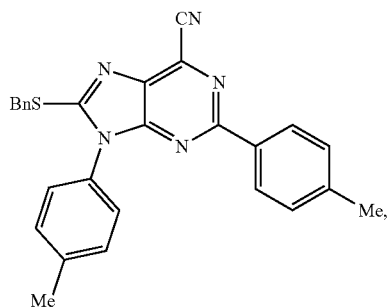
(28p)
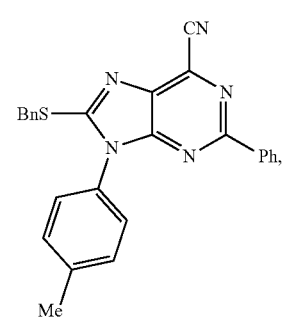
(28q)
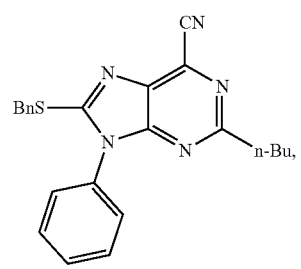
(28r)
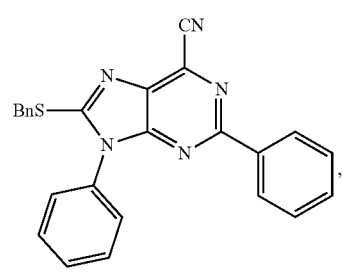
(28s)
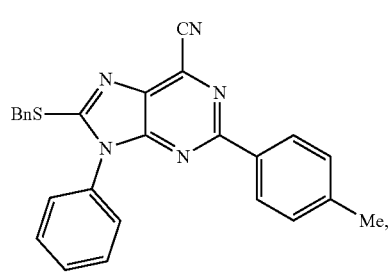
-continued
(30b)
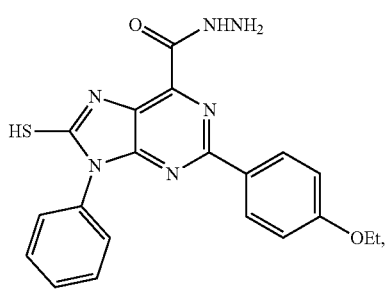
(30c)
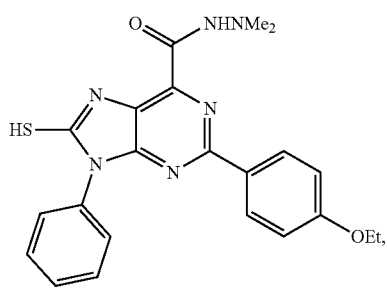
(30d)
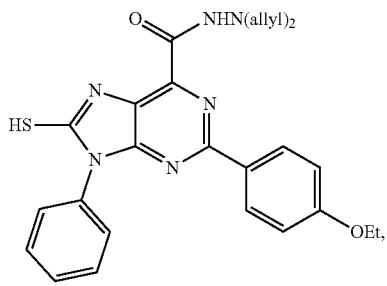
(30e)
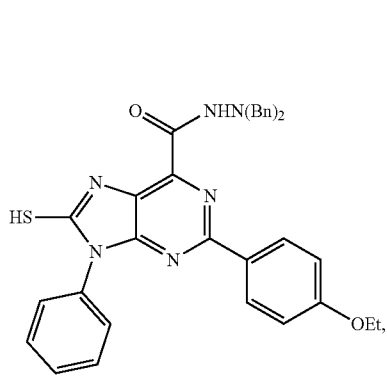
(30f)
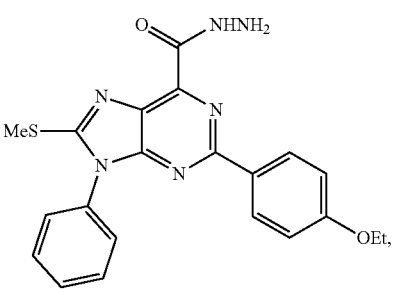

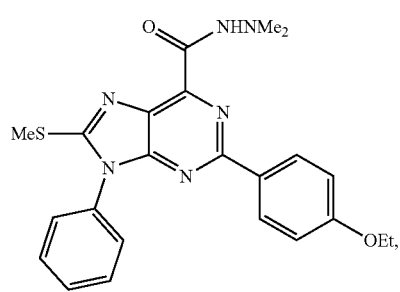 (30g)
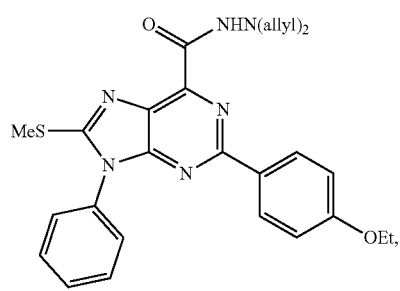 (30h)
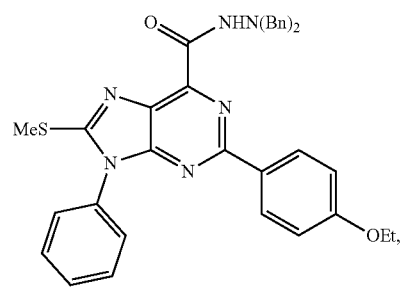 (30i)
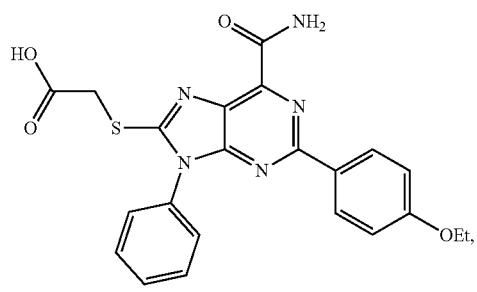 (11g)
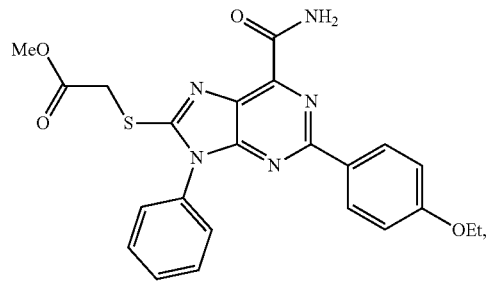 (11f)
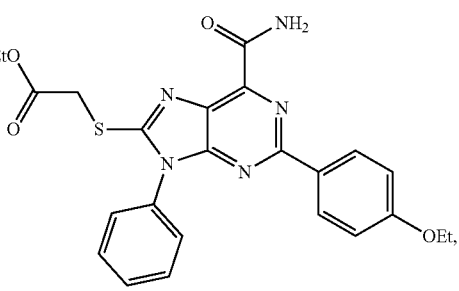 (11s)
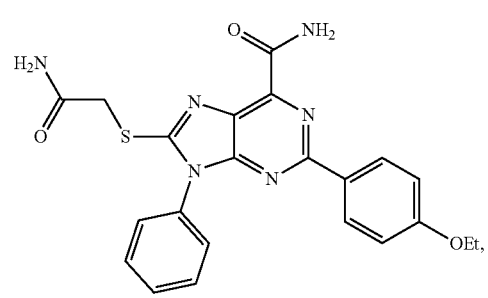 (11t)
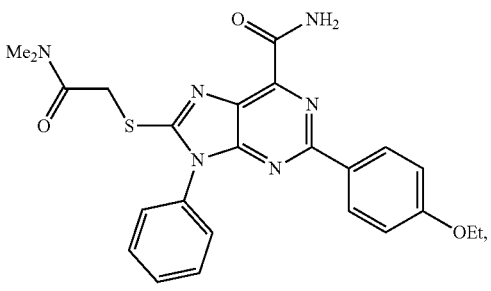 (11u)
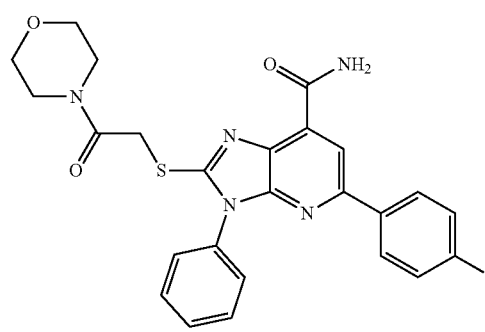 (11c)
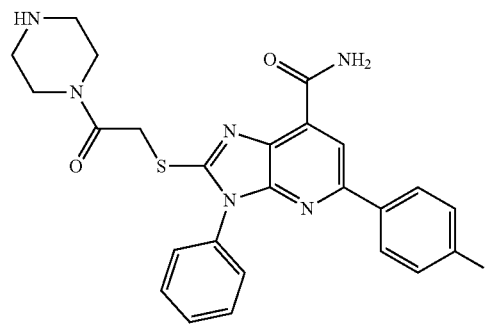 (11e)

-continued
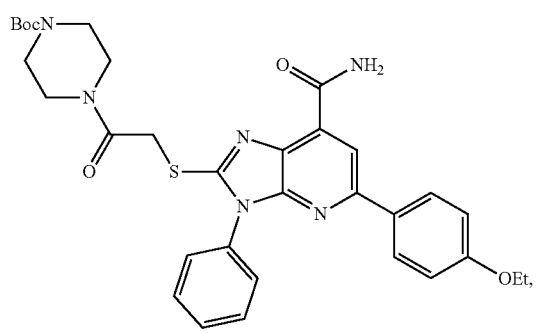
(11d)
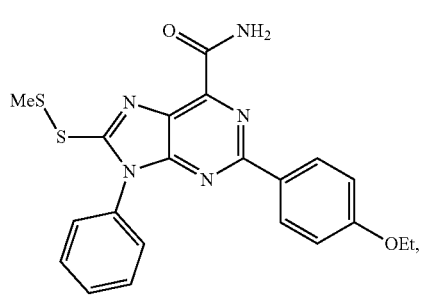
(26d)
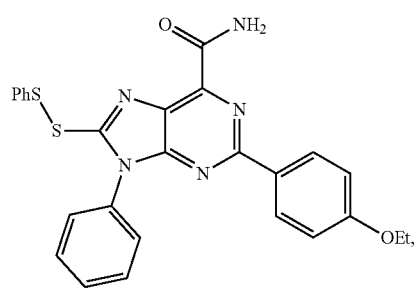
(26e)
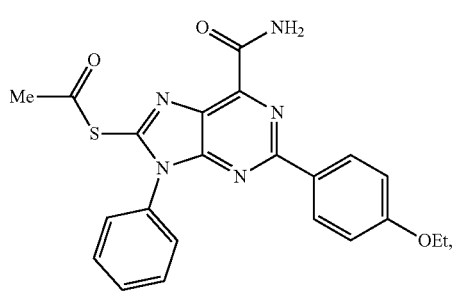
(26a)
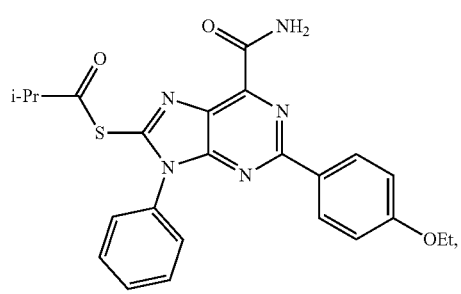
(26b)
-continued
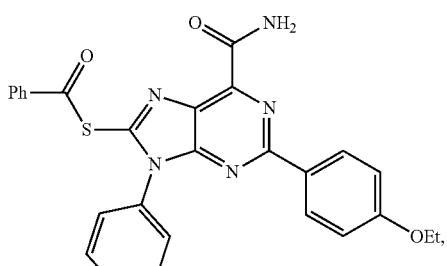
(26c)
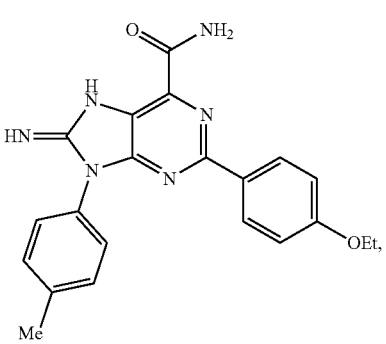
(32b'-toluene)
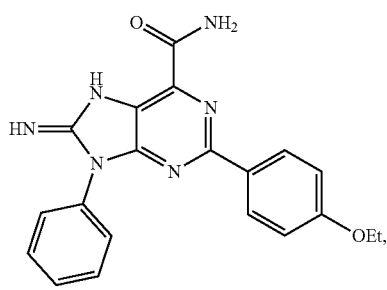
(32b')
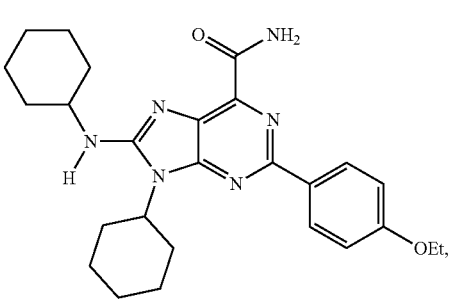
(32a)
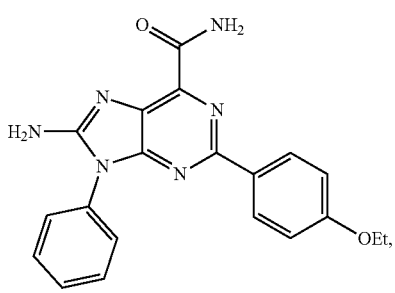
(32b)

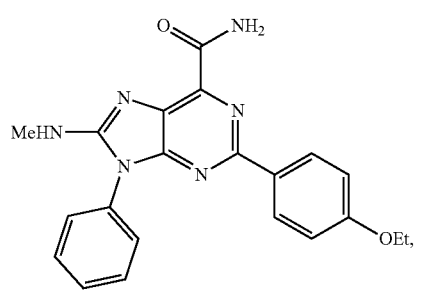 (32c)
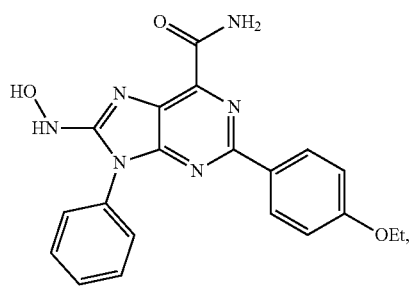 (32h)
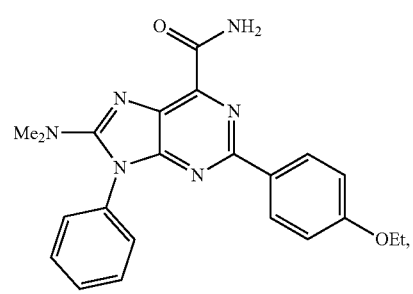 (32d)
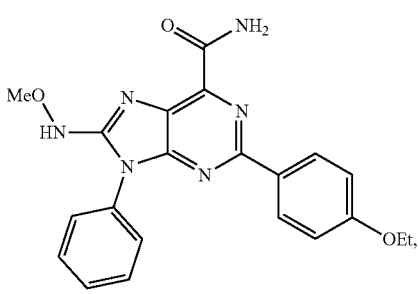 (32i)
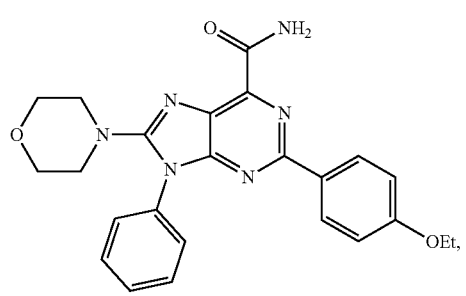 (32e)
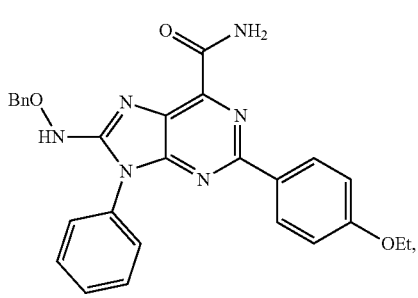 (32j)
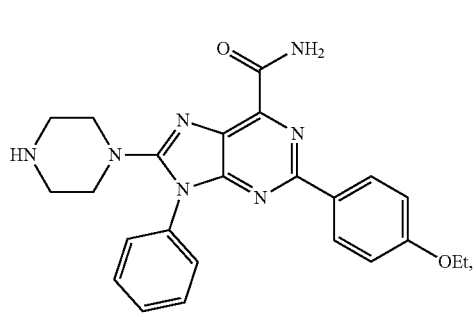 (32f)
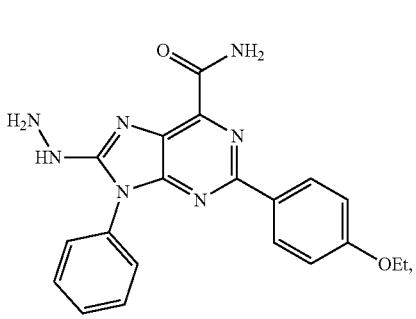 (32k)
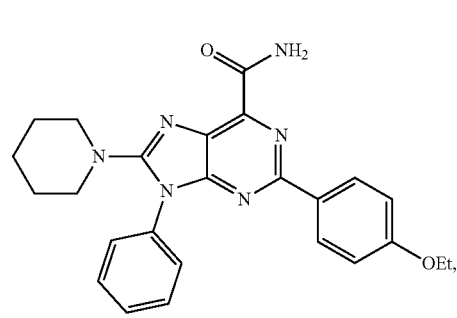 (32g)
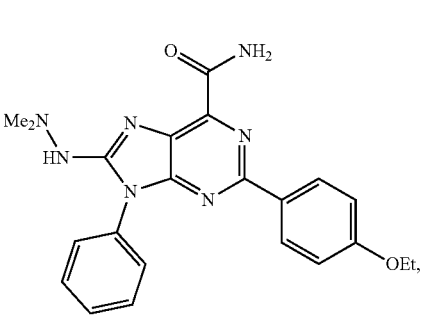 (32l)

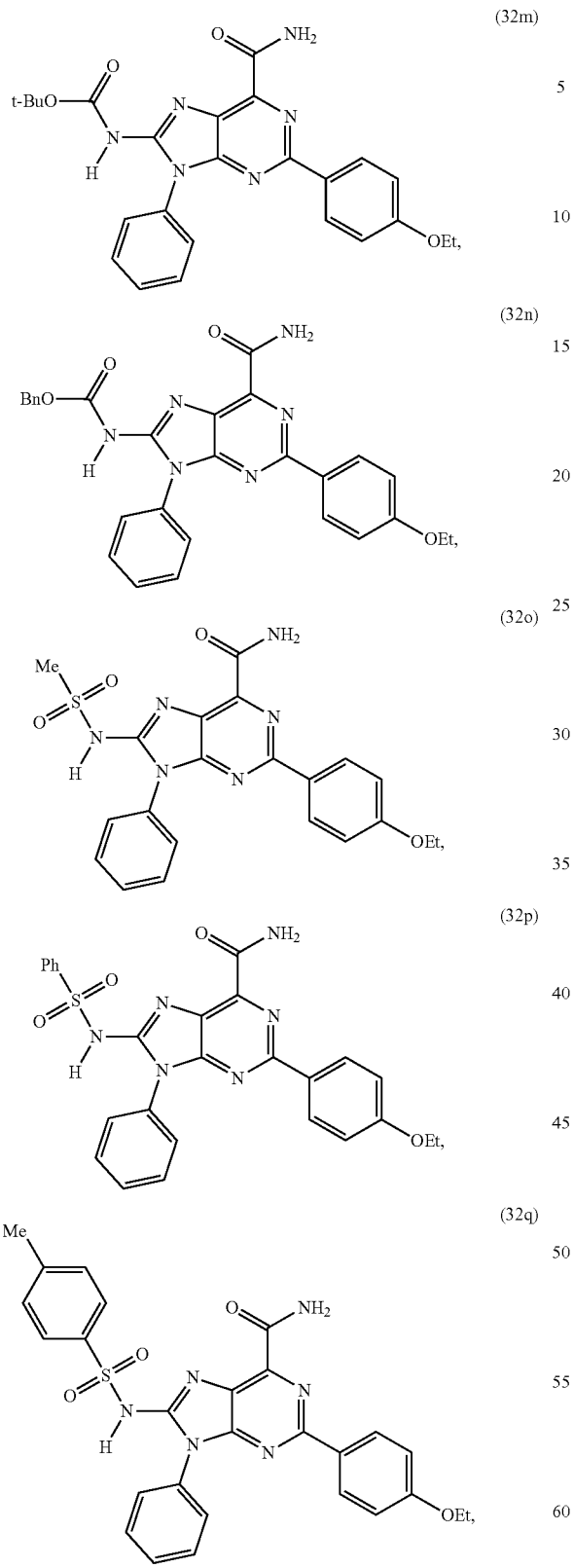
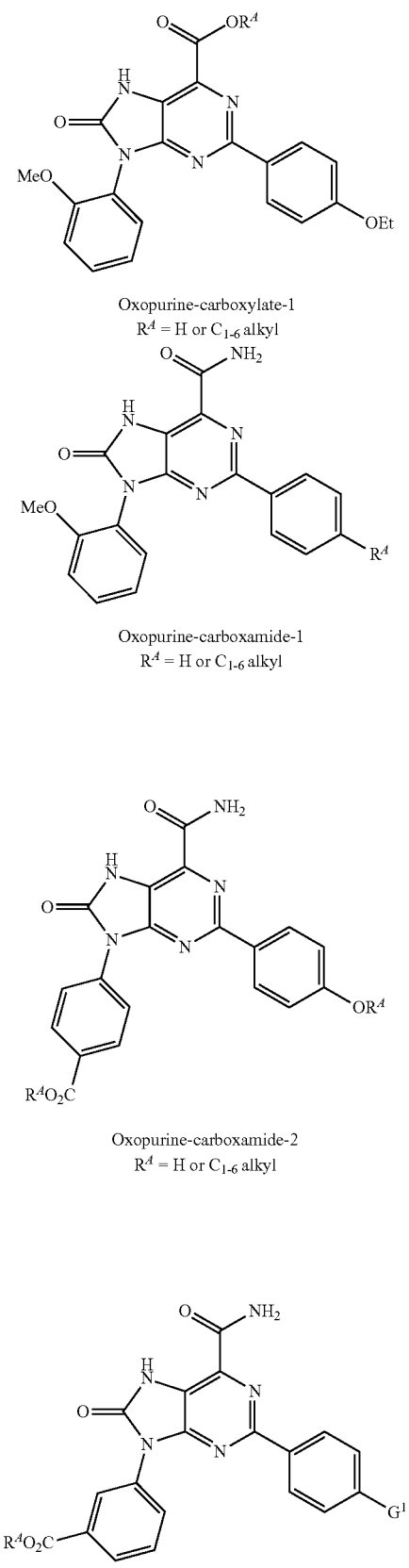
or a pharmaceutically acceptable salt thereof.
Further exemplary compounds of Formulas (I') and (I) include, but are not limited to:

-continued

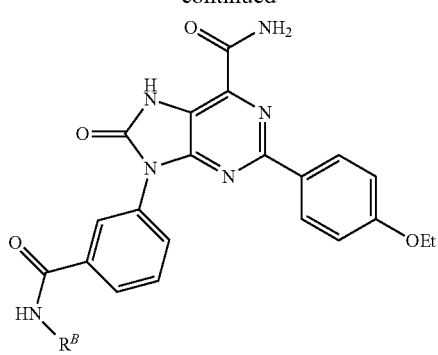

Oxopurine-carboxamide-4
$R^B$ = H or $C_{1-12}$ alkyl

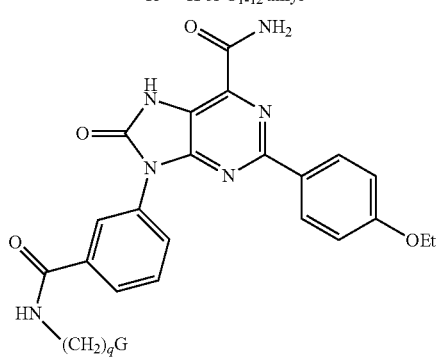

Oxopurine-carboxamide-5
G = $N_3$, $NH_2$, $NHCO_2$t-Bu,
NH-biotin
q = 1-12

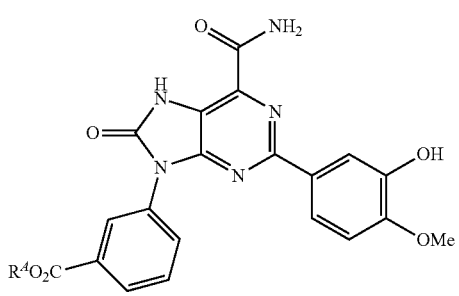

Oxopurine-carboxamide-3
$R^A$ = H or $C_{1-12}$ alkyl

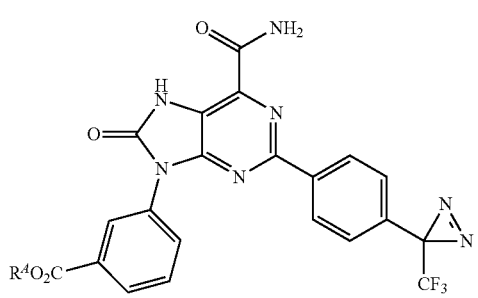

Oxopurine-carboxamide-6
$R^A$ = H or $C_{1-12}$ alkyl

-continued

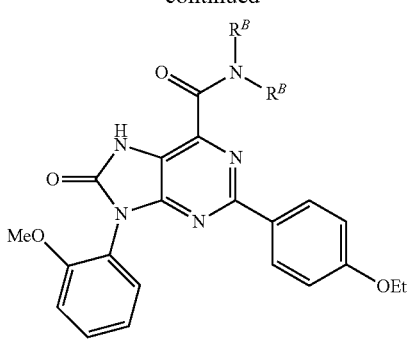

Oxopurine-carboxamide-7
$(R^B,R^B)$ = (Me,Me); or two
instances of $R^B$ are taken
together with the intervening
nitrogen to form piperidine,
moprholine, or piperazine.

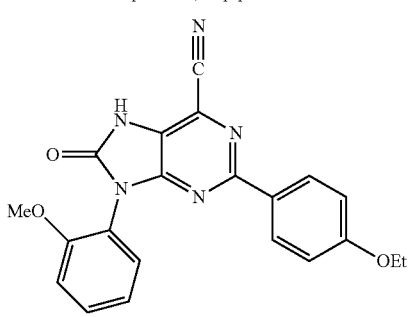

Oxopurine-carbonitrile-1

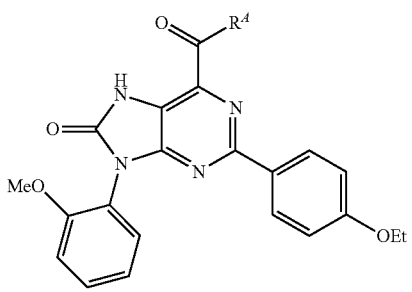

Oxopurine-carbonyl
$R^A$ = H or $C_{1-6}$ alkyl

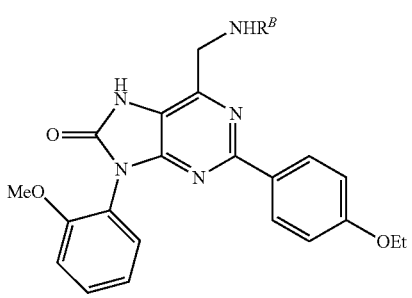

Aminomethyl-oxopurine
$R^B$ = H or $C_{1-6}$ alkyl

-continued

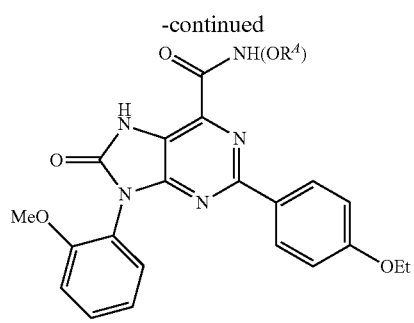

Oxopurine-(N-alkoxy)carboxamide
$R^A$ = H, Me, benzyl

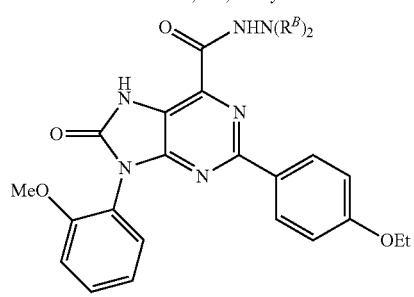

Oxopurine-carbohydrazide
$R^B$ = H, Me

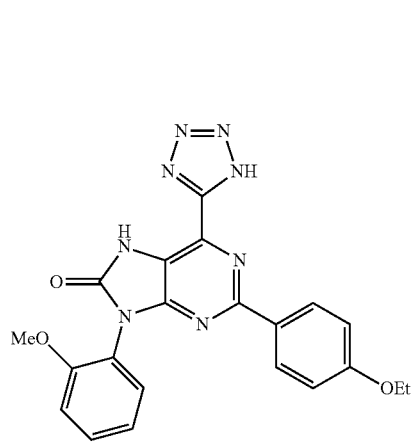

Oxopurine-tetrazole

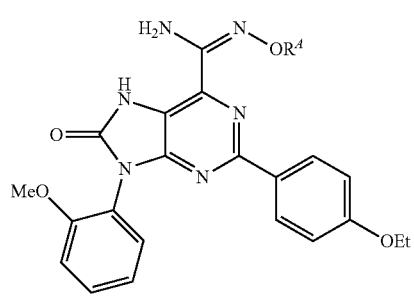

Oxopurine-(N-alkoxy)imidamide
$R^A$ = H, Me, benzyl.

-continued

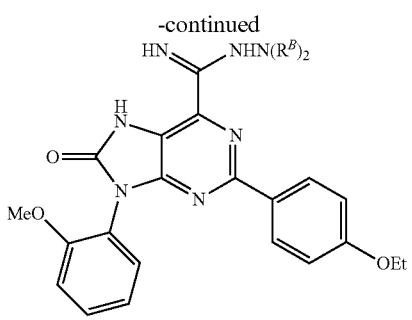

Oxopurine-imidohydrazide
$R^B$ = H, Me

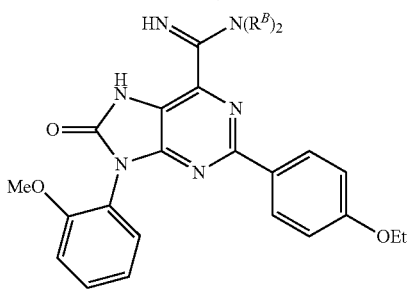

Oxopurine-imidamide
$R^B$ = H or $C_{1-6}$ alkyl

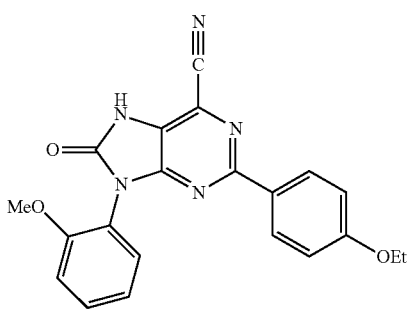

Oxopurine-carbonitrile-3
$R^3$ = Me, allyl, benzyl

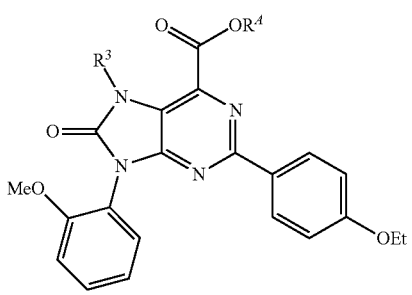

Oxopurine-carboxylate-2
$R^A$ = H or $C_{1-6}$ alkyl
$R^3$ = Me, allyl, benzyl

-continued

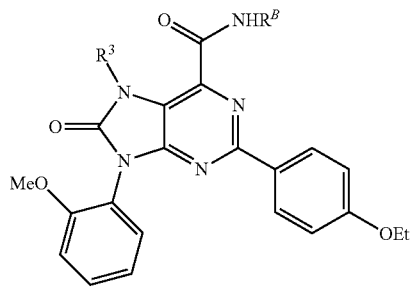

Oxopurine-carboxamide-9
$R^3$ = Me, allyl, benzyl
$R^B$ = H or $C_{1-6}$ alkyl

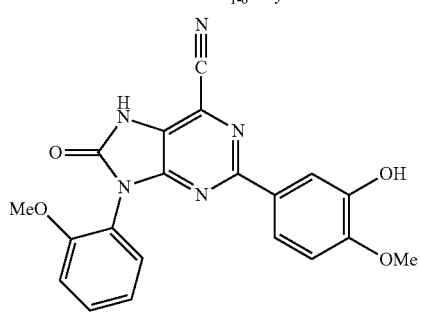

Oxopurine-carbonitrile-1

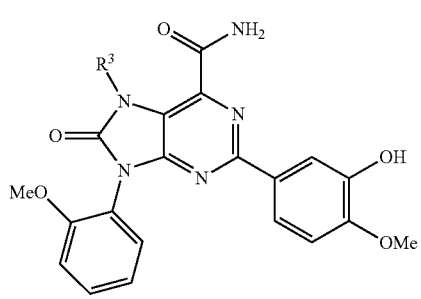

Oxopurine-carboxamide-7
$R^3$ = Me, allyl, benzyl

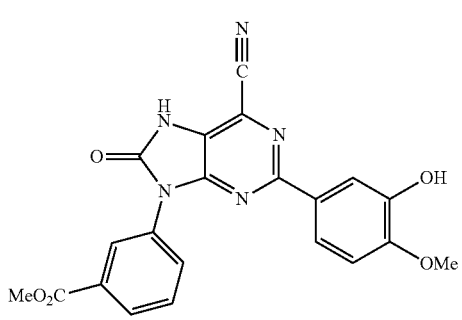

Oxopurine-carbonitrile-2

-continued

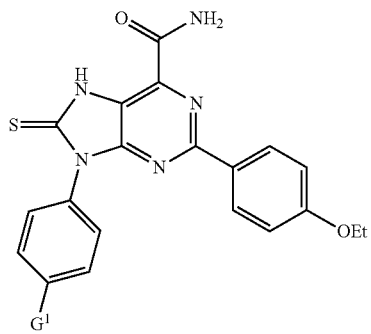

Thixopurine-carboxamide
$R^1$ = H, Me

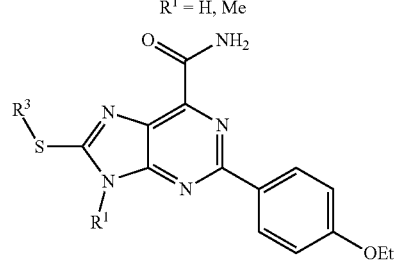

Mercaptopurine-carboxamide-2
$R^1$ = n-Bu, Ph, 4-MeC$_6$H$_4$
$R^3$ = H, Me, allyl, benzyl

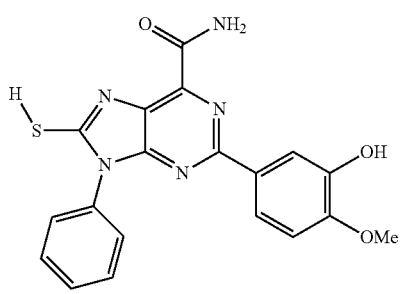

Mercaptopurine-carboxamide-1

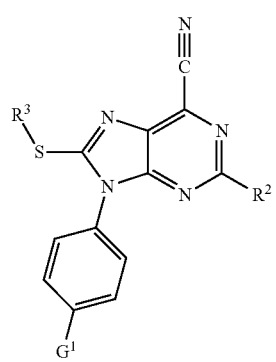

Mercaptopurine-carbonitrile
$G^1$ = H, Me
$R^2$ = n-Bu, Ph, 4-MeC$_6$H$_4$
$R^3$ = H, Me, allyl, benzyl -continued

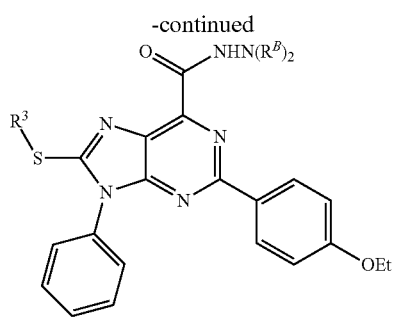

Mercaptopurine-carbohydrazide
R³ = H, Me, allyl, benzyl.
R^B = H, Me.

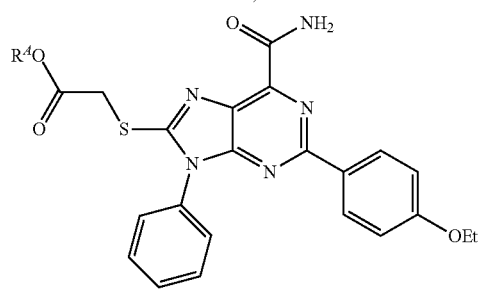

Mercaptopurine-carboxamide-3
R³ = H, Me, Et

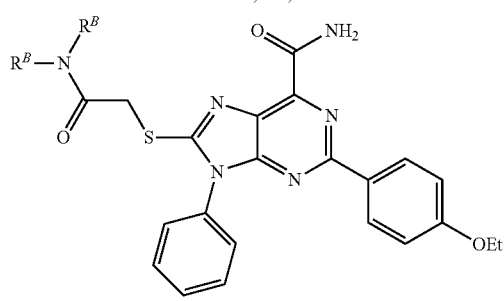

Mercaptopurine-carboxamide-4
(R^B,R^B) = (H,H) (Me,Me); or two instances of R^B are taken together with the intervening nitrogen to form moprholine, piperazine or Boc-piperazine

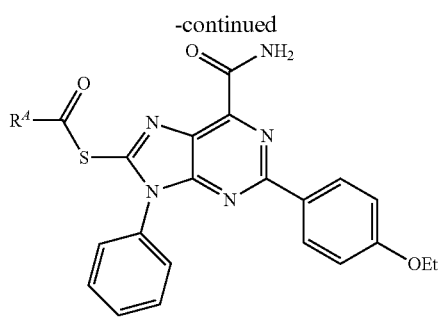

Mercaptopurine-carboxamide-5
R^A = Me, Ph

-continued

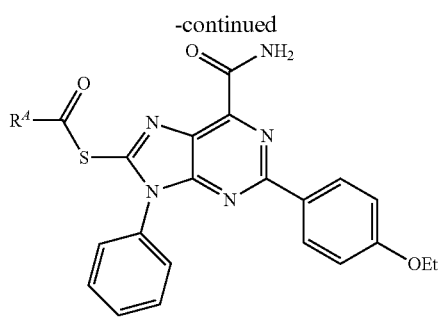

Mercaptopurine-carboxamide-6
R^A = Me, i-Pr, Ph

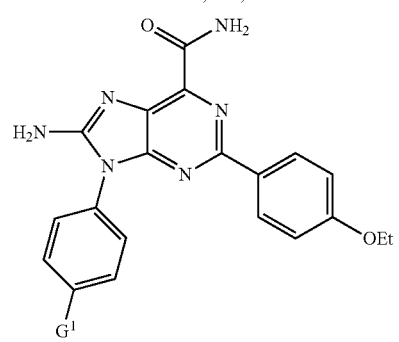

Aminopurine-carboxamide-1
G¹ = H, Me

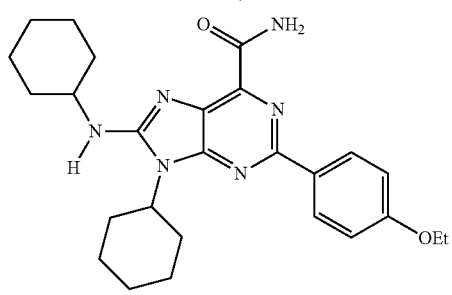

Aminopurine-carboxamide-2

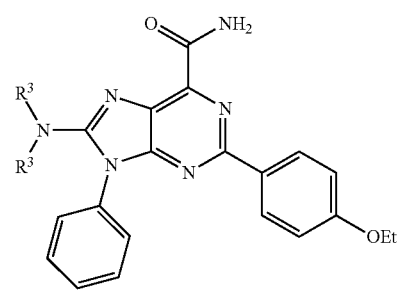

Aminopurine-carboxamide-3
(R³,R³) = (H,H), (H, Me), (Me,Me); or two instances of R³ are taken together with the intervening nitrogen to form piperidine, morpholine, or piperazine

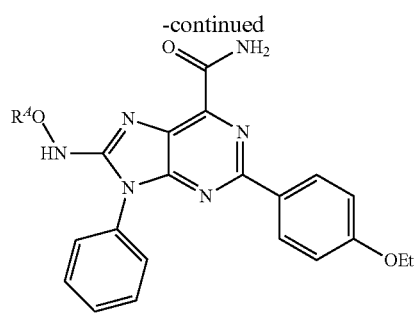
(N-Alkoxyamino)purine-carboxamide
R$^A$ = H, Me, Bn
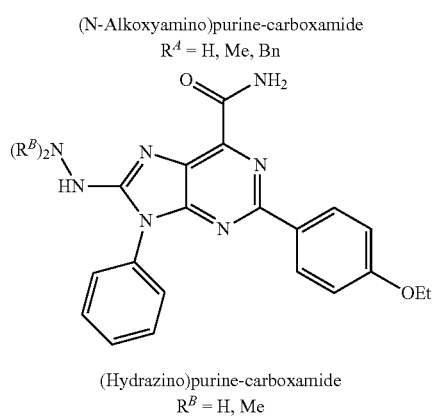
(Hydrazino)purine-carboxamide
R$^B$ = H, Me
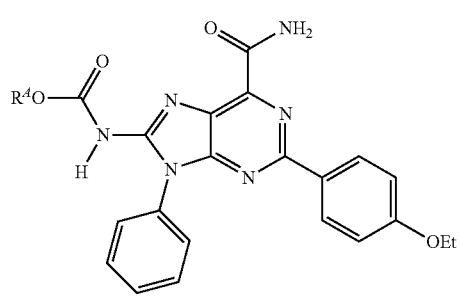
(Alkoxycarbonylamino)purine-carboxamide
R$^A$ = t-Bu, PhCH$_2$
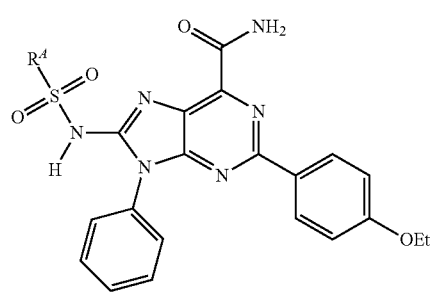
(Sulfonamino)purine-carboxamide
R$^A$ = Me, Ph, 4-MeC$_6$H$_4$
or a pharmaceutically acceptable salt thereof.
Additional exemplary compounds of Formula (I) include, but are not limited to:
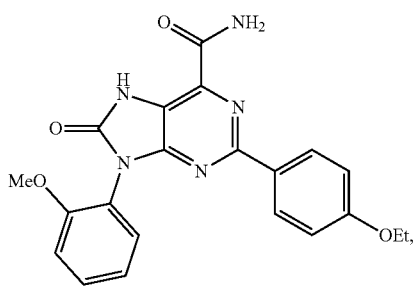
5a
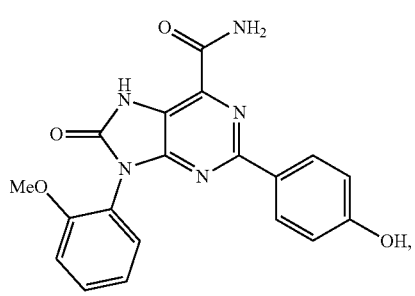
5b
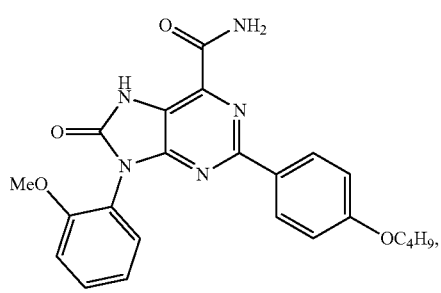
5c
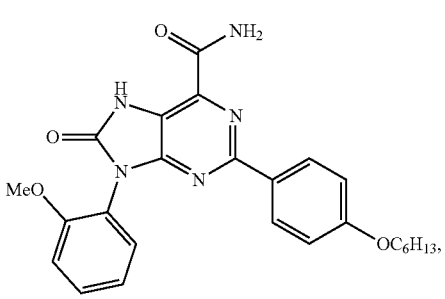
5d
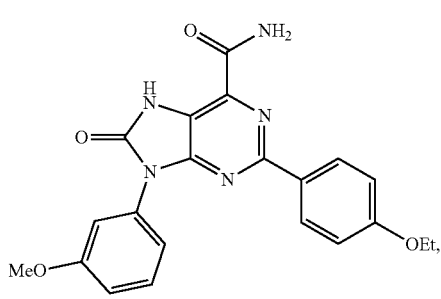
5e

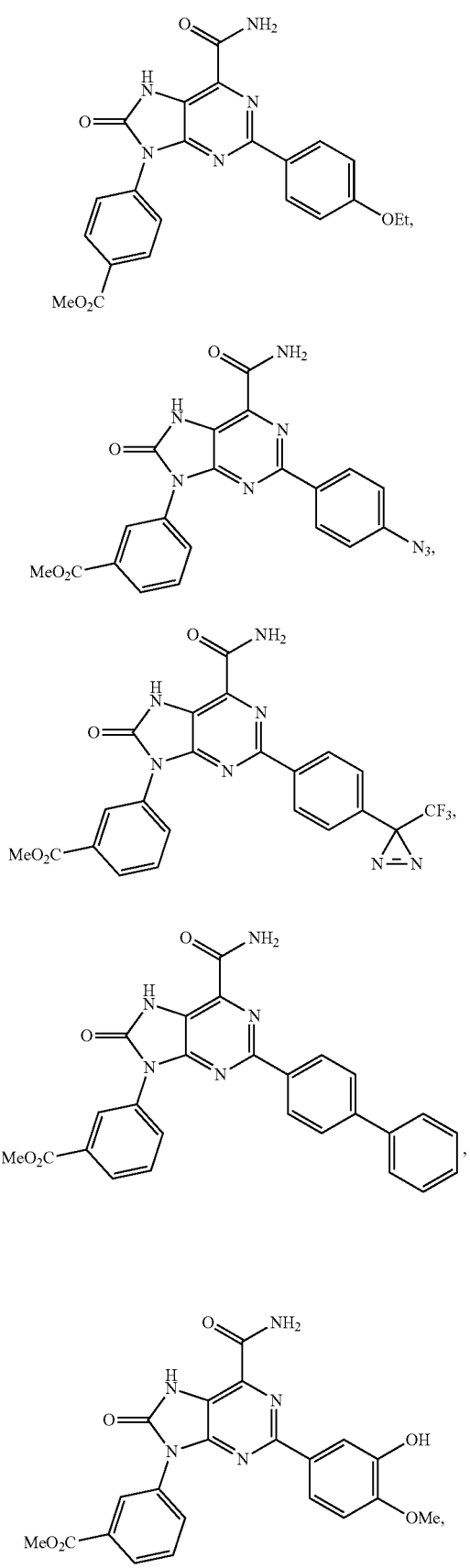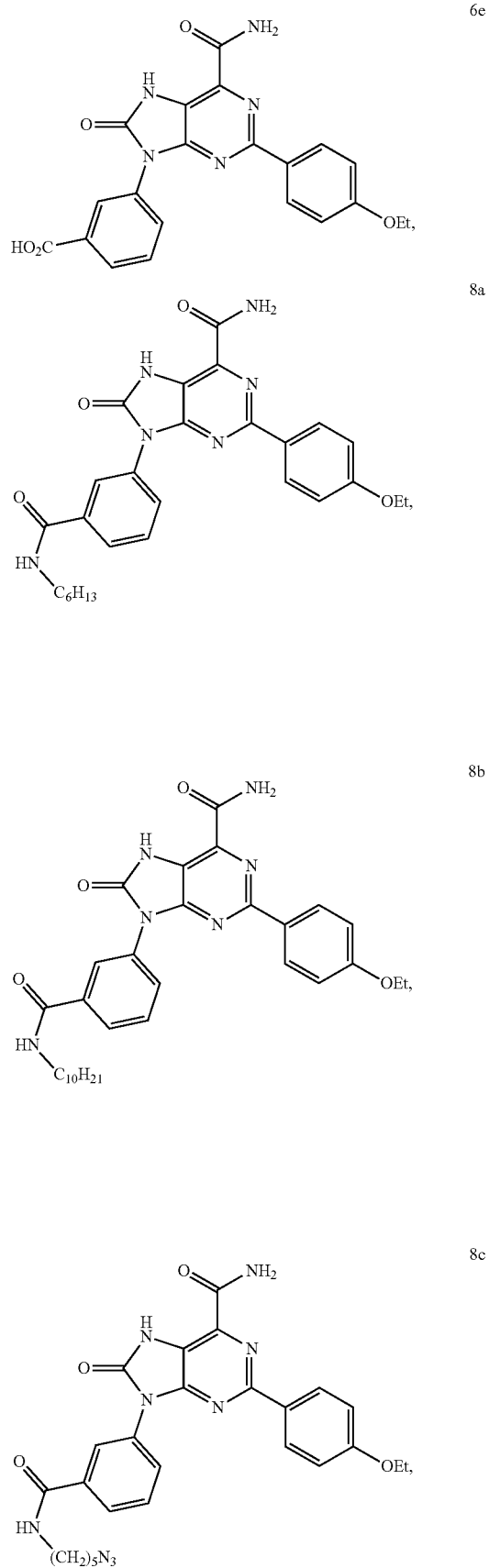

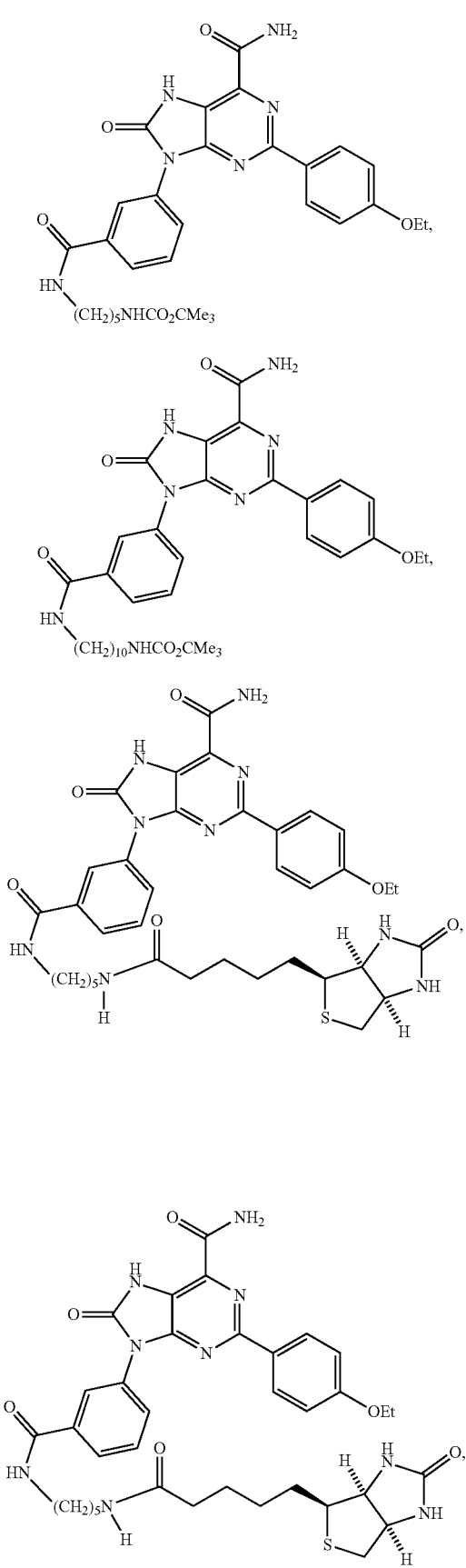
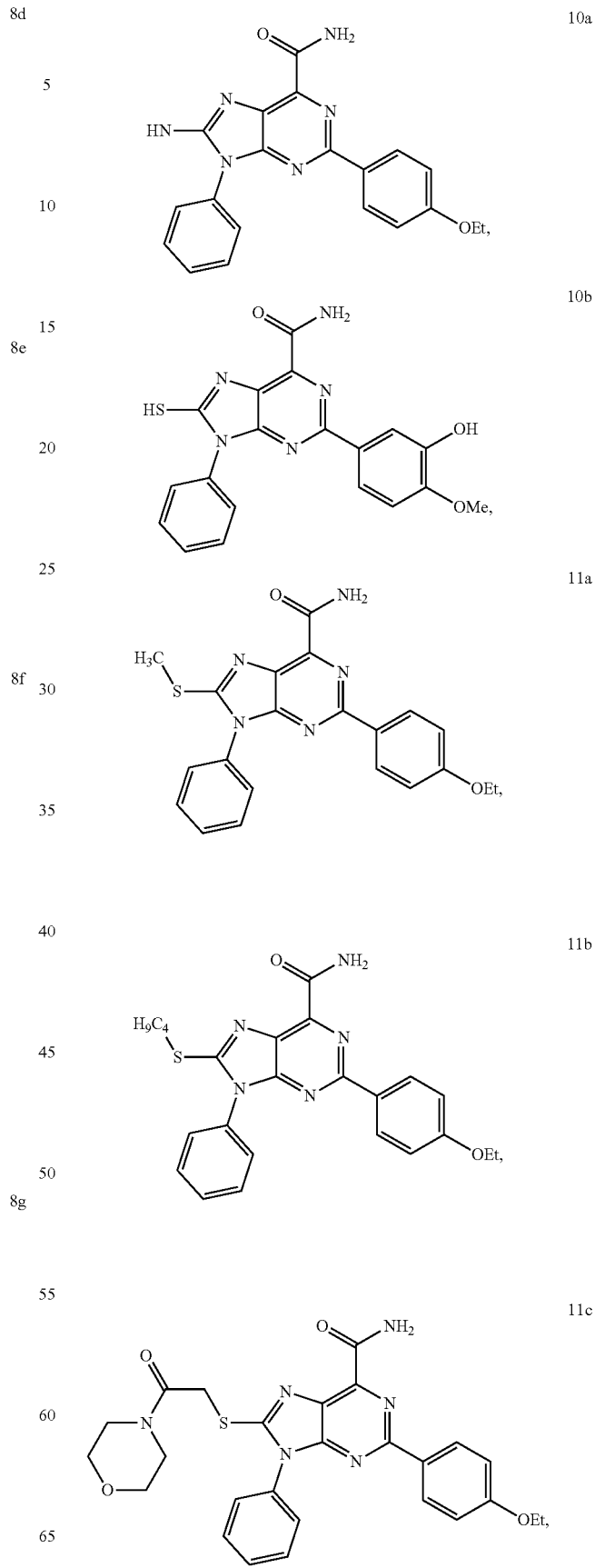

11d
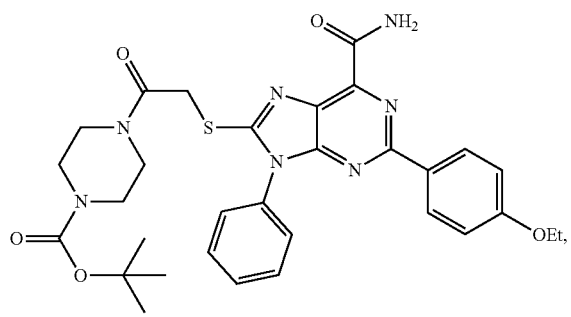
11e
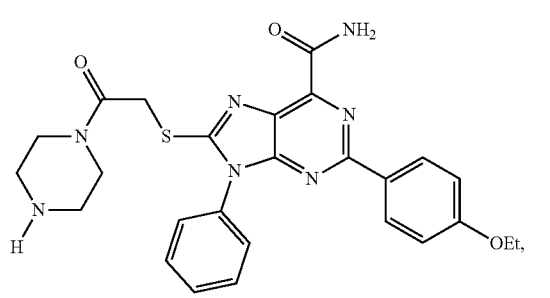
11f
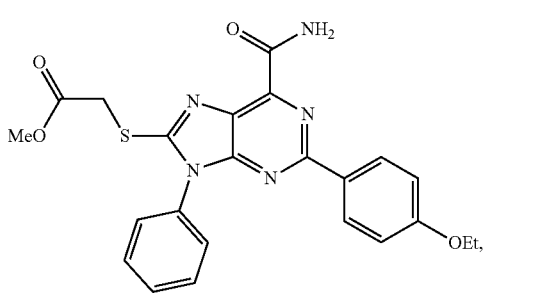
11g
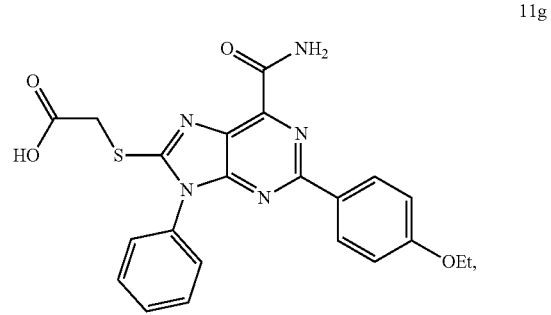
12a
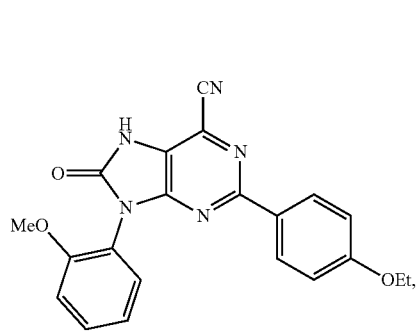
13a
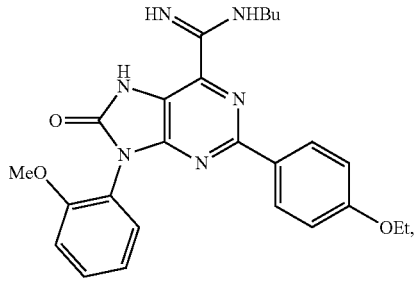
14a
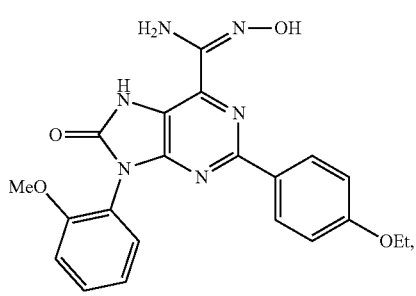
15a
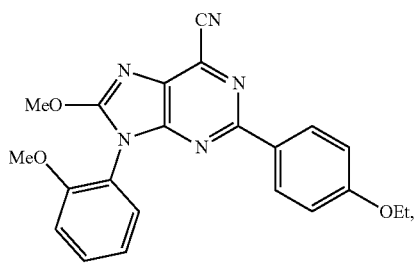
16a
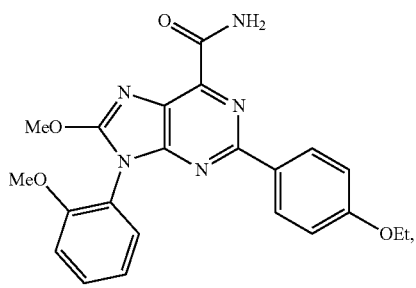
or a pharmaceutically acceptable salt thereof.
Further exemplary compounds of Formulas (I') and (I) include, but are not limited to:

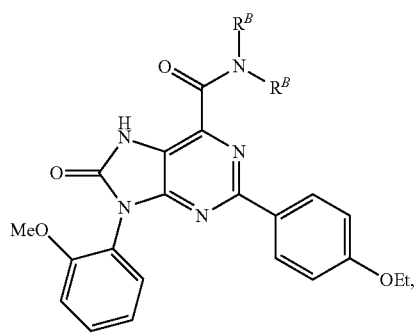

Oxopurine-carboxamide-8
($R^B$,$R^B$) = (Me,Me); or two
instances of $R^B$ are taken
together with the intervening
nitrogen to form piperidine,
moprholine, or piperazine.

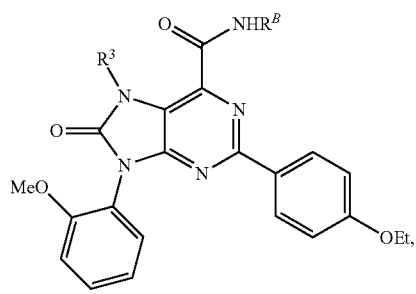

Oxopurine-carboxamide-9
$R^3$ = Me, allyl, benzyl
$R^B$ = H or $C_{1-6}$alkyl

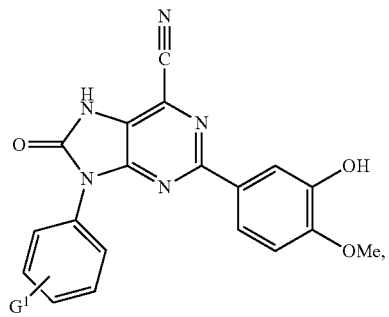

Oxopurine-carbonitrile-2
$G^1$ = 2-OMe, 3-NO$_2$, 3-CO$_2$Me,
4-CONHEt, 3,5-difluoro.

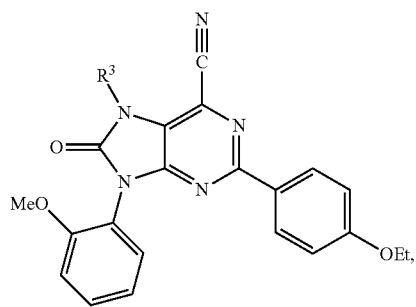

Oxopurine-carbonitrile-3
$R^3$ = H, Me, allyl, benzyl

-continued

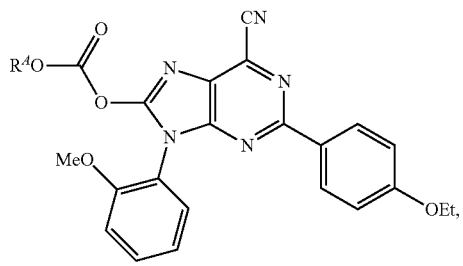

(Carbonato)purine-carbonitrile
$R^A$ = Me, Et, allyl, benzyl, phenyl

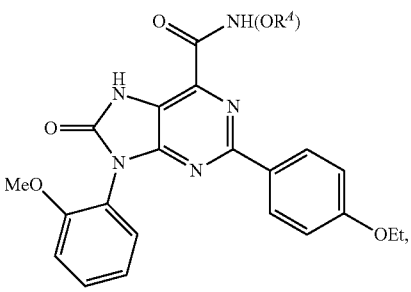

Oxopurine-(N-alkoxy)-carboxamide
$R^A$ = H, Me, benzyl

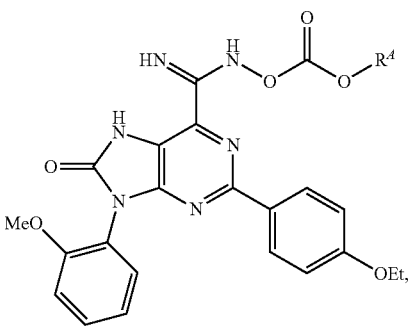

Oxopurine-(N-carbonato)imidamide

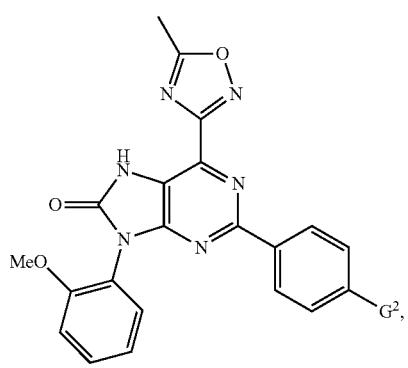

Oxopurine-oxadiazole-1
$G^2$ = H, Me, OEt, NO$_2$

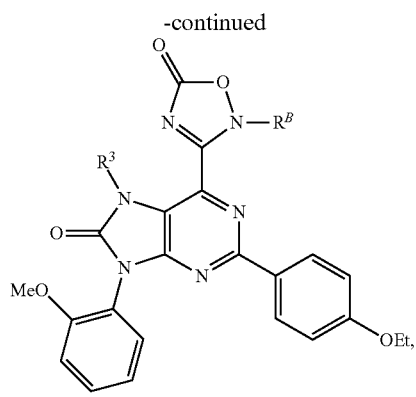

Oxopurine-oxadiazole-2
$R^3 = R^B$ = Me, allyl, benzyl

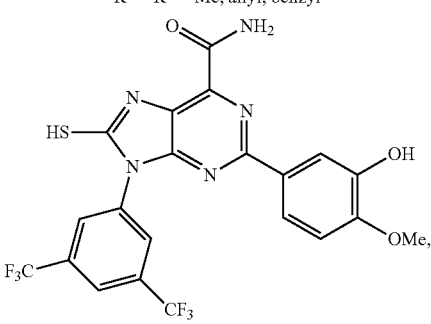

Mercaptopurine-carboxamide-2

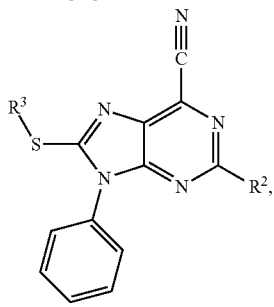

Mercaptopurine-carbonitrile-2
$R^2$ = cyclohexyl, Ph, 4-MeC$_6$H$_4$
$R^3$ = H, Me, allyl, benzyl, acetyl.

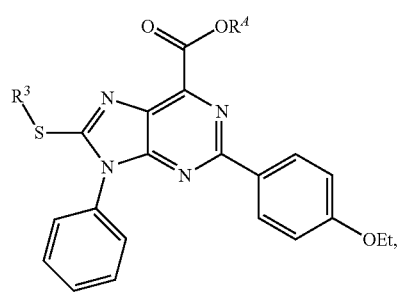

Mercaptopurine-carbxylate
$R^3$ = H, Me, allyl, benzyl.
$R^A$ = H, C$_{1-6}$alkyl.

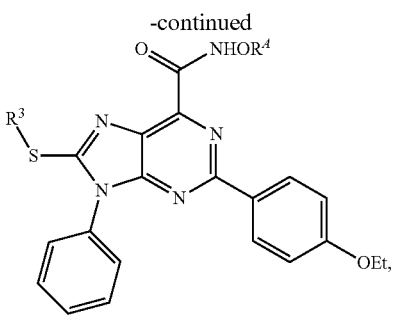

Mercaptopurine-(N-alkoxy)carboxamide
$R^3$ = H, Me, allyl, benzyl.
$R^A$ = H, Me, Et, benzyl.

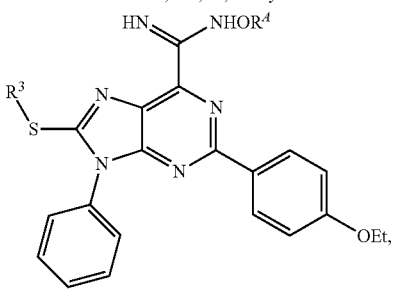

Mercaptopurine-(N-alkoxy)imidamide
$R^3$ = H, Me, allyl, benzyl.
$R^A$ = H, Me, Et, benzyl.

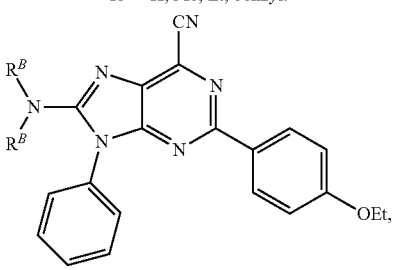

Aminopurine-carbonitrile
$(R^B, R^B)$ = (H,H), (Me, Me); or two
instances of $R^B$ are taken
together with the intervening
nitrogen to form
morpholine, piperazine, or Boc-
piperazine

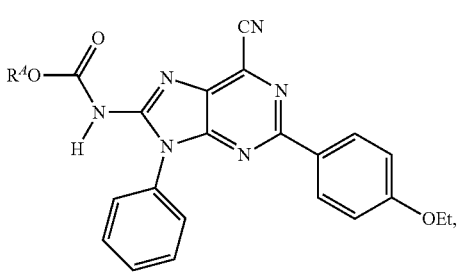

(Alkoxycarbonylamino)purine-carbonitrile
$R^A$ = Et, t-Bu, PhCH$_2$

-continued

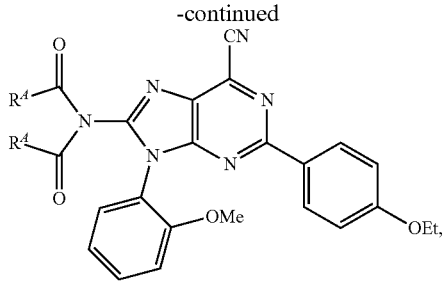

(Diacylamino)purine-carbonitrile
($R^A$,$R^A$) = (Me,Me), (Ph,Ph),
($CH_2CH_2$), (CH=CH).

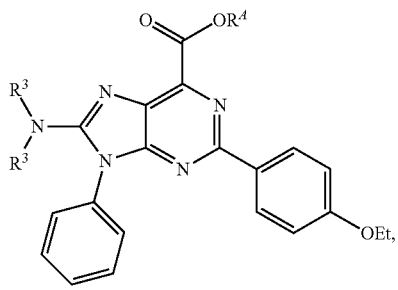

Aminopurine-carboxylate
$R^A$ = H, $C_{1-6}$alkyl.
($R^3$,$R^3$) = (H,H), (H,Me), (Me,Me); or
two instances of $R^3$ are taken
together with the intervening
nitrogen to form
piperidine, morpholine, or piperazine.

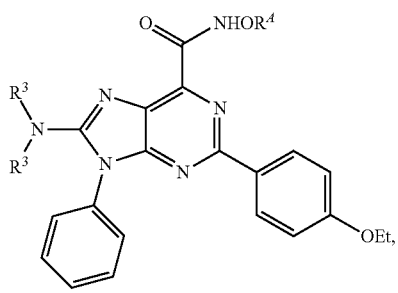

Aminopurine-(N-alkoxy)carboxamide
$R^A$ = H, Me, Et, benzyl.
($R^3$,$R^3$) = (H,H), (H,Me), (Me,Me); or
two instances of $R^3$ are taken
together with the intervening
nitrogen to form
piperidine, morpholine, or piperazine.

-continued

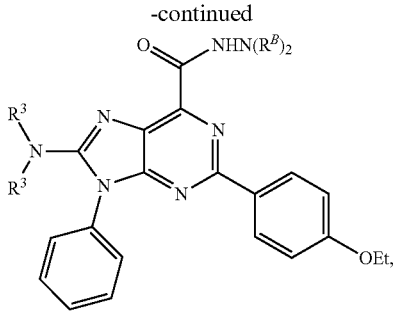

Aminopurine-carbohydrazide
$R^B$ = H, Me.
($R^3$,$R^3$) = (H,H), (H,Me), (Me,Me); or
two instances of $R^3$ are taken
together with the intervening
nitrogen to form
piperidine, morpholine, or piperazine.

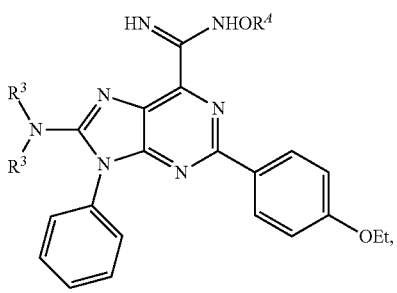

Aminopurine-(N-alkoxy)imidamide
$R^A$ = H, Me, Et, benzyl.
($R^3$,$R^3$) = (H,H), (H,Me), (Me,Me); or
two instances of $R^3$ are taken
together with the intervening
nitrogen to form
piperidine, morpholine, or piperazine.

or a pharmaceutically acceptable salt thereof.

Additional exemplary compounds of Formulas (I') and (I) include, but are not limited to:

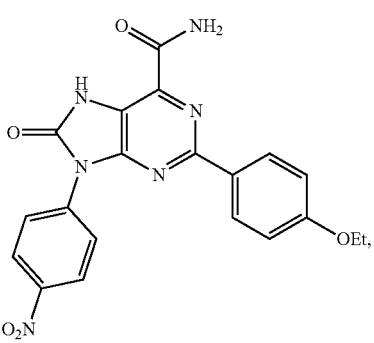

(5k)

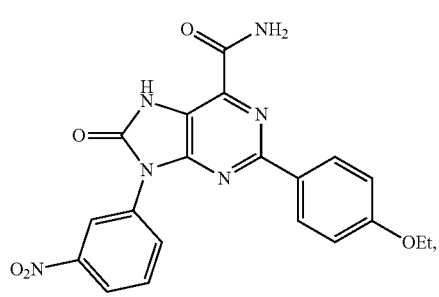
(5l)
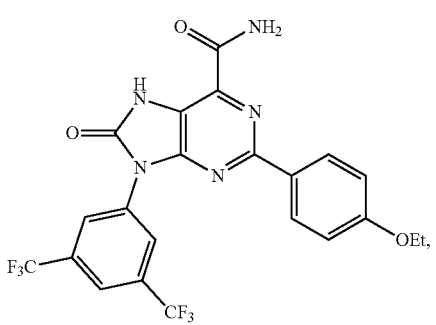
(5m)
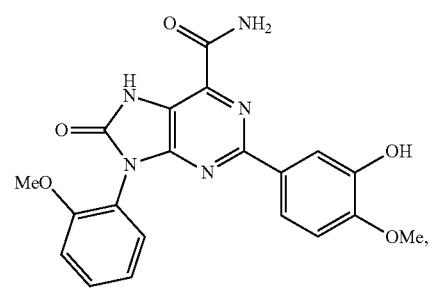
(5n)
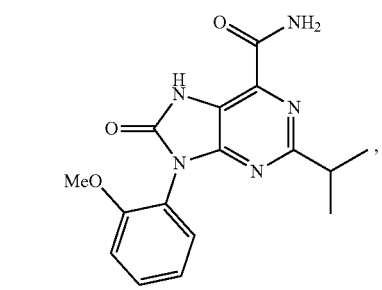
(5o)
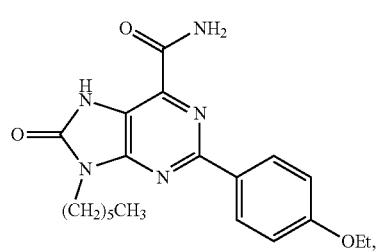
(5p)
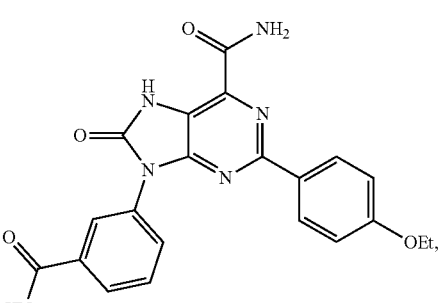
(5q)
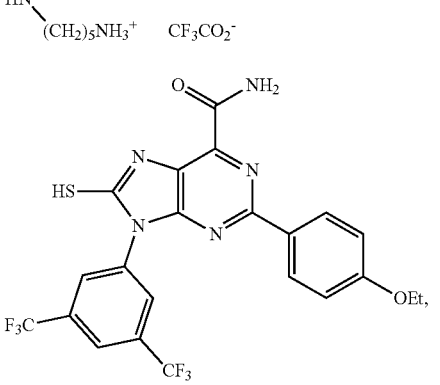
(10c)
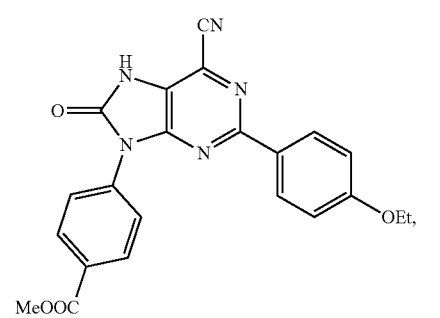
(12b)
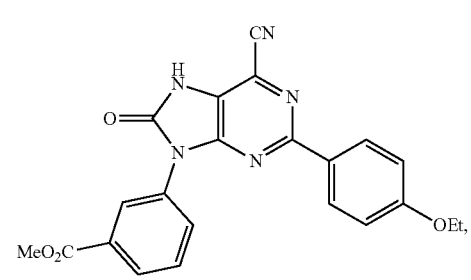
(12c)
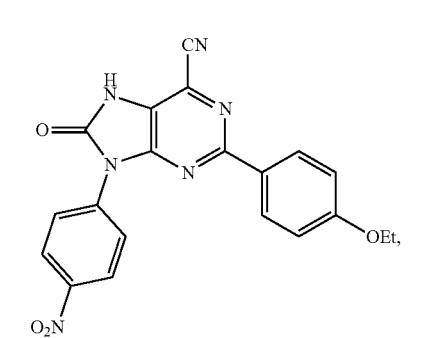
(12d)

(12e)
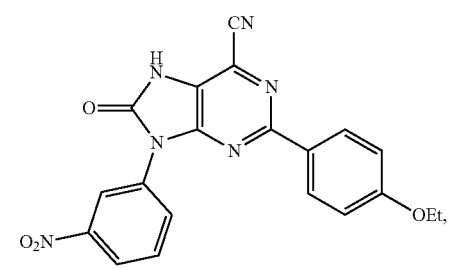
(12g)
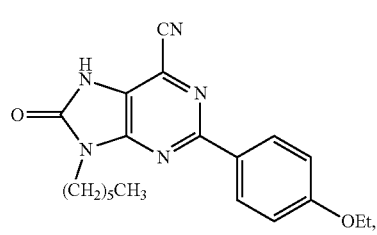
(14b)
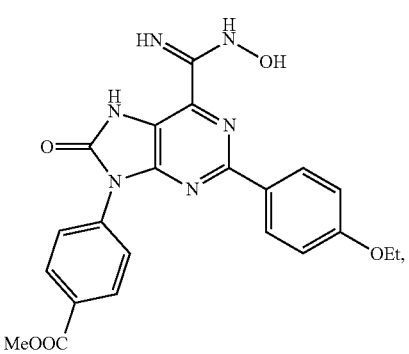
(14c)
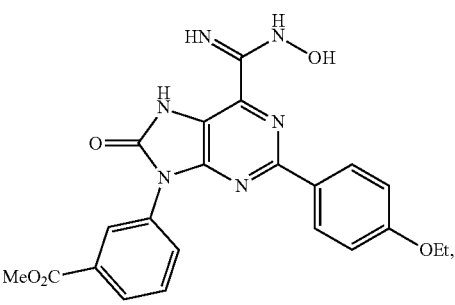
(14d)
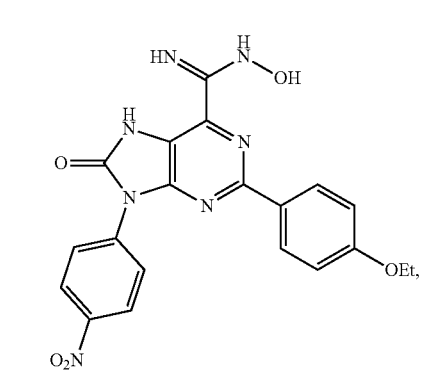
(14e)
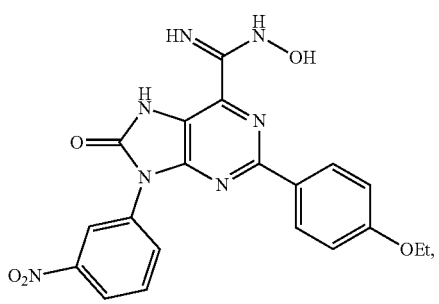
(14f)
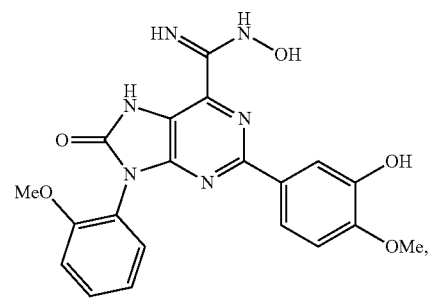
(14g)
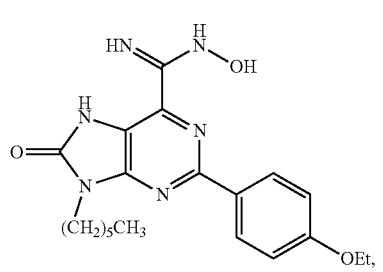
(14a')
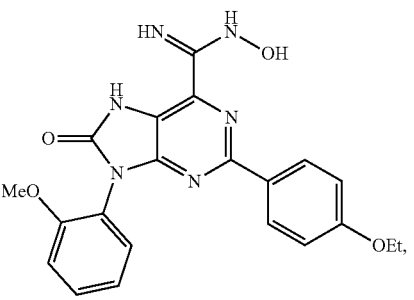
(14h)
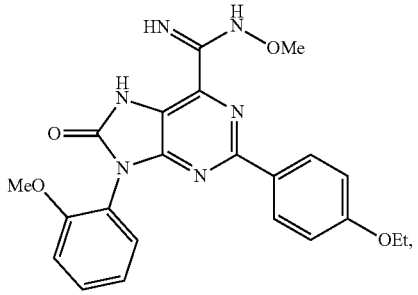

(14i)
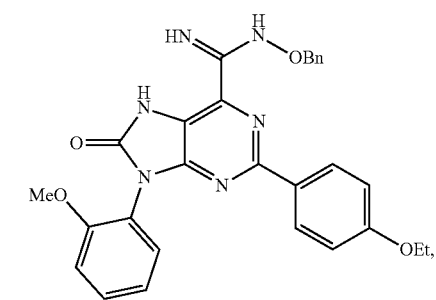
(16a')
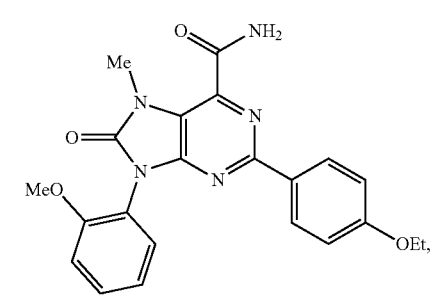
(17a)
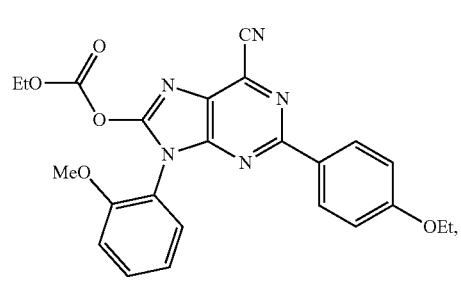
(17b)
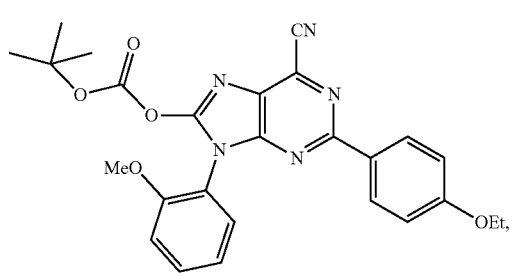
(17c)
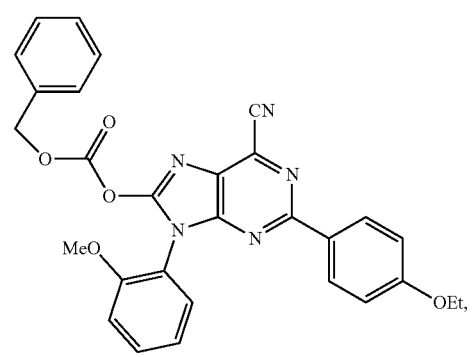
(17d)
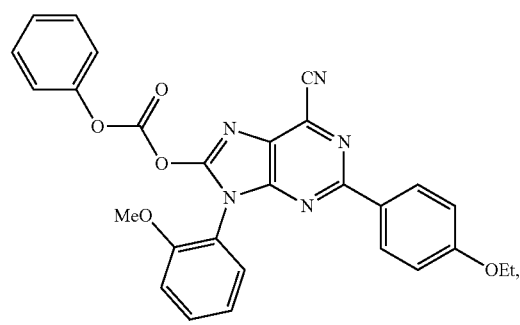
(18a)
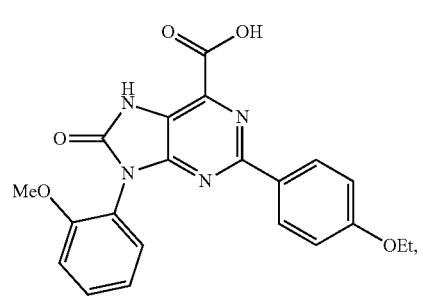
(18b)
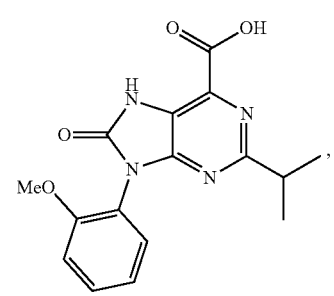
(19c)
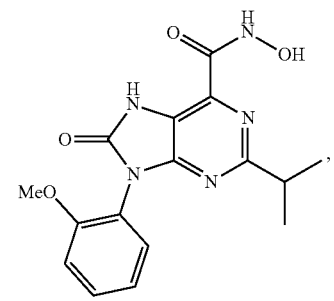
(19d)
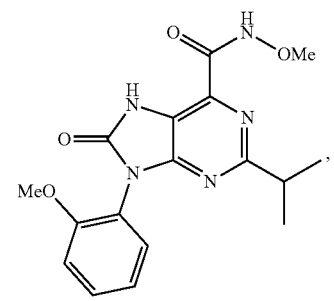

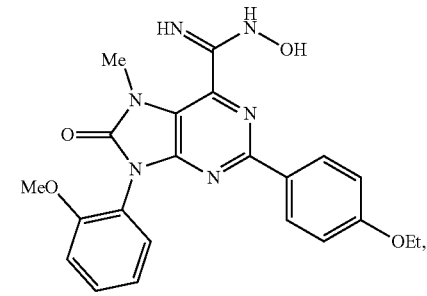
(21a)
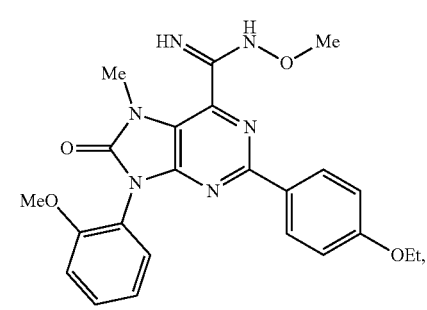
(21b)
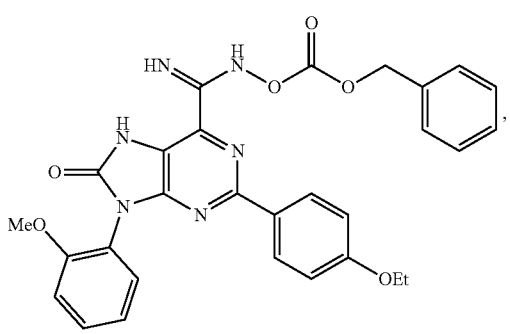
(22a)
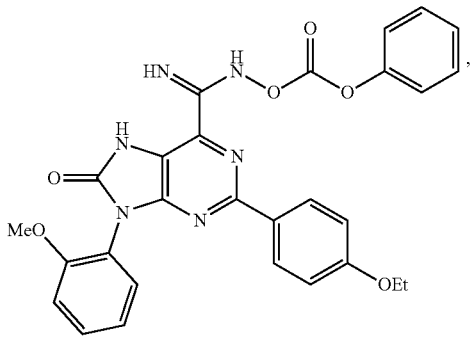
(22b)
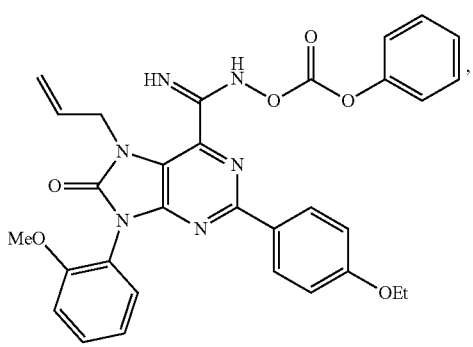
(23a)
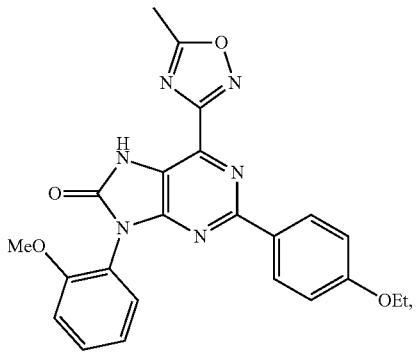
(24a)
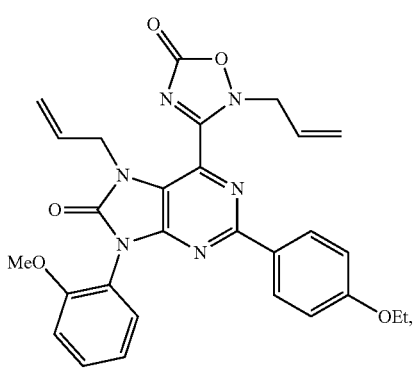
(25a)
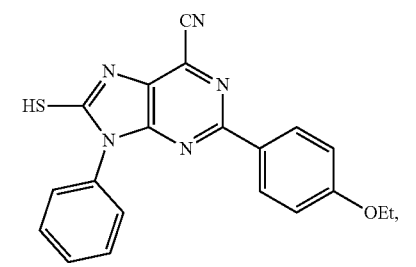
(27a)
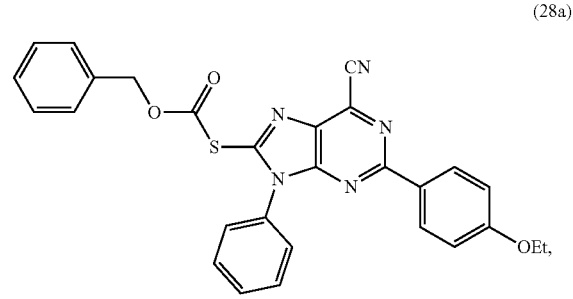
(28a)
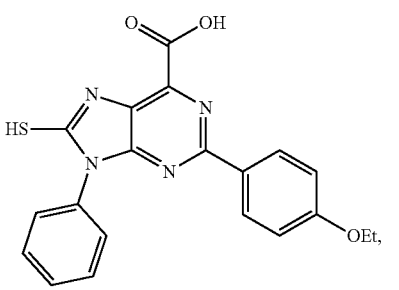
(29a)

(30a)
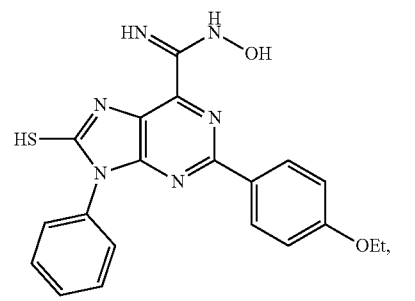

(31a)
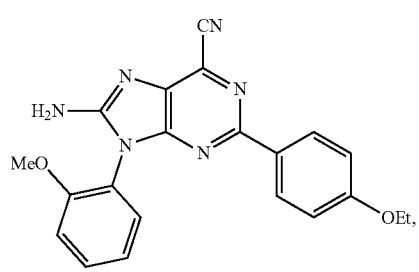

(33a)
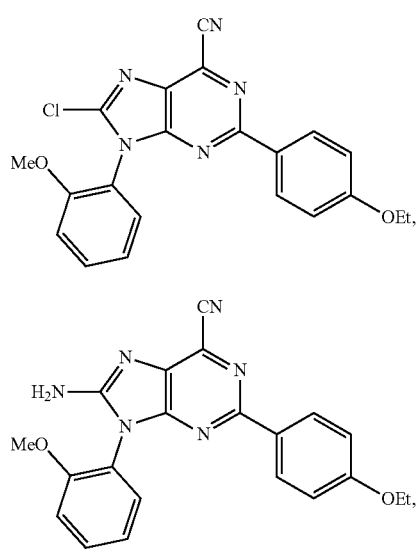

(33b)
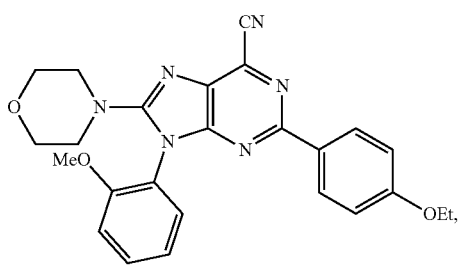

(34a)
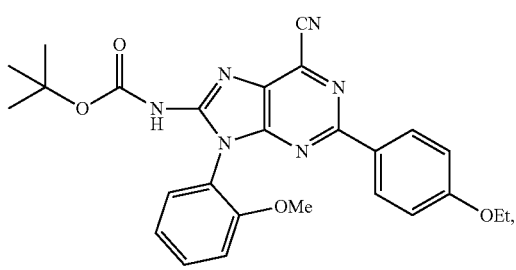

(35a)
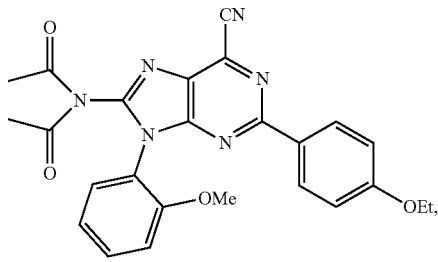

(36a)
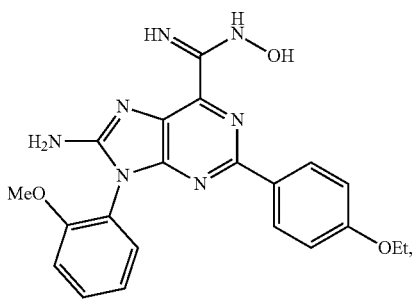

or a pharmaceutically acceptable salt thereof.

In another aspect, the present disclosure provides pharmaceutical compositions including one or more of the compounds described herein, and a pharmaceutically acceptable excipient.

In another aspect, the present disclosure provides methods for treating a proliferative disease (e.g., cancer) in a subject in need thereof. In some embodiments, the method provided herein is for treating lung cancer, such as non-small cell lung cancer. In some embodiments, the subject is resistant to an anti-cancer agent, e.g., a tyrosine kinase inhibitor. In some embodiments, the subject is resistant to gefitinib, erlotinib, cetuximab, matuzumab, or panitumumab.

In some embodiments, the method provided herein is for treating breast cancer. In some embodiments, the subject has a triple-negative breast cancer diagnosis.

In certain embodiments, the provided method comprises administering to a subject in need thereof a pharmaceutical composition comprising a compound of Formulas (I') or (I) in combination with a second anti-cancer drug. In certain embodiments, the second anti-cancer drug is selected from the group consisting of imatinib mesylate (Gleevec), BAY43-9006, Brostallicin, lenalidomide (Revlimid), thalidomide (Thalomid), docetaxel (Taxotere), erlotinib (Tarceva), vatalinib (PTK-787), VEGF-trap, fenretidine, bortezomib, bevacizumab (Avastin), pertuzumab, and rituximab.

In certain embodiments, the provided method comprises administering to a subject in need thereof a pharmaceutical composition comprising a compound of Formulas (I') or (I) in combination with a second anticancer drug. In certain embodiments, the second anticancer drug is selected from the group consisting of doxorubicin (Adriamycin), imatinib mesylate (Gleevec), gefitinib (Iressa), erlotinib (Tarceva), paclitaxel (Taxol), docetaxel (Taxotere), BAY43-9006, brostallicin, lenalidomide (Revlimid), thalidomide (Thalomid), vatalinib (PTK-787), VEGF-trap, fenretidine, bortezomib, bevacizumab (Avastin), pertuzumab, and rituximab.

In another aspect, the present invention provides kits comprising a compound provided herein or a pharmaceutical composition thereof. The kits may include a single dose or multiple doses of the provided compound. The kits may be useful in a method of the disclosure. In certain embodiments, the kit further includes instructions for using the compound or pharmaceutical composition. The provided kits may be useful for the treatment of proliferative diseases such as cancer. In certain embodiments, the kits described herein further include instructions for administering the provided compound or packaging information. The kit may also optionally include a device for administration of the compound or composition (e.g., a syringe for parenteral administration).

Also described herein are any of the compounds and pharmaceutical compositions as described herein for use in treating a proliferative disease such as cancer (e.g., lung cancer), and uses of such compounds/pharmaceutical compositions for manufacturing a medicament for use in treating any of the proliferative diseases as described herein.

The details of certain embodiments of the invention are set forth herein. Other features, objects, and advantages of the invention will be apparent from the Detailed Description, the Examples, and the Claims.

Definitions

Any of the compounds described herein may be in a variety of forms, such as, but not limited to, salts, solvates, hydrates, tautomers, and isomers. The following definitions are more general terms used throughout the present application:

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 rt electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl").

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

As used herein, nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined below:

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{bb}$ is, independently, selected from hydrogen, —OH, —OR$^{aa}$, —N(R$^{cc}$)$_2$, —CN, —C(=O)R$^{aa}$, —C(=O)N(RC)$_2$, —CO$_2$R, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_2$-10 alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein X is a counterion;

each instance of R is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$+X, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, NR$^{ff}$CO$_2$R$^{ee}$, NRC$^{ff}$(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_1$-6 perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X, —NH(C$_{1-6}$ alkyl)$_2$+X, —NH$_2$(C$_{1-6}$ alkyl)+X, —NH$_3$+X, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OC$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide,-o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo) fluorenylmethyl carb amate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N'-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethyl ammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxy enzylideneamine, N-diphenylmethyl eneamine, N-[(2-pyridyl)mesityl]methyleneamine, N—(N',N'-dimethyl aminomethylene) amine, N,N'-isopropylidenediamine, N-p-nitrob enzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrob enzenesulfenamide (Nps), 2,4-dinitrobenzenesulfenamide, pentachlorob enzenesulfenamide, 2-nitro-4-methoxybenzenesulfenamide, triphenylmethylsulfenamide, and 3-nitropyridinesulfenamide (Npys).

Oxygen protecting groups include, but are not limited to, —R$^{aa}$, N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl acetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulas (I') or (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound, and x is a number greater than 0.

As used herein, the term "tautomer" includes two or more interconvertible forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; thioketone-to-enethiol; amide-to-imide; lactam-to-lactim; thiolactam-to-thiolactim; enamine-to-imine; and enamine-to-(a different) enamine tautomerizations.

As used herein, the term "isomer" includes any and all positional isomers, geometric isomers and stereoisomers (e.g., enantiomers, diastereomers, etc.). For example, "isomer" includes 1,3-transpositional isomers; ortho-, meta- and para-isomers; cis- and trans-isomers; E- and Z-isomers; R- and S-enantiomers; diastereomers; dextro- and levorotatory isomers; racemic mixtures thereof, and other mixtures thereof, as falling within the scope of the invention.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Simple aliphatic or aromatic esters, amides, and anhydrides derived from acidic groups pendant on the compounds of this invention are particular prodrugs.

A "subject" or a "patient" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)). The subject or the "patient" may also include any non-human animals including, but not limited to, primates, such as cynomolgus monkeys, rhesus monkeys, or commercially relevant animals such as cattle, pigs, horses, sheep, goats, cats, dogs, mice, rats, rabbits and birds (e.g., commercially relevant birds such as chickens, ducks, geese, and/or turkeys). In certain embodiments, the non-human animal is a mammal, a primate, a rodent, an avian, an equine, an ovine, a bovine, a caprine, a feline, or a canine. The non-human animal may be a male or female and at any stage of development. A non-human animal may be a transgenic animal.

The terms "administer," "administering," or "administration," as used herein refer to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual, or to a subject at risk of developing symptoms, prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a provided compound refers to an amount sufficient to elicit a desired biological response, i.e., treating the condition. As will be appreciated by those of ordinary skill in this art, the effective amount of a provided compound may vary depending on such factors as the desired biological endpoint, the pharmacokinetics of the compound, the condition being treated, the mode of administration, and the age and health of the subject.

A "therapeutically effective amount" of a provided compound of Formulae is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a provided compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: (1) the pathological proliferation of normally quiescent cells; (2) the pathological migration of cells from their normal location (e.g., metastasis of neoplastic cells); (3) the pathological expression of proteolytic enzymes such as matrix metalloproteinases (e.g., collagenases, gelatinases, and elastases); or (4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein "inhibition", "inhibiting", "inhibit" and "inhibitor", and the like, refer to the ability of a compound to reduce, slow, halt, or prevent the activity of a particular biological process involving cancer in a cell relative to vehicle.

As used herein, the term "EGFR" represents any form of EGFR including but are not limited to full-length EGFR (isoform a), soluble EGFR isoforms (sEGFR) produced by normal and tumor cells (e.g. sEGFR isoforms b, c and d are encoded by EGFR variants 2 (v2), 3 (v3) and 4 (v4) mRNA resulting from gene alternative splicing). In certain embodiments, EGFR is the full length isoform a. In certain embodiments, EGFR is sEGFR.

BRIEF DESCRIPTION OF THE DRAWINGS

Non-limiting embodiments of the present disclosure will be described by way of example with reference to the accompanying FIGURES, which are schematic and are not intended to be drawn to scale. In the FIGURES, each identical or nearly identical component illustrated is typically represented by a single numeral. For purposes of clarity, not every component is labeled in every FIGURE, nor is every component of each embodiment of the invention shown where illustration is not necessary to allow those of ordinary skill in the art to understand the invention.

FIG. 1 shows the in vitro and in vivo antitumor activities of compound 5a (GRC0321). Panel A shows the inhibitory activities of compound 5a against different human non-small-cell lung cancer cell lines. The cells were treated with compound 5a for 72 hours, and cell proliferation was examined by MTT assay. Data are expressed as the mean of four determinations. Panel B shows data on the in vitro antitumor activity of compound 5a, including its inhibitory effects on non-small cell lung cancer cell growth in vitro (colony formation of the H1975 cells). Panel C shows the in vivo antitumor efficacy of compound 5a in a mouse model, including data on the mean tumor volumes of mice in both the treatment and vehicle groups on the days before treatment and throughout treatment.

DETAILED DESCRIPTION OF THE INVENTION

The present disclosure provides compounds of Formula (I) and Fomula (I') as described herein. The compounds described herein are useful in treating and/or preventing proliferative diseases (e.g., cancer). Exemplary proliferative diseases include, but are not limited to, cancers, benign neoplasms, diseases associated with angiogenesis, inflammatory diseases, autoinflammatory diseases, and autoimmune diseases. In certain embodiments, the disease is cancer. Exemplary cancers include, but are not limited to, lung cancer, large bowl cancer, pancreas cancer, biliary tract cancer, or endometrial cancer. Also provided in the present disclosure are pharmaceutical compositions, kits, methods of using the compounds described herein for treating proliferative diseases such as cancer.

Compounds

As generally described above, provided herein are compounds of Formula (I'):

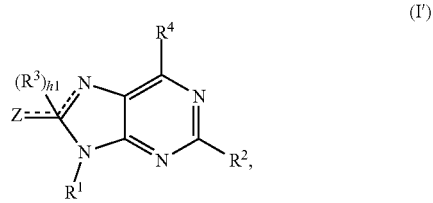
(I')

or a pharmaceutically acceptable salt, solvate, hydrate, polymorph, co-crystal, tautomer, stereoisomer, isotopically labeled derivative, or prodrug thereof, wherein $Z^1$, $R^1$, $R^2$, $R^3$, $R^{4a}$, and h1 are as defined herein. In certain embodiments, a compound of Formula (I') is of Formula (I).

As generally described above, provided herein are compounds of Formula (I):

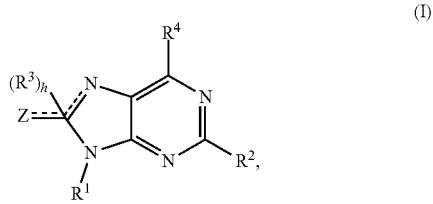
(I)

or a pharmaceutically acceptable salt, solvate, hydrate, polymorph, co-crystal, tautomer, stereoisomer, isotopically labeled derivative, or prodrug thereof, wherein Z, $R^1$, $R^2$, $R^3$, $R^4$, and h are as defined herein.

Formula (I) includes Z attached to the aromatic ring. In certain embodiments, Z can be N. In certain embodiments, Z can be O. In certain embodiments, Z can be S. In certain embodiments, Z can be $NR^B$, in which $R^B$ is as defined herein. In certain embodiments, Z can be $SR^3$, in which $R^3$ is as defined herein.

Formula (I') includes $Z^1$ attached to the aromatic ring. In certain embodiments, $Z^1$ can be Cl. In certain embodiments, $Z^1$ can be N. In certain embodiments, $Z^1$ can be O. In certain embodiments, $Z^1$ can be S. In certain embodiments, $Z^1$ can be $NR^B$, in which $R^B$ is as defined herein. In certain embodiments, $Z^1$ can be $SR^3$, in which $R^3$ is as defined herein. In certain embodiments, when $Z^1$ is independently Cl, S or N, as valency permits, h1 is 0, 1 or 2. In certain embodiments, when $Z^1$ is O, h1 is 1.

In certain embodiments, $Z^1$ can be N, h1 is 2, and both instances of $R^3$ are H. In certain embodiments, $Z^1$ can be N, h1 is 2, and both instances of $R^3$ are H.

In some embodiments, substituent $R^1$ in Formula (I) or Formula (I') can be optionally substituted alkyl. In certain embodiments, $R^1$ can be optionally substituted methyl, optionally substituted ethyl, or optionally substituted butyl. In certain embodiments, $R^1$ can be optionally substituted hexyl. In certain embodiments, $R^1$ can be optionally substituted n-hexyl. In certain embodiments, $R^1$ can be optionally substituted alkenyl. In certain embodiments, $R^1$ can be optionally substituted alkynyl. In certain embodiments, $R^1$ can be optionally substituted carbocyclyl. In certain embodiments, $R^1$ can be:

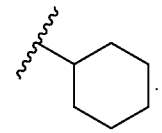

In certain embodiments, $R^1$ can be optionally substituted aryl. In certain embodiments, $R^1$ can be

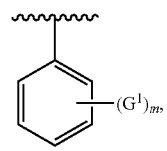

wherein $G^1$ and m are as defined herein. In certain embodiments, $R^1$ can be:

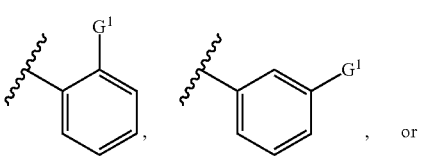

, or

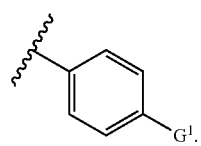

In certain embodiments, $R^1$ can be

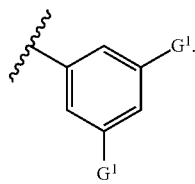

In certain embodiments, $R^1$ can be

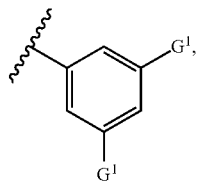

wherein $G^1$ is hydrogen, $NO_2$, $CF_3$, or optionally substituted $C_{1-6}$ alkyl. In certain embodiments, $R^1$ can be:

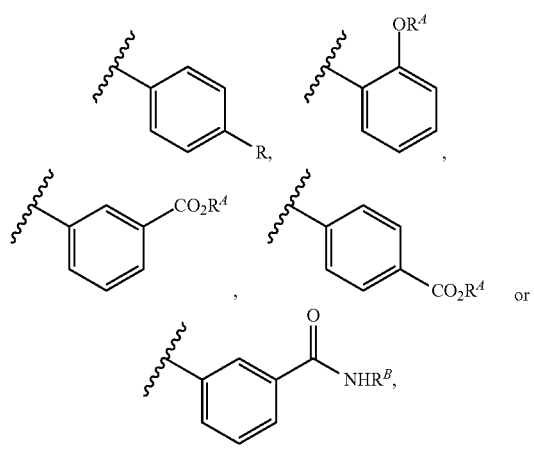

wherein R, $R^A$ and $R^B$ are as defined herein. In certain embodiments, $R^1$ can be:

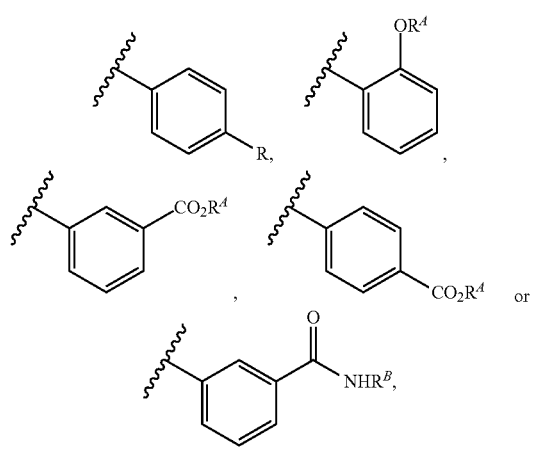

wherein R, $R^A$ and $R^B$ are as defined herein. In certain embodiments, $R^1$ can be:

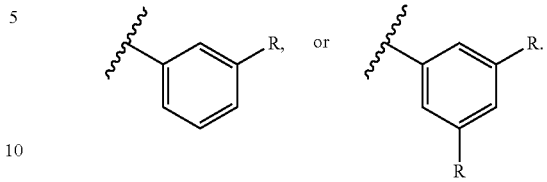

In certain embodiments, $R^1$ can be:

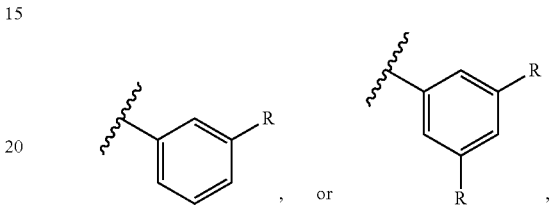

wherein R is as defined herein. In certain embodiments, R can be hydrogen or optionally substituted $C_{1-6}$ alkyl. In certain embodiments, $R^A$ can be hydrogen or optionally substituted $C_{1-6}$ alkyl. In certain embodiments, $R^B$ can be hydrogen or optionally substituted $C_{1-6}$ alkyl.

In certain embodiments, $R^1$ can be:

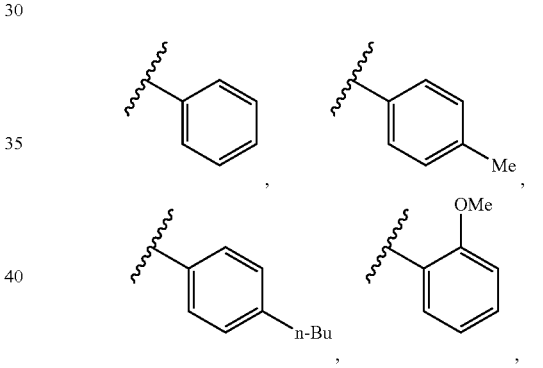

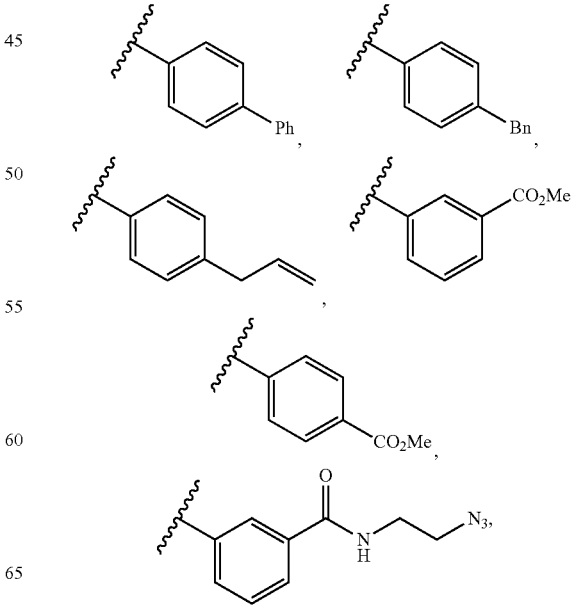

-continued

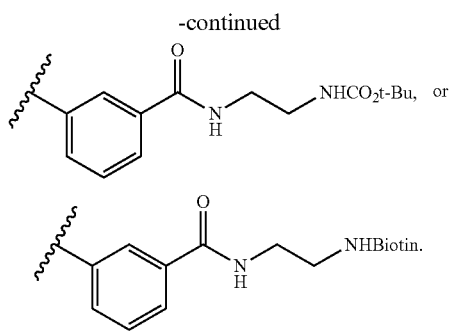

In certain embodiments, R¹ can be:

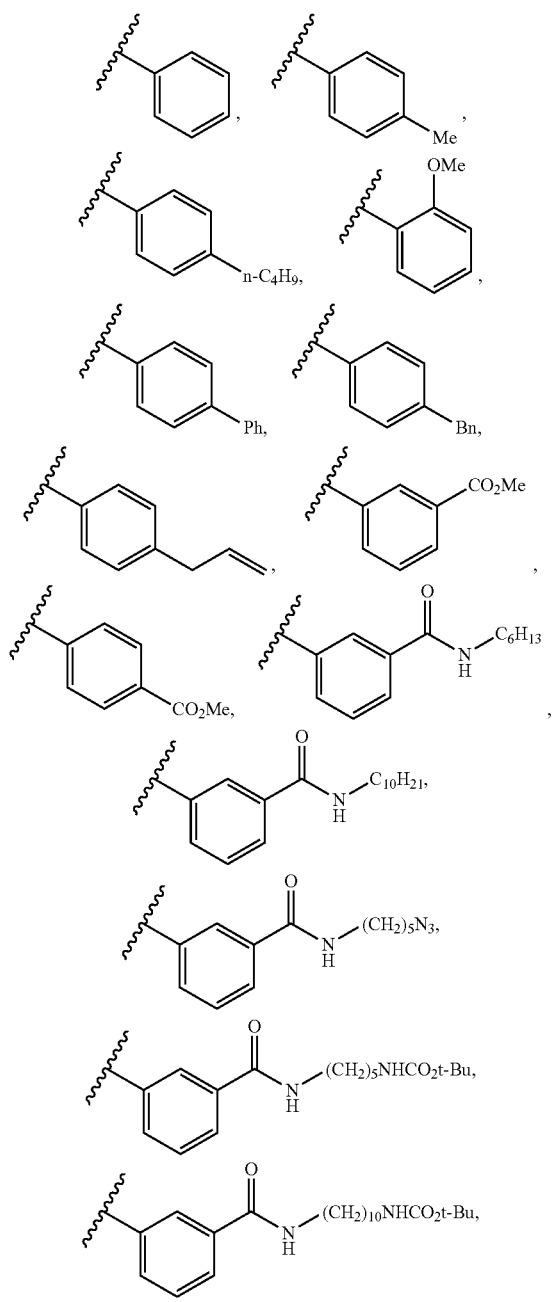

-continued

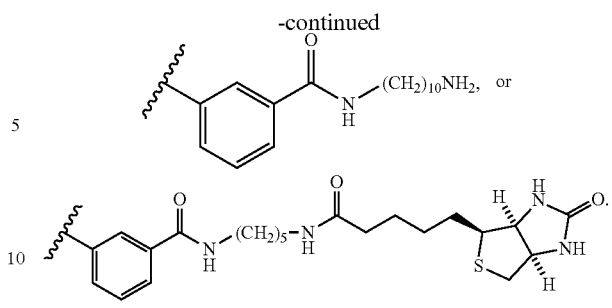

In certain embodiments, R¹ can be:

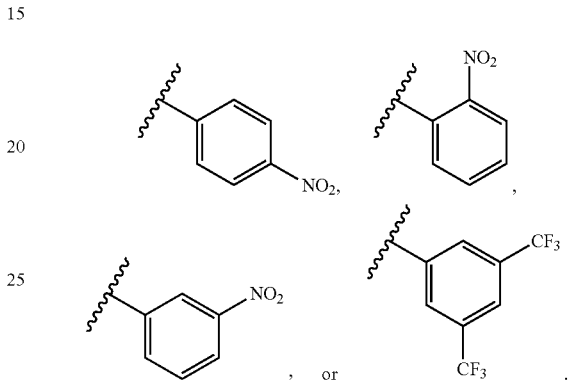

As generally defined herein, m can be 0, 1, 2, 3, 4, or 5. In certain embodiments, m can be 0. In certain embodiments, m can be 1. In certain embodiments, m can be 2. In certain embodiments, m can be 3. In certain embodiments, m can be 4. In certain embodiments, m can be 5.

As generally defined herein, G¹ can be hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —SR$^A$, —NHR$^B$, —N(R$^B$)$_2$, —C(=O)R$^A$, —C(=O)OR$^A$, —OC(=O)R$^A$, —C(=O)NHR$^B$, —C(=O)N(R$^B$)$_2$, —NR$^B$C(=O)R$^A$, —OC(=O)N(R$^B$)$_2$, —NR$^B$C(=O)OR$^A$, —NR$^B$C(=O)N(R$^B$)$_2$, —S(=O)R$^A$, —OS(=O)$_2$R$^A$, —SO$_2$R$^A$, NR$^B$SO$_2$R$^A$, or —SO$_2$N(R$^B$)$_2$. In certain embodiments, G¹ can be hydrogen. In certain embodiments, G¹ can be halogen (e.g., F, Cl, Br, or I). In certain embodiments, G¹ can be —CN. In certain embodiments, G¹ can be —NO$_2$. In certain embodiments, G¹ can be —N$_3$. In certain embodiments, G¹ can be optionally substituted alkyl (e.g., Me, i-Pr, or n-Bu). In certain embodiments, G¹ can be optionally substituted C$_{1-6}$ alkyl. In certain embodiments, G¹ can be CF$_3$. In certain embodiments, G¹ can be methyl. In certain embodiments, G¹ can be i-Pr. In certain embodiments, G¹ can be n-Bu. In certain embodiments, G¹ can be optionally substituted alkenyl. In certain embodiments, G¹ can be optionally substituted alkynyl. In certain embodiments, G¹ can be optionally substituted carbocyclyl. In certain embodiments, G¹ can be optionally substituted aryl (e.g., phenyl or benzyne) In certain embodiments, G¹ can be phenyl. In certain embodiments, G¹ can be 4-Me-C$_6$H$_4$ (tolyl). In certain embodiments, G¹ can be optionally substituted heterocyclyl. In certain embodiments, G¹ can be optionally substituted heteroaryl. In certain embodiments, G¹ can be —OR$^A$, wherein R$^A$ is as defined herein (e.g., —OH or —OMe). In certain embodiments, R$^A$ can be hydrogen. In certain embodiments, R$^A$ can be optionally substituted $C_{1-6}$ alkyl (e.g., methyl or ethyl). In certain embodiments, $G^1$ can be —$SR^A$, wherein $R^A$ is as defined herein. In certain embodiments, $G^1$ can be —$NH(R^B)$. In certain embodiments, $G^1$ can be —$N(R^B)_2$ and $R^B$ is as defined herein. In certain embodiments $R^B$ can be optionally substituted alkyl. In certain embodiments, $G^1$ can be —C(=O) $R^A$, and $R^A$ is as defined herein. In certain embodiments, $G^1$ can be —C(=O)$OR^A$, and $R^A$ is as defined herein (e.g., —$CO_2$Me or —$CO_2$H). In certain embodiments, $R^A$ can be hydrogen, optionally substituted alkyl, or an oxygen protecting group. In certain embodiments, $R^A$ can be unsubstituted $C_{1-6}$ alkyl (e.g. methyl or ethyl). In certain embodiments, $G^1$ can be —C(=O)$N(R^B)_2$, wherein $R^B$ is defined herein. In certain embodiments, at least one instance of $R^B$ can be independently hydrogen, optionally substituted alkyl, or a nitrogen protecting group.

In certain embodiments, $G^1$ can be —C(=O)$NHR^B$ and $R^B$ can be optionally substituted alkyl (e.g., —C(=O)NH (optionally substituted $C_{1-12}$ alkyl) (e.g., —C(=O)NHMe). In certain embodiments, $R^B$ can be unsubstituted alkyl. In certain embodiments, $R^B$ can be substituted alkyl. In certain embodiments, $R^B$ can be —$(CH_2)_qG$, wherein q and G are defined herein. In certain embodiments, q can be 2. In certain embodiments, q can be 3. In certain embodiments, q can be 4. In certain embodiments, q can be 5. In certain embodiments, q can be 6. In certain embodiments, q can be 7. In certain embodiments, q can be 8. In certain embodiments, q can be 9. In certain embodiments, q can be 10. In certain embodiments, q can be 11. In certain embodiments, q can be 12. In certain embodiments, G can be hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OH, optionally substituted alkoxy, optionally substituted acyl, or —$N(R^{a1})_2$. In certain embodiments, G can be hydrogen. In certain embodiments, G can be optionally substituted $C_{1-6}$ alkyl. In certain embodiments, each instance of $R^{a1}$ can be independently hydrogen, optionally substituted alkyl, optionally substituted acyl; or a nitrogen protecting group. In certain embodiments, $R^B$ can be —$(CH_2)_2N_3$. In certain embodiments, $R^B$ can be —$(CH_2)_qCH_3$. In certain embodiments, $R^B$ can be —$(CH_2)_qNHR^{a1}$ In certain embodiments, $R^B$ can be —$(CH_2)$—$NH_2$ or —$(CH_2)$—NHBoc. In certain embodiments, $G^1$ can be —C(=O)NH$(CH_2)_2$NH (Biotin). In certain embodiments, $G^1$ can be —C(=O)NH$(CH_2)_2$NHCO$_2$t-Bu. In certain embodiments, $R^B$ can be —$(CH_2)_q$NHC(=O) $(CH_2)$t-T; wherein t can be 1, 2, 3, 4, 5, 6, 7, 8, 9, or 10; and T can be a label. In certain embodiments, T can be biotin.

As used herein, a "label" refers to a moiety that has at least one element, isotope, or functional group incorporated into the moiety which enables detection of the inventive polypeptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). It will be appreciated that the label may be attached to the inventive polypeptide at any position that does not interfere with the biological activity or characteristic of the inventive polypeptide that is being detected.

In general, a label can fall into any one (or more) of five classes: (a) a label which contains isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; (b) a label which contains an immune moiety, which may be antibodies or antigens, which may be bound to enzymes (e.g., such as horseradish peroxidase); (c) a label which is a colored, luminescent, phosphorescent, or fluorescent moieties (e.g., such as the fluorescent label FITC); (d) a label which has one or more photoaffinity moieties; and (e) a label which has a ligand moiety with one or more known binding partners (such as biotin-streptavidin, FK506-FKBP, etc.). Any of these type of labels as described above may also be referred to as "diagnostic agents" as defined herein.

In certain embodiments, a label comprises a radioactive isotope, preferably an isotope which emits detectable particles (e.g. β particles). In certain embodiments, the label comprises one or more photoaffinity moieties for the direct elucidation of intermolecular interactions in biological systems. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

In certain embodiments, t can be 0. In certain embodiments, t can be 1. In certain embodiments, t can be 2. In certain embodiments, t can be 3. In certain embodiments, t can be 4.

In certain embodiments, t can be 5. In certain embodiments, t can be 6. In certain embodiments, t can be 7. In certain embodiments, t can be 8. In certain embodiments, t can be 9. In certain embodiments, t can be 10.

In certain embodiments, $G^1$ can be —C(=O)$R^A$ and $R^A$ can be optionally substituted alkyl. In certain embodiments, $R^1$ can be optionally substituted heterocyclyl. In certain embodiments, $R^1$ can be optionally substituted heteroaryl.

In some embodiments, substituent $R^2$ in Formula (I') or (I) can be hydrogen. In certain embodiments, $R^2$ can be optionally substituted alkyl (e.g., methyl, ethyl, or propyl). In certain embodiments, $R^2$ can be optionally substituted propyl. In certain embodiments, $R^2$ can be isopropyl. In certain embodiments, $R^2$ can be optionally substituted alkenyl. In certain embodiments, $R^2$ can be optionally substituted alkynyl. In certain embodiments, $R^2$ can be optionally substituted carbocyclyl. In certain embodiments, $R^2$ can be optionally substituted cyclohexyl. In certain embodiments, $R^2$ can be optionally substituted aryl. In certain embodiments, $R^2$ can be phenyl. In certain embodiments, $R^2$ can be

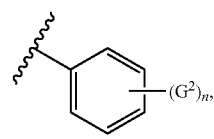

and $G^2$ and n are as defined herein. In certain embodiments, $R^2$ can be

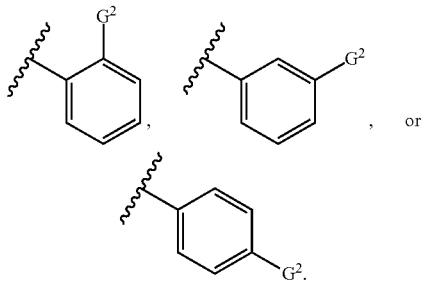

In certain embodiments, $R^2$ can be:

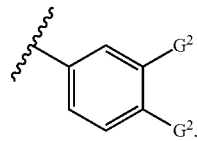

In certain embodiments, $R^2$ can be

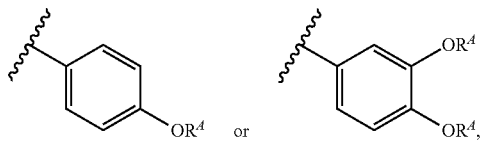

and $R^A$ are as defined herein. In certain embodiments, $R^2$ can be

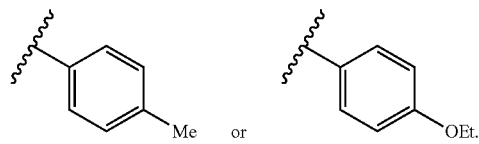 [SMILES: *c1ccc(C)cc1 ; *c1ccc(OCC)cc1]

As generally defined herein, n can be 0, 1, 2, 3, 4, or 5. In certain embodiments, n can be 0. In certain embodiments, n can be 1. In certain embodiments, n can be 2. In certain embodiments, n can be 3. In certain embodiments, n can be 4. In certain embodiments, n can be 5.

As generally defined herein, $G^2$ can be hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —SR$^A$, —NHR$^B$, —N(R$^B$)$_2$, —C(=O)R$^A$, —C(=O)OR$^A$, —OC(=O)R$^A$, —C(=O)NHR$^B$, —C(=O)N(R$^B$)$_2$, —NR$^B$C(=O)R$^A$, —OC(=O)N(R$^B$)$_2$, —NR$^B$C(=O)OR$^A$, —NR$^B$C(=O)N(R$^B$)$_2$, —S(=O)R$^A$, —OS(=O)$_2$R$^A$, —SO$_2$R$^A$, —NR$^B$SO$_2$R$^A$, or —SO$_2$N(R$^B$)$_2$. In certain embodiments, $G^2$ can be hydrogen. In certain embodiments, $G^2$ can be halogen (e.g., F, Cl, Br, or I). In certain embodiments, $G^2$ can be —CN. In certain embodiments, $G^2$ can be —NO$_2$. In certain embodiments, $G^2$ can be —N$_3$. In certain embodiments, $R^2$ can be unsubstituted $C_{1-6}$ alkyl (e.g., methyl or ethyl). In certain embodiments, $G^2$ can be substituted $C_{1-6}$ alkyl (e.g, —CH$_2$C(=O)OR$^A$). In certain embodiments, $G^2$ can be n-butyl. In certain embodiments, $G^2$ can be n-hexyl. In certain embodiments, $G^2$ can be optionally substituted aryl. In certain embodiments, $G^2$ can be optionally substituted heteroaryl. In certain embodiments, $G^2$ can be 3-trifluoromethyl-3H-diazirin-3-yl. In certain embodiments, $G^2$ can be —OR$^A$, and $R^A$ can be optionally substituted $C_{1-6}$ alkyl. In certain embodiments, $G^2$ can be —OH. In certain embodiments, $G^2$ can be —OMe. In certain embodiments, $G^2$ can be —OEt. In certain embodiments, $R^2$ can be:

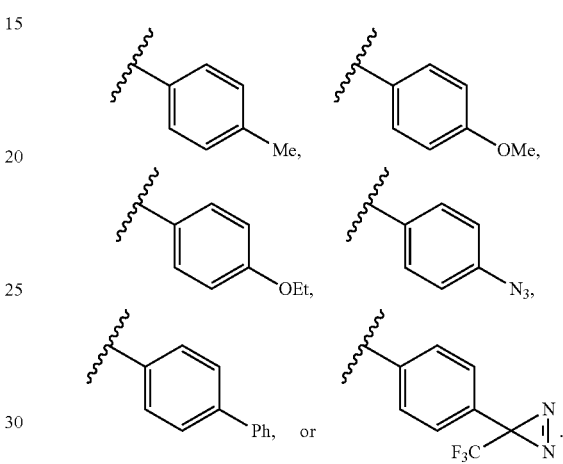

In certain embodiments, $R^2$ can be:

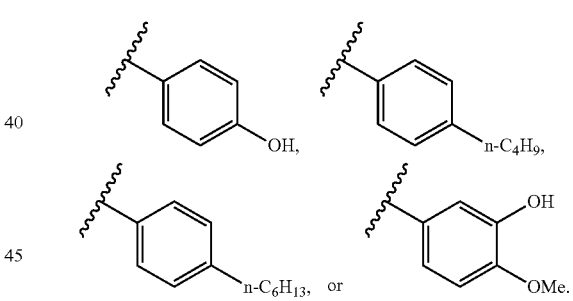

In certain embodiments, $R^2$ can be optionally substituted heterocyclyl. In certain embodiments, $R^2$ can be optionally substituted heteroaryl.

Formula (I) includes one or more instances of substituent $R^3$. In certain embodiments, h can be 1. In certain embodiments, h can be 2. Formula (I') includes zero, one, or two instances of substituent $R^3$. In certain embodiments, h1 can be 1. In certain embodiments, h1 can be 1. In certain embodiments, h1 can be 2. In some embodiments, each instance of substituent $R^3$ in Formula (I) or Formula (I') can be independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^A$, —SR$^A$, —NHR$^B$, —N(R$^B$)$_2$, —C(=O)R$^A$, —C(=O)OR$^A$, —C(=O)N$_{HRB}$, —C(=O)N(R$^B$)$_2$, —NR$^B$C(=O)R$^A$, or —SO$_2$R$^A$. In certain embodiments, at least one instance of $R^3$ can be hydrogen, optionally substituted $C_{1-6}$ alkyl, optionally substituted alkenyl, optionally substituted carbocyclyl, or optionally substituted aryl. In certain embodiments, at least one instance of $R^3$ is H, and at least one instance of $R^3$ is t-Boc. In certain embodiments, at least one instance of $R^3$ can be hydrogen. In certain embodiments, one instance of $R^3$ can be hydrogen and one instance of $R^3$ can be methyl. In certain embodiments, at least one instance of $R^3$ can be optionally substituted $C_{1-6}$ alkyl. In certain embodiments, at least one instance of $R^3$ can be methyl. In certain embodiments, at least one instance of $R^3$ can be of the formula —$(CH_2)_pC(=O)OR^A$; wherein p can be 0, 1, 2, 3, 4, 5, or 6; and $R^A$ can be hydrogen or optionally substituted alkyl. In certain embodiments, at least one instance of $R^3$ can be of the formula —$(CH_2)_pC(=O)OR^A$; wherein p can be 0, 1, or 2; and $R^A$ can be hydrogen or optionally substituted alkyl. In certain embodiments, at least one instance of $R^3$ can be of the formula —$(CH_2)_pC(=O)N(R^B)_2$, wherein p and $R^B$ are as defined herein. In certain embodiments, at least one instance of $R^3$ can be of the formula —$(CH_2)_pC(=O)N(R^B)_2$, wherein p is 0, 1, or 2; and $R^B$ is optionally substituted $C_{1-6}$ alkyl, nitrogen protecting group, or two instances of $R^B$ are taken together to form optionally substituted heterocyclyl. In certain embodiments, at least one instance of $R^B$ can be optionally substituted $C_{1-6}$ alkyl. In certain embodiments, at least one instance of $R^B$ can be a nitrogen protecting group. In certain embodiments, two instances of $R^B$ are H. In certain embodiments, two instances of $R^B$ are Me. In certain embodiments, two instances of $R^B$ are taken together with the intervening nitrogen to form optionally substituted heterocyclyl. In certain embodiments, at least one instance of $R^3$ can be —$(CH_2)_pC(=O)NH_2$. In certain embodiments, at least one instance of $R^3$ can be —$(CH_2)_pC(=O)NMe_2$. In certain embodiments, two instances of $R^B$ are taken together with the intervening nitrogen to form morpholine. In certain embodiments, two instances of $R^B$ are taken together with the intervening nitrogen to form piperazine. In certain embodiments, two instances of $R^B$ are taken together with the intervening nitrogen to form Boc-piperazine. In certain embodiments, two instances of $R^B$ are taken together with the intervening nitrogen to form piperadine. In certain embodiments, at least one instance of $R^3$ can be acetyl. In certain embodiments, at least one instance of $R^3$ can be optionally substituted alkenyl. In certain embodiments, at least one instance of $R^3$ can be allyl. In certain embodiments, at least one instance of $R^3$ can be optionally substituted carbocyclyl. In certain embodiments, at least one instance of $R^3$ can be cyclohexyl. In certain embodiments, $R^3$ can be optionally substituted aryl (e.g., benzyl). In certain embodiments, $R^3$ can be benzyl. In certain embodiments, at least one instance of $R^3$ can be —$OR^A$, wherein $R^A$ can be as defined herein (e.g., OH, OMe or OBn). In certain embodiments, at least one instance of $R^3$ can be —$N(R^B)_2$, wherein $R^B$ is as defined herein. In certain embodiments, at least one instance of $R^3$ can be —$NH_2$ or —$NMe_2$. In certain embodiments, at least one instance of $R^3$ can be —$C(=O)R^A$, wherein $R^A$ is as defined herein. In certain embodiments, two instances of $R^3$ can be —$C(=O)R^A$. In certain embodiments, at least one instance of $R^3$ can be —$C(=O)Me$ or —$C(=O)i$-Pr. In certain embodiments, at least one instance of $R^3$ can be —$C(=O)Me$. In certain embodiments, both instances of $R^3$ are —$C(=O)$(allyl). In certain embodiments, h is 2, and both instances of $R^3$ are —$C(=O)Me$. In certain embodiments, both instances of $R^3$ are —$C(=O)Et$. In certain embodiments, both instances of $R^3$ are —$C(=O)Ph$. In certain embodiments, h1 is 2, and both instances of $R^3$ are —$C(=O)Me$. In certain embodiments, at least one instance of $R^3$ can be —$C(=O)Ph$. In certain embodiments, at least one instance of $R^3$ can be —$C(=O)OR^A$ (e.g., —$C(=O)Ot$-Bu or —$C(=O)OBn$). In certain embodiments, at least one instance of $R^3$ can be —$C(=O)OMe$. In certain embodiments, at least one instance of $R^3$ can be —$C(=O)OEt$. In certain embodiments, at least one instance of $R^3$ can be —$C(=O)O$(t-Bu). In certain embodiments, at least one instance of $R^3$ can be —$C(=O)OBn$. In certain embodiments, at least one instance of $R^3$ can be —$C(=O)OPh$. In certain embodiments, at least one instance of $R^3$ can be —$SR^A$, wherein $R^A$ is as defined herein. In certain embodiments, at least one instance of $R^3$ can be —$SMe$, In certain embodiments, at least one instance of $R^3$ can be —$SPh$, In certain embodiments, at least one instance of $R^3$ can be —$SO_2R^A$ (e.g., —$SO_2Me$, —$SO_2Ph$, or —$SO_2(4\text{-MeC}_6H_4)$). In certain embodiments, two instances of $R^3$ can be taken together with Z to form optionally substituted heterocyclyl, wherein Z is N. In certain embodiments, Z is N. In certain embodiments, Z is O. In certain embodiments, Z is S. In certain embodiments, two instances of $R^3$ can be taken together with Z to form morpholine. In certain embodiments, two instances of $R^3$ can be taken together with Z to form piperidine. In certain embodiments, two instances of $R^3$ can be taken together with Z to form piperazine.

In some embodiments, substituent $R^4$ in Formula (I) can be independently optionally substituted alkyl, —$C(=O)N(R^B)_2$, —$CN$, —$C(=O)OR^A$, —$C(=O)NR^B(OR^A)$, —$C(=O)R^A$, —$C(=O)NHN(R^B)_2$, —$C(=NH)NHOR^A$, —$C(=NOR^A)NH_2$, —$C(=NH)NHN(R^B)_2$, —$C[=NHN(R^B)_2]NH_2$, —$C(=NH)N(R^B)_2$, or tetrazole. In certain embodiments, $R^4$ can be optionally substituted $C_{1-6}$ alkyl. In certain embodiments, $R^4$ can be —$CH_2N(R^B)_2$, and $R^B$ can be hydrogen or optionally substituted $C_{1-6}$ alkyl. In certain embodiments, one instance of $R^B$ can be hydrogen and the other instance of $R^B$ can be optionally substituted $C_{1-6}$ alkyl. In certain embodiments, $R^4$ can be —$C(=O)N(R^B)_2$ (e.g., —$C(=O)NH_2$ or —$C(=O)NMe_2$). In certain embodiments, one instance of $R^B$ can be hydrogen and the other instance of $R^B$ can be optionally substituted $C_{1-6}$ alkyl. In certain embodiments, both instances of $R^B$ can be hydrogen. In certain embodiments, two instances of $R^B$ are taken together with the intervening nitrogen to form piperidine. In certain embodiments, two instances of $R^B$ are taken together with the intervening nitrogen to form morpholine. In certain embodiments, two instances of $R^B$ are taken together with the intervening nitrogen to form piperizine. In certain embodiments, $R^4$ can be —$CN$. In certain embodiments, $R^4$ can be —$C(=O)R^A$, and $R^A$ is as defined herein. In certain embodiments, $R^4$ can be —$C(=O)N_3$. In certain embodiments, $R^4$ can be —$C(=O)OR^A$, and $R^A$ is as defined herein. In certain embodiments, $R^4$ can be —$C(=O)OH$. In certain embodiments, $R^4$ can be —$C(=O)OMe$. In certain embodiments, $R^A$ can be optionally substituted $C_{1-6}$ alkyl. In certain embodiments, $R^4$ can be —$C(=O)NHR^B$ and $R^B$ as defined herein.

In certain embodiments, $R^4$ can be —$C(=O)NHN(R^B)_2$. In certain embodiments, $R^4$ can be —$C(=O)NHNH_2$. In certain embodiments, two instances of $R^B$ are taken together with the intervening nitrogen to form optionally substituted heterocyclyl. In certain embodiments, $R^4$ can be —$C(=O)NR^B(OR^A)$ and $R^A$ is as defined herein. In certain embodiments, $R^4$ can be —$C(=NH)NHOR^A$ and $R^A$ is as defined herein. In certain embodiments, $R^4$ can be —$C(=NH)NHOH$. In certain embodiments, $R^4$ can be —$C(=NH)NHOMe$. In certain embodiments, $R^4$ can be —$C(=NH)NHOEt$. In certain embodiments, $R^4$ can be —$C(=NH)NHOBn$. In certain embodiments, $R^4$ can be —$C(=NH)NHOC(=O)OBn$. In certain embodiments, $R^4$ can be —C(=NH)NHOC(=O)OPh. In certain embodiments, R$^4$ can be —C(=NH)NHOC(=O)OPh. In certain embodiments, R$^4$ can be —C(=NH)NHOBn. In certain embodiments, R$^4$ can be —C(=NOR$^A$)NH$_2$, and R$^A$ is as defined herein. In certain embodiments, R$^4$ can be —C(=NOH)NH$_2$ In certain embodiments, R$^4$ can be —C(=NH)NHN(R$^B$)$_2$. In certain embodiments, R$^4$ can be —C(=NH)N(R$^B$)$_2$)NH$_2$. In certain embodiments, R$^4$ can be —C(=NHN(R$^B$)$_2$)NMe$_2$. In certain embodiments, R$^4$ can be —C(=NH)N(R$^B$)$_2$ and R$^B$ is as defined herein. In certain embodiments, R$^B$ can be optionally substituted C$_{1-6}$ alkyl. In certain embodiments, R$^B$ can be —OR$^X$, and R$^X$ is as defined herein. In certain embodiments, R$^4$ can be —C(=O)NH(OH). In certain embodiments, R$^4$ can be —C(=O)NH(OMe). In certain embodiments, R$^4$ can be —C(=O)NH(OEt). In certain embodiments, R$^4$ can be —C(=NH)(NH$_2$). In certain embodiments, R$^4$ can be —C(=NH)NMe$_2$. In certain embodiments, R$^4$ can be tetrazole.

In some embodiments, substituent R$^{4a}$ in Formula (I') can be independently optionally substituted alkyl, —C(=O)N(R$^B$)$_2$, —CN, —C(=O)OR$^A$, —C(=O)NR$^B$(OR$^A$), —C(=O)R$^A$, —C(=O)NHN(R$^B$)$_2$, —C(=NH)NHOR$^A$, —C(=NOR$^A$)NH$_2$, —C(=NH)NHN(R$^B$)$_2$, —C[=NHN(R$^B$)$_2$]NH$_2$, —C(=NH)N(R$^B$)$_2$, or nitrogen-containing heterocycle. In certain embodiments, R$^{4a}$ can be optionally substituted C$_{1-6}$ alkyl. In certain embodiments, R$^{4a}$ can be —CH$_2$N(R$^B$)$_2$, and R$^B$ can be hydrogen or optionally substituted C$_{1-6}$ alkyl. In certain embodiments, one instance of R$^B$ can be hydrogen and the other instance of R$^B$ can be optionally substituted C$_{1-6}$ alkyl. In certain embodiments, R$^{4a}$ can be —C(=O)N(R$^B$)$_2$ (e.g., —C(=O)NH$_2$ or —C(=O)NMe$_2$). In certain embodiments, one instance of R$^B$ can be hydrogen and the other instance of R$^B$ can be optionally substituted C$_{1-6}$ alkyl. In certain embodiments, both instances of R$^B$ can be hydrogen. In certain embodiments, two instances of R$^B$ are taken together with the intervening nitrogen to form piperidine. In certain embodiments, two instances of R$^B$ are taken together with the intervening nitrogen to form morpholine. In certain embodiments, two instances of R$^B$ are taken together with the intervening nitrogen to form piperizine. In certain embodiments, R$^{4a}$ can be —CN. In certain embodiments, R$^4$ can be —C(=O)R$^A$, and R$^A$ is as defined herein. In certain embodiments, R$^{4a}$ can be —C(=O)N$_3$. In certain embodiments, R$^{4a}$ can be —C(=O)OR$^A$, and R$^A$ is as defined herein. In certain embodiments, R$^4$ can be —C(=O)OH. In certain embodiments, R$^{4a}$ can be —C(=O)OMe. In certain embodiments, R$^4$ can be optionally substituted C$_{1-6}$ alkyl. In certain embodiments, R$^{4a}$ can be —C(=O)NHR$^B$ and R$^B$ as defined herein.

In certain embodiments, R$^{4a}$ can be —C(=O)NHN(R$^B$)$_2$. In certain embodiments, R$^{4a}$ can be —C(=O)NHNH$_2$. In certain embodiments, R$^{4a}$ can be —C(=O)NH(n-Bu). In certain embodiments, two instances of R$^B$ are taken together with the intervening nitrogen to form optionally substituted heterocyclyl. In certain embodiments, R$^{4a}$ can be —C(=O)NR$^B$(OR$^A$) and R$^A$ is as defined herein. In certain embodiments, R$^{4a}$ can be —C(=NH)NHOR$^A$ and R$^A$ is as defined herein. In certain embodiments, R$^{4a}$ can be —C(=NH)NHOH. In certain embodiments, R$^{4a}$ can be —C(=NH)NHOMe. In certain embodiments, R$^{4a}$ can be —C(=NH)NHOBn. In certain embodiments, R$^{4a}$ can be —C(=NH)NHOC(=O)OBn. In certain embodiments, R$^{4a}$ can be —C(=NH)NHOC(=O)OPh. In certain embodiments, R$^{4a}$ can be —C(=NOR$^A$)NH$_2$ and R$^A$ is as defined herein. In certain embodiments, R$^{4a}$ can be —C(=NOH)NH$_2$ In certain embodiments, R$^{4a}$ can be —C(=NH)NHN(R$^B$)$_2$. In certain embodiments, R$^{4a}$ can be —C(=NH)N(R$^B$)$_2$)NH$_2$. In certain embodiments, R$^{4a}$ can be —C(=NHN(R$^B$)$_2$)NMe$_2$. In certain embodiments, R$^{4a}$ can be —C(=NH)N(R$^B$)$_2$ and R$^B$ is as defined herein. In certain embodiments, R$^B$ can be optionally substituted C$_{1-6}$ alkyl. In certain embodiments, R$^B$ can be —OR$^X$, and R$^X$ is as defined herein. In certain embodiments, R$^{4a}$ can be —C(=O)NH(OH). In certain embodiments, R$^{4a}$ can be —C(=O)NH(OMe). In certain embodiments, R$^{4a}$ can be —C(=NH)(NH$_2$). In certain embodiments, R$^{4a}$ can be —C(=NH)NMe$_2$. In certain embodiments, R$^{4a}$ can be a nitrogen-containing heterocycle (e.g., tetrazole, piperidine, piperizine, etc.). In certain embodiments, R$^{4a}$ can be optionally substituted 1-oxa-2,4-diazole. In certain embodiments, R$^{4a}$ can be a nitrogen-containing heterocycle, in which at least one instance of heterocycle is optionally substituted 1-oxa-2,4-diazole. In certain embodiments, R$^{4a}$ can be tetrazole. In certain embodiments, R$^{4a}$ can be of the formula:

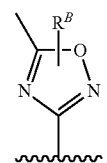

and R$^B$ is as defined herein. In certain embodiments, R$^{4a}$ can be of the formula:

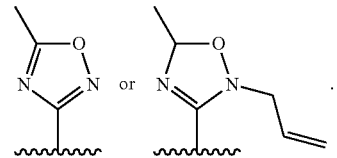

In some embodiments, the compound of Formula (I) can be of one of the following formulae: Formula (IA), Formula (IB), or a pharmaceutically acceptable salt, solvate, hydrate, polymorph, co-crystal, tautomer, stereoisomer, isotopically labeled derivative, or prodrug thereof.

In some embodiments, the compound of Formulas (I') or (I) can be of the formula of (Ia'-2), (Ia'-3), (IB-1), (IB'-2), (IB'-3), or (IB-4).

In some embodiments, the compound of Formula (I) can be of the formula of compounds 5a-11g, or a pharmaceutically acceptable salt, solvate, hydrate, polymorph, co-crystal, tautomer, stereoisomer, isotopically labeled derivative, or prodrug thereof.

In some embodiments, the compound of Formulas (I') or (I) can be of the formula of compounds 5a-36a. In some embodiments, the compound of Formulas (I') or (I) can be of the formula of compounds (5i), (8c), (8d), (8f), (8g), (10a)-(10d), (11a)-(11g), (12a)-(12g), (13a), (14b)-(14g), (15a'), (15a)-(15c), (16a), (16a'), (17a)-(17d), (18a), (18b), (19a)-(19d), (20a), (20b), (21a), (21b), (22a), (22b), (23a), (24a), (25a), (26a), (27a), (28a), (29a), (30a), (31a), (32a), (33a), (33b), (34a), (35a), and (36a), or a pharmaceutically acceptable salt, solvate, hydrate, polymorph, co-crystal, tautomer, stereoisomer, isotopically labeled derivative, or prodrug thereof.

In some embodiments, the compound of Formulas (I') or (I) can be of the formula of the compounds described herein, or a pharmaceutically acceptable salt, solvate, hydrate, polymorph, co-crystal, tautomer, stereoisomer, isotopically labeled derivative, or prodrug thereof.

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis,* 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating and/or preventing proliferative diseases (e.g., cancer).

In certain embodiments, the compound described herein is provided in an effective amount in the pharmaceutical composition. In certain embodiments, the effective amount is a therapeutically effective amount (e.g., amount effective for treating a proliferative disease in a subject in need thereof). In certain embodiments, the proliferative disease is cancer. In certain embodiments, the proliferative disease is lung cancer. In certain embodiments, the effective amount is a therapeutically effective amount (e.g., amount effective for treating a proliferative disease in a subject in need thereof). In certain embodiments, the amount of any of the compounds described herein is effective to inhibit the growth of cancer cells, e.g., those described herein, in a cancer patient. In certain embodiments, the effective amount is a prophylactically effective amount (e.g., amount effective for preventing a proliferative disease in a subject in need thereof).

The compounds and formulations of the present invention are suitable for use in treating a proliferative disease such as cancer, either alone or in combination with a second anticancer agent. Therefore, the invention provides pharmaceutical compositions comprising a compound of Formula (I'), Formula (I), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient and a second anticancer agent or treatment. Exemplary second anti-cancer agent or treatment includes, but is not limited to, camptothecin, doxorubicin, cisplatin, irinotecan (CPT-11), alkylating agents, topoisomerase I and II inhibitors, and radiation treatment. Furthermore, the compounds of the invention may be used in combination with anti-cancer drugs such as Gleevec, BAY43-9006, and Brostallicin, and other anti-cancer drugs as described herein, and find particular use in patients that are resistant to these anti-cancer drugs.

In some embodiments, the pharmaceutical composition comprising a compound as described herein and a second anti-cancer agent or treatment can be administered simultaneously, separately, or sequentially in the treatment of a patient, such as a cancer patient. In some embodiments, the patient is a cancer patient that is resistant to at least one anti-cancer drug, such as Gleevec, BAY43-9006, or Brostallicin. In some embodiments, the second anti-cancer agent and the compound as described herein are provided as a single composition. In other embodiments, the second anti-cancer agent and the compound as described herein are provided separately as parts of a kit. Such kits may further include instructions for use.

Pharmaceutical compositions described herein can be prepared by any method known in the art of pharmacology. In general, such preparatory methods include the steps of bringing the compound of Formula (I'), or Formula (I) into association with a carrier and/or one or more other accessory ingredients, and then, if necessary and/or desirable, shaping and/or packaging the product into a desired single- or multi-dose unit.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between about 0.1% and about 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof. In certain embodiments, the composition of the instant disclosure is encapsulated in a carrier vehicle. In certain embodiments, the encapsulating carrier vehicle is selected from the group consisting of vesicles, rigid vesicles, elastic vesicles, monolayer vesicles, multi-layer vesicles, liposomes, niosomes, proniosomes, Transfersomes®, ethosomes, L-595-PEG-8-L vesicles, nanoemulsions, nanosomes, nanoparticles and a combination thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, I solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

The compounds and compositions provided herein can be administered by any route, including enteral (e.g., oral), parenteral, intravenous, intramuscular, intra-arterial, intracranial, intramedullary, intrathecal, subcutaneous, intraventricular, transdermal, intradermal, interdermal, rectal, intravaginal, intraperitoneal, topical (such as by powders, ointments, creams, and/or drops), by any means that facilitate in vivo or ex vivo transport of the compound or composition as described herein in, into, or through tissue/skin of a subject (such as iontophoresis), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), transfusion, perfusion, regional administration via blood and/or lymph supply, and/or direct administration to an affected site, such as intra-tumoral. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I') or Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower, higher, or the same as that administered to an adult.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification and/or manipulation of pharmaceutical compositions suitable for administration to humans in order to render the compositions suitable for administration to various animals is well understood, and the ordinarily skilled veterinary pharmacologist can design and/or perform such modification/manipulation using techniques that are routinely used by said veterinary pharmacologist to arrive at the desired composition form with a reasonable expectation of success.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, disease or condition, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination are lower than those utilized individually. In some embodiments, the therapeutic effect achieved by administration of said combination therapy described herein is additive when compared to the therapeutic effect resulting from separate administrations of said compound or composition, and said one or more additional pharmaceutical agents. In some embodiments, additive effects are shown as in vitro cytotoxic antitumor activities (using e.g., MTT assays).

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound as described herein and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment

The present disclosure also provides methods of using any of the compounds of Formulas (I') or (I) as described herein, or a pharmaceutically acceptable salt, solvate, hydrate, polymorph, co-crystal, tautomer, stereoisomer, isotopically labeled derivative, and prodrug thereof, or a pharmaceutical composition thereof, for the treatment or prevention of a proliferative disease such as cancer (e.g., lung cancer, breast cancer, large bowel cancer, pancreas cancer, biliary tract cancer, or endometrial cancer), benign neoplasm, angiogenesis, inflammatory disease, autoinflammatory disease, or autoimmune disease) in a subject. In certain embodiments, the invention provides a method for treating cancer, the method comprising administering to a subject in need thereof an effective amount (e.g., prophylactically or therapeutically effective amount) of the provided compound or pharmaceutical composition thereof. In certain embodiments, the subject is a human. In certain embodiments, the subject is a mammal. In certain embodiments, the subject has cancer. In certain embodiments, the subject is suspected of having cancer or is at risk of having cancer.

In some embodiments, a provided compound is useful in treating cancer. In some embodiments, a provided compound is useful to delay the onset of, slow the progression of, or ameliorate the symptoms of cancer. In some embodiments, a provided compound is administered in combination with other compounds, drugs, or therapeutics to treat cancer. In some embodiments, a provided compound is administered in combination with a second anti-cancer agent to treat cancer.

In some embodiments, compounds described herein are useful for treating cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

The compounds and pharmaceutical compositions described herein are useful in treating and/or preventing proliferative diseases in a subject. In certain embodiments, the proliferative disease is cancer. In some embodiments, the cancer is lung cancer. In some embodiments, the lung cancer is small cell lung cancer. In some embodiments, the lung cancer is non-small cell lung cancer. In some embodiments, the cancer is breast cancer. In some embodiments, the breast cancer is triple-negative breast cancer. In some embodiments, the cancer is large bowel cancer. In some embodiments, the cancer is pancreas cancer. In some embodiments, the cancer is biliary tract cancer or endometrial cancer.

In some embodiments, the subject is a cancer patient resistant to an anti-cancer agent. In some embodiments, the cancer patient is resistant to a tyrosine kinase inhibitor. In some embodiments, the cancer patient is resistant to an EGFR inhibitor. In some embodiments, the cancer patient is resistant to a tyrosine kinase inhibitor. In some embodiments, the cancer patient is resistant to an EGFR inhibitor. In some embodiments, the cancer patient is resistant to gefitinib, erlotinib, cetuximab, matuzumab, or panitumumab. In some embodiments, the subject is a human cancer patient (e.g., breast cancer patient) who carry cancer cells that does not express estrogen receptor (ER), progesterone receptor (PR) and/or Her2/neu.

In still another aspect, the present invention provides methods of inhibiting EGFR activity or EGFR signaling in a biological sample or a subject.

In certain embodiments, the compound is administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, active or passive immunotherapy, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol); epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse or rat), dog, or non-human primate. In certain embodiments, the subject is a non-human transgenic animal such as a transgenic mouse or transgenic pig.

Examples

In order that the invention described herein may be more fully understood, the following examples are set forth. It should be understood that these examples are for illustrative purposes only and are not to be construed as limiting this invention in any manner.

All reagents and solvents were reagent grade and were used without further purification unless otherwise specified. All solvents were anhydrous grade unless indicated otherwise.

$CH_2Cl_2$ was distilled from $CaH_2$. All non-aqueous reactions were performed in dried glassware and with continuous stirring under argon or nitrogen atmosphere. Reactions were monitored by thin-layer chromatography on 0.25 mm E. Merck silica gel 60 $F_{254}$ glass plates using $KMnO_4$, p-anisaldehyde, ninhydrin and iodine vapor as visualizing agents. E. Merck silica gel 60 (0.040-0.063 mm particle sizes) and LiChroprep RP-18 (0.040-0.063 mm particle sizes) were used for column chromatography. Melting points were recorded on a Yanaco melting point apparatus. Infrared (IR) spectra were recorded on Thermo Nicolet iS-5 FT-IR spectrometer. Nuclear magnetic resonance (NMR) spectra was obtained on Bruker Avanced-400 (400 MHz) or Bruker AVIII (400 MHz) NMR. Chemical shifts (δ) are given in parts per million (ppm) relative to $CHCl_3$ ($δ_H$ 7.24), $CDCl_3$ ($δ_C$ 77.0 for the central line of triplet), $CD_2HOD$ ($δ_H$ 3.31), $CD_3OD$ ($δ_C$ 49.0), $(CD_2H)_2SO$ ($δ_H$ 2.50), and $(CD_3)_2SO$ ($δ_C$ 39.5). Coupling constants (J) are given in Hertz (Hz) and the splitting patterns are reported as s (singlet), d (doublet), t (triplet), q (quartet), quint (quintet), m (multiplet) and br (broad). The ESI-HRMS experiments were conducted on a Bruker Daltonics BioTOF III high-resolution mass spectrometer.

The Examples show the syntheses of compounds, e.g., 8-oxopurine compound 5. (Booth, et al., J. Org. Chem. 2001, 66, 8436. Mortensen, D. S.; et al. U.S. Pat. No. 8,383,634B2, 2013.) The methods for elaboration of substituents and functional group transformation are reported in appropriate examples. (Higashino, et al., Chem. Pharm. Bull. 1982, 30, 4521. Dyer, et al., J. Org. Chem. 1963, 6, 289.)

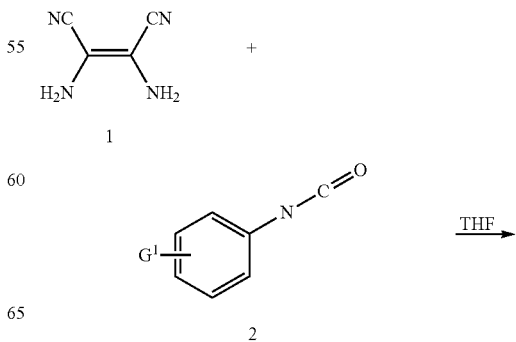

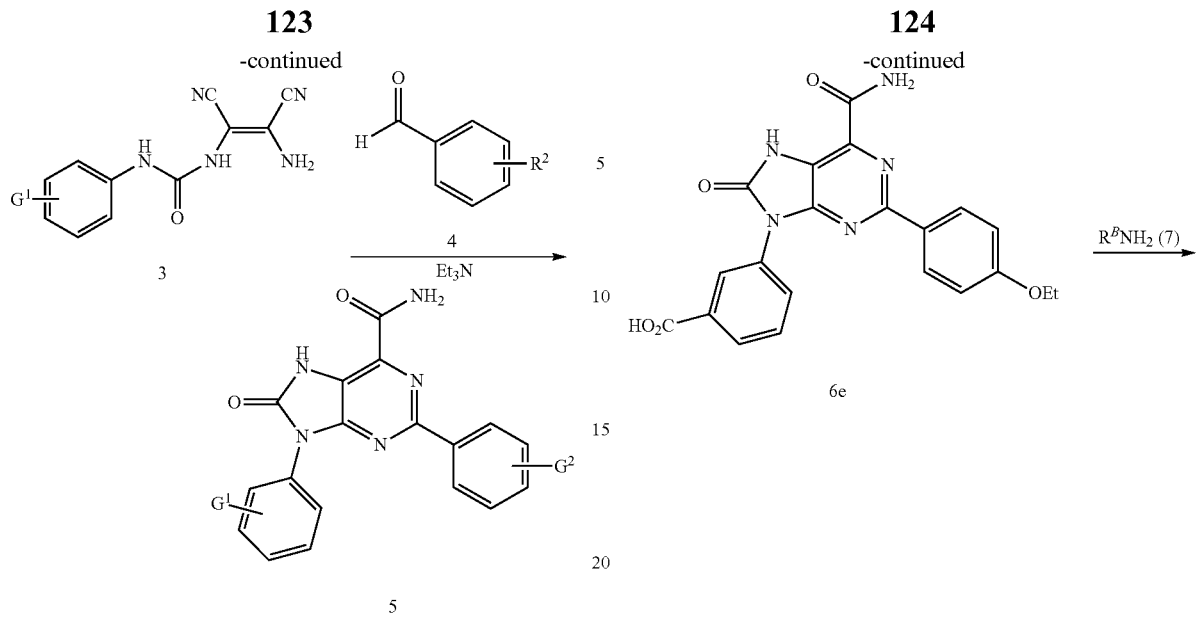
The Examples shows the syntheses of compound 8-thio-purine compounds 8 bearing aminocarbonyl substituents on the 9-phenyl ring.
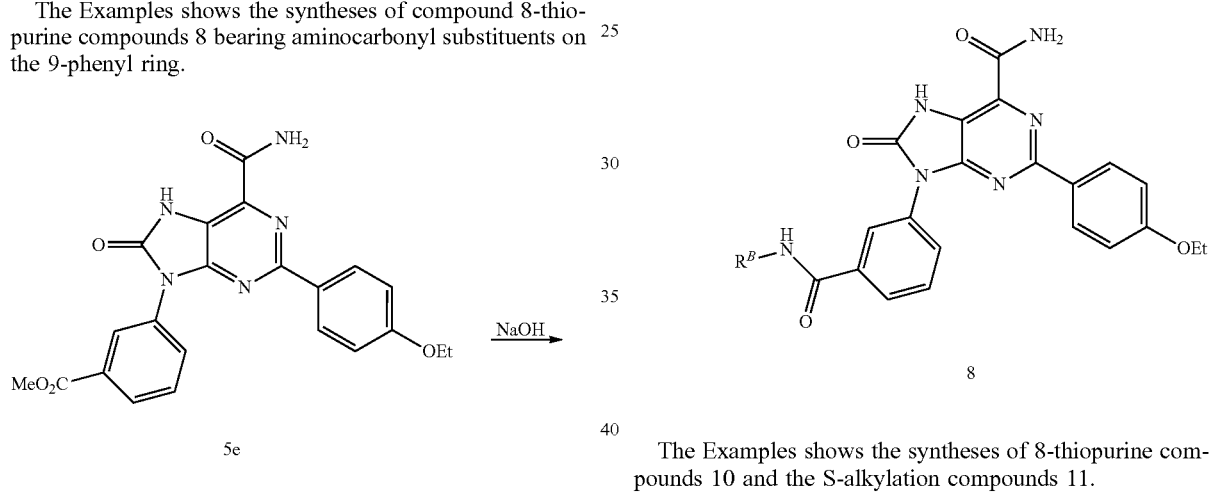
The Examples shows the syntheses of 8-thiopurine compounds 10 and the S-alkylation compounds 11.
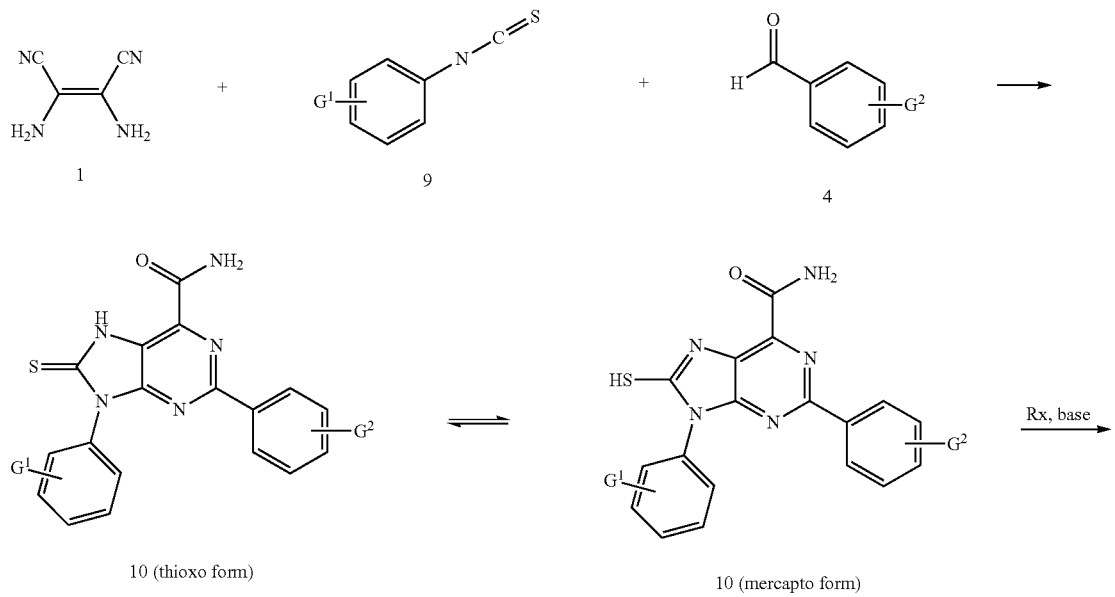

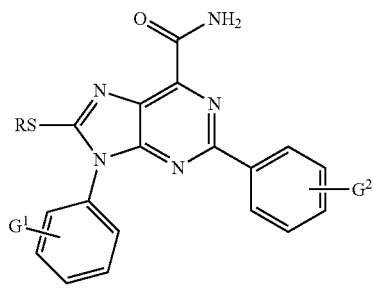

11

The methods for elaboration of substituents and functional group transformation are reported in appropriate Examples. (Higashino, et al., *Chem. Pharm. Bull.* 1982, 30, 4521. Dyer, et al., *J. Org. Chem.* 1963, 6, 289.)

2-(4-Ethoxyphenyl)-9-(2-methoxyphenyl)-8-oxopurine-6-carboxamide (5a)

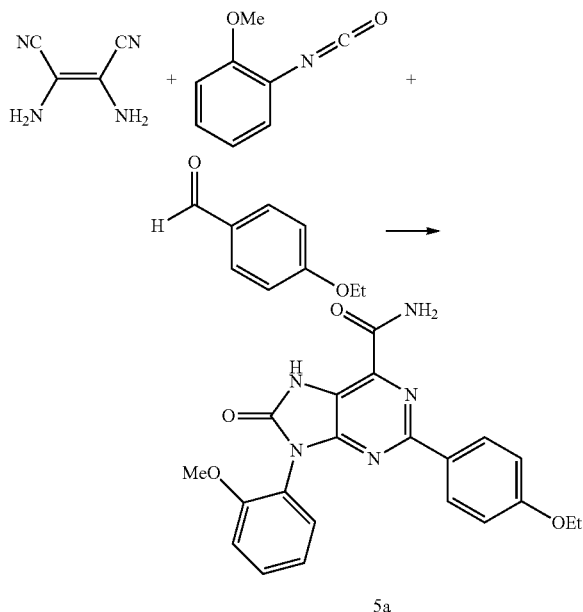

5a

A mixture of diaminomaleonitrile (217 mg, 2 mmol) and 2-methoxyphenyl isocyanate (0.28 mL, 2.1 mmol) in anhydrous THF (15 mL) was stirred at room temperature for 24 h under an atmosphere of argon. The mixture was concentrated under reduced pressure. The residual solids were filtered, and rinsed with cold ethanol and diethyl ether to yield a urea compound (310 mg, 60% yield). $C_{12}H_{11}N_5O_2$; white solid; mp=175.2-176.5 OC (decomposed); IR $v_{max}$ (KBr) 3426, 3331, 2995, 2840, 2241, 2208, 1664, 1560 cm$^1$; $^1$H NMR (400 MHz, DMSO-d$_6$) δ 8.25 (1H, br s), 8.20 (1H, br s), 8.04 (1H, dd, J=8.0, 1.6 Hz), 7.12 (2H, s), 7.00 (1H, dd, J=8.0, 1.2 Hz), 6.94 (1H, td, J=7.2, 1.6 Hz), 6.87 (1H, td, J=7.0, 1.2 Hz), 3.84 (3H, s); $^{13}$C NMR (100 MHz, DMSO-d$_6$) δ 152.0, 147.5, 128.3, 126.2, 122.2, 120.6, 118.2, 117.0, 114.2, 110.8, 90.5, 55.8. ESI-HRMS calculated for $C_{12}H_{12}N_5O_2$: 258.0991, found: m/z 258.0991 [M+H]$^+$. Anal. Cacld for ($C_{21}H_{19}N_5O_4$·½ H$_2$O): C, 60.86; H, 4.86; N, 16.90. Found: C, 60.76; H, 5.00; N, 16.74.

To a suspension of the above-prepared urea compound (218 mg, 0.85 mmol) and 4-ethoxybenzaldehyde (0.24 mL, 1.74 mmol) in methanol (10 mL), triethylamine (125 μL, 0.89 mmol) was added. The mixture was stirred at room temperature, and the solids dissolved in approximately 1 h. The solution was stirred for another 24 h, during which the solid precipitates gradually formed. The mixture was filtered and washed with cold ethanol and diethyl ether to yield the purine-type 5a (182.1 mg, 53% yield). $C_{21}H_{19}N_5O_4$; white solid; mp=261.3-263.2° C.; IR $v_{max}$ (KBr) 3507, 3454, 3290, 3235, 2972, 1744, 1702, 1577 cm$^1$; $^1$H NMR (400 MHz, DMSO-d$_6$) δ 11.62 (1H, s, N$_7$—H), 8.47 (1H, s, amide), 8.26 (2H, d, J=8.8 Hz, H-2" & H-6"), 7.91 (1H, s, amide), 7.53 (1H, dd, J=8.2, 7.6 Hz, H-4'), 7.46 (1H, d, J=7.6 Hz, H-6'), 7.27 (1H, d, J=8.2 Hz, H-3'), 7.13 (1H, dd, J=8.2, 7.6 Hz, H-5'), 6.93 (2H, d, J=8.8 Hz, H-3" & H-5"), 4.05 (2H, q, J=6.8 Hz, OCH$_2$), 3.73 (3H, s, OCH$_3$), 1.32 (3H, t, J=6.8 Hz, CH$_3$); $^{13}$C NMR (100 MHz, DMSO-d$_6$) δ 165.6, 160.2, 160.2, 155.4, 154.8, 153.4, 152.8, 132.7, 130.8, 130.1, 129.2 (2×), 129.1, 120.7, 120.6, 114.0 (2×), 112.7, 63.1, 55.8, 14.5; ESI-HRMS (negative mode) calculated for $C_{21}H_{18}N_5O_4$: 404.1359, found: m/z 404.1374 [M−H]$^-$. Anal. Cacld for ($C_{21}H_{19}N_5O_4$·½H$_2$O): C, 60.86; H, 4.86; N, 16.90. Found: C, 60.76; H, 5.00; N, 16.74.

2-(4-Hydroxyphenyl)-9-(2-methoxyphenyl)-8-oxopurine-6-carboxamide (5b)

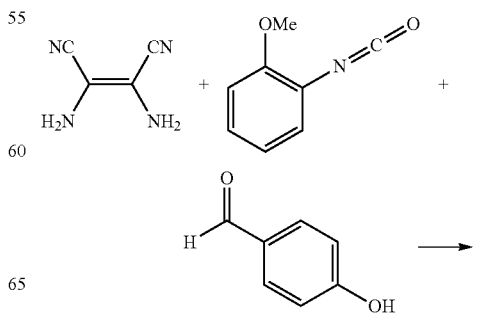

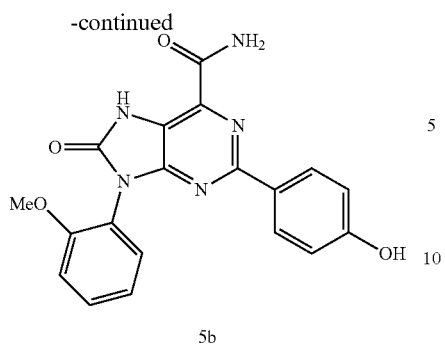

5b

By a procedure similar to that for 5a, the condensation reaction of diaminomaleonitrile, 2-methoxyphenyl isocyanate and 4-hydroxybenzaldehyde gave the purine compound 5b (33% yield). $C_{19}H_{15}N_5O_4$; pale orange solid; mp=370.2-371.8° C.; IR $\nu_{max}$ (KBr) 3472, 3441, 3255, 1732, 1686, 1599, 1510 cm$^{-1}$; $^1$H NMR (400 MHz, DMSO-d$_6$) δ 11.58 (1H, br s), 9.77 (1H, s), 8.40 (1H, s), 8.17 (2H, d, J=7.8 Hz), 7.92 (1H, s), 7.54 (1H, dd, J=8.0, 7.6 Hz), 7.47 (1H, d, J=7.6 Hz), 7.28 (1H, d, J=8.0 Hz), 7.14 (1H, dd, J=8.0, 7.6 Hz), 6.78 (2H, d, J=7.8 Hz), 3.73 (3H, s); $^{13}$C NMR (100 MHz, DMSO-d$_6$) δ 165.7, 159.4, 155.4, 155.3, 153.3, 152.8, 132.8, 130.8, 130.2, 127.9 (2×), 120.8, 120.7 (2×), 119.1 (2×), 112.7 (2×), 55.9; ESI-HRMS calculated for $C_{19}H_{16}N_5O_4$: 378.1202, found: m/z 378.1201 [M+H]$^+$. Anal. Cacld for ($C_{19}H_{15}N_5O_4$·½CH$_3$OH): C, 59.54; H, 4.36; N, 17.80. Found: C, 59.50; H, 3.98; N, 18.24.

2-(4-Butoxyphenyl)-9-(2-methoxyphenyl)-8-oxopurine-6-carboxamide (5c)

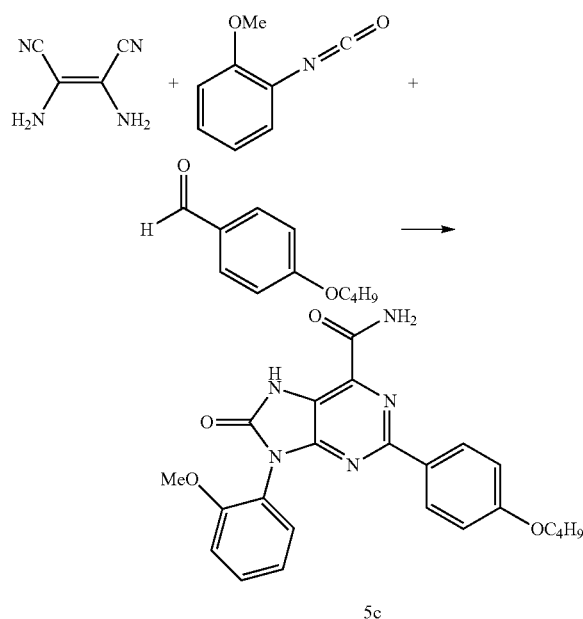

5c

By a procedure similar to that for 5a, the condensation reaction of diaminomaleonitrile, 2-methoxyphenyl isocyanate and 4-butoxybenzaldehyde gave the purine compound 5c (34% yield). $C_{23}H_{23}N_5O_4$; white solid; mp=268.7-270.2° C.; IR $\nu_{max}$ (KBr) 3453, 3277, 3215, 2954, 1744, 1702, 1577 cm$^{-1}$; $^1$H NMR (400 MHz, DMSO-d$_6$) δ 11.62 (1H, s), 8.45 (1H, s), 8.27 (2H, d, J=8.2 Hz), 7.94 (1H, s), 7.53 (1H, dd, J=8.0, 7.6 Hz), 7.47 (1H, d, J=7.6 Hz), 7.27 (1H, d, J=8.0 Hz), 7.14 (1H, t, J=7.6 Hz), 6.94 (2H, d, J=8.2 Hz), 3.98 (2H, t, J=6.0 Hz), 3.73 (3H, s), 1.67 (2H, m), 1.42 (2H, m), 0.91 (3H, t, J=7.2 Hz); $^{13}$C NMR (100 MHz, DMSO-d$_6$) δ 165.7, 160.4, 155.4, 154.9, 153.4, 152.8, 132.8, 130.8, 130.2, 129.24 (2×), 129.16, 120.71, 120.68, 114.1 (2×), 112.8, 67.2, 55.9, 30.7, 18.7, 13.7; ESI-HRMS calculated for $C_{23}H_{24}N_5O_4$: 434.1828, found: m/z 434.1833 [M+H]$^+$. Anal. Cacld for $C_{23}H_{23}N_5O_4$: C, 63.73; H, 5.35; N, 16.16. Found: C, 63.81; H, 5.19; N, 15.85.

2-(4-Hexoxyphenyl)-9-(2-methoxyphenyl)-8-oxopurine-6-carboxamide (5d)

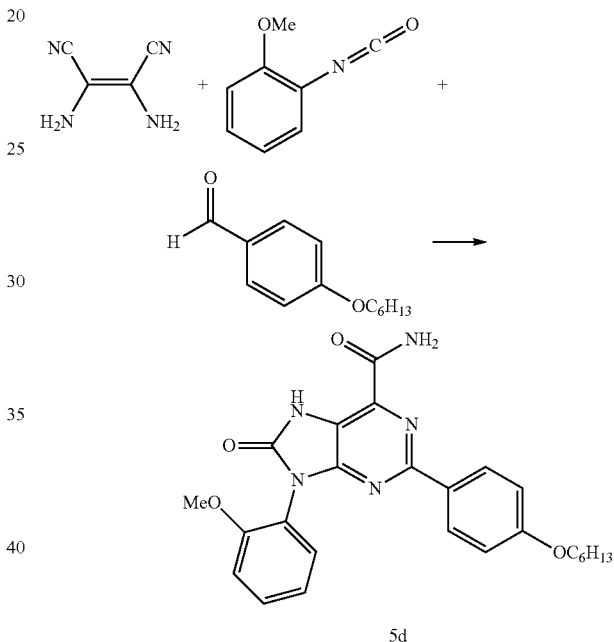

5d

By a procedure similar to that for 5a, the condensation reaction of diaminomaleonitrile, 2-methoxyphenyl isocyanate and 4-hexoxybenzaldehyde produced the purine compound 5d (50% yield). $C_{25}H_{27}N_5O_4$; yellow solid; mp=219.7-220.3° C.; IR $\nu_{max}$ (KBr) 3443, 3301, 3129, 2949, 2855, 1760, 1725, 1674 cm$^{-1}$; $^1$H NMR (400 MHz, DMSO-d$_6$) δ 11.62 (1H, br s), 8.45 (1 H, s), 8.27 (2H, d, J=8.8 Hz), 7.94 (1H, s), 7.54 (1H, ddd, J=8.0, 7.6, 1.6 Hz, H-4'), 7.47 (1H, dd, J=7.6, 1.6 Hz, H-6'), 7.27 (1H, dd, J=8.0, 1.0 Hz, H-3'), 7.14 (1H, ddd, J=8.0, 7.6, 1.0 Hz, H-5'), 6.93 (2H, d, J=8.8 Hz), 3.97 (2H, t, J=6.8 Hz), 3.73 (3H, s), 1.69 (2H, quin, J=6.8 Hz), 1.44-1.35 (2H, m), 1.33-1.25 (4H, m), 0.86 (3H, t, J=7.2 Hz); $^{13}$C NMR (100 MHz, DMSO-d$_6$) δ 165.7, 160.4, 155.4, 154.9, 153.4, 152.8, 132.8, 130.8, 130.2, 129.24 (2×), 129.18, 120.72, 120.68, 114.1 (2×), 112.8, 67.5, 55.9, 31.0, 28.6, 25.2, 22.0, 13.9; ESI-HRMS calculated for $C_{25}H_{28}N_5O_4$: 462.2141, found: m/z 462.2145 [M+H]$^+$. Anal. Cacld for ($C_{25}H_{27}N_5O_4$·½H$_2$O): C, 63.82; H, 6.00; N, 14.88. Found: C, 64.01; H, 5.83; N, 14.81.

2-(4-Ethoxyphenyl)-9-(3-methoxycarbonyl)phenyl-8-oxopurine-6-carboxamide (5e)

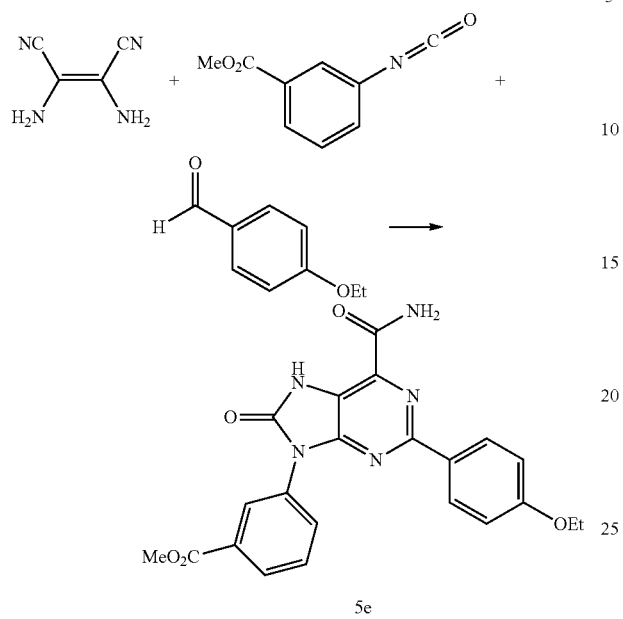

5e

By a procedure similar to that for 5a, the condensation reaction of diaminomaleonitrile, 3-(methoxycarbonyl)phenyl isocyanate and 4-ethoxybenzaldehyde produced the purine compound 5e (39% yield). $C_{22}H_{19}N_5O_5$; orange solid; mp=330.5-332.0 OC; IR $v_{max}$ (KBr) 3456, 3285, 3217, 2983, 2942, 1753, 1701, 1597, 1578 cm$^{-1}$; $^1$H NMR (400 MHz, DMSO-d$_6$) δ 11.74 (1H, br s, N$_7$—H), 8.48 (1H, s, amide), 8.43 (1H, t, J=2.0 Hz, H-2'), 8.39-8.36 (2H, m, H-4' & H-6'), 8.10-8.01 (2H, m, H-2" & H-6"), 7.94 (1H, s, amide), 7.76 (1H, dd, J=8.8, 7.4 Hz, H-5'), 6.99-6.96 (2H, m, H-3" & H-5"), 4.08 (2H, q, J=7.2 Hz), 3.91 (3H, s, CO$_2$CH$_3$), 1.34 (3H, t, J=7.2 Hz); $^{13}$C NMR (100 MHz, DMSO-d$_6$) δ 165.6, 165.6, 160.3, 154.6, 152.6, 133.3, 133.1, 130.5, 130.5, 130.3, 129.4, 129.2 (4×), 128.1, 126.5, 114.2 (2×), 63.2, 52.4, 14.6; ESI-HRMS calculated for $C_{22}H_{20}N_5O_5$: 434.1464, found: m/z 434.1479 [M+H]$^+$. Anal. Cacld for ($C_{22}H_{19}N_5O_5 \cdot 1/2H_2O$): C, 59.72; H, 4.56; N, 15.83. Found: C, 59.85; H, 4.55; N, 16.15.

2-(4-Ethoxyphenyl)-9-(4-methoxycarbonyl)phenyl-8-oxopurine-6-carboxamide (5f)

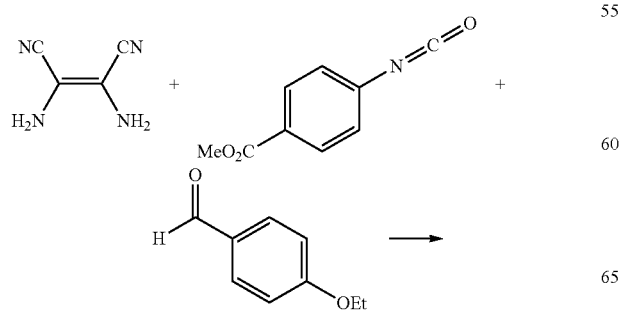

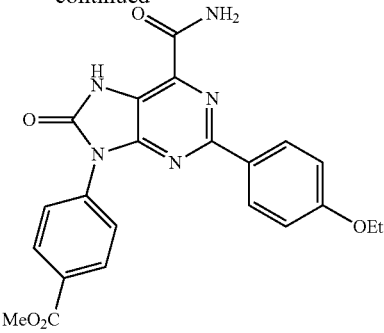

5f

By a procedure similar to that for 5a, the condensation reaction of diaminomaleonitrile, 4-(methoxycarbonyl)phenyl isocyanate and 4-ethoxybenzaldehyde produced the purine compound 5f (52% yield). $C_{22}H_{19}N_5O_5$; orange solid; mp=264.0-265.3° C.; IR $v_{max}$ (KBr) 3439, 3371, 3235, 2983, 1754, 1727, 1685, 1597, 1576 cm$^{-1}$; $^1$H NMR (400 MHz, DMSO-d$_6$) δ 11.74 (1H, br s), 8.46 (1H, s), 8.38 (2H, br d, J=8.8 Hz), 8.17 (2H, br d, J=8.8 Hz), 7.97 (2H, br d, J=8.8 Hz), 7.95 (1H, s), 6.96 (2H, br d, J=8.8 Hz), 4.06 (2H, q, J=7.2 Hz), 3.90 (3H, s), 1.33 (3H, t, J=7.2 Hz); $^{13}$C NMR (100 MHz, DMSO-d$_6$) δ 165.7, 165.6, 160.3, 154.8, 152.4, 152.3, 137.1, 133.3, 129.8 (2×), 129.3 (2×), 129.1, 128.3, 125.7 (2×), 119.3, 114.2 (2×), 63.2, 52.3, 14.6; ESI-HRMS (negative mode) calculated for $C_{22}H_{18}N_5O_5$: 432.1308, found: m/z 432.1218 [M–H]$^-$. Anal. Cacld for ($C_{22}H_{19}N_5O_5 \cdot H_2O$): C, 58.53; H, 4.69; N, 15.51. Found: C, 58.23; H, 4.72; N, 15.87.

2-(4-Azidophenyl)-9-(3-methoxycarbonyl)phenyl-8-oxopurine-6-carboxamide (5g)

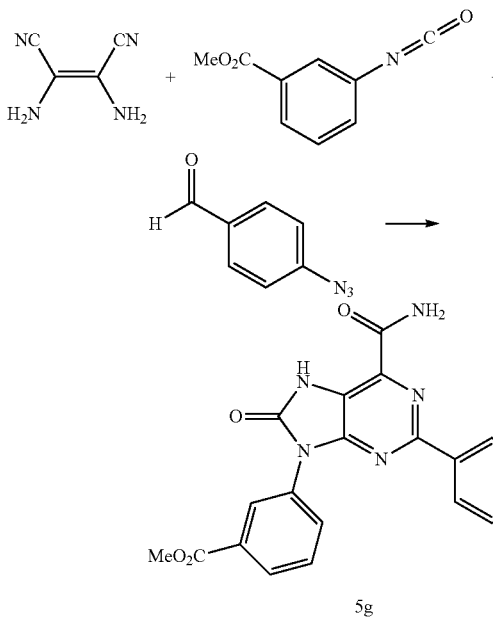

5g

By a procedure similar to that for 5a, the condensation reaction of diaminomaleonitrile, 3-(methoxycarbonyl)phenyl isocyanate and 4-azidobenzaldehyde gave the purine compound 5g (60% yield). $C_{20}H_{14}N_8O_4$; white solid; mp=262.7-264.4 OC (decomposed); IR $\nu_{max}$ (KBr) 3461, 3219, 2128, 1755, 1720, 1702, 1596, 1576 cm$^{-1}$; $^1$H NMR (400 MHz, DMSO-d$_6$) δ 11.82 (1H, s), 8.52 (1H, s), 8.48 (1H, d, J=8.4 Hz), 8.41 (1H, s), 8.05 (2H, t, J=10 Hz), 7.96 (1H, s, br), 7.76 (1H, t, J=8.0 Hz), 7.18 (2H, d, J=6.8 Hz), 3.90 (3H, s); $^{13}$C NMR (100 MHz, DMSO-d$_6$) δ 165.6, 165.5, 153.7, 152.7, 141.1, 133.7, 133.3, 133.0, 130.5, 130.4 (2×), 129.5 (2×), 129.2 (2×), 128.2, 126.6, 119.1 (2×), 52.4; ESI-HRMS calculated for $C_{20}H_{13}N_8O_4$: 429.1060, found: m/z 429.1056 [M+H]$^+$.

2-(3-Trifluoromethyl-3H-diazirin-3-yl)phenyl-9-(3-methoxycarbonyl)phenyl-8-oxopurine-6-carboxamide (5h)

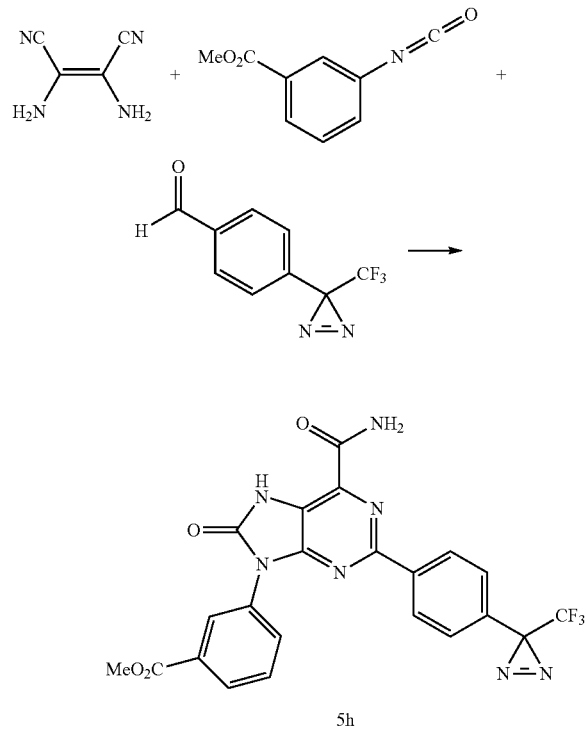

5h

By a procedure similar to that for 5a, the condensation reaction of diaminomaleonitrile, 3-(methoxycarbonyl)phenyl isocyanate and 4-(3-trifluoromethyl-3H-diazirin-3-yl) benzaldehyde gave the purine compound 1h (30% yield). $C_{22}H_{14}F_3N_7O_4$; white solid; mp=236.6-238.5 OC (decomposed); IR $\nu_{max}$ (KBr) 3459, 3286, 2090, 1750, 1700, 1598, 1500 cm$^{-1}$; $^1$H NMR (400 MHz, DMSO-d$_6$) δ 11.91 (1H, s, br), 8.54 (2H, d, J=8.4 Hz), 8.39 (1H, s), 8.05 (2H, t, J=7.6 Hz), 7.97 (1H, s), 7.75 (1H, t, J=8.0 Hz), 7.34 (2H, d, J=8.4 Hz), 3.90 (3H, s); $^{13}$C NMR (100 MHz, DMSO-d$_6$) δ 165.6, 165.4, 153.1, 152.8, 138.5, 133.2, 133.0, 130.7, 130.4, 130.4, 129.5, 129.0 (2×), 128.3, 128.2 (2×), 126.7, 126.5 (2×), 120.5, 120.4, 52.4; ESI-HRMS (negative mode) calculated for $C_{22}H_{13}F_3N_7O_4$: 496.0981, found: m/z 496.0981 [M−H]$^−$.

2-Biphenyl-9-(3-methoxycarbonylphenyl)-8-oxopurine-6-carboxamide (5i)

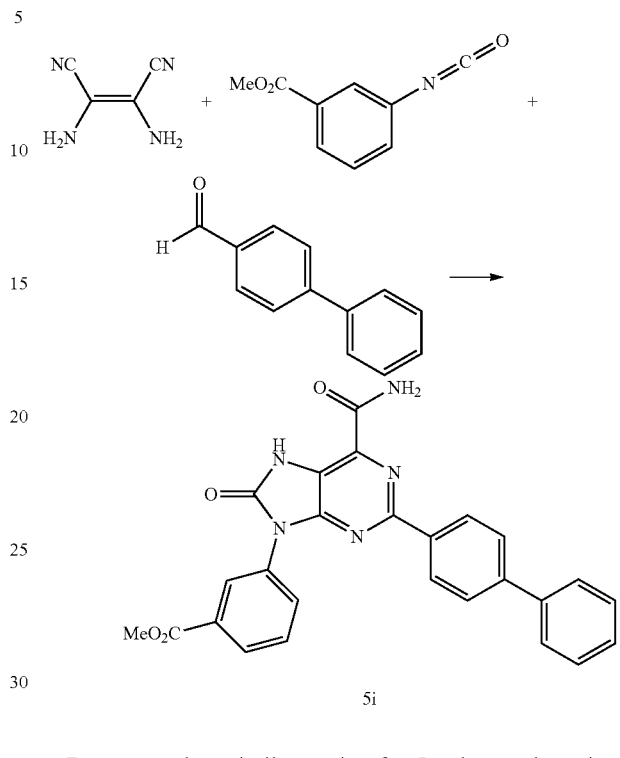

5i

By a procedure similar to that for 5a, the condensation reaction of diaminomaleonitrile, 3-(methoxycarbonyl)phenyl isocyanate and 4-phenylbenzaldehyde produced the purine compound 5i (31 mg, 56% yield). $C_{26}H_{19}N_5O_4$; white solid; mp=302.3-302.8° C.; IR $\nu_{max}$ (KBr) 3510, 3455, 3297, 3228, 3064, 3027, 2835, 1728, 1701, 1686, 1594 cm$^{-1}$; $^1$H NMR (400 MHz, DMSO-d$_6$) δ 11.74 (1H, s), 8.54 (1H, s), 8.43 (2H, d, J=8.8 Hz), 7.97 (1H, s), 7.72-7.69 (4H, m), 7.55 (1H, dd, J=8.8, 7.6 Hz), 7.52-7.44 (3H, m), 7.40-7.35 (1H, m), 7.30 (1H, d, J=8.0 Hz), 7.16 (1H, td, J=7.6, 0.8 Hz), 3.75 (3H, s); $^{13}$C NMR (100 MHz, DMSO-d$_6$) δ 165.6, 155.4, 154.4, 153.4, 141.5, 139.5, 135.9, 132.8, 130.8, 130.2, 129.0 (4×), 128.1 (3×), 127.8, 126.7 (4×), 126.6, 120.7, 112.8, 55.8; ESI-HRMS calculated for $C_{26}H_{19}N_5O_4$: 618.2499, found: m/z 618.2486 [M+H]$^+$. Anal. Cacld for ($C_{26}H_{19}N_5O_4 \cdot ¼H_2O$): C, 58.53; H, 4.69; N, 15.51. Found: C, 58.23; H, 4.72; N, 15.87.

2-(3-Hydroxy-4-methoxyphenyl)-9-(3-methoxycarbonylphenyl)-8-oxopurine-6-carboxamide (5j)

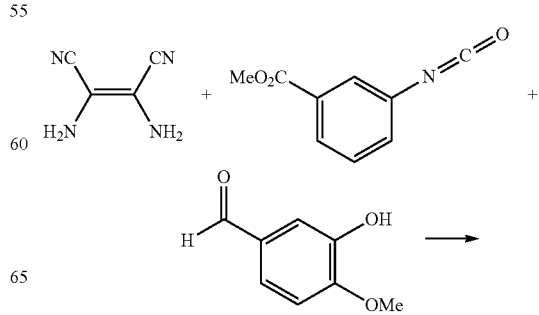

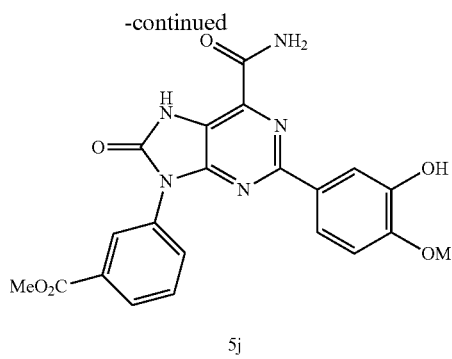

5j

By a procedure similar to that for 5a, the condensation reaction of diaminomaleonitrile, 3-(methoxycarbonyl)phenyl isocyanate and 3-hydroxy4-methoxybenzaldehyde gave the title compound 5j (36% yield). $C_{21}H_{17}N_5O_6$; black solid; mp=333.3-334.3° C.; IR $\nu_{max}$ (KBr) 3437, 3173, 3085, 2958, 2835, 1719, 1678, 1648, 1585 cm$^{-1}$; $^1$H NMR (400 MHz, DMSO-d$_6$) δ 13.25 (1H, br, s), 9.05 (1H, s), 8.48 (1H, s), 8.22 (1H, s), 8.21 (1H, d, J=1.4 Hz), 8.14 (1H, dt, J=7.8, 1.4 Hz), 7.91 (2H, dd, J=8.8, 2.0 Hz), 7.77 (1H, d, J=7.8 Hz), 7.73 (1H, s), 6.95 (1H, d, J=8.8 Hz), 3.89 (3H, s), 3.80 (3H, s); $^{13}$C NMR (100 MHz, DMSO-d$_6$) δ 173.3, 165.5, 165.1, 156.6, 155.1, 149.9, 146.2, 135.1, 134.2, 133.6, 133.6, 130.5, 129.6, 129.5, 129.2, 120.9, 120.0, 114.8, 111.6, 55.6, 52.4.

2-(4-Ethoxyphenyl)-9-(4-nitrophenyl)-8-oxopurine-6-carboxamide (5k)

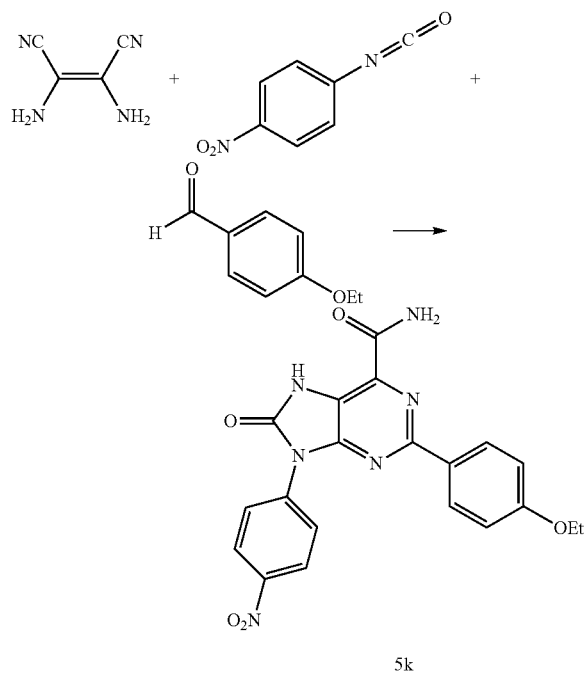

5k

Under an atmosphere of argon, a solution of diaminomaleonitrile (270 mg, 2.5 mmol) and 4-nitrophenyl isocyanate (440 mg, 2.7 mmol) in anhydrous THF (18 mL) was stirred at room temperature for 24 h. The mixture was concentrated under reduced pressure, and washed successively with cold EtOH and Et$_2$O to give a urea compound (294 mg, 43% yield). A mixture of the above-prepared urea compound (294 mg, 1.1 mmol), 4-ethoxybenzaldehyde (0.30 mL, 2.2 mmol), and triethylamine (0.40 mL, 2.8 mmol) in MeOH (25 mL) was stirred at room temperature for 25 h. The solids were collected by filtration, and washed successively with cold EtOH and Et$_2$O to give compound 5k (242 mg, 54% yield). $C_{20}H_{16}N_6O_5$; brown solid; mp=307.6-309.0 OC; $^1$H NMR (400 MHz, DMSO-d$_6$) δ 11.87 (1H, br s), 8.52-8.48 (3H, m), 8.43 (2H, d, J=7.6 Hz), 8.17-8.15 (2H, m), 7.98 (1H, br s), 7.00 (2H, d, J=7.2 Hz), 4.09 (2H, q, J=7.2 Hz), 1.35 (3H, t, J=6.8 Hz); $^{13}$C NMR (125 MHz, DMSO-d$_6$) δ 165.7, 160.5, 154.9, 152.4, 145.8, 138.8, 133.6, 129.5 (2×), 129.1, 126.4 (3×), 124.4 (3×), 114.3 (2×), 63.3, 14.7; ESI-HRMS (negative mode) calcd for $C_{20}H_{15}N_6O_5$: 419.1104, found: m/z 419.1114 [M–H]$^-$.

2-(4-Ethoxyphenyl)-9-(3-nitrophenyl)-8-oxopurine-6-carboxamide (5l)

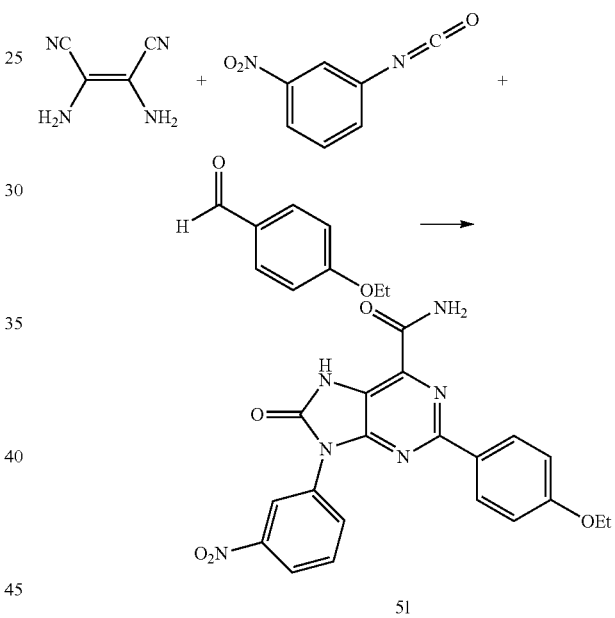

5l

Under an atmosphere of argon, a solution of diaminomaleonitrile (270 mg, 2.5 mmol) and 4-nitrophenyl isocyanate (440 mg, 2.7 mmol) in anhydrous THF (15 mL) was stirred at room temperature for 25 h. The mixture was concentrated under reduced pressure, and washed successively with cold EtOH and Et$_2$O to give a urea compound (289 mg, 42% yield). A mixture of the above-prepared urea compound (150 mg, 0.55 mmol), 4-ethoxybenzaldehyde (0.10 mL, 0.72 mmol), and triethylamine (0.40 mL, 2.8 mmol) in MeOH (10 mL) was stirred at room temperature for 25 h. The solids were collected by filtration, and washed successively with cold EtOH and Et$_2$O to give compound 5l (135 mg, 87% yield). $C_{20}H_{16}N_6O_5$; yellow solid; mp=322.8-324.3° C.; $^1$H NMR (400 MHz, DMSO-d$_6$) δ 11.85 (1H, br s), 8.77 (1H, s), 8.52 (1H, s), 8.41 (2H, d, J=4.0 Hz), 8.20 (2H, d, J=4.4 Hz), 7.98 (1H, br s), 7.92 (1H, t, J=8.0 Hz), 6.99 (2H, d, J=4.0 Hz), 4.09 (2H, q, J=6.4 Hz), 1.35 (3H, t, J=6.0 Hz); $^{13}$C NMR (100 MHz, DMSO-d$_6$) δ 165.3, 160.2, 154.7, 152.3, 152.2, 147.8, 133.9, 133.3, 131.6, 130.1 (2×), 129.1

(2×), 129.0, 121.9, 120.2, 114.1 (2×), 63.1, 14.4; ESI-HRMS (negative mode) calcd for $C_{20}H_{15}N_6O_5$: 419.1104, found: m/z 419.1123 [M−H]⁻.

9-(3,5-Bis(trifluoromethyl)phenyl)-2-(4-ethoxyphenyl)-8-oxopurine-6-carboxamide (5m)

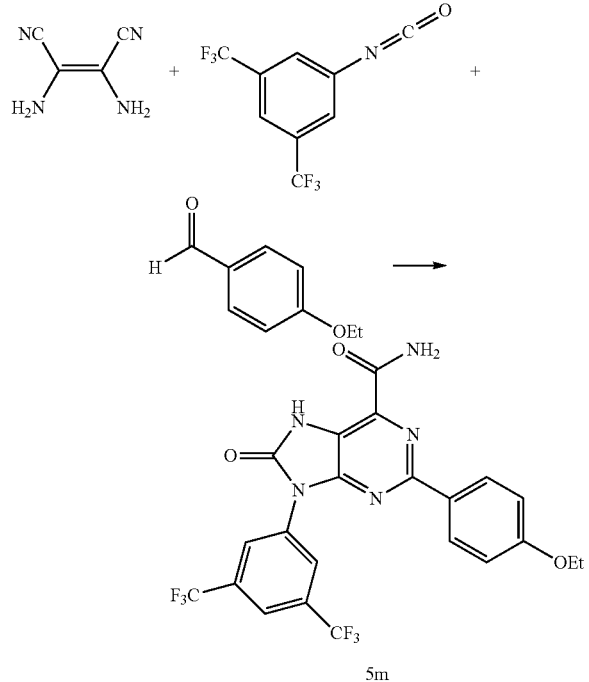

5m

A solution of diaminomaleonitrile (434 mg, 4.01 mmol) and 3,5-bis(trifluoromethyl)phenyl isocyanate (0.77 mL, 4.2 mmol) in anhydrous THF (20 mL) was stirred at room temperature for 40 h. The crude product was then concentrated under reduced pressure, and washed with EtOH to give a urea compound (643 mg, 44% yield). A mixture of the above-prepared urea compound (363 mg, 0.55 mmol), 4-ethoxybenzaldehyde (0.15 mL, 1.1 mmol), and triethylamine (0.09 mL, 0.6 mmol) in MeOH (5.2 mL) was stirred at room temperature for 16 h. The mixture was concentrated under reduced pressure. The residual solids were filtered, and washed with MeOH to give compound 5m (163 mg, 58% yield). $C_{22}H_{15}F_6N_5O_3$; white solid; mp 288-290 OC; TLC (EtOAc/hexane=1:2) $R_f$=0.2; IR $v_{max}$ (neat) 3441, 2989, 2924, 1737, 1677, 1593, 1483, 1445, 1388, 1285, 1186, 1125, 1049, 893, 844, 703, 688 cm⁻¹; ¹H NMR (400 MHz, DMSO-d₆) δ 11.95 (1H, br), 8.63 (2H, s), 8.54 (1H, s), 8.40 (2H, d, J=8.8 Hz), 8.25 (1H, s), 8.00 (1H, s), 7.00 (2H, d, J=8.8 Hz), 4.10 (2H, q, J=7.2 Hz), 1.35 (3H, t, J=7.2 Hz); ¹³C NMR (100 MHz, DMSO-d₆) δ 165.6 (2×), 160.5, 154.7, 152.6, 152.4, 135.0, 133.6, 133.8 (q, $^1J_{C-F}$=27.0 Hz) (2×), 129.1 (3×), 126.4, 126.2, 124.2, 122.1, 120.8, 114.4 (2×), 63.3, 14.7; ESI-HRMS calcd for $C_{22}H_{14}F_6N_5O_3$: 510.1001, found: m/z 510.0983 [M−H]⁻. Anal. Calcd for ($C_{22}H_{15}F_6N_5O_3$—$H_2O$): C, 49.91; H, 3.24; N, 13.23. Found: C, 49.86; H, 3.12; N, 13.16.

2-(3-Hydroxy-4-methoxyphenyl)-9-(2-methoxyphenyl)-8-oxopurine-6-carboxamide (5n)

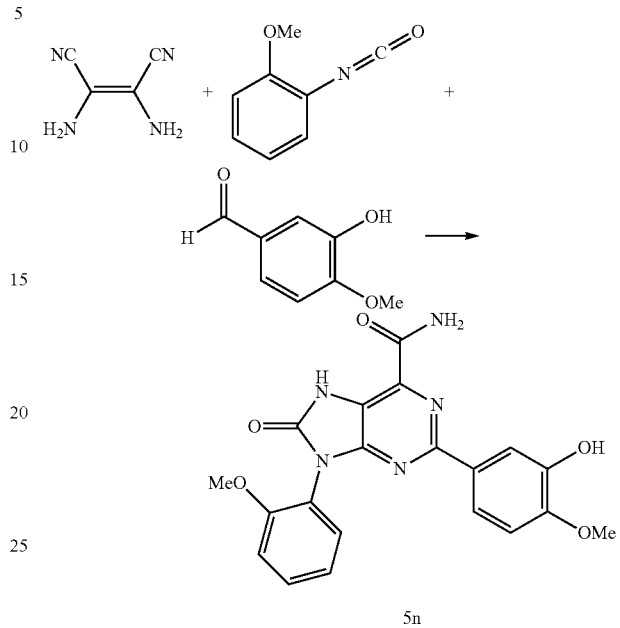

5n

To a solution of diaminomaleonitrile (400 mg, 3.7 mmol) in anhydrous THF (20 mL) was added 2-methoxyphenyl isocyanate (0.52 mL, 3.9 mmol) at 0° C. The mixture was stirred at room temperature for 42 h. The mixture was concentrated under reduced pressure, and washed with Et₂O to give a urea compound. A mixture of the above-prepared urea compound, 3-hydroxy-4-methoxybenzaldehyde (619 mg, 4.1 mmol) and triethylamine (0.57 mL, 4.1 mmol) in MeOH (20 mL) was stirred at room temperature for 24 h. The mixture was concentrated under reduced pressure, and the residual solids were washed successively with Et₂O, EtOH, MeOH, CH₂Cl₂, and CH₃CN to give compound 5n (818 mg, 54% yield). $C_{20}H_{17}N_5O_5$; pale yellow solid; mp 319-321° C.; IR $v_{max}$ (neat) 3434, 3240, 2840, 1737, 1696, 1597, 1513, 1471, 1445, 1391, 1262, 1171, 1129, 1030, 954, 878, 760, 707 cm⁻¹; ¹H NMR (400 MHz, DMSO-d₆) δ 8.37 (1H, br), 7.96 (1H, br), 7.87 (1H, dd, J=8.4, 2.0 Hz), 7.70 (1H, d, J=2.0 Hz), 7.55 (1H, t, J=7.6 Hz), 7.48 (1H, d, J=7.6 Hz), 7.29 (1H, d, J=8.4 Hz), 7.15 (1H, t, J=7.6 Hz), 6.94 (1H, d, J=8.4 Hz), 3.80 (3H, s), 3.75 (3H, s); ¹³C NMR (100 MHz, DMSO-d₆) δ 165.7, 155.4, 155.1, 153.3, 152.9, 149.6, 146.2, 132.8, 130.8, 130.2, 129.7, 120.8, 120.7, 119.5, 119.3, 114.6, 112.8, 111.6, 55.9, 55.6; ESI-HRMS calcd for $C_{20}H_{18}N_5O_5$: 408.1308, found: m/z 408.1324 [M+H]⁺. Anal. Cacld for ($C_{20}H_{17}N_5O_5 \cdot H_2O$): C, 56.47; H, 4.50; N, 16.46. Found: C, 56.76; H, 4.38; N, 16.84.

2-Isopropyl-9-(2-methoxyphenyl)-8-oxopurine-6-carboxamide (5o)

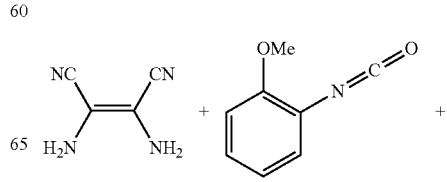

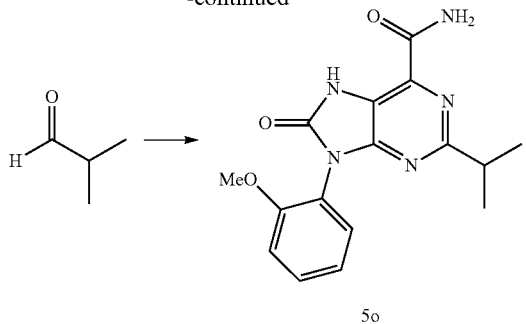

A mixture of diaminomaleonitrile (868 mg, 8 mmol) and 2-methoxyphenyl isocyanate (1.12 mL, 8.4 mmol) in anhydrous THF (50 mL) was stirred at room temperature for 24 h under an atmosphere of argon. The mixture was concentrated under reduced pressure. The residual solids were filtered, and rinsed with cold ethanol and diethyl ether to yield a urea compound (1.24 g, 60% yield).

To a suspension of the above-prepared urea compound (984 mg, 3.83 mmol) and isobutyraldehyde (0.70 mL, 7.65 mmol) in methanol (25 mL), triethylamine (0.50 mL, 3.83 mmol) was added. The mixture was stirred at room temperature for 4 days. After the urea compound totally consumed, solvent was removed under reduced pressure and the residue was purified by column chromatography (50% to 75% EtOAc/Hexane) to yield the purine-type compound 5o (110 mg, 9% yield). $C_{16}H_{17}N_5O_3$; yellow oil; $^1$H NMR (500 MHz, DMSO-$d_6$) δ 11.55 (1H, s), 8.06 (1H, s), 7.92 (1H, s), 7.51 (1H, ddd, J=8.3, 7.6, 1.7 Hz), 7.42 (1H, dd, J=7.7, 1.7 Hz), 7.25 (1H, dd, J=8.4, 1.0 Hz), 7.11 (1H, td, J=7.6, 1.2 Hz), 3.72 (3H, s), 3.03-2.92 (1H, m), 1.20 (6H, dd, J=6.9, 4.8 Hz); $^{13}$C NMR (126 MHz, DMSO-$d_6$) δ 165.6, 165.4, 155.3, 153.1, 152.8, 132.3, 130.7, 130.2, 120.8, 120.7, 120.5, 112.7, 55.8, 36.3, 21.8, 21.7. ESI-HRMS (posititve mode) calculated for $C_{16}H_{17}N_5O_3$: 328.1404, found: m/z 328.1414 [M+H]$^+$.

2-(4-Ethoxyphenyl)-9-hexyl-8-oxopurine-6-carboxamide (5p)

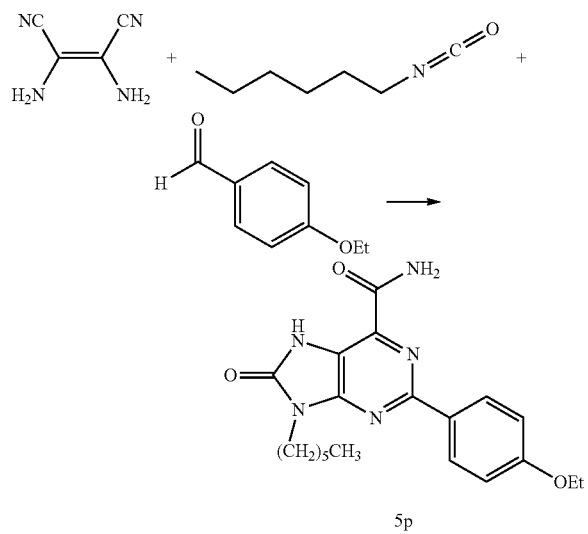

A mixture of diaminomaleonitrile (1 g, 9.25 mmol) and hexyl isocyanate (1.22 mL, 8.35 mmol) in anhydrous THF (25 mL) was stirred at room temperature for 17 h. The mixture was concentrated under reduced pressure. The residual solids were filtered, and rinsed with Et$_2$O and EtOAc to give a urea compound (1.77 g, 90% yield). $C_{11}H_{17}N_5O$; white solid; TLC (EtOAc/hexane=1:1) $R_f$=0.7; $^1$H NMR (400 MHz, DMSO-$d_6$) δ 7.36 (1H, s), 6.94 (2H, s), 6.38 (1H, s), 2.98-3.01 (2H, m), 1.39 (2H, s), 1.25 (6H, s), 0.85-0.87 (3H, m); $^{13}$C NMR (100 MHz, DMSO-$d_6$) δ 154.6, 125.3, 117.2, 114.4, 91.8, 40.2, 31.0, 29.6, 26.0, 22.1, 13.9; ESI-HRMS calcd for $C_{11}H_{16}N_5O$: 234.1355, found: m/z 234.1346 [M–H]$^-$.

A mixture of the above-prepared urea compound (1.7 g, 7.23 mmol), 4-ethoxybenzaldehyde (2.0 mL, 14.5 mmol), and triethylamine (1.06 mL, 7.57 mmol) in MeOH (25 mL) was stirred at room temperature for 25 h. The mixture was concentrated under reduced pressure, and rinsed with Et$_2$O and MeOH. The residual solids were further purified by flash chromatography on a silica gel column with elution of MeOH/CH$_2$Cl$_2$ (1:20 to 1:9) to give compound 5p (1.02 g, 37% yield). $C_{20}H_{25}N_5O_3$; yellow solid; TLC (EtOAc/hexane=1:1) $R_f$=0.5; $^1$H NMR (400 MHz, DMSO-$d_6$) δ 11.45 (1H, br), 8.48 (2H, d, J=8.8 Hz), 8.43 (1H, s), 7.90 (1H, s), 7.011 (2H, d, J=8.8 Hz), 4.10 (2H, q, J=7.2 Hz), 3.89 (2H, t, J=6.8 Hz), 1.76 (2H, t, J=6.8 Hz), 1.36 (3H, t, J=7.2 Hz), 1.24-1.30 (6H, m), 0.83 (3H, t, J=6.8 Hz); $^{13}$C NMR (100 MHz, DMSO-$d_6$) δ 165.7, 160.3, 154.6, 153.8, 153.1, 132.3, 129.4, 129.3 (2×), 119.0, 114.2 (2×), 63.2, 40.1, 30.7, 27.4, 25.7, 22.0, 14.6, 13.9; ESI-HRMS calcd for $C_{20}H_{24}N_5O_3$: 382.1879, found: m/z 382.1890 [M–H]$^-$.

2-(4-Ethoxyphenyl)-9-(3-carboxy)phenyl-8-oxopurine-6-carboxamide (6e)

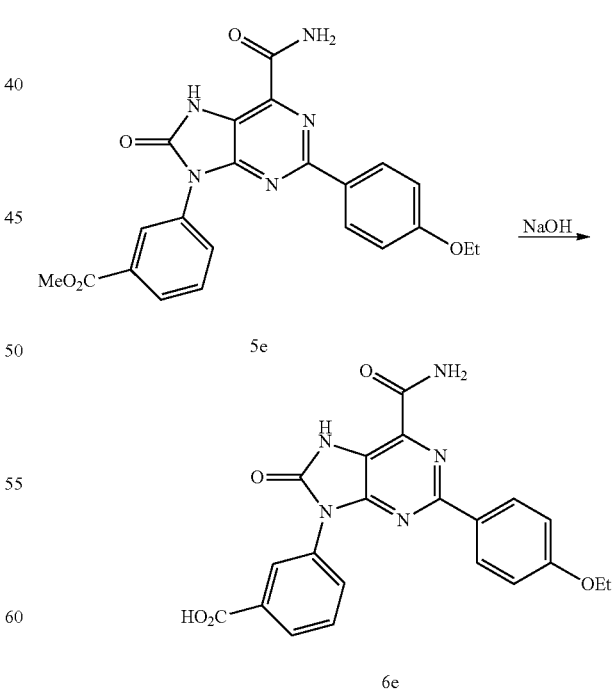

To a suspension of ester 5e (100 mg, 0.23 mmol) in pyridine (10 mL), we added 1 M NaOH$_{(aq.)}$ (1 mL). The mixture was stirred at room temperature for 17 h, in which the solids dissolved. The mixture was stirred for another 5 h until solid precipitates formed. The mixture was concentrated under reduced pressure. The residue was dissolved in methanol and acidified to pH 1.0 by adding 1 M HCl$_{(aq)}$. The suspension was subjected to centrifuge at 8000 rpm for 15 min at 4° C., and the acid compound 6e was collected as orange solids (74.8 mg, 78%). $C_{21}H_{17}N_5O_5$; orange solid; mp=343.7-345.6° C.; IR $v_{max}$ (KBr) 3446, 2987, 2913, 2509, 1750, 1704, 1600 cm$^{-1}$; $^1$H NMR (400 MHz, DMSO-d$_6$) δ 11.72 (1H, s), 8.47 (1H, s), 8.41-8.34 (3H, m), 8.02 (2H, dd, J=8.0, 2.0 Hz), 7.93 (1H, s), 7.73 (1H, dd, J=8.0, 7.6 Hz), 6.98-6.95 (2H, m), 4.07 (2H, q, J=6.8 Hz), 1.33 (3H, t, J=6.8 Hz); $^{13}$C NMR (100 MHz, DMSO-d$_6$) δ 166.7, 165.6, 160.3, 154.7, 152.7, 152.6, 133.1, 133.1, 131.6, 130.2, 129.3 (4×), 128.4, 126.9, 119.3, 114.2 (2×), 63.2, 14.6; ESI-HRMS (negative mode) calculated for $C_{21}H_{16}N_5O_5$: 418.1151, found: m/z 418.1159 [M−H]$^-$. Anal. Cacld for ($C_{21}H_{15}N_5Na_2O_5\cdot CH_3OH$): C, 53.34; H, 3.87; N, 14.14. Found: C, 53.39; H, 4.01; N, 14.21.

2-(4-Ethoxyphenyl)-9-(3-hexylcarbamoyl)phenyl-8-oxopurine-6-carboxamide (8a)

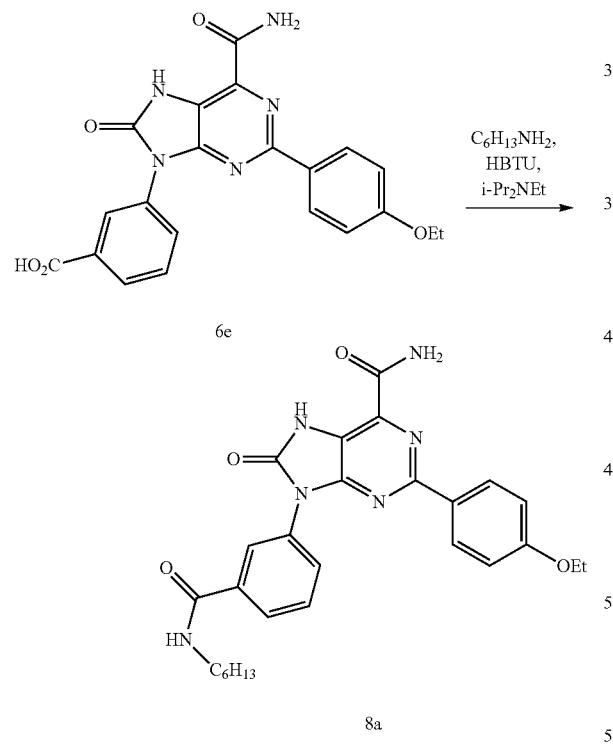

To a solution of acid 6e (42 mg, 0.06 mmol) in anhydrous DMF (5 mL) were added N,N,N,N-tetramethyl-O-(1H-benzotriazol-1-yl)uronium hexafluorophosphate (HBTU, 28 mg, 0.073 mmol), N,N-diisopropylethylamine (DIEA, 18 μL, 0.073 mmol) and hexylamine (110 μL, 0.073 mmol). The mixture was stirred at room temperature under argon for 20 h, and then concentrated under reduced pressure. The residue was diluted with CH$_2$Cl$_2$, and washed successively with 1 M HCl$_{(aq)}$, saturated NaHCO$_3$ $_{(aq)}$ and brine. The organic phase was dried over MgSO$_4$, filtered, and purified by silica gel chromatography (CH$_2$Cl$_2$/MeOH=19:1) to afford the desired amide product 8a (13 mg, 46% yield). $C_{27}H_3ON_6O_4$; yellow solid; mp=306.8-307.4° C.; TLC (CH$_2$Cl$_2$/MeOH=9:1) R$_f$=0.50; IR $v_{max}$ (KBr) 3436, 3301, 3113, 2966, 2925, 2844, 1746, 1704, 1640, 1594 cm$^{-1}$; $^1$H NMR (400 MHz, DMSO-d$_6$) δ 11.73 (1H, br, s), 8.55 (1H, t, J=5.6 Hz), 8.51 (1H, br, s), 8.35 (2H, d, J=8.8 Hz), 8.21 (1H, s), 7.95-7.84 (3H, m), 7.67 (1H, t, J=8.0 Hz), 6.96 (2H, d, J=8.8 Hz), 4.07 (2H, q, J=6.8 Hz), 1.58-1.48 (2H, m), 1.38-1.20 (11H, m), 0.88-0.82 (3H); $^{13}$C NMR (100 MHz, DMSO-d$_6$) δ 165.9, 165.6, 160.5, 155.0, 152.9, 135.7, 133.3, 133.0, 129.4 (2×), 129.2, 129.0, 126.5, 125.4, 114.4 (2×), 63.4, 31.2, 29.2, 26.3, 22.2, 14.7, 14.1; ESI-HRMS (negative mode) calculated for $C_{27}H_{31}N_6O_4$: 501.2250, found: m/z 501.2251 [M−H]$^-$.

2-(4-Ethoxyphenyl)-9-(3-dodecylcarbamoyl)phenyl-8-oxopurine-6-carboxamide (8b)

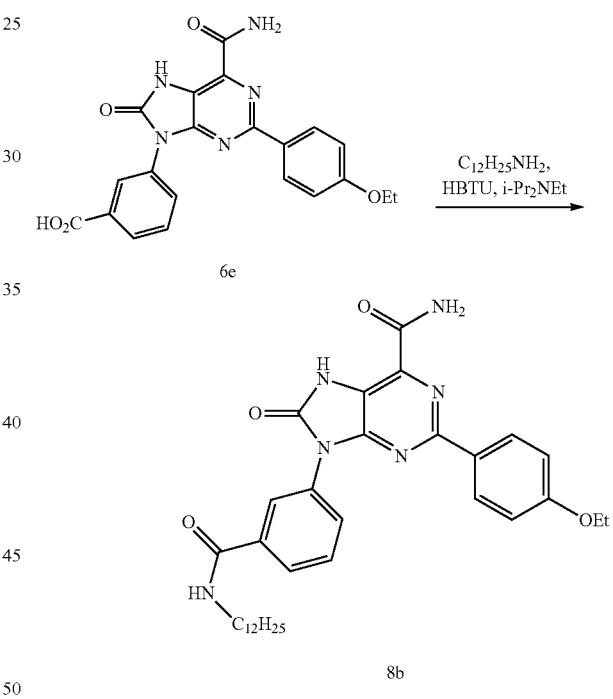

By a procedure similar to that for 8a, the condensation reaction of 6e (40 mg, 0.10 mmol) with dodecylamine (22 mg, 0.11 mmol) in the presence of HBTU (44 mg, 0.11 mmol) and DIEA (20 μL, 0.11 mmol) at room temperature for 17 h afforded the desired amide product 8b (16 mg, 37% yield). $C_{33}H_{42}N_6O_4$; yellow oil; TLC (CH$_2$Cl$_2$/MeOH=9:1) R$_f$=0.33; IR $v_{max}$ (KBr) 3461, 3269, 2958, 2921, 2844, 1744, 1697, 1598 cm$^{-1}$; $^{13}$C NMR (100 MHz, DMSO-d$_6$) δ 165.6, 165.2, 160.9, 160.3, 154.8, 152.8, 152.7, 135.6, 133.1, 132.8, 129.2 (2×), 128.9, 128.7, 126.3, 125.2, 114.1 (2×), 63.1, 44.4, 31.3, 29.2, 29.0, 28.9, 28.8, 28.7, 28.6, 26.4, 26.0, 22.0, 14.6, 13.9; ESI-HRMS (negative mode) calculated for $C_{33}H_{41}N_6O_4$: 585.3189, found: m/z 585.3184 [M−H]$^-$.

2-(4-Ethoxyphenyl)-9-[3-(5-azidopentylcarbamoyl)]phenyl-8-oxopurine-6-carboxamide (8c)

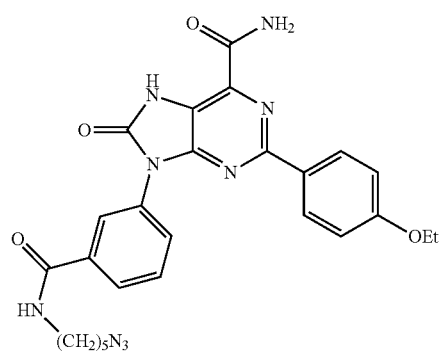

8c

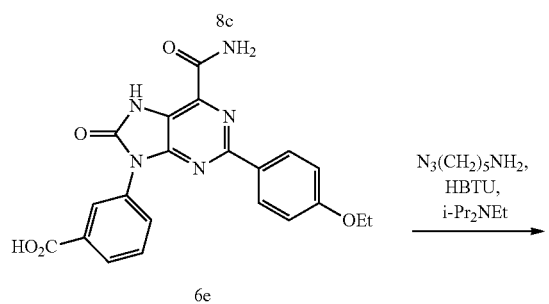

6e

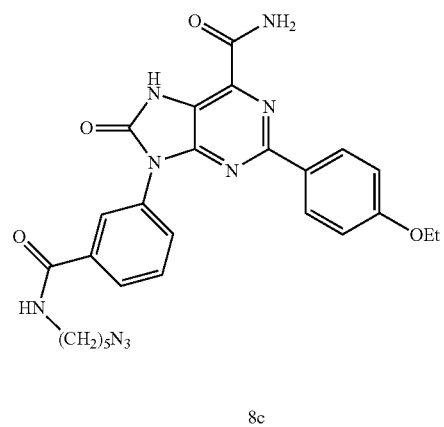

8c

By a procedure similar to that for 8a, the condensation reaction of 6e (25 mg, 0.06 mmol) with 5-azidopentylamine (10 mg, 0.072 mmol) in the presence of HBTU (27 mg, 0.072 mmol) and DIEA (13 µL, 0.072 mmol) at room temperature for 18 h afforded the desired amide product 8c (17 mg, 54% yield). $C_{26}H_{27}N_9O_4$; yellow solid; mp=265.6-267.4° C.; TLC ($CH_2Cl_2$/MeOH=19:1) $R_f$=0.38; IR $\nu_{max}$ (KBr) 3436, 3298, 2933, 2864, 2096, 1746, 1701, 1654, 1578 cm$^{-1}$; $^1$H NMR (400 MHz, DMSO-$d_6$) δ 11.73 (1H, s), 8.58 (1H, t, J=5.6 Hz), 8.48 (1H, s), 8.36 (2H, d, J=8.8 Hz), 8.21 (1H, s), 7.93 (2H, d, J=7.6 Hz), 7.87 (1H, d, J=8.8 Hz), 7.68 (1H, t, J=8.0 Hz), 6.96 (2H, d, J=9.2 Hz), 4.07 (2H, q, J=6.8 Hz), 1.60-1.50 (4H, m), 1.42-1.29 (9H, m); $^{13}$C NMR (100 MHz, DMSO-$d_6$) δ 165.6, 165.2, 160.3, 154.8, 152.7, 135.5, 133.0, 132.8, 129.2 (2×), 128.9, 128.8, 126.3, 125.3, 114.1 (2×), 63.1, 50.6, 28.5, 27.9, 23.6, 14.6; ESI-HRMS (negative mode) calculated for $C_{26}H_{26}N_9O_4$: 528.2108, found: m/z 528.2131 [M–H]$^-$.

2-(4-Ethoxyphenyl)-9-[3-(5-tert-butoxycarbonylamino)pentylcarbamoyl]phenyl-8-oxopurine-6-carboxamide (8d)

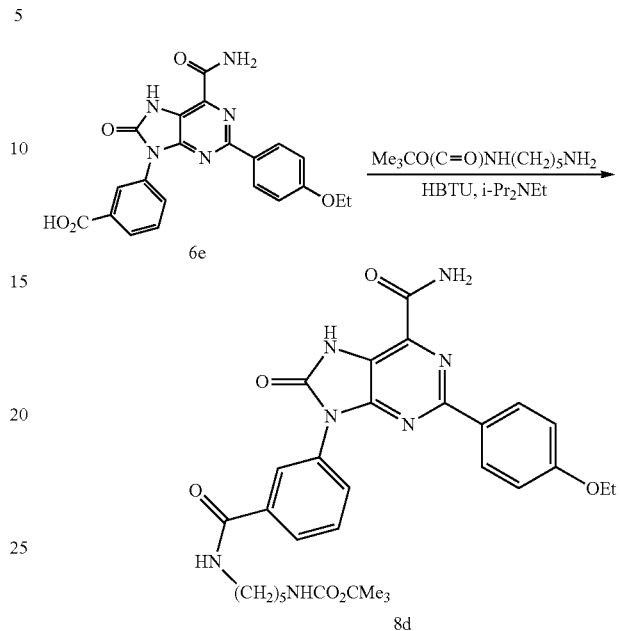

By a procedure similar to that for 8a, the condensation reaction of 1o (72 mg, 0.17 mmol) with 5-(tert-butoxycarbonylamino)pentyl amine (70 mg, 0.34 mmol) in the presence of HBTU (78 mg, 0.21 mmol) and DIEA (36 µL, 0.21 mmol) at room temperature for 18 h afforded the desired amide product 8d (63 mg, 62%). $C_{31}H_{37}N_7O_6$; yellow solid; mp=182.2-183.1° C.; TLC ($CH_2Cl_2$/MeOH=19:1) $R_f$=0.13; IR $\nu_{max}$ (KBr) 3356, 2976, 2932, 2865, 1684, 1651, 1597 cm$^{-1}$; $^1$H NMR (400 MHz, DMSO-$d_6$) δ 11.70 (1H, s, $N_7$—H), 8.52 (1H, t, J=5.2 Hz, NHBoc), 8.45 (1H, s, amide), 8.32 (2H, d, J=8.8 Hz), 8.16 (1H, s, amide), 7.88-7.84 (2H, m), 7.83 (1H, d, J=8.8 Hz), 7.64 (1H, dd, J=8.0, 7.6 Hz, H-5'), 6.94 (2H, br d, J=8.8 Hz), 6.71 (1H, t, J=5.2 Hz, amide), 4.03 (2H, q, J=6.8 Hz), 3.22 (2H, t, J=6.0 Hz), 2.84 (2H, t, J=6.8 Hz), 1.54-1.44 (2H, m), 1.40-1.21 (16H, m); $^{13}$C NMR (100 MHz, DMSO-$d_6$) δ 165.6, 165.2, 160.3, 155.6, 154.8, 152.7, 152.7, 135.6, 133.1, 132.8, 129.2 (2×), 128.9, 126.3, 125.3, 119.2, 114.1 (2×), 77.3, 63.2, 29.2, 29.0, 28.8, 28.2 (3×), 23.7, 14.7; ESI-HRMS (negative mode) calculated for $C_{31}H_{36}N_7O_6$: 602.2727, found: m/z 602.2714 [M–H]$^-$. Anal. Calcd for ($C_{31}H_{37}N_7O_6 \cdot 2\ H_2O$): C, 58.20; H, 6.46; N, 15.33. Found: C, 58.51; H, 6.05; N, 15.22.

2-(4-Ethoxyphenyl)-9-[3-(10-tert-butoxycarbonylamino)decylcarbamoyl]phenyl-8-oxopurine-6-carboxamide (8e)

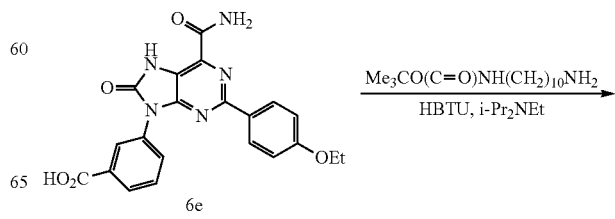

-continued

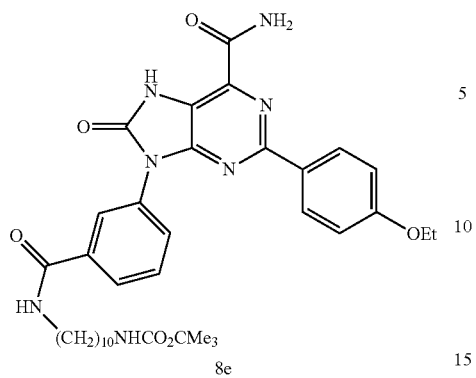

8e

By a procedure similar to that for 8a, the condensation reaction of 6e (72 mg, 0.17 mmol) with 10-(tert-butoxycarbonylamino)decylamine (27 mg, 0.10 mmol) in the presence of HBTU (37 mg, 0.10 mmol) and DIEA (17 μL, 0.10 mmol) at room temperature for 18 h afforded the desired amide product 8e (26 mg, 56% yield). $C_{36}H_{47}N_7O_6$; yellow solid; mp=257.3-258.4° C.; TLC ($CH_2Cl_2$/MeOH=9:1) $R_f$=0.38; IR $\nu_{max}$ (KBr) 3440, 3350, 3289, 2987, 2934, 2860, 1735, 1686, 1663, 1637 cm$^{-1}$; $^1$H NMR (400 MHz, DMSO-d$_6$) δ 11.72 (1H, br, s), 8.55 (1H, t, J=5.2 Hz), 8.47 (1H, s), 8.36 (2H, d, J=8.4 Hz), 8.21 (1H, s), 7.93 (2H, d, J=8.4 Hz), 7.87 (1H, d, J=8.0 Hz), 7.68 (1H, t, J=8.0 Hz), 6.95 (2H, t, J=8.8 Hz), 6.70 (1H, br, s), 4.06 (2H, q, J=6.4 Hz), 2.86 (4H, d, J=6.8 Hz), 1.52 (3H, t, J=6.4 Hz), 1.39-1.17 (24H, m); $^{13}$C NMR (125 MHz, DMSO-d$_6$) δ 165.6, 165.2, 160.3, 155.6, 154.8, 152.8, 152.7, 135.6, 133.1, 132.8, 129.2 (2×), 128.9, 128.7, 126.3, 125.2, 119.2, 114.1 (2×), 77.2, 63.1, 29.4, 29.2, 29.0, 29.0, 28.9, 28.8, 28.7, 28.5, 28.2 (3×), 26.5, 26.2, 26.0, 14.6; ESI-HRMS calculated for $C_{36}H_{46}N_7O_6$: 674.3666, found: m/z 674.3667 [M+H]+.

Biotin-Annexed Compound (8f)

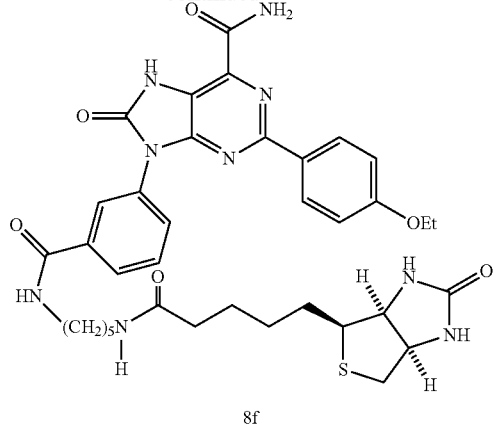

8f

A solution of 8d (63 mg, 0.11 mmol) and TFA (2 mL) in $CH_2Cl_2$ (2 mL) was stirred at room temperature for 1 h, and then, it was concentrated under reduced pressure to afford the corresponding amine. To a solution of the above-prepared amine compound in anhydrous DMF (5 mL), HBTU (43 mg, 0.11 mmol), DIEA (27 μL, 0.11 mmol) and a solution of D-(+)-biotin (28 mg, 0.11 mmol) in anhydrous DMF (3 mL) were added. The mixture was stirred at room temperature for 24 h under an atmosphere of argon, and then, it was concentrated under reduced pressure. Methanol (10 mL) was added, and the mixture was centrifuged at 8000 rpm for 15 min at 4° C. The biotin-annexed compound 8f was collected as yellow solids (48 mg, 73% yield). $C_{36}H_{43}N_9O_6S$; mp=223.4-224.1 OC (decomposed); $[α]^{25}_D$=+272 (DMSO, c=1); IR $\nu_{max}$ (KBr) 3297, 2930, 2860, 1736, 1697, 1598 cm$^{-1}$; $^1$H NMR (400 MHz, DMSO-d$_6$) δ 11.74 (1H, s), 8.56 (1H, t, J=5.6 Hz), 8.50 (1H, s), 8.35 (2H, d, J=8.8 Hz), 8.21 (1H, s), 7.94 (1H, s, H-2'), 7.92 (1H, d, J=8.0 Hz), 7.87 (1H, d, J=8.8 Hz), 7.76-7.65 (2H, m), 6.96 (2H, d, J=8.8 Hz), 6.40 (1H, s, biotin-NH), 6.33 (1H, s, biotin-NH), 4.32-4.25 (1H, m), 4.13-4.03 (3H, m), 3.30-3.23 (2H, m), 3.10-2.98 (3H, m), 2.82-2.76 (1H, m), 2.56 (1H, d, J=12.4 Hz), 2.02 (2H, t, J=7.6 Hz), 1.64-1.37 (8H, m), 1.37-1.20 (7H, m); $^{13}$C NMR (100 MHz, DMSO-d$_6$) δ 171.8, 165.6, 165.3, 162.7, 160.3, 154.7, 152.7, 135.5, 133.1, 132.9, 129.2 (2×), 129.0, 128.8, 126.3, 125.3, 114.1 (2×), 63.2, 61.0, 59.2, 55.4, 39.8, 38.3, 35.2, 28.9, 28.8, 28.2, 28.0, 25.3, 23.9, 14.6; ESI-HRMS (negative mode) calculated for $C_{36}H_{44}N_9O_6S$: 730.3135, found: m/z 730.3154 [M+H]$^+$. Anal. Cacld for ($C_{36}H_{43}N_9O_6S·2½H_2O$): C, 55.80; H, 6.24; N, 16.27; S, 4.14. Found: C, 56.03; H, 6.07; N, 15.78; S, 4.56.

Biotin-Annexed Compound (8g)

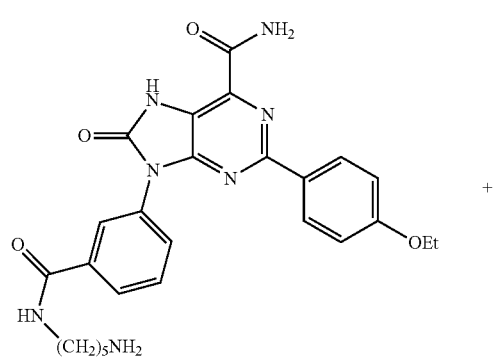

+

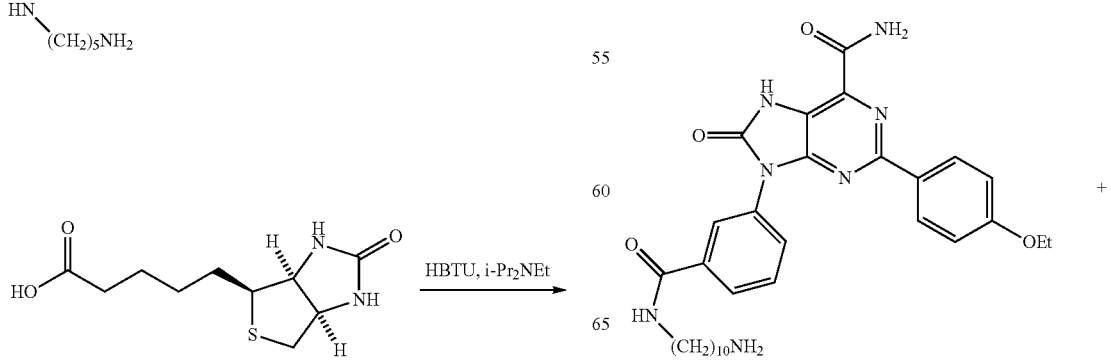

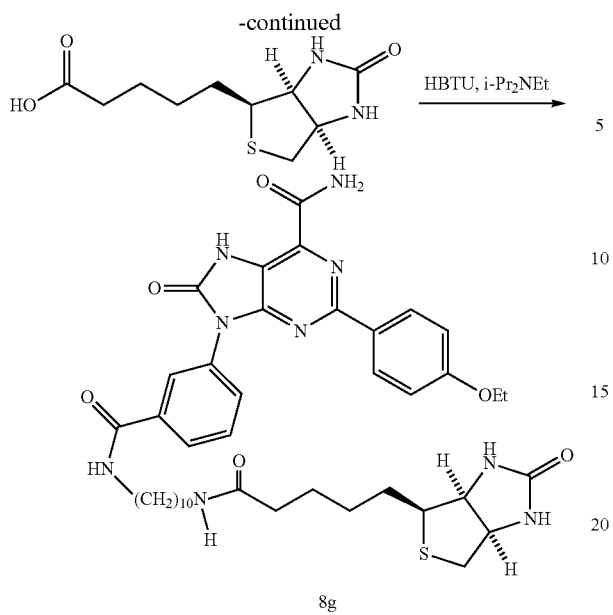

8g

A solution of compound 8e (48 mg, 0.08 mmol) and TFA (2 mL) in CH$_2$Cl$_2$ (2 mL) was stirred at room temperature for 1 h, and then concentrated under reduced pressure to afford the corresponding amine compound. To a solution of the above-prepared amine compound in anhydrous DMF (5 mL) were added HBTU (37 mg, 0.098 mmol), DIEA (60 μL, 0.24 mmol) and a solution of D-(+)-biotin (28 mg, 0.11 mmol) in anhydrous DMF (3 mL). The mixture was stirred at room temperature under argon for 24 h, and then concentrated under reduced pressure. Methanol (10 mL) was added, and the mixture was centrifuged at 8000 rpm for 15 min at 4° C. The biotin-annexed compound 8g was collected as yellow solids (25 mg, 45% yield). C$_{41}$H$_{53}$N$_9$O$_6$S; mp=243.4-235.8 OC (decompose); [α]$^{25}$$_D$=+0.29 (DMSO, c=1); IR ν$_{max}$ (KBr) 3448, 3293, 2925, 2853, 1696, 1641, 1560 cm$^{-1}$; $^1$H NMR (400 MHz, DMSO-d$_6$) δ 9.06 (1H, s), 8.49 (1H, t, J=4.8 Hz), 8.35 (1H, s), 8.21 (2H, d, J=8.8 Hz), 7.97 (1H, d, J=7.6 Hz), 7.75 (1H, d, J=8.0 Hz), 7.71 (1H, d, J=5.2 Hz), 7.58 (2H, t, J=8.0 Hz), 6.92 (2H, d, J=8.4 Hz), 6.40 (1H, s), 6.34 (1H, s), 4.32-4.25 (1H, m), 4.14-4.08 (1H, m), 4.05 (2H, q, J=6.7 Hz), 3.29-3.23 (2H, m), 3.16 (1H, s, br), 3.10-3.03 (1H, m), 3.02-2.94 (2H, m), 2.84 (1H, s, br), 2.79 (1H, dd, J=15.3, 5.2 Hz), 2.56 (1H, d, J=12.4 Hz), 2.02 (2H, t, J=7.2 Hz), 1.64-1.40 (6H, m), 1.38-1.17 (17H, m); $^{13}$C NMR (125 MHz, DMSO-d$_6$) δ 171.7, 166.4, 165.9, 162.7, 161.0, 158.9, 155.3, 149.7, 137.9, 136.1, 135.5, 135.2, 131.7, 130.7, 128.2 (2×), 128.0, 127.1, 124.1, 123.7, 113.8 (2×), 63.0, 61.0, 59.2, 55.4, 40.1, 39.9, 39.8, 39.6, 38.3, 35.2, 29.2, 29.0, 28.8, 28.7, 28.2, 26.5, 26.4, 25.3, 14.7; ESI-HRMS calculated for C$_{41}$H$_{54}$N$_9$O$_6$S: 800.3918, found: m/z 800.3924 [M+H]$^+$.

2-(4-Ethoxyphenyl)-9-phenyl-8-mercaptopurine-6-carboxamide (10a)

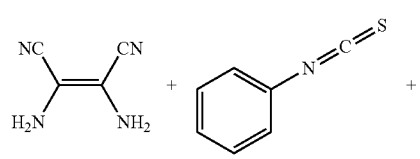

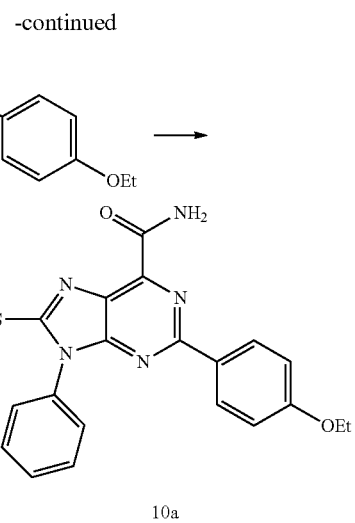

10a

Under an atmosphere of argon, a mixture of diaminomaleonitrile (108 mg, 1.0 mmol) and phenyl isothiocyanate (, 0.125 mL, 1.05 mmol) in anhydrous THF (10 mL) was stirred at room temperature for 22 h, and then concentrated under reduced pressure. Methanol (10 mL) was added to the residual solids, and the mixture was stirred for another 4 h. To the methanolic solution were added 4-ethoxybenzaldehyde (146 μL, 1.05 mmol) and triethylamine (146 μL, 1.05 mmol). The mixture was stirred at room temperature for 24 h, and concentrated under reduced pressure. The residual solids were washed successively with Et$_2$O and MeOH to give compound 10a (174 mg, 22% yield). C$_{20}$H$_{17}$N$_5$O$_2$S; yellow solid; mp=321.2-321.8 OC (decompose); IR ν$_{max}$ (KBr) 3413, 3059, 2977, 2643, 1683, 1659, 1597, 1593, 1580 cm$^{-1}$; $^1$H NMR (400 MHz, DMSO-d$_6$) δ 13.17 (1H, s), 8.56 (1H, br, s), 8.31 (2H, d, J=8.8 Hz), 8.00 (1H, br, s), 7.64-7.52 (5H, m), 6.96 (2H, dt, J=9.2, 2.8 Hz), 4.06 (2H, q, J=7.2 Hz), 1.33 (3H, t, J=6.8 Hz); $^{13}$C NMR (100 MHz, DMSO-d$_6$) δ 173.5, 165.1, 160.5, 156.3, 155.1, 135.0, 133.7, 129.5 (4×), 128.9, 128.8 (2×), 128.6 (2×), 114.2 (2×), 63.2, 14.5; ESI-HRMS calculated for C$_{20}$H$_{18}$N$_5$O$_2$S: 392.1181, found: m/z 392.1180 [M+H]$^+$.

2-(3-Hydroxy-4-methoxyphenyl)-8-mercapto-9-phenylpurine-6-carboxamide (10b)

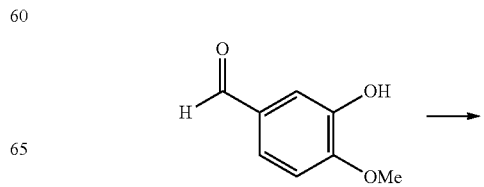

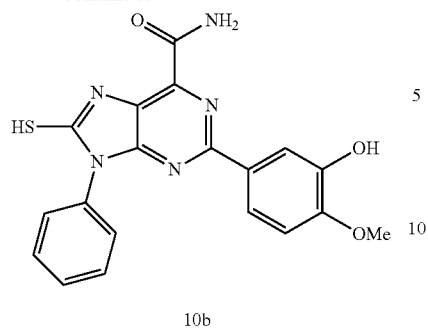

10b

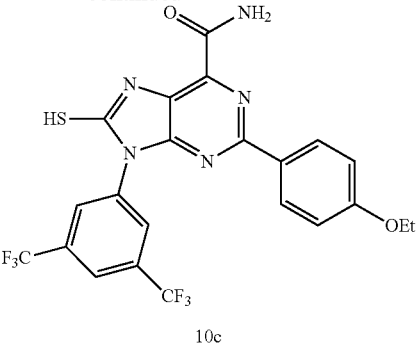

10c

Under an atmosphere of argon, a solution of diaminomaleonitrile (108 mg, 1.0 mmol) and phenyl isothiocyanate (0.13 mL, 1.05 mmol) in anhydrous THF (10 mL) was stirred at room temperature for 16 h. The mixture was concentrated under reduced pressure. Methanol (10 mL) was added to the residual solids, and the mixture was stirred for another 4 h. The solution containing the above-prepared thiourea intermediate 3-hydroxy-4-methoxybenzaldehyde (159 mg, 1.05 mmol) and triethylamine (146 μL, 1.05 mmol) was stirred at room temperature for 24 h, and concentrated under reduced pressure. The residual solids were washed successively with $Et_2O$ and MeOH to give compound 10b (97 mg, 25% yield). $C_{19}H_{15}N_5O_3S$; yellow solid; mp=368.9-369.7 OC (decompose); IR $\nu_{max}$ (KBr) 3416, 3046, 2938, 2835, 1677, 1655, 1583, 1571 cm$^{-1}$; $^1$H NMR (400 MHz, DMSO-d$_6$) δ 13.18 (1H, s), 9.06 (1H, s), 8.46 (1H, s), 8.02 (1H, s), 7.92 (1H, dd, J=8.6, 2.0 Hz), 7.73 (1H, d, J=2.0 Hz), 7.64-7.52 (5H, m), 6.95 (1H, d, J=8.6 Hz), 3.80 (3H, s); $^{13}$C NMR (100 MHz, DMSO-d$_6$) δ 173.4, 165.2, 156.6, 155.1, 149.9, 146.2, 135.0, 133.8, 129.3, 129.0 (2×), 128.7 (2×), 120.9, 119.8, 114.8, 111.6, 55.6. ESI-HRMS (negative mode) calculated for $C_{19}H_{14}N_5O_3S$: 392.0817, found: m/z 392.0816 [M−H]$^-$.

9-(3,5-Bis(trifluoromethyl)phenyl)-2-(4-ethoxyphenyl)-8-mercaptopurine-6-carboxamide (10c)

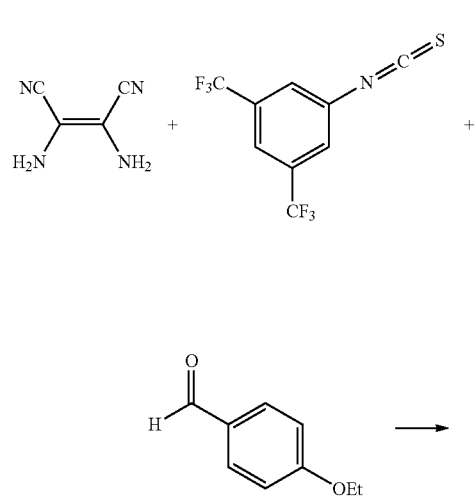

To a solution of diaminomaleonitrile (200 mg, 1.85 mmol) in anhydrous THF (10 mL) was added 3,5-bis(trifluoromethyl)phenyl isothiocyanate (0.35 mL, 1.94 mmol) at 0° C. The mixture was stirred at room temperature for 20 h, concentrated under reduced pressure, and purified by flash chromatography on a silica gel column with elution of EtOAc/hexane (1:4) to give a thiourea compound (151 mg, 22% yield). A mixture of the above-prepared thiourea compound (50 mg, 0.13 mmol), 4-ethoxybenzaldehyde (14 μL, 0.14 mmol) and triethylamine (19 μL, 0.14 mmol) in MeOH (1 mL) was stirred at room temperature for 14 h. The mixture was concentrated under reduced pressure, and the residual solids were washed successively with $Et_2O$ and MeOH to give compound 10c (39 mg, 56% yield). $C_{22}H_{15}F_6N_5O_2S$; pale yellow solid; mp 299-301° C.; $^1$H NMR (400 MHz, DMSO-d$_6$) δ 13.49 (1H, br), 8.63 (1H, br), 8.52 (2H, s), 8.32-8.34 (3H, m), 8.06 (1H, br), 6.98 (2H, d, J=8.4 Hz), 4.08 (2H, q, J=6.8 Hz), 1.34 (3H, t, J=6.8 Hz); ESI-HRMS calcd for $C_{22}H_{14}F_6N_5O_2S$: 526.0772, found: m/z 526.0781 [M−H]$^-$.

2-(4-Hydroxyphenyl)-8-mercapto-9-phenylpurine-6-carboxamide (10d)

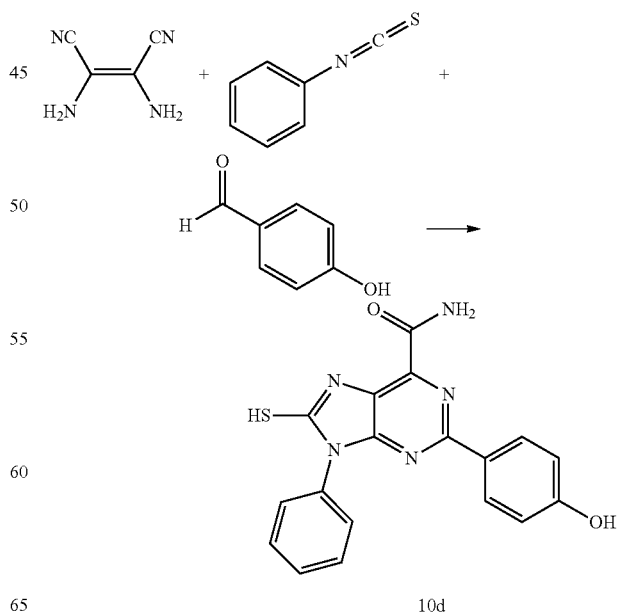

10d

A solution of diaminomaleonitrile (200 mg, 1.85 mmol) and phenyl isothiocyanate (0.23 mL, 1.93 mmol) in anhydrous THF (10 mL) was stirred at room temperature for 21 h. The mixture was concentrated under reduced pressure to give a thiourea intermediate as dark brown solids. A mixture of the above-prepared thiourea intermediate, 4-hydroxybenzaldehyde (0.38 mL, 3.8 mmol) and triethylamine (0.27 mL, 2.0 mmol) in MeOH (10 mL) was stirred at room temperature for 65 h. The mixture was concentrated under reduced pressure, and the residual solids were washed successively with $Et_2O$, $CH_2Cl_2$, MeOH, THF, $CH_3CN$, acetone and EtOH to give compound 10d. $C_{18}H_{13}N_5O_2S$; brown solid; mp 361-363° C.; TLC ($CH_2Cl_2$/MeOH=20:1) $R_f$=0.1; IR $v_{max}$ (neat) 3445, 1684, 1589, 1501, 1448, 1395, 1334, 1239, 1163, 844, 768, 699 cm$^{-1}$; $^1$H NMR (400 MHz, DMSO-d$_6$) δ 13.17 (1H, br), 9.87 (1H, br), 8.52 (1H, br), 8.23 (2H, d, J=8.4 Hz), 8.02 (1H, br), 7.54-7.64 (5H, m), 6.80 (2H, d, J=8.4 Hz); $^{13}$C NMR (100 MHz, DMSO-d$_6$) δ 173.4, 165.2, 159.8, 156.7, 155.1, 135.0, 133.8, 129.6 (2×), 128.9 (3×), 128.6 (3×), 127.4, 115.2 (2×); ESI-HRMS calcd for $C_{18}H_{12}N_5O_2S$: 362.0712, found: m/z 362.0728 [M−H]$^−$.

2-(4-Ethoxyphenyl)-8-(methylthio)-9-phenylpurine-6-carboxamide (11a)

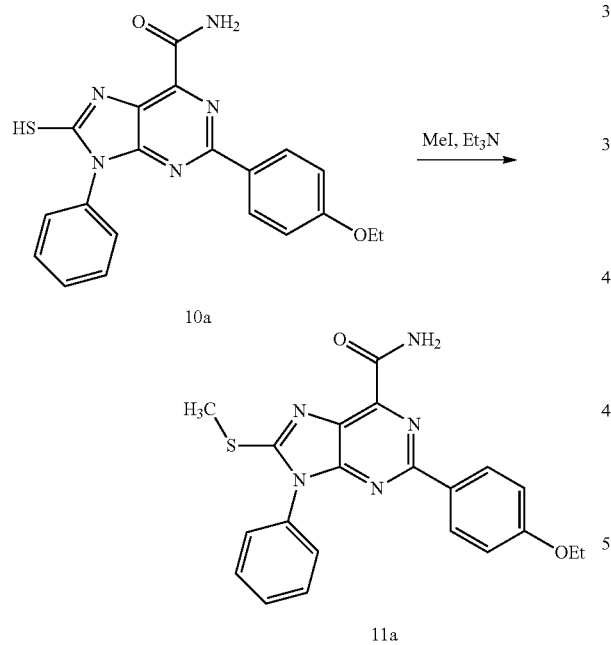

To a solution of mercaptopurine compound 10a (48 mg, 0.12 mmol) in anhydrous DMF (10 mL) were added triethylamine (24 μL, 0.17 mmol), and iodomethane (20 μL, 0.32 mmol) at 0° C. The mixture was warmed to room temperature, stirred for 18 h, and then concentrated under reduced pressure. The mixture was filtered, and washed successively with EtOAc, 1 M HCl$_{(aq)}$, $H_2O$, NaHCO$_{3(sat)}$, $H_2O$, cold EtOH and $Et_2O$ to give the methylation compound 11a (38 mg, 78% yield). $C_{21}H_{19}N_5O_2S$; white solid; mp=309.7-311.0° C. (decomposed); IR $v_{max}$ (KBr) 3412, 3293, 3054, 2990, 1659, 1609, 1597, 1577 cm$^{-1}$; $^1$H NMR (400 MHz, DMSO-d$_6$) δ 8.45 (1H, br, s), 8.30 (2H, dt, J=9.6, 2.8 Hz), 8.01 (1H, br, s), 7.71-7.61 (5H, m), 6.99 (2H, dt, J=9.6, 2.8 Hz), 4.07 (2H, q, J=6.8 Hz), 3.30 (3H, s), 1.33 (3H, t, J=6.8 Hz); $^{13}$C NMR (125 MHz, DMSO-d$_6$) δ 164.7, 160.4, 159.0, 157.2, 156.3, 143.9, 132.7, 129.8, 129.8, 129.7, 129.5 (2×), 129.4 (2×), 127.4 (2×), 114.3 (2×), 63.2, 14.6, 13.9; ESI-HRMS calculated for $C_{21}H_{20}N_5O_2S$: 406.1338, found: m/z 406.1339 [M+H]$^+$.

8-(Butylthio)-2-(4-ethoxyphenyl)-9-phenylpurine-6-carboxamide (11b)

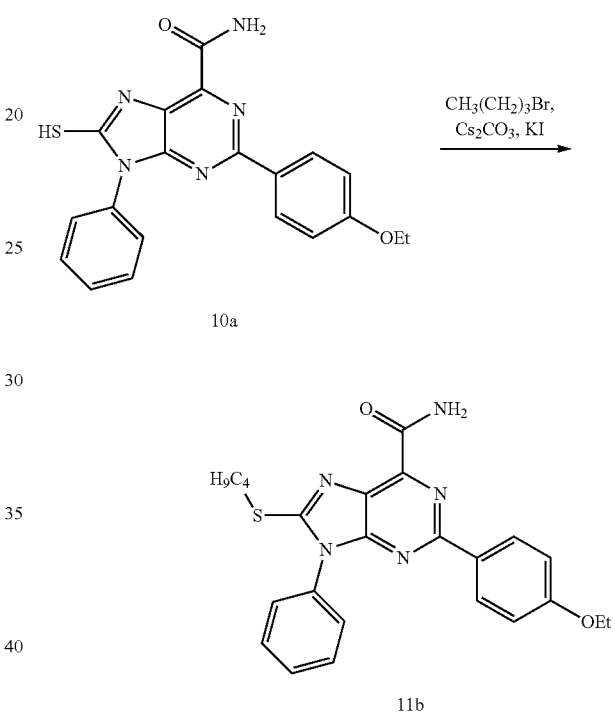

To a solution of mercaptopurine compound 10a (40 mg, 0.10 mmol) in anhydrous DMF (10 mL) were added $Cs_2CO_3$ (36 mg, 0.11 mmol), KI (4 mg, 0.024 mmol) and 1-bromobutane (22 μL, 0.20 mmol) at 0° C. The mixture was warmed to room temperature, stirred for 21 h, and then concentrated under reduced pressure. The residual solids washed successively with EtOAc, 1 M HCl$_{(aq)}$, $H_2O$, NaHCO$_{3(sat.)}$, $H_2O$, cold EtOH and $Et_2O$ to give compound 11b (34 mg, 50% yield). $C_{24}H_{25}N_5O_2S$; white solid; mp=276.7-277.1° C.; IR $v_{max}$ (KBr) 3359, 3138, 3060, 2970, 2930, 2868, 1700, 1599, 1577 cm$^{-1}$; $^1$H NMR (400 MHz, DMSO-d$_6$) δ 8.44 (1H, s), 8.29 (2H, d, J=8.4 Hz), 8.02 (1H, s), 7.72-7.60 (5H, m), 6.98 (2H, d, J=8.8 Hz), 4.07 (2H, q, J=6.8 Hz), 3.41 (2H, t, J=7.2 Hz), 1.75 (2H, quint, J=7.2 Hz), 1.48-1.36 (2H, m), 1.36-1.30 (3H, m), 0.91 (3H, t, J=7.2 Hz); $^{13}$C NMR (100 MHz, DMSO-d$_6$) δ 164.6, 160.4, 158.3, 157.0, 156.3, 143.9, 132.7, 129.7 (4×), 129.4, 129.4 (2×), 127.5 (2×), 114.3 (2×), 63.2, 31.0, 30.5, 21.2, 14.5, 13.4; ESI-HRMS calculated for $C_{24}H_{26}N_5O_2S$: 448.1807, found: m/z 448.1800 [M+H]$^+$.

151

2-(4-Ethoxyphenyl)-8-[(morpholinocarbonyl)methylthio]-9-phenylpurine-6-carboxamide (11c)

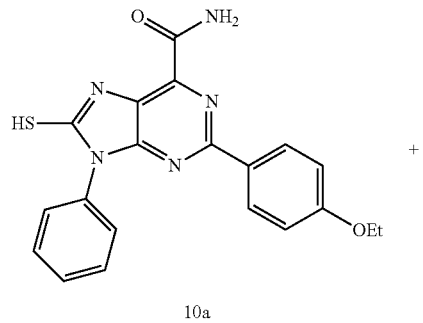

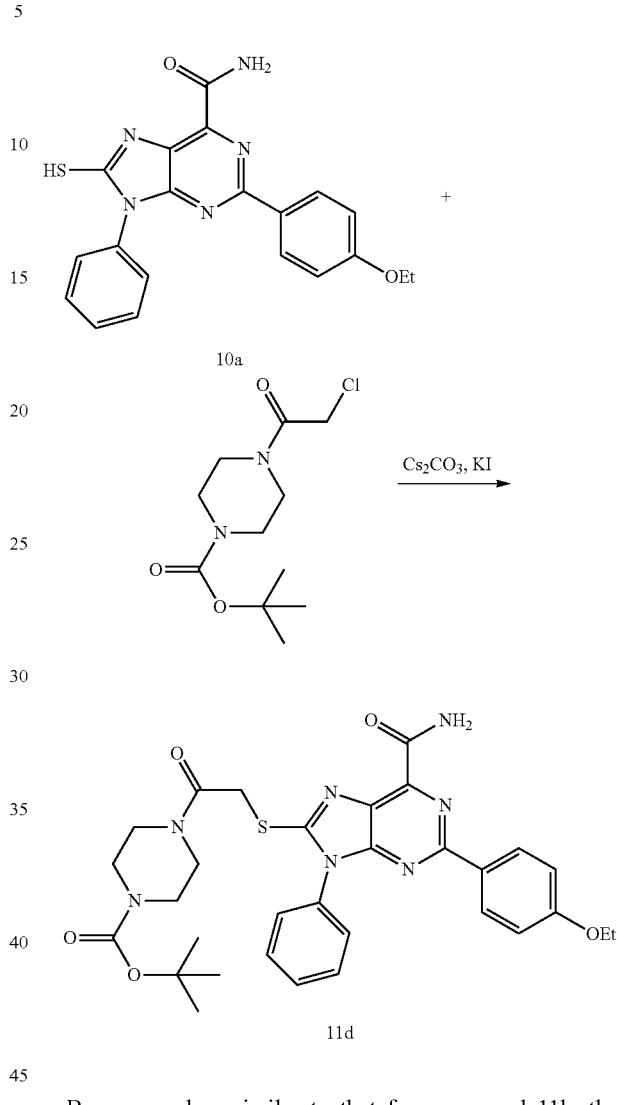

By a procedure similar to that for 11b, the reaction of mercaptopurine compound 10a (96 mg, 0.25 mmol) with 2-chloro-1-morpholinoethanone (60 mg, 0.37 mmol) at room temperature for 16 h in the presence of $Cs_2CO_3$ (96 mg, 0.29 mmol) and KI (8 mg, 0.048 mmol) afforded the desired S-substituted product 11c (124 mg, 97%). $C_{26}H_{26}N_6O_4S$; pink solid; mp=167.3-168.9 OC (decomposed); IR $v_{max}$ (KBr) 3378, 3199, 2970, 2904, 2864, 1641, 1578 cm$^{-1}$; $^1$H NMR (400 MHz, DMSO-d$_6$) δ 8.44 (1H, s), 8.30 (2H, d, J=9.2 Hz), 8.05 (1H, s), 7.74-7.61 (5H, m), 6.99 (2H, d, J=9.2 Hz), 4.52 (2H, s), 4.07 (2H, q, J=7.2 Hz), 3.66 (4H, s), 3.55 (2H, d, J=4.4 Hz), 3.46 (2H, d, J=4.4 Hz), 1.33 (3H, d, J=4.4 Hz); $^{13}$C NMR (100 MHz, DMSO-d$_6$) δ 165.3, 164.6, 160.4, 157.7, 157.0, 156.5, 144.1, 132.6, 129.8 (3×), 129.6, 129.5 (2×), 129.3, 127.4 (2×), 114.3 (2×), 66.0, 65.9, 63.2, 46.0, 42.1, 35.2, 14.6; ESI-HRMS calculated for $C_{26}H_{27}N_6O_4S$: 541.1634, found: m/z 541.1627 [M+H]$^+$.

152

2-(4-Ethoxyphenyl)-9-phenyl-8-{[(4-tert-butoxycarbonyl)piperazinocarbonyl]methylthio}purine-6-carboxamide (11d)

By a procedure similar to that for compound 11b, the reaction of mercaptopurine compound 10a (78 mg, 0.20 mmol) with tert-butyl 4-(2-chloroacetyl)piprazine-1-carboxylate (78 mg, 0.30 mmol) in the presence of $Cs_2CO_3$ (72 mg, 0.22 mmol) and KI (7 mg, 0.04 mmol) at room temperature for 16 h afforded the desired S-substituted product 11d (76 mg, 62%). $C_{31}H_{35}N_7O_5S$; white solid; mp=225.6-226.5 OC (decomposed); IR $v_{max}$ (KBr) 3384, 3165, 3058, 2977, 2922, 1707, 1667, 1652, 1588, 1577 cm$^{-1}$; $^1$H NMR (400 MHz, CDCl$_3$) δ 8.27 (2H, d, J=8.8 Hz), 7.60-7.49 (5H, m), 6.86 (2H, d, J=8.8 Hz), 6.70 (1H, br, s), 4.50 (2H, s), 4.02 (2H, q, J=6.8 Hz), 3.67 (2H, d, J=4.8 Hz), 3.57 (2H, d, J=5.2 Hz), 3.50 (2H, d, J=4.8 Hz), 3.41 (2H, d, J=5.2 Hz), 2.32 (1H, br, s), 1.43 (9H, s), 1.38 (3H, t, J=6.8 Hz); $^{13}$C NMR (100 MHz, CDCl$_3$) δ 165.8, 165.6, 160.9, 158.6, 157.4, 154.4, 142.1, 132.5, 130.1, 129.7 (4×), 129.6 (2×), 129.4, 127.0 (2×), 114.2 (2×), 80.3, 63.4, 46.0 (2×), 42.0 (2×), 36.2, 28.2 (3×), 14.7; ESI-HRMS calculated for $C_{31}H_{36}N_7O_5S$: 618.2499, found: m/z 618.2486 [M+H]$^+$.

2-(4-Ethoxyphenyl)-9-phenyl-8-[(piperazinocarbonyl)methylthio]purine-6-carboxamide (11e, as the trifluoroacetate salt)

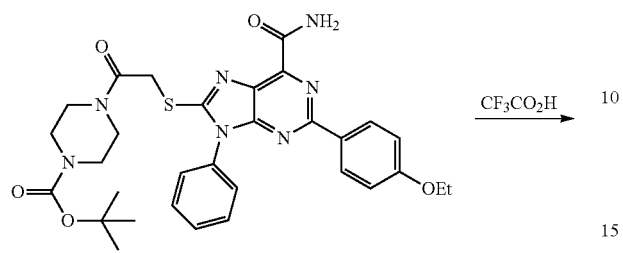

11d

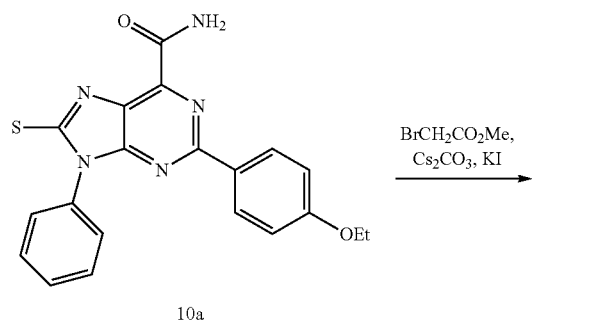

11e

A solution of compound 11d (63 mg, 0.11 mmol) and TFA (2 mL) in CH$_2$Cl$_2$ (2 mL) was stirred at room temperature for 1 h, and then concentrated under reduced pressure to afford the corresponding amine 11e as the TFA salt. C$_{28}$H$_{28}$F$_3$N$_7$O$_5$S; yellow solid; mp=242.9-243.5 (decomposed); IR $v_{max}$ (KBr) 3473, 3367, 2974, 2933, 1777, 1669, 1601, 1574 cm$^{-1}$; $^1$H NMR (400 MHz, DMSO-d$_6$) δ 8.80 (2H, br, s), 8.47 (1H, s), 8.31 (2H, d, J=8.8 Hz), 7.93 (1H, s), 7.76-7.65 (5H, m), 6.99 (2H, d, J=8.8 Hz), 4.56 (2H, s), 4.07 (2H, q, J=6.8 Hz), 3.88 (2H, br, s), 3.67 (2H, br, s), 3.26 (2H, br, s), 3.10 (2H, br, s), 1.33 (3H, t, J=6.8 Hz); $^{13}$C NMR (100 MHz, DMSO-d$_6$) δ 165.7, 164.8, 160.5, 158.7, 158.3, 158.0, 157.6, 157.0, 156.4, 144.2, 132.6, 129.9 (2×), 129.5 (2×), 129.3, 127.4 (2×), 114.3 (2×), 63.2, 42.8, 42.8, 42.6, 34.9, 14.5; ESI-HRMS calculated for C$_{26}$H$_{28}$N$_7$O$_3$S: 518.1974, found: m/z 518.1992 [M+H]$^+$.

2-(4-Ethoxyphenyl)-8-(methoxycarbonylmethylthio)-9-phenylpurine-6-carb oxamide (11f)

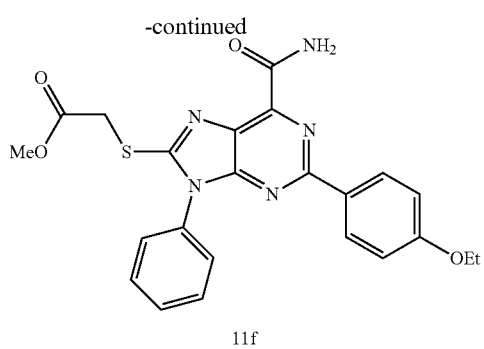

11f

By a procedure similar to that for compound 11b, the reaction of compound 10a (96 mg, 0.25 mmol) with methyl bromoacetate (35 μL, 0.37 mmol) in the presence of Cs$_2$CO$_3$ (96 mg, 0.29 mmol) and KI (8 mg, 0.05 mmol) at room temperature for 23 h afforded the desired S-substituted product 1f (92 mg, 62%). C$_{23}$H$_{21}$N$_5$O$_4$S; white solid; mp=237.6-239.0° C. (decompose); IR $v_{max}$ (KBr) 3391, 3191, 2991, 2942, 1743, 1663, 1577 cm$^{-1}$; $^1$H NMR (400 MHz, DMSO-d$_6$) δ 8.45 (1H, s), 8.29 (2H, d, J=8.8 Hz), 8.16 (1H, s), 7.75-7.62 (5H, m), 7.00 (2H, d, J=8.8 Hz), 4.33 (2H, s), 4.07 (2H, q, J=7.2 Hz), 3.71 (3H, s), 1.33 (3H, t, J=7.2 Hz); $^{13}$C NMR (100 MHz, DMSO-d$_6$) δ 168.6, 164.2, 160.5, 157.0 (2×), 156.9 (2×), 156.7, 155.1 (2×), 144.1 (2×), 132.4, 130.0, 129.9, 129.5, 129.3, 127.3, 114.3, 63.2, 52.9, 33.5, 14.5; ESI-HRMS calculated for C$_{23}$H$_{22}$N$_5$O$_4$S: 464.1393, found: m/z 464.1375 [M+H]$^+$.

8-(Carboxymethylthio)-2-(4-ethoxyphenyl)-9-phenylpurine-6-carboxamide (11g, as the sodium salt)

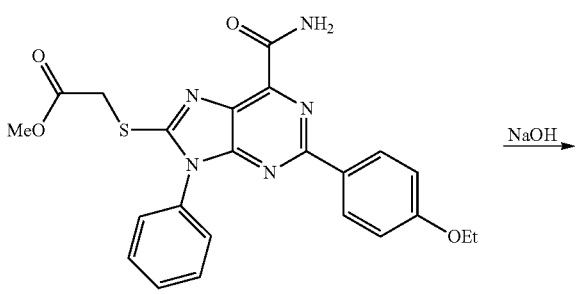

11f

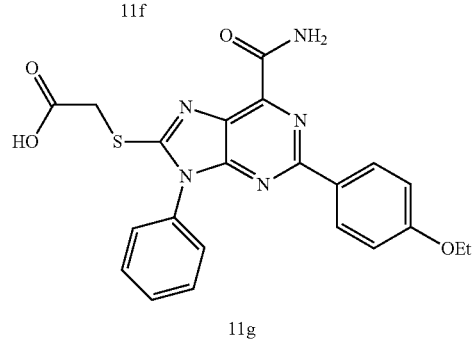

11g

To a suspension of ester 11f (60 mg, 0.23 mmol) in pyridine (10 mL) was added 1 M NaOH$_{(aq.)}$ (3 mL). The mixture was stirred at room temperature for 17 h, in which the solids dissolved. The mixture was concentrated under reduced pressure. To the residue was added ethanol, and the suspension was subjected to centrifuge at 8000 rpm for 15 min at 4° C. three times. The acid compound 1g was collected as pink solids (42 mg, 69%). $C_{22}H_{18}N_5NaO_4S$; mp=216.1-217.2 OC (decompose); IR $\nu_{max}$ (KBr) 3594, 3173, 3085, 2958, 2835, 1719, 1678, 1648, 1585 cm$^{-1}$; $^1$H NMR (400 MHz, DMSO-d$_6$) δ 8.53 (1H, s), 8.29 (2H, d, J=8.8 Hz), 8.06 (1H, s), 7.73-7.61 (5H, m), 6.98 (2H, d, J=8.8 Hz), 4.07 (2H, q, J=7.2 Hz), 3.89 (2H, s), 1.33 (3H, t, J=7.2 Hz); $^{13}$C NMR (100 MHz, DMSO-d$_6$) δ 167.7, 164.8, 160.6, 160.3, 157.0, 156.0, 142.8, 132.9, 130.0, 129.8, 129.7, 129.6, 129.5 (2×), 129.4 (2×), 127.5 (2×), 114.2 (2×), 63.2, 14.6; ESI-HRMS calculated for $C_{22}H_{19}N_5NaO_4S$: 472.1055, found: m/z 472.1042 [M+H]$^+$.

2-(4-Ethoxyphenyl)-9-(2-methoxyphenyl)-8-oxopurine-6-carbonitrile (12a)

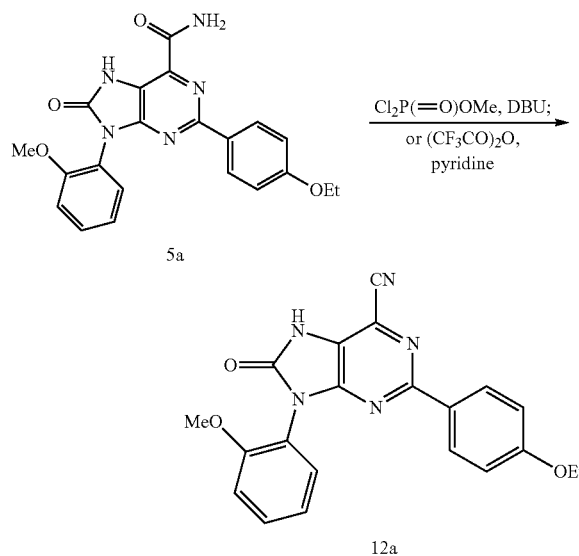

A mixture of the amide compound 5a (165 mg, 0.41 mmol) and 1,8-diazabicyclo[5.4.0]undec7-ene (DBU) (0.17 mL, 1.22 mmol) in anhydrous pyridine (3.5 mL) was stirred for 10 min at room temperature. Methyl dichlorophosphate (83 µL, 0.79 mmol) was added, and the mixture was stirred at room temperature for 72 h. The mixture was concentrated under reduced pressure, and purified by flash chromatography on a silica gel column with elution of EtOAc/hexane (1:2) to give the nitrile compound 12a (75 mg, 47% yield).

Alternatively, a mixture of compound 5a (1.18 g, 3.0 mmol) and trifluoroacetic anhydride (0.63 mL, 4.51 mmol) in pyridine (24 mL) was stirred at 0° C. for 2 h. After then, another batch of trifluoroacetic anhydride (0.63 mL, 4.51 mmol) was added. The mixture was stirred at 0° C. for another 1 h. The solution was concentrated under reduced pressure, rinsed with Et$_2$O, and extracted with CH$_2$Cl$_2$ and H$_2$O. The organic phase was dried over MgSO$_4$, filtered, and concentrated to give compound 12a (1.06 g, 91% yield). The purity of compound 3a was 96.3% as shown by HPLC on a Platisil Silica column (Dikma, 4.6×250 mm, 5 m particle size), $t_R$=19.8 min (EtOAc/hexane=1:2) at a flow rate of 1.0 mL/min.

12a: $C_{21}H_{17}N_5O_3$; white solid; mp 288-290 OC; TLC (EtOAc/hexane=1:2) R$_f$=0.2; IR $\nu_{max}$ (neat) 3227, 2365, 2349, 2251, 1756, 1601, 1151, 1474, 1405, 1258, 1168, 1004, 849, 780, 751, 673 cm$^{-1}$; $^1$H NMR (400 MHz, DMSO-d$_6$) δ 8.04 (2H, d, J=8.8 Hz), 7.54-7.58 (1H, m), 7.47 (1H, dd, J=6.0, 1.6 Hz), 7.30 (1H, d, J=8.4 Hz), 7.16 (1H, t, J=7.6 Hz), 7.00 (2H, d, J=8.8 Hz), 4.05 (2H, q, J=7.2 Hz), 3.76 (3H, s), 1.32 (3H, t, J=7.2 Hz); 13C NMR (100 MHz, DMSO-d$_6$) δ 160.6, 156.5, 155.2, 152.8, 152.3, 131.1, 129.9, 128.8 (2×), 128.5, 124.4, 120.7, 119.9, 114.6, 114.5 (2×), 114.0, 112.9, 63.2, 55.9, 14.5; ESI-HRMS calcd for $C_{21}H_{18}N_5O_3$: 388.1404, found: m/z 388.1404 [M+H]$^+$.

2-(4-Ethoxyphenyl)-9-(4-methoxycarbonylphenyl)-8-oxopurine-6-carbonitrile (12b)

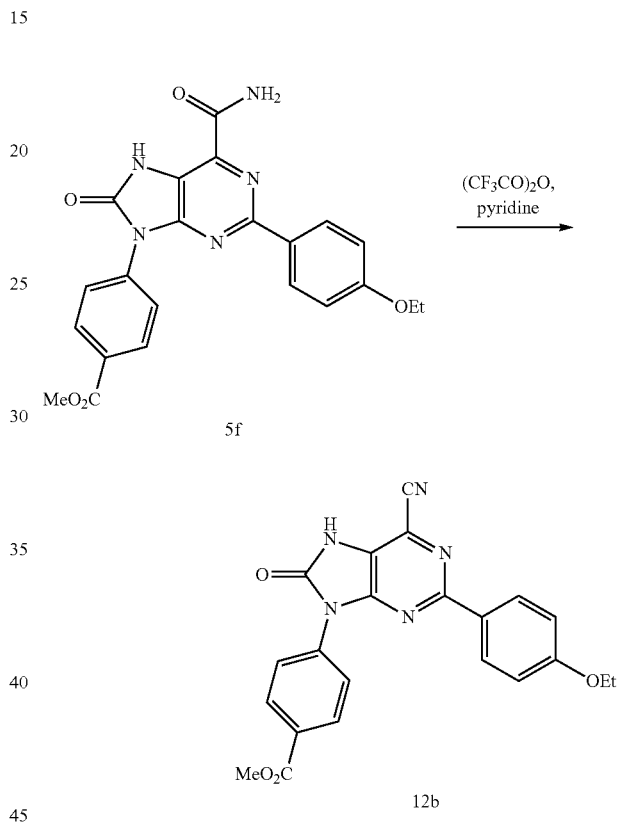

A mixture of amide compound 5f (216 mg, 0.50 mmol) and trifluoroacetic anhydride (0.20 mL, 1.4 mmol) in pyridine (6 mL) was stirred at room temperature for 3 h. The mixture was quenched with H$_2$O, and concentrated under reduced pressure. The residue was extracted with H$_2$O and CH$_2$Cl$_2$. The organic phase was dried over MgSO$_4$, filtered, concentrated under reduced pressure, and purified by flash chromatography on a silica gel column (hexane/EtOAc=1:1) to give compound 12b (116 mg, 56% yield). $C_{22}H_{17}N_5O_4$; yellow solid; mp=311.1-312.2 OC; $^1$H NMR (400 MHz, DMSO-d$_6$) δ 8.18 (2H, d, J=8.0 Hz), 8.11 (2H, d, J=8.4 Hz), 7.92 (2H, d, J=8.4 Hz), 6.98 (2H, d, J=8.4 Hz), 4.05 (2H, q, J=7.6 Hz), 3.91 (3H, s), 1.33 (3H, t, J=6.8 Hz); $^{13}$C NMR (100 MHz, DMSO-d$_6$) δ 165.6, 160.6, 156.3, 152.0, 136.3, 129.8 (2×), 128.9 (2×), 128.8, 128.4, 125.6 (2×), 124.4, 114.5 (2×), 114.4 (2×), 114.3, 63.2, 52.2, 14.4; ESI-HRMS (negative mode) calcd for $C_{22}H_{16}N_5O_4$: 414.1202, found: m/z 414.1182 [M−H]$^-$.

157

2-(4-Ethoxyphenyl)-9-(3-methoxycarbonylphenyl)-8-oxopurine-6-carbonitrile (12c)

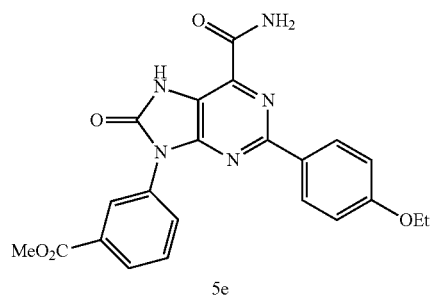

5e

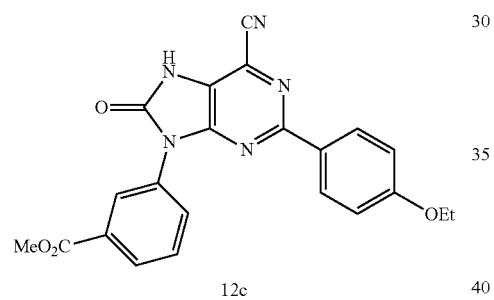

12c

A mixture of compound 5e (50 mg, 0.12 mmol) and trifluoroacetic anhydride (25 μL, 0.18 mmol) in pyridine (2 mL) was stirred at room temperature for 1 h. After then, another batch of trifluoroacetic anhydride (25 μL, 0.18 mmol) was added. The mixture was stirred at room temperature for additional 2 h, concentrated under reduced pressure, and washed with Et$_2$O and MeOH to give compound 12c (34 mg, 71% yield). The purity of compound 3c was 97.7% as shown by HPLC on a Platisil Silica column (Dikma, 4.6×250 mm, 5 m particle size), $t_R$=5.3 min (EtOAc/hexane=1:1) at a flow rate of 1.0 mL/min. $C_{22}H_{17}N_5O_4$; white solid; mp 297-299° C.; TLC (EtOAc) $R_f$=0.8; IR $\nu_{max}$ (neat) 3399, 1760, 1707, 1646, 1597, 1403, 1251, 1167, 1045, 1026, 783, 753, 726 cm$^{-1}$ 1H NMR (400 MHz, DMSO-d$_6$) δ 8.39 (1H, s), 8.13 (2H, d, J=8.8 Hz), 8.06 (2H, t, J=8.0 Hz), 7.78 (1H, t, J=8.0 Hz), 7.00 (2H, d, J=8.8 Hz), 4.08 (2H, q, J=7.2 Hz), 3.92 (3H, s), 1.34 (3H, t, J=7.2 Hz); $^{13}$C NMR (100 MHz, DMSO-d$_6$) δ 165.5, 160.7, 156.2, 152.4, 152.3, 132.7, 130.6, 130.5, 129.7 (2×), 128.8, 128.6, 128.4, 126.6, 124.5, 114.6, 114.5 (2×), 1140, 63.3, 52.5, 14.6; ESI-HRMS calcd for $C_{22}H_{16}N_5O_4$: 414.1202, found: m/z 414.1209 [M−H]$^−$.

158

2-(4-Ethoxyphenyl)-9-(4-nitrophenyl)-8-oxopurine-6-carbonitrile (12d)

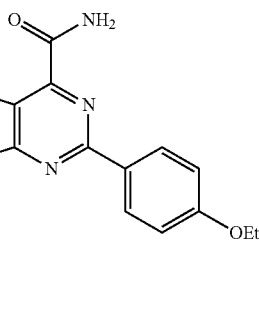

5k

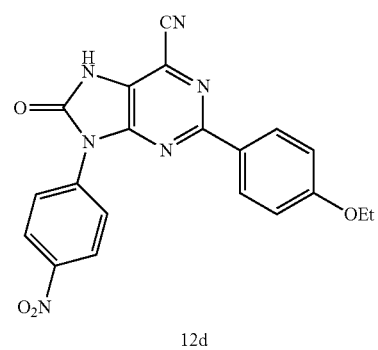

12d

A mixture of amide compound 5k (242.4 mg, 0.58 mmol) and trifluoroacetic anhydride (0.30 mL, 2.1 mmol) in pyridine (12 mL) was stirred at room temperature for 3 h. The mixture was quenched with H$_2$O, and concentrated under reduced pressure. The residue was extracted with H$_2$O and CH$_2$Cl$_2$. The organic phase was dried over MgSO$_4$, filtered, concentrated under reduced pressure, and purified by flash chromatography on a silica gel column (hexane/EtOAc=1:1) to give compound 12d (91 mg, 39% yield). $C_{20}H_{14}N_6O_4$; yellow solid; mp=293.2-294.8° C.; $^1$HNMR (400 MHz, DMSO-d$_6$) δ 8.50 (2H, d, J=8.0 Hz), 8.18 (2H, d, J=8.0 Hz), 8.11 (2H, d, J=8.4 Hz), 7.03 (2H, d, J=8.0 Hz), 4.09 (2H, q, J=6.8 Hz), 1.34 (3H, t, J=6.0 Hz); $^{13}$C NMR (100 MHz, DMSO-d$_6$) δ 160.7, 156.3, 152.00, 151.8, 146.0, 137.9, 129.0 (2×), 128.2, 126.3 (2×), 124.5 (2×), 121.1, 114.5 (2×), 114.4, 114.3, 63.3, 14.5; ESI-HRMS (negative mode) calcd for $C_{20}H_{13}N_6O_4$: 401.0998, found: m/z 401.1010 [M−H]$^−$.

2-(4-Ethoxyphenyl)-9-(3-nitrophenyl)-8-oxopurine-6-carbonitrile (12e)

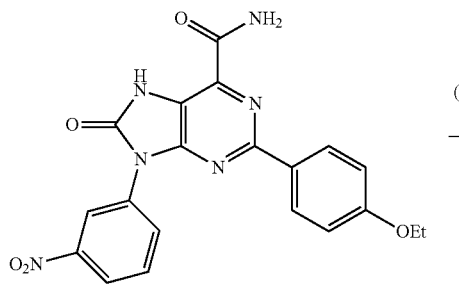

5l

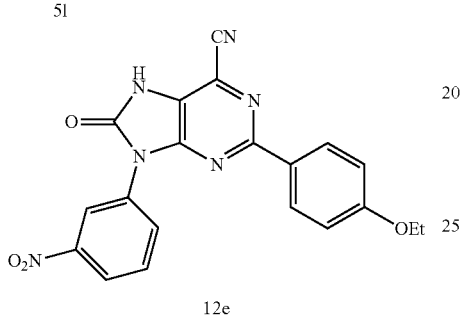

12e

A mixture of amide compound 5l (121 mg, 0.29 mmol) and trifluoroacetic anhydride (0.20 mL, 1.4 mmol) in pyridine (7 mL) was stirred at room temperature for 3 h. The mixture was quenched with H$_2$O, and concentrated under reduced pressure. The residue was extracted with H$_2$O and CH$_2$Cl$_2$. The organic phase was dried over MgSO$_4$, filtered, concentrated under reduced pressure, and purified by flash chromatography on a silica gel column (hexane/EtOAc=1:1) to give compound 12e (99 mg, 85% yield). C$_{20}$H$_{14}$N$_6$O$_4$; yellow solid; mp=296.1-297.8° C.; $^1$HNMR (400 MHz, DMSO-d$_6$) δ 8.71 (1H, t, J=2.0 Hz), 8.35 (1H, dd, J=4.2, 2.4 Hz), 8.28-8.26 (1H, m), 8.13 (2H, d, J=8.8 Hz), 7.94 (1H, t, J=8.0 Hz), 6.01 (2H, d, J=8.8 Hz), 4.08 (2H, q, J=7.2 Hz), 1.34 (3H, t, J=7.2 Hz); 13C NMR (125 MHz, DMSO-d$_6$) δ 160.8, 156.2, 152.3, 152.2, 147.9, 133.4, 132.0, 130.7, 129.0 (2×), 128.4, 124.8, 122.8, 120.6, 114.6 (3×), 114.2, 63.4, 14.7; ESI-HRMS (negative mode) calcd for C$_{20}$H$_{13}$N$_6$O$_4$: 401.0998, found: m/z 401.1005 [M–H]$^-$.

2-(3-Hydroxy-4-methoxyphenyl)-9-(2-methoxyphenyl)-8-oxopurine-6-carbonitrile (12f)

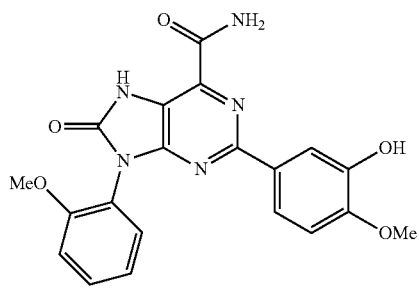

5n

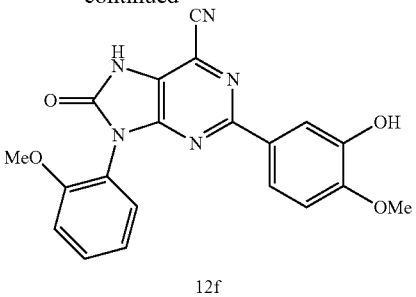

12f

A mixture of compound 5n (100 mg, 0.25 mmol) and trifluoroacetic anhydride (53 µL, 0.38 mmol) in pyridine (2 mL) was stirred at room temperature for 1 h. After then, another batch of trifluoroacetic anhydride (53 µL, 0.38 mmol) was added. The mixture was stirred at 0° C. for additional 1 h, concentrated under reduced pressure, and extracted with CH$_2$Cl$_2$ and H$_2$O. The organic phase was dried over MgSO$_4$, filtered, and concentrated under reduced pressure to give pale brown solids. The solids were washed successively with Et$_2$O, CH$_2$Cl$_2$, and CH$_3$CN to give compound 12f (56 mg, 58% yield). The purity of compound 12f was 97.0% as shown by HPLC on a Platisil Silica column (Dikma, 4.6×250 mm, 5 µm particle size), t$_R$=5.7 min (EtOAc/hexane=2:1) at a flow rate of 1.0 mL/min. C$_{20}$H$_{15}$N$_5$O$_4$; pale yellow solid; mp 294-296° C.; TLC (EtOAc/hexane=1:1) R$_f$=0.3; IR ν$_{max}$ (neat) 3426, 2924, 2844, 2349, 2236, 1741, 1631, 1521, 1475, 1395, 1285, 1251, 1110. 1019, 882 cm$^{-1}$; $^1$H NMR (400 MHz, DMSO-d$_6$) δ 9.25 (1H, br), 7.55-7.59 (3H, m), 7.48 (1H, d, J=7.6 Hz), 7.31 (1H, d, J=8.4 Hz), 7.16 (1H, t, J=7.6 Hz), 6.96 (1H, d, J=9.6 Hz), 3.78 (3H, s), 3.76 (3H, s); $^{13}$C NMR (100 MHz, DMSO-d$_6$) δ 156.5, 155.3, 152.7, 152.4, 150.0, 146.4, 131.1, 129.9 (2×), 128.9, 120.8, 120.0, 119.0, 114.6, 114.1, 114.0, 112.9, 111.9, 56.0, 55.5; ESI-HRMS calcd for C$_{20}$H$_{14}$N$_5$O$_4$: 388.1046, found: m/z 388.1046 [M–H]$^-$.

2-(4-Ethoxyphenyl)-9-hexyl-8-oxopurine-6-carbonitrile (12g)

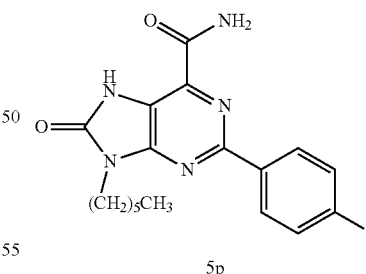

5p

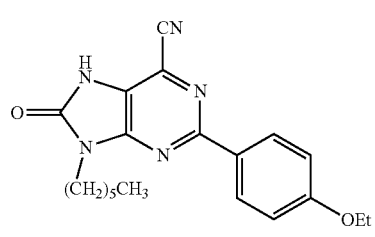

12g

A mixture of compound 5p (100 mg, 0.26 mmol) and trifluoroacetic anhydride (56 μL, 0.41 mmol) in pyridine (1.8 mL) was stirred at 0° C. for 1 h. After then, another batch of trifluoroacetic anhydride (56 μL, 0.41 mmol) was added. The mixture was stirred at 0° C. for additional 4 h. The mixture was concentrated under reduced pressure, and extracted with $CH_2Cl_2$ and $H_2O$. The organic phase was dried over $MgSO_4$, filtered, and concentrated to give pale brown solid. The solids were collected, and rinsed successively with $Et_2O$, $CH_2Cl_2$, and MeOH to give compound 12g (25 mg, 26% yield). $C_{20}H_{23}N_5O_2$; pale yellow solid; TLC (EtOAc/hexane=1:1) $R_f$=0.7; $^1$H NMR (400 MHz, $CDCl_3$) δ 10.67 (1H, br), 8.26 (2H, d, J=7.2 Hz), 6.91 (2H, d, J=7.2 Hz), 4.00-4.08 (4H, m), 1.84 (2H, t, J=6.8 Hz), 1.41 (3H, t, J=6.8 Hz), 1.27-1.38 (6H, m), 0.86 (3H, t, J=6.8 Hz); $^{13}$C NMR (100 MHz, $CDCl_3$) δ 161.3, 158.3, 153.8, 152.1, 129.4 (2×), 128.7, 122.5, 115.8, 114.3 (2×), 113.9, 63.6, 40.1, 31.2, 28.0, 26.3, 22.5, 14.7, 14.0; ESI-HRMS calcd for $C_{20}H_{22}N_5O_2$: 364.1774, found: m/z 364.1749 [M–H]⁻.

2-(4-Ethoxyphenyl)-9-(2-methoxyphenyl)-8-oxopurine-6-(N-butyl)carboximidamide (13a)

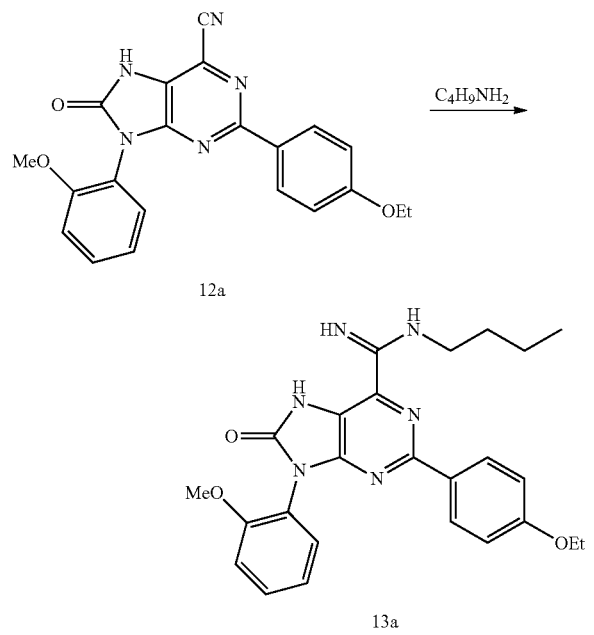

Compound 12a (10 mg, 0.03 mmol) and butylamine (5 μL, 0.05 mmol) in anhydrous THF (0.3 mL) and MeOH (0.1 mL) was stirred at 60° C. for 48 h. After cooling to room temperature, the solution was concentrated under reduced pressure, and the solids were washed successively with $H_2O$, MeOH, and THF to give compound 13a (8 mg, 69% yield). $C_{25}H_{28}N_6O_3$; white solid; mp 375-377° C.; IR $v_{max}$ (neat) 3369, 3254, 2962, 2928, 1680, 1620, 1601, 1574, 1513, 1464, 1403, 1372, 1247, 1175, 1140, 1049, 749, 699 cm⁻¹; TLC (EtOAc) $R_f$=0.3; $^1$H NMR (400 MHz, DMSO-$d_6$) δ 8.62-8.63 (1H, m), 8.29 (2H, d, J=7.2 Hz), 7.58 (1H, s), 7.49 (1H, t, J=8.0 Hz), 7.36 (1H, d, J=6.4 Hz), 7.27 (1H, d, J=8.8 Hz), 7.11 (1H, t, J=7.2 Hz), 6.95 (2H, d, J=7.6 Hz), 4.06 (2H, q, J=7.0 Hz), 3.73 (3H, s), 3.42-3.46 (2H, m), 1.59-1.62 (2H, m), 1.38-1.41 (2H, m), 1.32-1.35 (3H, t, J=7.0 Hz), 0.93 (3H, t, J=7.2 Hz); $^{13}$C NMR (100 MHz, DMSO-$d_6$) δ 159.7, 159.3, 159.1, 155.6, 155.4, 152.1, 130.1, 130.0, 129.9, 129.5, 128.8 (2×), 128.3, 122.4, 120.6, 114.1 (2×), 112.8, 63.1, 55.8, 30.4, 19.6, 14.6, 13.8; ESI-HRMS calcd for $C_{25}H_{27}N_6O_3$: 459.2145, found: m/z 459.2141 [M–H]⁻.

2-(4-Ethoxyphenyl)-9-(2-methoxyphenyl)-8-oxopurine-6-(N-hydroxy)carboximidamide (14a')

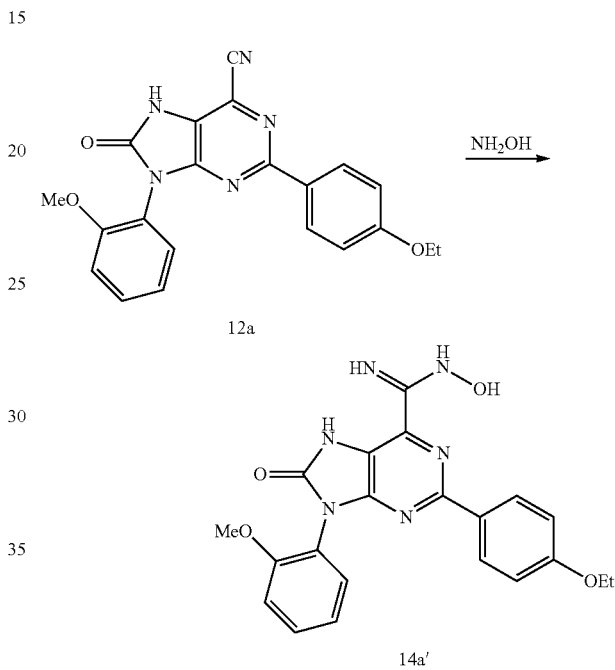

A mixture of compound 10a (500 mg, 1.3 mmol), hydroxylamine hydrochloride (350 mg, 5.2 mmol), and sodium acetate trihydrate (700 mg, 5.2 mmol) in THF (20 mL) and MeOH (20 mL) was stirred at 60° C. for 2 h. After cooling to room temperature, the solution was concentrated under reduced pressure and washed successively with $H_2O$, MeOH, and THF to give compound 14a' (455 mg, 84% yield). The purity of compound 14a' was 99.1% as shown by HPLC on a Platisil Silica column (Dikma, 4.6×250 mm, 5 μm particle size), $t_R$=8.26 min (EtOAc/hexane=4:1) at a flow rate of 1.0 mL/min. $C_{21}H_{20}N_6O_4$; pale yellow solid; mp 241-243° C.; TLC (EtOAc) $R_f$=0.2; IR $v_{max}$ (neat) 3357, 2975, 2927, 2844, 1720, 1660, 1600, 1509, 1469, 1398, 1247, 1163, 1116, 1044, 1008, 881, 794, 758, 663 cm⁻¹; $^1$H NMR (400 MHz, $(CD_3)_2CO$) δ 9.52-9.56 (2H, m), 8.31 (2H, m), 7.52 (2H, td, J=6.0, 1.6 Hz), 7.28 (1H, d, J=8.4 Hz), 7.16 (1H, td, J=6.4, 1.2 Hz), 6.93 (2H, dd, J=4.8, 2.0 Hz), 6.11 (2H, br) 4.08 (2H, q, J=6.8 Hz), 3.80 (3H, s), 1.37 (3H, t, J=7.2 Hz); $^{13}$C NMR (100 MHz, $(CD_3)_2CO$) δ 161.8 (2×), 157.5, 157.0, 153.1, 153.0, 151.2, 134.8, 131.6, 131.2, 130.1 (2×), 122.5, 121.6, 117.2, 115.0 (2×), 113.6, 64.2, 56.4, 15.1; ESI-HRMS calcd for $C_{21}H_{21}N_6O_4$: 421.1619, found: m/z 421.1614 [M+H]⁺.

163

2-(4-Ethoxyphenyl)-9-(4-methoxycarbonylphenyl)-8-oxopurine-6-(N-hydroxy)carboximidamide (14b)

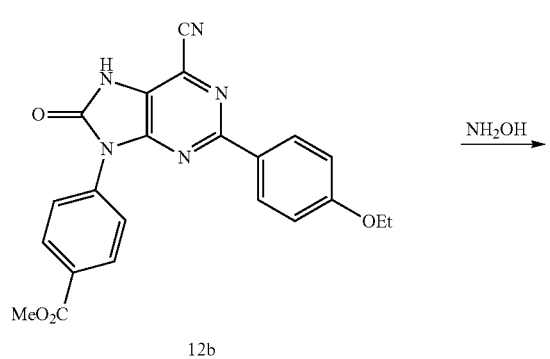

A mixture of nitrile compound 12b (70 mg, 0.17 mmol) and hydroxylamine hydrochloride (47 mg, 0.68 mmol) and sodium acetate (92 mg, 0.68 mmol) in THF (6 mL) and MeOH (6 mL) was stirred at 70° C. for 1 h. The mixture was concentrated under reduced pressure, washed successively with cold MeOH and H$_2$O, and purified by flash chromatography on a silica gel column (hexane/EtOAc=1:1) to give compound 14b (69 mg, 90% yield). C$_{22}$H$_{20}$N$_6$O$_5$; yellow solid; mp=261.9-263.1° C.; $^1$H NMR (400 MHz, DMSO-d$_6$) δ 10.10 (1H, br s), 8.36 (2H, d, J=9.0 Hz), 8.18 (2H, d, J=8.4 Hz), 8.01 (2H, d, J=9.0 Hz), 6.99 (2H, d, J=8.4 Hz), 6.23 (2H, br s), 4.09 (2H, q, J=7.0 Hz), 3.91 (3H, s), 1.35 (3H, t, J=7.0 Hz); $^{13}$C NMR (125 MHz, DMSO-d$_6$) δ 165.8, 160.3, 155.3, 152.1, 150.4, 149.4, 137.2, 135.0, 129.9 (2×), 129.5, 129.2 (2×), 128.2, 125.8 (2×), 115.9, 114.2 (2×), 63.2, 52.4, 14.7; ESI-HRMS (negative mode) calcd for C$_{22}$H$_{19}$N$_6$O$_5$: 447.1417, found: m/z 447.1404 [M−H]$^−$.

164

2-(4-Ethoxyphenyl)-9-(3-methoxycarbonylphenyl)-8-oxopurine-6-(N-hydroxy)carboximidamide (14c)

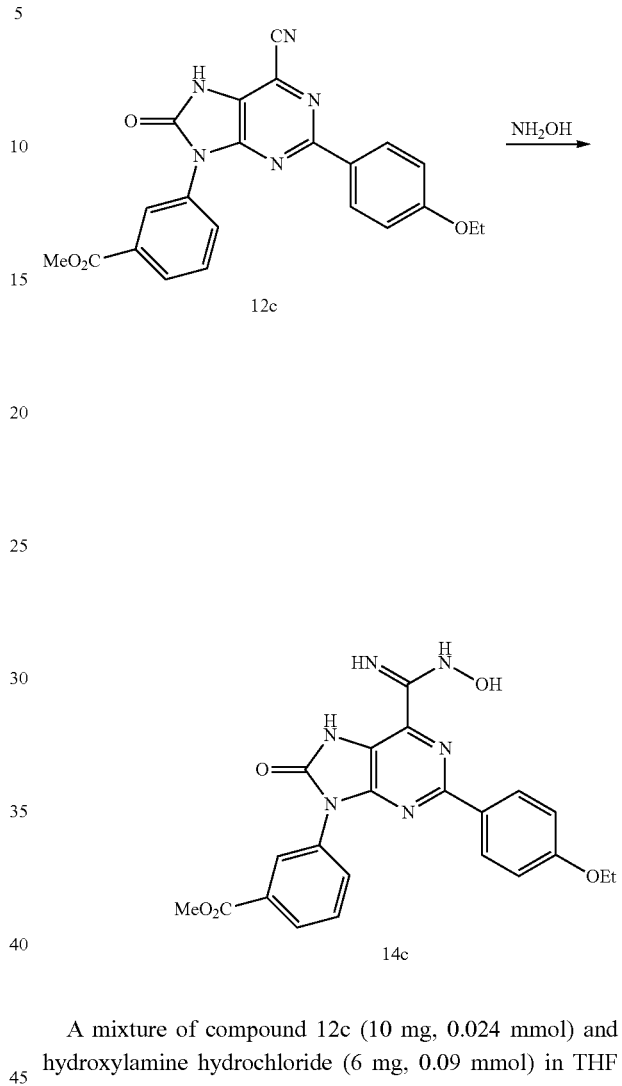

A mixture of compound 12c (10 mg, 0.024 mmol) and hydroxylamine hydrochloride (6 mg, 0.09 mmol) in THF (0.5 mL) and EtOH (0.5 mL) was stirred at room temperature for 10 min. After then, triethylamine (12 μL, 0.09 mmol) was added slowly into the solution. The mixture was stirred for additional 40 min, concentrated under reduced pressure, and washed successively with H$_2$O, Et$_2$O, CH$_2$Cl$_2$, MeOH and acetone to give compound 14c (10 mg, 97% yield). C$_{22}$H$_{20}$N$_6$O$_5$; white solid; mp 257-259° C.; TLC (EtOAc) R$_f$ '$_2$ 0.1; IR ν$_{max}$ (neat) 3437, 2958, 2913, 1658, 1506, 1456, 1407, 1258, 1114, 1068, 1038, 985, 962, 927 cm$^{-1}$; $^1$H NMR (400 MHz, DMSO-d$_6$) δ 10.70 (1H, br), 10.09 (1H, s), 8.45 (1H, s), 8.35 (2H, d, J=8.4 Hz), 8.11 (1H, d, J=8.0 Hz), 8.04 (1H, d, J=7.2 Hz), 7.77 (1H, t, J=8.0 Hz), 6.99 (2H, d, J=8.8 Hz), 6.23 (2H, br), 4.08 (2H, q, J=6.8 Hz), 3.92 (3H, s), 1.35 (3H, t, J=6.8 Hz); $^{13}$C NMR (100 MHz, DMSO-d$_6$) δ 165.7, 160.2, 155.2, 152.2, 150.6, 149.4, 134.8, 133.4, 130.5, 130.3, 129.5 (3×), 129.1, 128.0, 126.4, 115.8, 114.2 (2×), 63.2, 52.5, 14.6; ESI-HRMS calcd for C$_{22}$H$_{19}$N$_6$O$_5$: 447.1417, found: m/z 447.1411 [M−H]$^−$.

165

2-(4-Ethoxyphenyl)-9-(4-nitrophenyl)-8-oxopurine-6-(N-hydroxy)carboximidamide (14d)

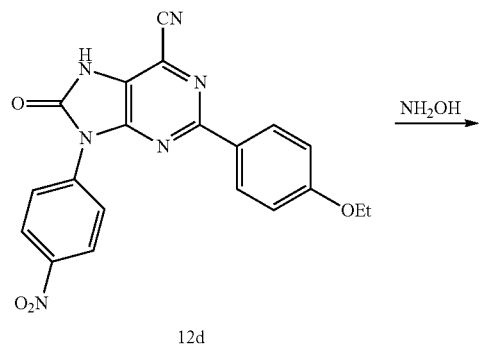

12d

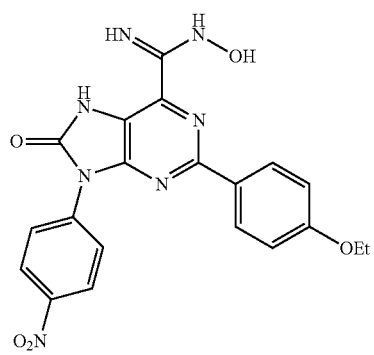

14d

A mixture of compound 12d (50 mg, 0.12 mmol) and hydroxylamine hydrochloride (28 mg, 0.41 mmol) and sodium acetate (56 mg, 0.41 mmol) in THF (5 mL) and MeOH (5 mL) was stirred at 70° C. for 1 h. The mixture was concentrated under reduced pressure, washed successively by cold MeOH and H$_2$O, and purified by flash chromatography on a silica gel column (hexane/EtOAc=1:1) to give compound 14d (20 mg, 37% yield). C$_{20}$H$_{17}$N$_7$O$_5$; yellow solid; mp=302.0-303.9 OC (decomposed); $^1$H NMR (400 MHz, DMSO-d$_6$) δ 10.11 (1H, br s), 8.48 (2H, d, J=8.4 Hz), 8.39 (2H, d, J=8.4 Hz), 8.19 (2H, d, J=8.8 Hz), 7.00 (2H, d, J=8.8 Hz), 6.24 (2H, br s), 4.09 (2H, q, J=6.8 Hz), 1.35 (3H, t, J=7.2 Hz); $^{13}$C NMR (125 MHz, DMSO-d$_6$) δ 160.3, 155.3, 151.9, 150.2, 149.3, 145.6, 138.9, 135.2, 129.3, 129.2 (2×), 126.1 (3×), 124.3 (2×), 114.2 (2×), 63.2, 14.6; ESI-HRMS (negative mode) calcd for C$_{20}$H$_{16}$N$_7$O$_5$: 434.1213, found: m/z 434.1210 [M−H]$^−$.

166

2-(4-Ethoxyphenyl)-9-(3-nitrophenyl)-8-oxopurine-6-(N-hydroxy)carboximidamide (14e)

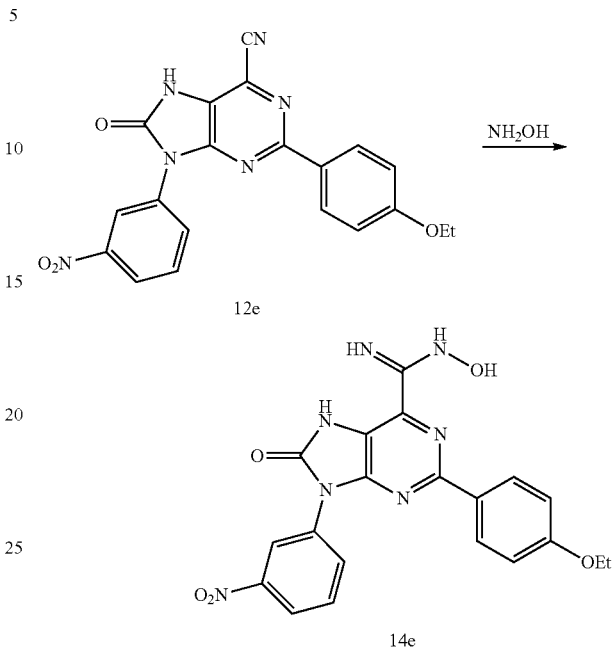

A mixture of compound 12e (40 mg, 0.10 mmol) and hydroxylamine hydrochloride (30 mg, 0.43 mmol) and sodium acetate (60 mg, 0.43 mmol) in THF (4 mL) and MeOH (4 mL) was stirred at 70° C. for 1 h. The mixture was concentrated under reduced pressure, washed successively with cold MeOH and H$_2$O, and purified by flash chromatography on a silica gel column (hexane/EtOAc=1:1) to give compound 14e (39 mg, 91% yield). C$_{20}$H$_{17}$N$_7$O$_5$; yellow solid; mp=247.0-248.1° C.; $^1$H NMR (400 MHz, DMSO-d$_6$) δ 10.14 (1H, br s), 8.79 (1H, s), 8.39-8.31 (4H, m), 7.92 (1H, t, J=8.0 Hz), 6.99 (2H, d, J=7.6 Hz), 4.09 (2H, q, J=6.8 Hz), 1.35 (3H, t, J=7.2 Hz); $^{13}$C NMR (125 MHz, DMSO-d$_6$) δ 160.28, 155.3, 152.0, 150.4, 149.4, 147.8, 134.9, 134.1, 131.9, 130.3, 129.3, 129.1 (2×), 122.0, 120.4, 115.9, 114.2 (2×), 63.2, 14.6; ESI-HRMS (negative mode) calcd for C$_{20}$H$_{16}$N$_7$O$_5$: 434.1213, found: m/z 434.1215 [M−H]$^−$.

2-(3-Hydroxy-4-methoxyphenyl)-9-(2-methoxyphenyl)-8-oxopurine-6-(N-hydroxy)carboximidamide (14f)

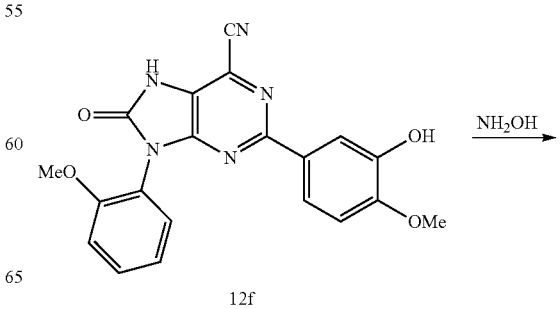

12f

167

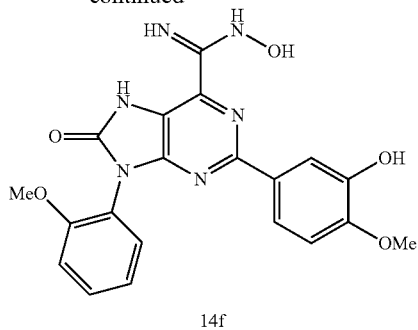

14f

A mixture of compound 12f (20 mg, 0.05 mmol), hydroxylamine hydrochloride (14 mg, 2.0 mmol) and sodium acetate trihydrate (28 mg, 2.0 mmol) in THF (1.6 mL) and MeOH (1.6 mL) was stirred at 60° C. for 1 h. The mixture was concentrated under reduced pressure, and washed successively with H$_2$O, CH$_2$Cl$_2$ and CH$_3$CN to give compound 14f (21 mg, 97% yield). The purity of compound 14f was 96.7% as shown by HPLC on a Platisil Silica column (Dikma, 4.6×250 mm, 5 m particle size), t$_R$=9.6 min (EtOAc/hexane=4:1) at a flow rate of 1.0 mL/min. C$_{20}$H$_{18}$N$_6$O$_5$; pale yellow solid; mp 226-228° C.; TLC (EtOAc/hexane=1:1) R$_f$=0.1; IR ν$_{max}$ (neat) 3365, 2916, 2848, 1722, 1661, 1611, 1509, 1441, 1403, 1266, 1026, 878, 798, 760 cm$^{-1}$; $^1$H NMR (400 MHz, DMSO-d$_6$) δ 10.56 (1H, br), 10.11 (1H, br), 9.11 (1H, br), 7.79 (1H, d, J=8.4 Hz), 7.70 (1H, d, J=2.0 Hz), 7.55 (1H, J=8.4 Hz), 7.51 (1H, d, J=6.8 Hz), 7.29 (1H, d, J=8.0 Hz), 7.15 (1H, d, J=7.6 Hz), 6.94 (1H, d, J=8.8 Hz), 6.14 (2H, br), 3.79 (3H, s), 3.75 (3H, s); $^{13}$C NMR (100 MHz, DMSO-d$_6$) δ 155.6, 155.5, 152.5, 151.5, 149.5, 149.3, 146.2, 134.2, 130.8, 130.3, 130.0, 120.8, 120.7, 119.2, 115.8, 114.4, 112.8, 111.7, 55.9, 55.6; ESI-HRMS calcd for C$_{20}$H$_{17}$N$_6$O$_5$: 421.1260, found: m/z 421.1250 [M−H]$^-$.

2-(4-Ethoxyphenyl)-9-hexyl-8-oxopurine-6 (N-hydroxy)-carboximidamide (14g)

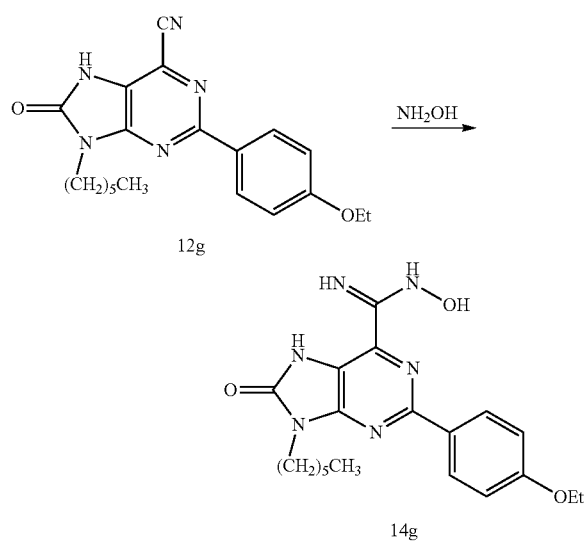

168

A mixture of compound 12g (15 mg, 0.04 mmol), hydroxylamine hydrochloride (11 mg, 0.16 mmol) and sodium acetate trihydrate (22 mg, 0.16 mmol) in THF (1.35 mL) and MeOH (1.3 mL) was stirred at room temperature for 1.5 h. The mixture was concentrated under reduced pressure, and purified by flash chromatography on a silica gel column with elution of MeOH/CH$_2$Cl$_2$ (1:20 to 1:9) to give compound 14g (12 mg, 75% yield). C$_{20}$H$_{26}$N$_6$O$_3$; pale yellow solid; TLC (EtOAc/hexane=1:1) R$_f$=0.3; $^1$H NMR (400 MHz, (CD$_3$)$_2$CO) δ 8.48 (2H, d, J=8.8 Hz), 7.00 (2H, d, J=8.8 Hz), 6.06 (1H, br), 4.13 (2H, q, J=7.2 Hz), 3.99 (2H, t, J=7.2 Hz), 1.86 (2H, t, J=6.8 Hz), 1.38-1.42 (6H, m), 1.30-1.33 (3H, m), 0.87 (3H, t, J=7.2 Hz); $^{13}$C NMR (100 MHz, (CD$_3$)$_2$CO) δ 161.7, 157.1, 154.0, 152.6, 151.0, 134.3, 131.2, 130.2, 130.1 (2×), 115.0 (2×), 64.2, 40.3, 32.0, 28.8, 27.0, 23.2, 15.1, 14.3; ESI-HRMS calcd for C$_{20}$H$_{25}$N$_6$O$_3$: 397.1988, found: m/z 397.1981 [M−H]$^-$.

2-(4-Ethoxyphenyl)-9-(2-methoxyphenyl)-7-methyl-8-oxopurine-6-carbonitrile (15a')

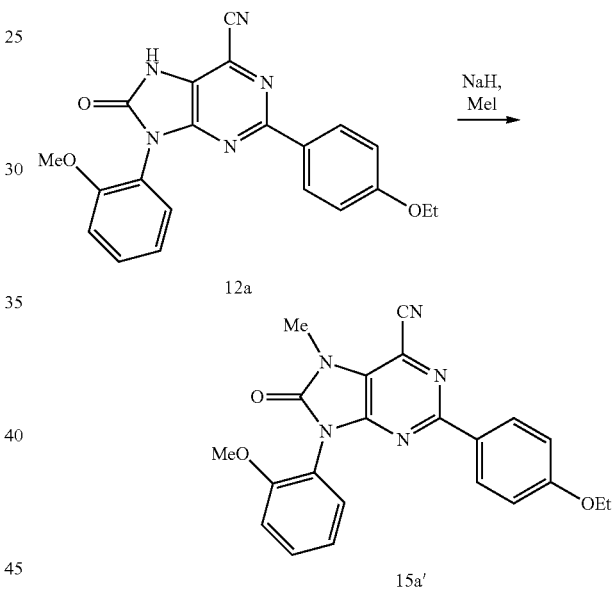

A mixture of compound 12a (20 mg, 0.052 mmol) and NaH (4 mg, 0.1 mmol) in anhydrous DMF (0.6 mL) was stirred for 15 min at room temperature. Methyl iodide (5 μL) was added, and the mixture was stirred at room temperature for additional 2 h. The solution was concentrated under reduced pressure, and washed successively with H$_2$O and Et$_2$O to give compound 15a (20 mg, 94% yield). The purity of compound 15a' was 95.1% as shown by HPLC on a Platisil Silica column (Dikma, 4.6×250 mm, 5 μm particle size), t$_R$=16.81 min (EtOAc/hexane=1:2) at a flow rate of 1.0 mL/min. C$_{22}$H$_{19}$N$_5$O$_3$; white solid; mp 235-237° C.; TLC (EtOAc/hexane=1:1) R$_f$=0.7; IR ν$_{max}$ (neat) 3418, 1745, 1604, 1509, 1445, 1403, 1251, 1159, 1019, 863, 779, 737, 696 cm$^{-1}$; $^1$H NMR (400 MHz, CDCl$_3$) δ 8.19 (2H, dt, J=4.8, 2.4 Hz), 7.49-7.53 (1H, m), 7.37 (1H, dd, J=6.0, 1.2 Hz), 7.09-7.14 (2H, m), 6.87 (2H, dt, J=5.2, 2.4 Hz), 4.05 (2H, q, J=7.2 Hz), 3.77 (3H, s), 3.76 (3H, s), 1.40 (3H, t, J=7.2 Hz); $^{13}$C NMR (100 MHz, CDCl$_3$) δ 161.3, 158.4, 155.3, 152.2, 151.7, 131.2, 129.6 (3×), 128.8, 123.7, 121.0, 119.9, 114.9, 114.7, 114.3 (2×), 112.5, 63.6, 55.9, 28.2, 14.7;

ESI-HRMS calcd for $C_{22}H_{20}N_5O_3$: 402.1566, found: m/z 402.1559 [M+H]$^+$. $C_{22}H_{19}N_5O_3$; white solid; TLC (EtOAc/hexane=1:1) $R_f$=0.7; $^1$H NMR (400 MHz, CDCl$_3$) δ 8.19 (2H, dt, J=4.8, 2.4 Hz), 7.49-7.53 (1H, m), 7.37 (1H, dd, J=6.0, 1.2 Hz), 7.09-7.14 (2H, m), 6.87 (2H, dt, J=5.2, 2.4 Hz), 4.05 (2H, q, J=7.2 Hz), 3.77 (3H, s), 3.76 (3H, s), 1.40 (3H, t, J=7.2 Hz); $^{13}$C NMR (100 MHz, CDCl$_3$) δ 161.3, 158.4, 155.3, 152.2, 151.7 131.2, 129.6 (3×), 128.8, 123.7, 121.0, 119.9, 114.9, 114.7, 114.3 (2×), 112.5, 63.6, 55.9, 28.2, 14.7; ESI-HRMS calcd for $C_{22}H_{20}N_5O_3$: 402.1566, found: m/z 402.1559 [M+H]$^+$.

7-Allyl-2-(4-ethoxyphenyl)-9-(2-methoxyphenyl)-8-oxopurine-6-carbonitrile (15b)

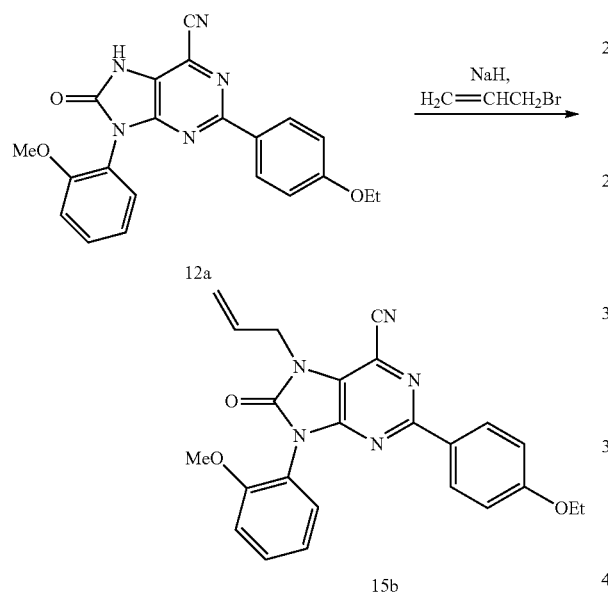

A mixture of compound 12a (30 mg, 0.077 mmol) and NaH (6 mg, 0.15 mmol) in anhydrous DMF (1.2 mL) was stirred for 10 min at room temperature. Allyl bromide (0.01 mL) was added and the mixture was stirred under room temperature for additional 4 h. The solution was quenched with water, and extracted with CH$_2$Cl$_2$ and H$_2$O. The organic phase was dried over MgSO$_4$, filtered, and purified by flash chromatography on a silica gel column with elution of EtOAc/hexane (1:4) to give compound 15b (14 mg, 42% yield). The purity of compound 15b was 96.1% as shown by HPLC on a Platisil Silica column (Dikma, 4.6×250 mm, 5 μm particle size), $t_R$=11.5 min (EtOAc/hexane=1:3) at a flow rate of 1.0 mL/min. $C_{24}H_{21}N_5O_3$; pale yellow solid; mp 144-146° C.; TLC (EtOAc/hexane=1:1) $R_f$=0.8; IR $v_{max}$ (neat) 3407, 2920, 2855, 1757, 1589, 1509, 1471, 1414, 1380, 1251, 1163, 1045, 836, 791, 760 cm$^{-1}$; $^1$H NMR (400 MHz, CDCl$_3$) δ 8.19 (2H, dt, J=9.2, 2.8 Hz), 7.49-7.53 (1H, m), 7.40 (1H, dd, J=7.8, 1.6 Hz), 7.09-7.15 (2H, m), 6.87 (2H, dt, J=9.6, 2.8 Hz), 5.99-6.09 (1H, m), 5.30-5.37 (2H, m), 4.81 (2H, dt, J=5.6, 1.6 Hz), 4.03 (2H, q, J=6.8 Hz), 3.76 (3H, s), 1.40 (3H, t, J=6.8 Hz); $^{13}$C NMR (100 MHz, CDCl$_3$) δ 161.3, 158.4, 155.3, 151.9 (2×), 131.2, 130.8, 129.6 (3×), 128.8, 122.8, 121.0, 120.0, 118.9, 115.2, 114.7, 114.3 (2×), 112.5, 63.5, 55.9, 43.6, 14.7; ESI-HRMS calcd for $C_{24}H_{22}N_5O_3$: 428.1723, found: m/z 428.1711 [M+H]$^+$.

7-Benzyl-2-(4-ethoxyphenyl)-9-(2-methoxyphenyl)-8-oxopurine-6-carbonitrile (15c)

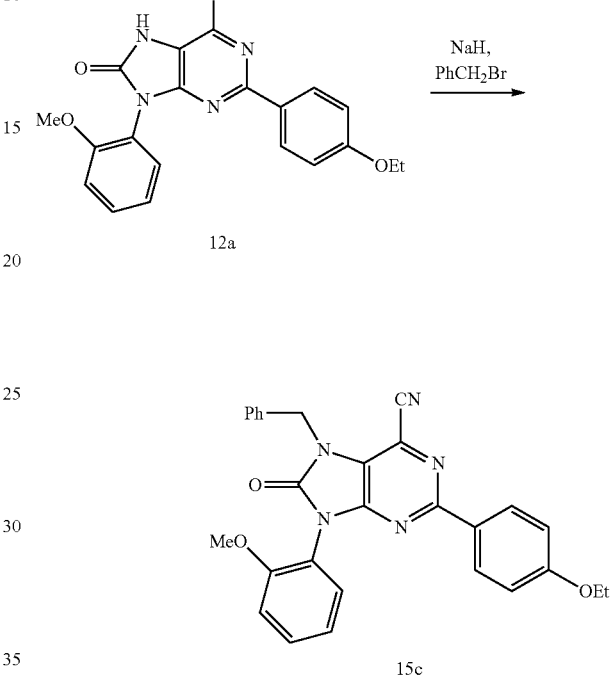

A mixture of compound 12a (30 mg, 0.077 mmol) and NaH (6 mg, 0.15 mmol) in anhydrous DMF (1.2 mL) was stirred for 10 min at room temperature. Benzyl bromide (0.014 mL) was added and the mixture was stirred under room temperature for additional 3 h. The solution was quenched with water, and extracted with CH$_2$Cl$_2$ and H$_2$O. The organic phase was dried over MgSO$_4$, filtered, and purified by flash chromatography on a silica gel column with elution of EtOAc/hexane (1:4) to give compound 15c (24 mg, 64% yield). The purity of compound 15c was 95.1% as shown by HPLC on a Platisil Silica column (Dikma, 4.6× 250 mm, 5 μm particle size), $t_R$=10.6 min (EtOAc/hexane=1:3) at a flow rate of 1.0 mL/min. $C_{28}H_{23}N_5O_3$; pale yellow solid; mp 164-166° C.; TLC (EtOAc/hexane=1:2) R=0.8; IR $v_{max}$ (neat) 3418, 2920, 2855, 2349, 1756, 1593, 1517, 1479, 1414, 1380, 1255, 1163, 1038, 855, 791, 749 cm$^{-1}$; $^1$H NMR (400 MHz, CDCl$_3$) δ 8.17 (2H, dd, J=4.8, 2.4 Hz), 7.50-7.53 (2H, m), 7.42 (1H, dd, J=6.4, 1.6 Hz), 7.31-7.38 (4H, m), 7.01-7.16 (2H, m), 6.86 (2H, dd, J=4.8, 2.4 Hz), 5.38 (2H, d, J=8.4 Hz), 4.04 (2H, q, J=7.2 Hz), 3.79 (3H, s), 1.40 (3H, t, J=7.2 Hz); 13C NMR (100 MHz, CDCl$_3$) 161.2, 158.4, 155.2, 152.4, 151.9, 135.1, 131.2, 129.6 (2×), 129.5 (2×), 129.0, 128.6, 128.3 (2×), 128.0, 122.8, 120.1, 122.0, 115.2, 114.9, 114.2 (2×), 112.5, 63.5, 55.9, 45.1, 14.7; ESI-HRMS calcd for $C_{28}H_{24}N_5O_3$: 478.1879, found: m/z 478.1885 [M+H]+.

2-(4-Ethoxyphenyl)-9-(2-methoxyphenyl)-7-methyl-8-oxopurine-6-carboxamide (16a')

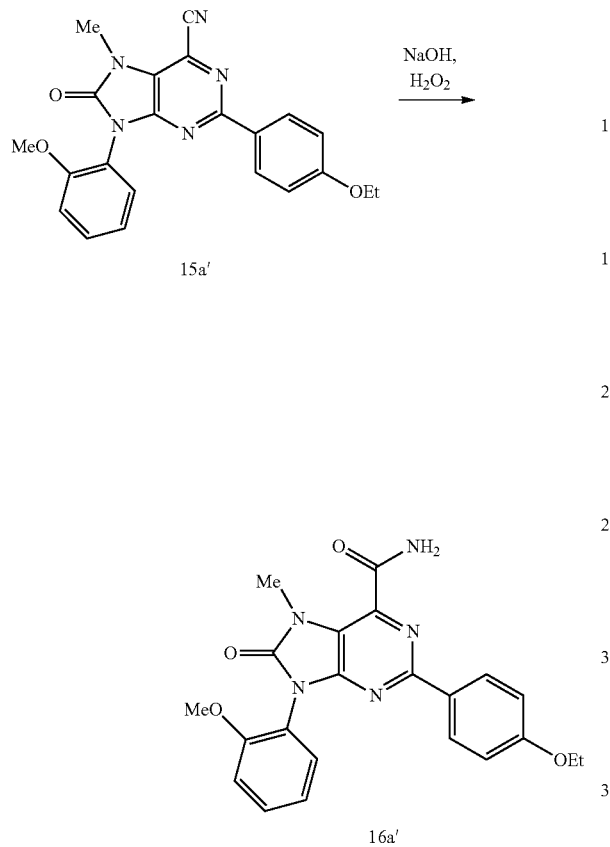

A mixture of nitrile compound 15a' (8 mg, 0.02 mmol) and 4.8 M NaOH$_{(aq)}$ (1 μL) in CH$_2$Cl$_2$ (0.5 mL) was carefully added H$_2$O$_2$ (0.08 mmol, 8 μL of 30% aqueous solution). The solution was stirred at room temperature for 48 h, and then extracted with CH$_2$Cl$_2$ and H$_2$O. The organic phase was dried over MgSO$_4$, filtered, and purified by flash chromatography on a silica gel column with elution of CH$_2$Cl$_2$/MeOH (40:1) to give compound 16a' (6 mg, 70% yield). The purity of compound 16a' was 98.7% as shown by HPLC on a Platisil Silica column (Dikma, 4.6×250 mm, 5 m particle size), $t_R$=14.8 min (EtOAc/hexane=2:1) at a flow rate of 1.0 mL/min. C$_{22}$H$_{21}$N$_5$O$_4$; white solid; mp 222-224° C.; TLC (CH$_2$Cl$_2$/MeOH=30:1) R$_f$=0.2; IR ν$_{max}$ (neat) 3433, 2932, 1631, 1513, 1448, 1251, 1080, 1049, 1019 cm$^{-1}$; $^1$H NMR (400 MHz, CDCl$_3$) δ 8.17 (2H, d, J=8.8 Hz), 8.00 (1H, br), 7.49 (1H, t, J=7.6 Hz), 7.38 (1H, dd, J=6, 1.6 Hz), 7.08-7.13 (2H, m), 6.88 (2H, d, J=9.2 Hz), 5.78 (1H, br), 4.05 (2H, q, J=7.2 Hz), 3.90 (3H, s), 3.77 (3H, s), 1.41 (3H, t, J=6.8 Hz); $^{13}$C NMR (100 MHz, CDCl$_3$) δ 166.0, 160.9, 155.6, 155.5, 153.5 153.0, 133.7, 130.8, 129.8, 129.3, 129.2 (2×), 121.0, 120.9 (2×), 114.2 (2×), 112.5, 63.5, 55.9, 32.7, 14.8; ESI-HRMS calcd for C$_{22}$H$_{22}$N$_5$O$_4$: 420.1672, found: m/z 420.1671 [M+H]+.

6-Cyano-2-(4-ethoxyphenyl)-9-(2-methoxyphenyl)purin-8-yl ethyl carbonate (17a)

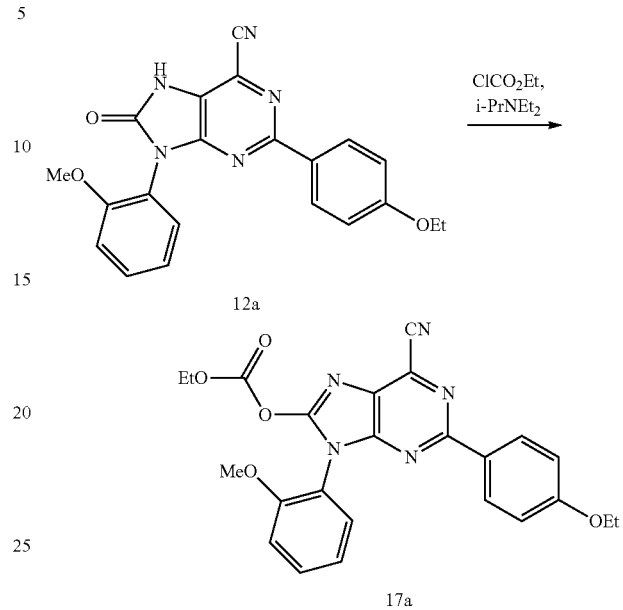

A mixture of compound 12a (10 mg, 0.026 mmol), ethyl chloroformate (7 μL, 0.07 mmol), and DIEA (15 μL, 0.09 mmol) in anhydrous CH$_2$Cl$_2$ (0.4 mL) was stirred at 0° C. for 3 h. The solution was concentrated under reduced pressure, and washed successively with H$_2$O, Et$_2$O, and CH$_2$Cl$_2$ to give compound 17a (8 mg, 67% yield). The purity of compound 17a was 99.6% as shown by HPLC on a Platisil Silica column (Dikma, 4.6×250 mm, 5 m particle size), $t_R$=19.3 min (EtOAc/hexane=1:3) at a flow rate of 1.0 mL/min. C$_{24}$H$_{21}$N$_5$O$_5$; white solid; mp 270-272° C.; TLC (EtOAc/hexane=1:2)R$_f$=0.4; IR ν$_{max}$ (neat) 3418, 2985, 2920, 2852, 1814, 1635, 1582, 1513, 1456, 1407, 1293, 1258, 1224, 1148, 1124, 1087, 992, 848, 787, 764 cm$^{-1}$; $^1$H NMR (400 MHz, CDCl$_3$) δ 8.20 (2H, d, J=9.2 Hz), 7.53 (1H, t, J=7.8 Hz), 7.36 (1H, dd, J=7.8, 2.0 Hz), 7.10-7.15 (2H, m), 6.88 (2H, d, J=8.8 Hz), 4.66 (2H, q, J=7.2 Hz), 4.05 (2H, q, J=7.2 Hz), 3.77 (3H, s), 1.51 (3H, t, J=7.2 Hz), 1.41 (3H, t, J=7.2 Hz); $^{13}$C NMR (100 MHz, CDCl$_3$) δ 162.0, 160.4, 155.5, 152.3, 148.1, 147.8, 131.6, 130.2 (2×), 129.6, 128.2, 122.0, 121.1, 119.6, 118.1, 114.7 (2×), 114.6, 112.7, 65.1, 63.7, 56.0, 14.7, 14.2; ESI-HRMS calcd for C$_{24}$H$_{24}$N$_5$O$_5$: 460.1621, found: m/z 460.1624 [M+H]+.

Tert-butyl 6-cyano-2-(4-ethoxyphenyl)-9-(2-methoxyphenyl)purin-8-yl carbonate (17b)

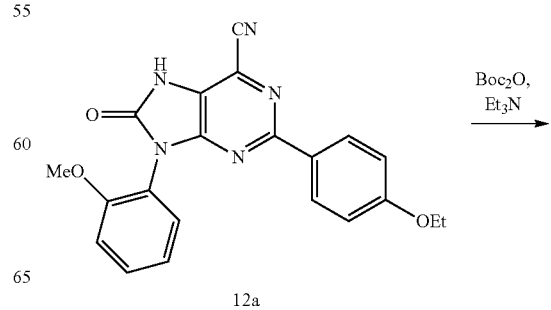

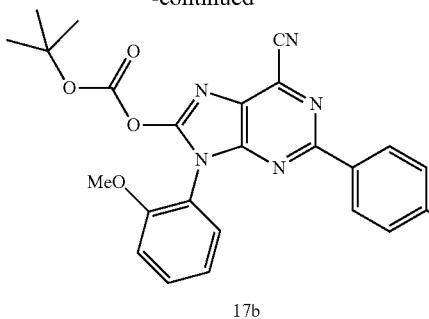

17b

Compound 12a (50 mg, 0.13 mmol), Boc anhydride (59 µL, 0.26 mmol) and triethylamine (0.1 mL, 0.73 mmol) in CH$_2$Cl$_2$ (3 mL) was stirred at room temperature for 4 h. The mixture was extracted with CH$_2$Cl$_2$ and H$_2$O. The organic phase was dried over MgSO$_4$, filtered, and purified by flash chromatography on a silica gel column with elution of EtOAc/hexane (1:5) to give compound 17b (44 mg, 70% yield). C$_{26}$H$_{25}$N$_5$O$_5$; pale yellow solid; mp 278-280 OC; TLC (EtOAc/hexane=1:4) R$_f$=0.3; IR $v_{max}$ (neat) 3441, 1794, 1650, 1612, 1520, 1479, 1388, 1262, 1152, 1042, 772 cm$^{-1}$; $^1$HNMR (400 MHz, CDCl$_3$) δ 8.20 (2H, dd, J=6.8, 2.0 Hz), 7.51 (1H, td, J=8.0, 1.6 Hz), 7.37 (1H, dd, J=7.6, 2.0 Hz), 7.09-7.14 (2H, m), 6.87 (2H, dd, J=6.8, 2.0 Hz), 4.05 (2H, q, J=6.8 Hz), 3.77 (3H, s), 1.70 (9H, s), 1.40 (3H, J=6.8 Hz); $^{13}$C NMR (100 MHz, CDCl$_3$) δ 161.7, 160.0, 155.3, 152.0, 148.0, 146.7, 131.5, 130.0 (2×), 129.5, 128.0, 121.5, 121.0, 119.3, 118.5, 114.7, 114.3 (2×), 112.4, 88.1, 63.6, 55.9, 27.9 (3×), 14.7; ESI-HRMS calcd for C$_{26}$H$_{26}$N$_5$O$_5$: 488.1934, found: m/z 488.1942 [M+H]$^+$. Anal. Cacld for (C$_{26}$H$_{25}$N$_5$O$_5$·½H$_2$O): C, 62.89; H, 5.28; N, 14.11. Found: C, 63.15; H, 5.04; N, 14.11.

Benzyl 6-cyano-2-(4-ethoxyphenyl)-9-(2-methoxyphenyl)purin-8-yl carbonate (17c)

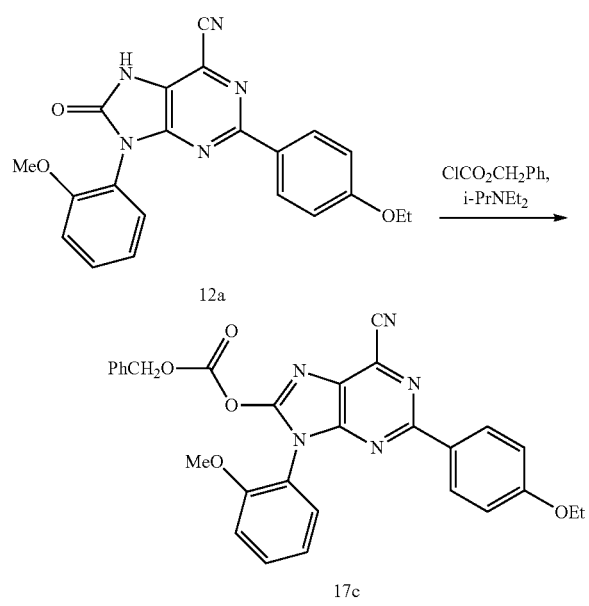

A mixture of compound 12a (50 mg, 0.13 mmol), benzyl chloroformate (55 µL, 0.39 mmol) and DIEA (75 µL, 0.18 mmol) in anhydrous CH$_2$Cl$_2$ (2 mL) was stirred at 0° C. for 3 h. The solution was concentrated under reduced pressure, and washed successively with H$_2$O, Et$_2$O, MeOH and EtOAc to give compound 17c (49 mg, 73% yield). The purity of compound 17c was 97.0% as shown by HPLC on a Platisil Silica column (Dikma, 4.6×250 mm, 5 m particle size), t$_R$=5.6 min (EtOAc/hexane=0.9:1.1) at a flow rate of 1.0 mL/min. C$_{29}$H$_{23}$N$_5$O$_5$; white solid; mp 228-230 OC; TLC (EtOAc/hexane=1:1) R$_f$=0.8; IR $v_{max}$ (neat) 3662, 3646, 3152, 1821, 1791, 1589, 1517, 1479, 1403, 1255, 1159, 1045, 1123, 783, 760 cm$^{-1}$; $^1$H NMR (400 MHz, DMSO-d$_6$) δ 8.06 (2H, d, J=8.8 Hz), 7.55-7.62 (3H, m), 7.48 (1H, dd, J=7.6, 2.0 Hz), 7.38-7.45 (3H, m), 7.33 (1H, d, J=7.2 Hz), 7.18 (1H, t, J=7.0 Hz), 7.02 (2H, J=8.8 Hz), 5.57 (2H, J=3.6 Hz), 4.07 (2H, q, J=7.2 Hz), 3.78 (3H, s), 1.33 (3H, t, J=7.2 Hz); $^{13}$C NMR (100 MHz, DMSO-d$_6$) δ 161.2, 158.6, 155.1, 152.5, 148.1, 147.4, 134.6, 131.6, 129.6, 129.3 (2×), 128.5 (3×), 128.3 (3×), 127.4, 120.8, 120.6, 119.1, 115.1, 114.7 (2×), 113.0, 68.9, 63.3, 56.0, 14.5; ESI-HRMS calcd for C$_{29}$H$_{24}$N$_5$O$_5$: 522.1777, found: m/z 522.1781 [M+H]+.

6-Cyano-2-(4-ethoxyphenyl)-9-(2-methoxyphenyl)purin-8-yl phenyl carbonate (17d)

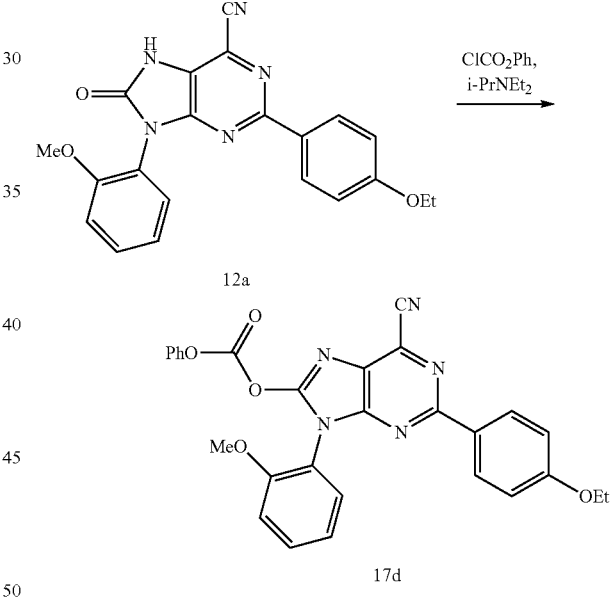

Compound 12a (20 mg, 0.052 mmol), phenyl chloroformate (20 µL, 0.16 mmol), and DIEA (30 µL, 0.18 mmol) in anhydrous CH$_2$Cl$_2$ (0.8 mL) was stirred at 0° C. for 2 h. The solution was concentrated under reduced pressure and washed successively with H$_2$O, Et$_2$O, and CH$_2$Cl$_2$ to give compound 17d (21 mg, 80% yield). C$_{28}$H$_{21}$N$_5$O$_5$; white solid; mp 247-249° C.; TLC (EtOAc/hexane=1:1)R$_f$=0.8; IR $v_{max}$ (neat) 3202, 2369, 2346, 1791, 1593, 1513, 1479, 1410, 1308, 1251, 1220, 1163, 1023, 851, 783, 749, 692 cm$^{-1}$; $^1$H NMR (400 MHz, CDCl$_3$) 8.23 (2H, dd, J=6.8, 2.0 Hz), 7.53-7.57 (1H, m), 7.37-7.47 (5H, m), 7.32-7.34 (1H, m), 7.12-7.18 (2H, m), 6.89 (2H, dd, J=7.2, 2.0 Hz), 4.06 (2H, q, J=7.0 Hz), 3.81 (3H, s), 1.41 (3H, t, J=7.2 Hz); $^{13}$C NMR (100 MHz, CDCl$_3$) 162.0, 160.6, 155.3, 152.4, 149.6, 147.5, 146.9, 131.7, 130.2 (2×), 129.8 (2×), 129.5, 127.8, 127.1, 122.3, 121.3 (2×), 121.1, 119.2, 117.8, 114.5, 114.4 (2×), 112.5, 63.6, 56.0, 14.7; ESI-HRMS calcd for C$_{28}$H$_{22}$N$_5$O$_5$: 508.1621, found: m/z 508.1623 [M+H]$^+$. Anal. Cacld for (C$_{28}$H$_{21}$N$_5$O$_5$·½H$_2$O): C, 65.11; H, 4.29; N, 13.56. Found: C, 65.41; H, 4.06; N, 13.44.

2-(4-Ethoxyphenyl)-9-(2-methoxyphenyl)-8-oxopurine-6-carboxylic acid (18a)

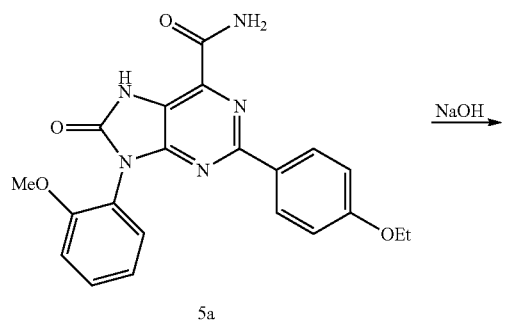

5a

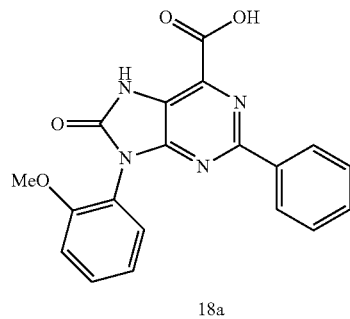

18a

A solution of compound 5a (100 mg, 0.25 mmol) in EtOH (10 mL) and 10 M NaOH(aq) (10 mL) was heated at 100° C. under reflux for 3 h. The white precipitate was collected by filtration, and washed successively with water, ice cold ethanol and Et$_2$O. The collected solids were dried in the air, suspended in THF (5 mL), and added 1 M HCl$_{(aq)}$ dropwise until the solids completely dissolved. The solution was subjected to recrystallization to give the carboxylic acid 18a (60 mg, 59% yield). C$_{21}$H$_{18}$N$_4$O$_5$; white solid; mp=192.6-193.9° C.; $^1$H NMR (600 MHz, DMSO-d$_6$) δ 11.67 (1H, s), 8.13 (2H, d, J=8.9 Hz), 7.58-7.53 (1H, m), 7.49 (1H, dd, J=7.7, 1.5 Hz), 7.29 (1H, d, J=8.2 Hz), 7.15 (1H, t, J=7.6 Hz), 6.97 (2H, d, J=8.9 Hz), 4.05 (2H, q, J=7.0 Hz), 3.75 (3H, s), 1.33 (3H, t, J=7.0 Hz); $^{13}$C NMR (151 MHz, DMSO-d$_6$) δ 165.2, 165.0, 160.1, 155.4, 155.4, 153.3, 152.6, 130.9, 130.1, 129.5, 128.8 (2×), 120.9, 120.7, 120.6, 114.2 (2×), 112.8, 63.1, 55.9, 14.6. ESI-HRMS calcd for C$_{21}$H$_{19}$N$_4$O$_5$: 407.1350, found: m/z 407.1349 [M+H]$^+$.

2-Isopropyl-9-(2-methoxyphenyl)-8-oxopurine-6-carboxylic acid (18b)

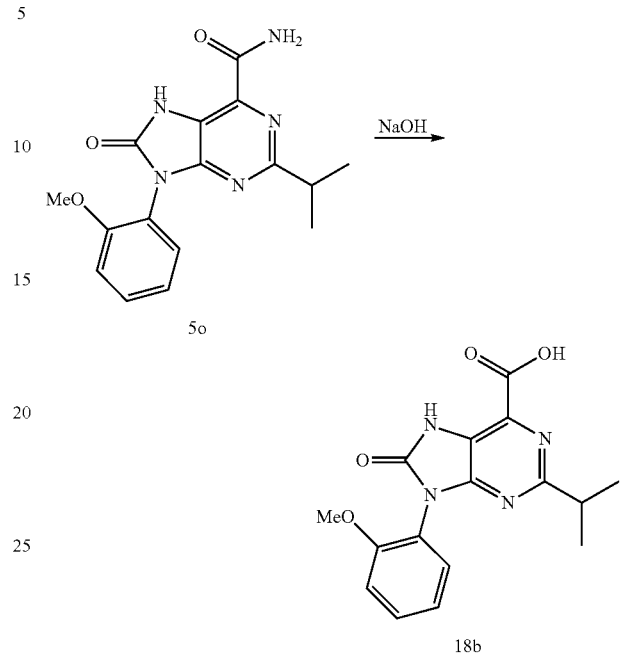

A solution of compound 5o (110 mg, 0.34 mmol) in MeOH (8 mL) and 10 M NaOH$_{(aq)}$ (8 mL) was heated at 100° C. under reflux for 3 h. The mixture was cooled in an ice bath, and adjusted to pH z 2 by addition of 6 M HCl$_{(aq)}$. The mixture was then extracted with EtOAc (3×). The organic phase was dried over Mg$_2$SO$_4$, and concentrated under reduced pressure to give the carboxylic acid 18b (104.8 mg, 94% yield). C$_{16}$H$_{16}$N$_4$O$_4$; white solid; $^1$H NMR (600 MHz, CD$_3$OD) δ 7.54 (1H, ddd, J=8.5, 7.6, 1.6 Hz), 7.41 (1H, dd, J=7.7, 1.6 Hz), 7.24 (1H, d, J=8.4 Hz), 7.13 (1H, td, J=7.6, 1.1 Hz), 3.79 (3H, s), 3.17 (1H, ddd, J=17.2, 8.7, 5.3 Hz), 1.25 (6H, dd, J=6.9, 3.7 Hz); $^{13}$C NMR (126 MHz, DMSO-d$_6$) δ 166.0, 165.0, 155.3, 153.1, 152.6, 130.8, 130.6, 130.1, 121.0, 120.7, 120.6, 112.8, 55.8, 36.5, 21.9, 21.7. ESI-HRMS calcd for C$_{16}$H$_{16}$N$_4$O$_4$: 329.1244, found: m/z 329.1253 [M+H]$^+$.

2-(4-Ethoxyphenyl)-9-(2-methoxyphenyl)-8-oxopurine-6-(N-hydroxy)carboxamide (19a)

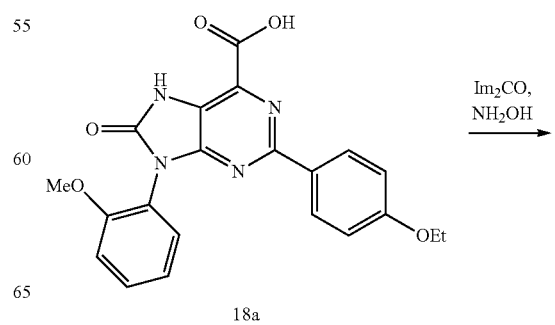

18a

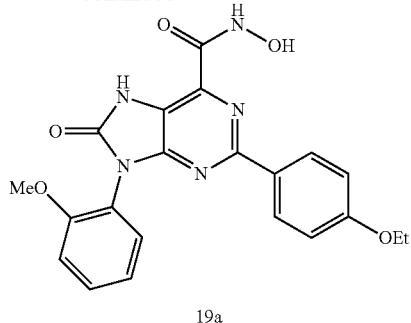

19a

Under an atmosphere of nitrogen, a mixture of acid compound 18a (51 mg, 0.13 mmol) and 1,1'-carbonyldiimidazole (30 mg, 0.19 mmol) in anhydrous THF (5 mL) was stirred at room temperature for 3 h. Hydroxylamine hydrochloride (17.2 mg, 0.25 mmol) was added, and the mixture was stirred at room temperature for 16 h. The white precipitate was filtered, and washed successively with ice-cold Et$_2$O, MeOH and THF to give hydroxamate compound 19a (9.3 mg, 17% yield). C$_{21}$H$_{19}$N$_5$O$_5$; white solid; mp=280° C. (decomposed); $^1$H NMR (600 MHz, DMSO-d$_6$) δ 11.69 (1H, s), 9.33 (1H, s), 8.30 (2H, d, J=8.6 Hz), 7.56-7.52 (1H, m), 7.47 (1H, d, J=7.4 Hz), 7.28 (1H, d, J=8.4 Hz), 7.14 (1H, t, J=7.6 Hz), 6.94 (2H, d, J=8.9 Hz), 4.06 (2H, q, J=7.0 Hz), 3.74 (3H, s), 1.33 (3H, t, J=7.0 Hz); $^{13}$C NMR (151 MHz, DMSO-d$_6$) δ 160.5, 160.3, 155.4, 155.0, 153.2, 152.9, 132.5, 130.9, 130.2, 129.4 (2×), 129.3, 120.8, 120.7, 118.9, 114.1 (2×), 112.9, 63.2, 56.0, 14.6. ESI-HRMS calculated for C$_{21}$H$_{20}$N$_5$O$_5$: 422.1459, found: m/z 422.1457 [M+H]$^+$.

2-(4-Ethoxyphenyl)-9-(2-methoxyphenyl)-8-oxopurine-6-(N-methoxy)carb oxamide (19b)

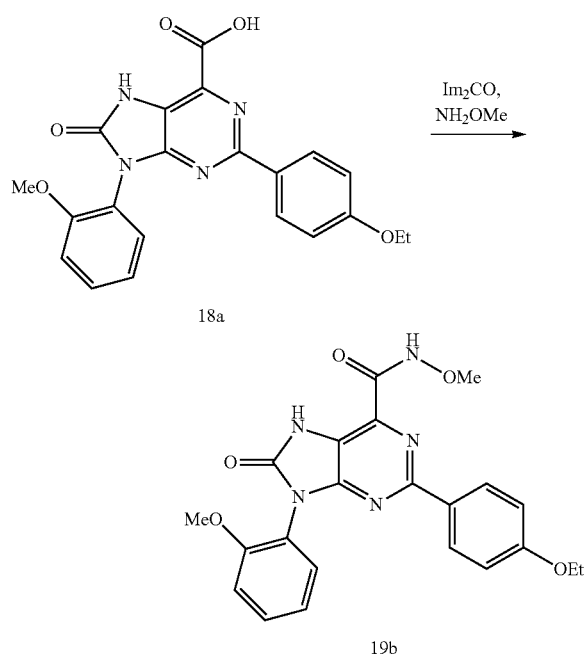

18a

19b

Under and atmosphere of nitrogen, a mixture of acid compound 18a (53 mg, 0.13 mmol) and 1,1'-carbonyldiimidazole (32 mg, 0.20 mmol) in anhydrous THF (5 mL) was stirred at room temperature for 1 h. A solution of methoxyamine hydrochloride (21.7 mg, 0.26 mmol) in water (1 mL) was added, and the mixture was stirred at room temperature for 3 h. THF was removed under reduced pressure, and the residue was extracted with CH$_2$Cl$_2$ (3×) and water. The organic phase was collected, dried over anhydrous MgSO$_4$, concentrated under reduced pressure, and purified by flash chromatography (1% to 5% MeOH in CH$_2$Cl$_2$ containing 10 mM NEt$_3$) on a silica gel column to give compound 19b (16.4 mg, 29% yield). C$_{22}$H$_{21}$N$_5$O$_5$; white solid; mp=260.5-261.6° C.; $^1$H NMR (600 MHz, DMSO-d$_6$) δ 12.22 (1H, s), 11.75 (1H, s), 8.29 (2H, d, J=8.9 Hz), 7.58-7.52 (1H, m), 7.48 (1H, dd, J=7.7, 1.6 Hz), 7.29 (1H, d, J=7.6 Hz), 7.15 (1 H, td, J=7.6, 1.1 Hz), 6.98-6.92 (2H, m), 4.06 (2H, q, J=7.0 Hz), 3.81 (3H, s), 3.74 (3H, s), 1.33 (3H, t, J=7.0 Hz); $^{13}$C NMR (151 MHz, DMSO-d$_6$) δ 160.5, 160.3, 155.3, 154.9, 153.2, 152.8, 131.7, 130.8, 130.1, 129.3 (2×), 129.1, 120.7, 120.6, 114.1 (2×), 112.8, 63.5, 63.1, 55.9, 14.5. ESI-HRMS calculated for C$_{22}$H$_{22}$N$_5$O$_5$: 436.1615, found: m/z 436.1633 [M+H]+.

2-Isopropyl-9-(2-methoxyphenyl)-8-oxopurine-6-hydroxamate (19c)

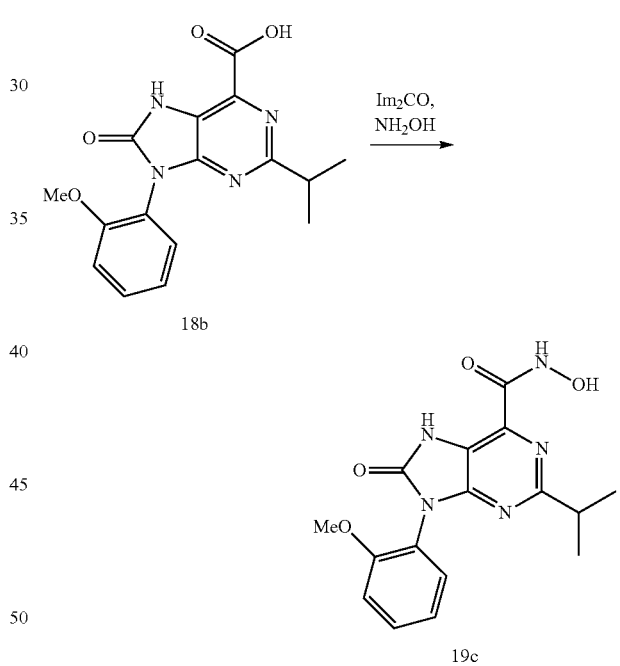

18b

19c

Under an atmosphere of nitrogen, a mixture of acid compound 18b (48 mg, 0.15 mmol) and 1,1'-carbonyldiimidazole (50 mg, 0.23 mmol) in anhydrous THF (5 mL) was stirred at room temperature for 2.5 h. Hydroxylamine hydrochloride (20.8 mg, 0.30 mmol) was added, and the mixture was stirred at room temperature for 3 h. Water (5 mL) was added to quench the reaction. THF was removed under reduced pressure, and the aqueous solution was extracted with EtOAc (3×). The organic phase was collected, dried over Mg$_2$SO$_4$, and concentrated under reduced pressure to give the hydroxamate compound 19c (22 mg, 43% yield). C$_{16}$H$_{17}$N$_5$O$_4$; orange solid; $^1$H NMR (600 MHz, DMSO-d$_6$) δ 11.57 (1H, s), 11.35 (1H, s), 9.29 (1H, s), 7.54-7.48 (1H, m), 7.42 (1H, dd, J=7.7, 1.7 Hz), 7.25 (1H, dd, J=8.4, 0.9

Hz), 7.11 (1H, td, J=7.6, 1.1 Hz), 3.73 (3H, s), 3.14-2.78 (1H, m), 1.21-1.16 (6H, m); $^{13}$C NMR (151 MHz, DMSO-d$_6$) δ 165.5, 155.3, 152.7, 150.3, 149.5, 132.1, 130.7, 130.1, 120.7, 120.6, 118.5, 112.7, 55.8, 36.4, 21.8, 21.6.

2-Isopropyl-9-(2-methoxyphenyl)-8-oxopurine-6-N-methoxy carboxamide (19d)

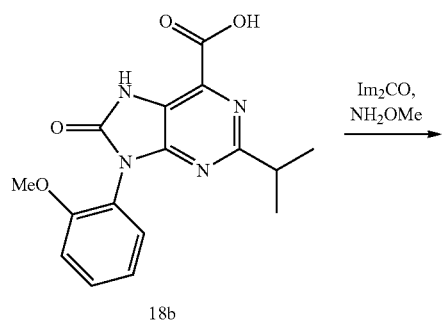

18b

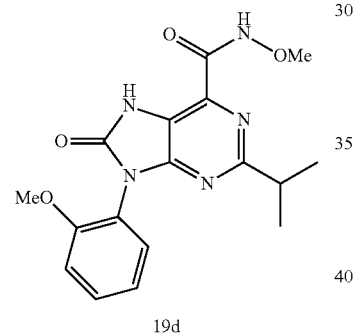

19d

Under an atmosphere of nitrogen, a mixture of acid compound 18b (12 mg, 0.04 mmol) and 1,1'-carbonyldiimidazole (9.7 mg, 0.06 mmol) in anhydrous THF (2 mL) was stirred at room temperature for 2 h. Methoxyamine hydrochloride (6.7 mg, 0.08 mmol) was added, and the mixture was stirred at room temperature for 2 h. Water (3 mL) was added to quench the reaction. THF was removed under reduced pressure, and the aqueous solution was extracted with EtOAc (3×). The organic phase was collected, dried over Mg$_2$SO$_4$, and concentrated under reduced pressure to give compound 19d (11 mg, 77% yield). C$_{17}$H$_{19}$N$_5$O$_4$; colorless oil; $^1$H NMR (600 MHz, DMSO-d$_6$) δ 11.92 (1H, s), 11.66 (1H, br s), 7.52 (1H, td, J=8.4, 1.7 Hz), 7.41 (1H, dd, J=7.7, 1.6 Hz), 7.25 (1H, d, J=7.7 Hz), 7.11 (1H, td, J=7.6, 1.0 Hz), 3.77 (3H, s), 3.72 (3H, s), 3.04-2.88 (1H, m), 1.19 (6H, dd, J=14.0, 7.1 Hz); $^{13}$C NMR (151 MHz, DMSO-d$_6$) δ 165.5, 160.5, 159.3, 155.3, 152.9, 152.8, 131.4, 130.8, 130.1, 120.6, 120.6, 112.7, 59.7, 55.8, 36.4, 21.8, 21.6.

2-(4-Ethoxyphenyl)-9-(2-methoxyphenyl)-8-oxopurine-6-carbohydrazide (20a)

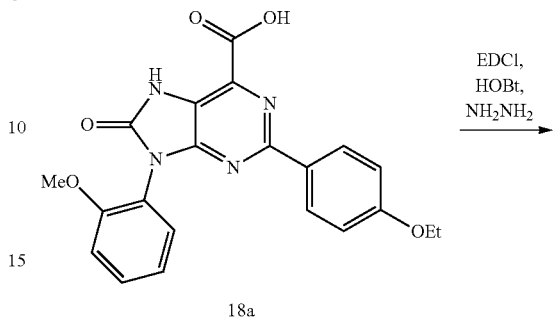

18a

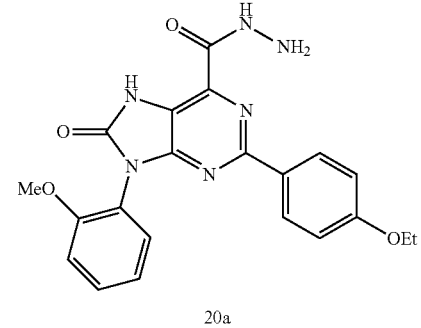

20a

A mixture of acid compound 18a (50 mg, 0.12 mmol), 1-ethyl-3-(3-dimethylaminopropyl)carbodiimide (EDCI, 26.8 mg, 0.14 mmol) and 1-hydroxybenzotriazole (HOBt, 21.4 mg, 0.14 mmol) in anhydrous DMF (5 mL) was stirred at room temperature for 2 h. The mixture was cooled to 0° C., and a solution of hydrazine monohydrate (12 mg, 0.24 mmol) in anhydrous DMF (0.5 mL) was added dropwise. The mixture was stirred at 0° C. for 1 h. After the reaction completed, water (15 mL) was added, and the suspended solids were collected by filtration. The crude product was purified by flash chromatography (1% to 5% MeOH in CH$_2$Cl$_2$ containing 10 mM NEt$_3$) on a silica gel column to give the hydrazide compound 20a (4.7 mg, 9% yield). C$_{21}$H$_{20}$N$_6$O$_4$; white solid; mp=273.7-274.5° C.; $^1$H NMR (600 MHz, DMSO-d$_6$) δ 11.84 (1H, s), 10.91 (1H, s), 8.20 (2H, d, J=8.9 Hz), 7.58-7.52 (1H, m), 7.49 (1H, d, J=6.9 Hz), 7.29 (1H, d, J=7.8 Hz), 7.15 (1H, td, J=7.6, 1.0 Hz), 6.98 (2H, d, J=8.9 Hz), 4.06 (2H, q, J=7.0 Hz), 3.75 (3H, s), 1.33 (3H, t, J=7.0 Hz); $^{13}$C NMR (151 MHz, DMSO-d$_6$) δ 160.3, 159.5, 155.4, 155.2, 155.0, 153.3, 152.9, 132.2, 130.9, 130.2, 129.4 (2×), 129.2, 120.8, 120.6, 114.2 (2×), 112.8, 63.2, 55.9, 14.6. ESI-HRMS calculated for C$_{21}$H$_{21}$N$_6$O$_4$: 421.1643, found: m/z 421.1627 [M+H]$^+$.

2-(4-Ethoxyphenyl)-9-(2-methoxyphenyl)-8-oxopurine-6-(N',N'-dimethyl)carbohydrazide (20b)

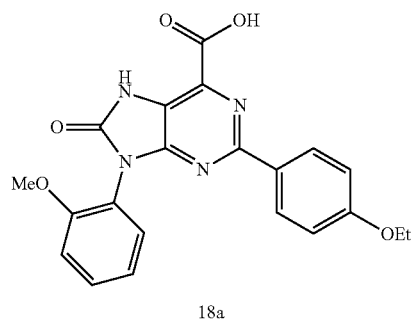

18a

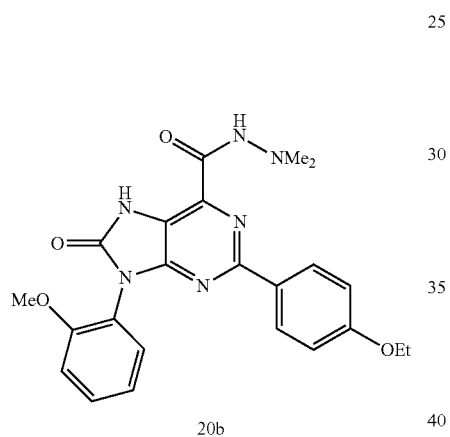

20b

Under an atmosphere of nitrogen, a mixture of acid compound 18a (102 mg, 0.25 mmol) and 1,1'-carbonyldiimidazole (62 mg, 0.38 mmol) in anhydrous THF (10 mL) was stirred at room temperature for 1 h. A solution of N',N'-dimethylhydrazine hydrochloride (48 mg, 0.50 mmol) in water (1 mL) was added, and the mixture was stirred at room temperature for 2 h. The yellow precipitate was collected by filtration, washed with ice-cold $Et_2O$, and purified by flash chromatography (0.5% to 5% MeOH in $CH_2Cl_2$) on a silica gel column to give compound 20b (53 mg, 47% yield). $C_{23}H_{24}N_6O_4$; yellow solid; mp=279.6-281.0 OC; $^1H$ NMR (500 MHz, $CDCl_3$) δ 9.30 (1H, s), 8.19 (2H, d, J=8.9 Hz), 7.48 (1H, ddd, J=8.3, 7.7, 1.6 Hz), 7.41 (1H, dd, J=7.7, 1.6 Hz), 7.15-7.05 (2H, m), 6.91-6.87 (2H, m), 4.05 (2H, d, J=7.0 Hz), 3.77 (3H, s), 2.79 (6H, s), 1.41 (3H, t, J=7.0 Hz); $^{13}C$ NMR (126 MHz, $CDCl_3$) δ 161.6, 160.9, 156.8, 155.4, 153.4, 152.5, 131.9, 130.9, 129.8, 129.4 (2×), 129.3, 120.9, 120.3, 119.2, 114.2 (2×), 112.4, 63.5, 55.9, 47.6 (2×), 14.7. ESI-HRMS calculated for $C_{23}H_{24}N_6O_4$: 449.1932, found: m/z 449.1953 [M+H]$^+$.

2-(4-Ethoxyphenyl)-9-(2-methoxyphenyl)-7-methyl-8-oxopurine-6-(N-hydroxy)carboximidamide (21a)

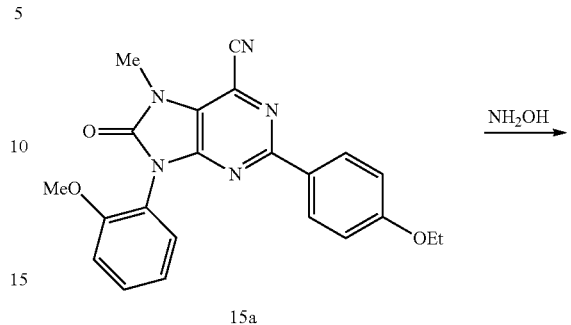

15a

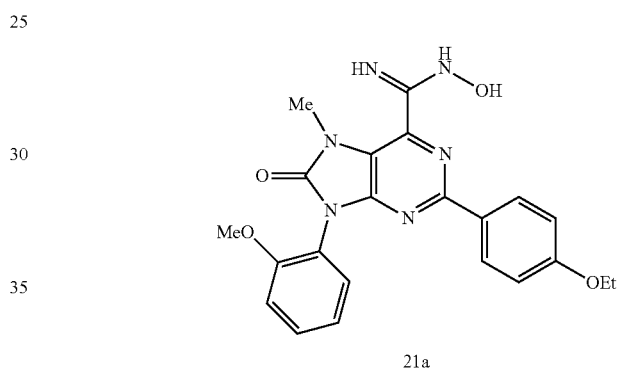

21a

Compound 15a (40 mg, 0.10 mmol), hydroxylamine hydrochloride (27 mg, 0.4 mmol), and sodium acetate trihydrate (54 mg, 0.4 mmol) in THF (2 mL) and MeOH (2 mL) was stirred at 60° C. for 1 h. The solution was concentrated under reduced pressure and washed successively with $H_2O$ and MeOH to give compound 21a (41 mg, 95% yield). The purity of compound 21a was 97.7% as shown by HPLC on an Platisil Silica column (Dikma, 4.6×250 mm, 5 μm particle size), $t_R$=9.2 min (EtOAc/hexane=2:1) at a flow rate of 1.0 mL/min. $C_{22}H_{22}N_6O_4$; white solid; mp 229-231° C.; TLC (EtOAc/hexane=1:1) $R_f$=0.4; IR $v_{max}$ (neat) 3357, 2927, 2855, 1814, 1749, 1604, 1509, 1479, 1399, 1258, 1045, 851, 787, 760 cm$^{-1}$; $^1H$ NMR (400 MHz, $(CD_3)_2CO$) δ 9.56 (1H, br), 8.25 (2H, dd, J=6.8, 2.4 Hz), 7.50-7.57 (2H, m), 7.41 (1H, dd, J=8.0, 1.2 Hz), 7.16 (1H, td, J=7.6, 1.2 Hz), 6.93 (2H, dd, J=6.8, 2.4 Hz), 5.93 (2H, br), 4.08 (2H, q, J=7.2 Hz), 3.79 (3H, s), 3.67 (3H, s), 1.37 (3H, J=6.8 Hz); $^{13}C$ NMR (100 MHz, $(CD_3)_2CO$) δ 161.7, 156.8 (2×), 154.0, 152.9, 150.1, 137.1, 131.6, 131.0, 130.8, 130.0 (2×), 122.5, 121.5, 119.8, 114.9 (2×), 113.4, 64.1, 56.3, 31.7, 15.1; ESI-HRMS calcd for $C_{22}H_{23}N_6O_4$: 435.1781, found: m/z 435.1798 [M+H]$^+$.

183

2-(4-Ethoxyphenyl)-9-(2-methoxyphenyl)-7-methyl-8-oxopurine-6-(N-methoxy)carboximidamide (21b)

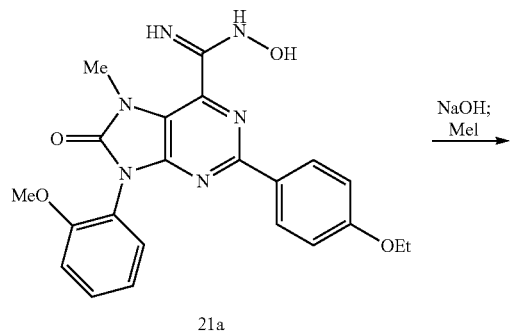

A mixture of compound 21a (20 mg, 0.05 mmol) and 1 M NaOH$_{(aq)}$ (47 µL, 0.05 mmol) in DMF (1 mL) was stirred at room temperature for 5 min. Methyl iodide (3.5 µL, 0.06 mmol) was added. The mixture was stirred at room temperature for 22 h, concentrated under reduced pressure, and washed with H$_2$O. The residual solids were collected, and purified by flash chromatography on a silica gel column with elution of EtOAc/hexane (1:3) to give compound 11b' (19 mg, 92% yield). The purity of compound 21b was 95.0% as shown by HPLC on a Platisil Silica column (Dikma, 4.6× 250 mm, 5 m particle size), $t_R$=7.9 min (EtOAc/hexane=1:1) at a flow rate of 1.0 mL/min. C$_{23}$H$_{24}$N$_6$O$_4$; white solid; mp 169-171° C.; TLC (EtOAc/hexane=1:1) R$_f$=0.6; IR ν$_{max}$ (neat) 3479, 3361, 2924, 2855, 1737, 1646, 1604, 1574, 1517, 1464, 1391, 1247, 1156, 1049, 844, 794, 756 cm$^{-1}$; $^1$H NMR (400 MHz, CDCl$_3$) δ 8.17 (2H, dd, J=6.8, 1.2 Hz), 7.45-7.49 (1H, m), 7.37 (2H, dd, J=7.6, 1.2 Hz), 7.08-7.12 (1H, m), 6.86 (2H, dd, J=7.2, 1.6 Hz), 5.50 (2H, br), 4.03 (2H, q, J=6.8 Hz), 3.97 (3H, s), 3.77 (3H, s), 3.76 (3H, s), 1.39 (3H, J=6.8 Hz); $^{13}$C NMR (100 MHz, CDCl$_3$) δ 160.6, 156.3, 155.5, 153.4, 151.9, 148.7, 134.8, 130.7, 129.8, 129.7, 129.2 (2×), 120.9, 120.8, 118.8, 114.1 (2×), 112.4, 63.5, 61.9, 55.8, 31.9, 14.7; ESI-HRMS calcd for C$_{23}$H$_{25}$N$_6$O$_4$: 449.1937, found: m/z 449.1956 [M+H]$^+$.

184

2-(4-Ethoxyphenyl)-9-(2-methoxyphenyl)-8-oxopurine-6-[N-(benzyloxycarbonyl)oxy]carboximidamide (22a)

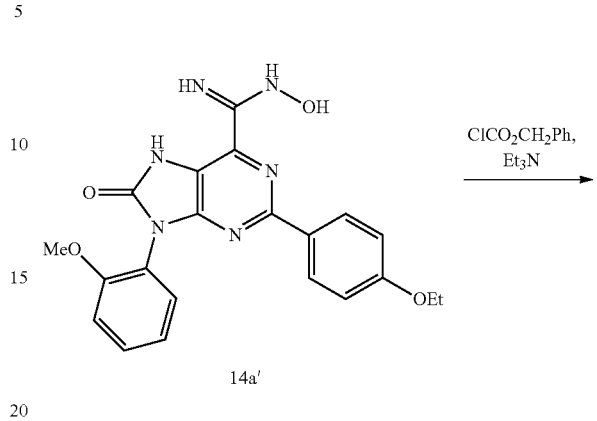

To a solution of compound 14a' (20 mg, 0.05 mmol) and triethylamine (7 µL, 0.05 mmol) in anhydrous acetone (1 mL) was added benzyl chloroformate (7 µL, 0.05 mmol). The mixture was stirred at 0° C. for 2 h, concentrated under reduced pressure, and washed successively with H$_2$O, Et$_2$O and acetone to give compound 22a (18 mg, 66% yield). C$_{29}$H$_{26}$N$_6$O$_6$; yellow solid; mp 246-248° C.; TLC (EtOAc/hexane=1:1) R$_f$=0.8; $^1$H NMR (400 MHz, DMSO-d$_6$) δ 10.6 (1H, s), 8.28 (2H, dd, J=8.8, 1.2 Hz), 7.56-7.58 (1H, m), 7.51-7.54 (3H, m), 7.38-7.49 (5H, m), 7.29 (2H, d, J=8.4 Hz), 7.16 (1H, t, J=7.6 Hz), 6.95 (2H, dd, J=8.8, 1.2 Hz), 5.30 (1H, s), 4.06 (2H, q, J=7.2 Hz), 3.75 (3H, s), 1.33 (3H, t, J=6.8 Hz); $^{13}$C NMR (100 MHz, DMSO-d$_6$) δ 160.3, 155.8, 155.4, 154.0, 153.3, 152.2, 152.1, 135.4, 131.9, 130.9, 130.2, 129.2 (2×), 128.5 (4×), 128.4 (3×), 120.7, 120.5, 117.3, 114.1, 112.8, 69.4, 63.1, 55.9, 14.6; ESI-HRMS calcd for C$_{29}$H$_{25}$N$_6$O$_6$: 553.1836, found: m/z 553.1865 [M−H]$^-$.

185

2-(4-Ethoxyphenyl)-9-(2-methoxyphenyl)-8-oxopurine-6-[N-(phenoxycarbonyl)oxy]carboximidamide (22b)

186

7-Allyl-2-(4-ethoxyphenyl)-9-(2-methoxyphenyl)-8-oxopurine-6-[N-(phenoxycarbonyl)oxy]carboximidamide (23a)

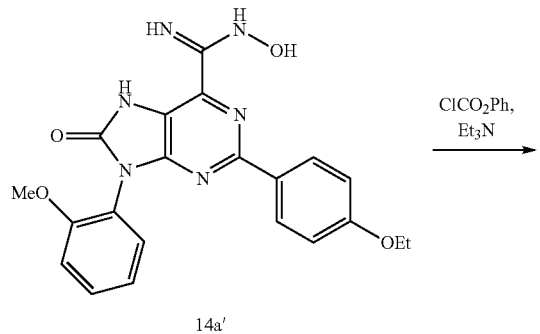

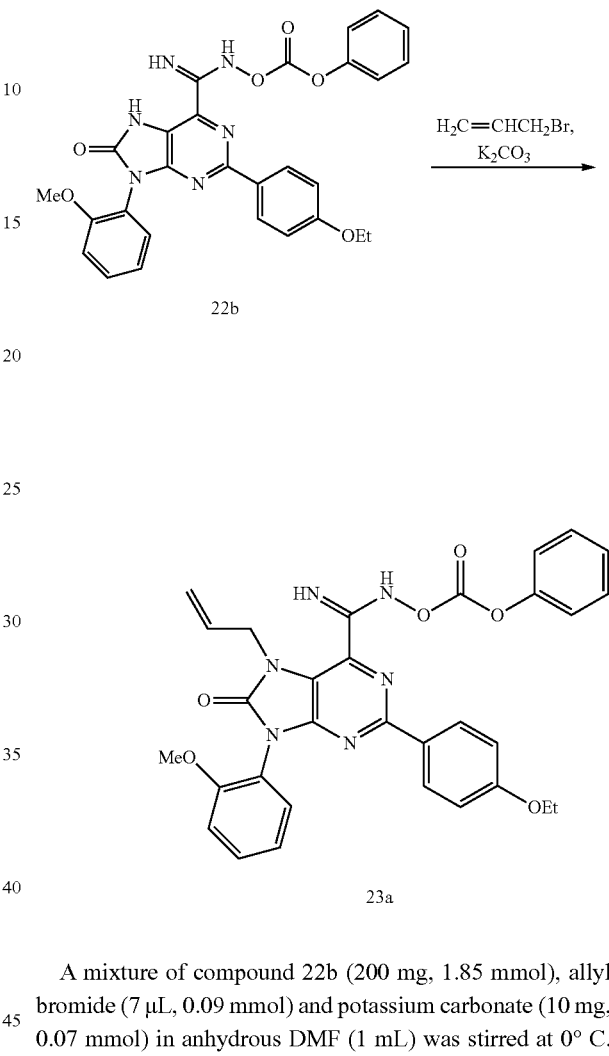

To a solution of compound 14a' (60 mg, 0.14 mmol) and triethylamine (78 μL, 0.58 mmol) in anhydrous acetone (3 mL) was added phenyl chloroformate (39 μL, 0.32 mmol). The mixture was stirred at 0° C. for 2 h, concentrated under reduced pressure, and washed successively with $H_2O$, $Et_2O$, MeOH and acetone to give compound 22b (44 mg, 59% yield). $C_{28}H_{24}N_6O_6$; pale yellow solid; mp=209-211° C.; TLC (EtOAc/hexane=1:1) $R_f$=0.5; $^1H$ NMR (400 MHz, $CDCl_3$) δ 9.26 (1H, br), 8.21 (2H, d, J=8.8 Hz), 7.40-7.50 (4H, m), 7.24-7.30 (3H, m), 7.08-7.13 (2H, m), 6.88 (2H, d, J=8.8 Hz), 4.05 (2H, q, J=7.2 Hz), 3.77 (3H, s), 1.40 (3H, t, J=7.2 Hz); $^{13}C$ NMR (100 MHz, $CDCl_3$) δ 160.9, 157.2, 155.5, 153.2, 152.5, 152.3, 151.8, 151.0, 130.8, 130.5, 129.8, 129.6 (3×), 129.3 (2×), 126.3, 120.9 (3×), 120.5, 117.1, 114.2 (2×), 112.5, 63.5, 55.9, 14.7; ESI-HRMS calcd for $C_{28}H_{25}N_6O_6$: 541.1836, found: m/z 541.1888 $[M+H]^+$.

A mixture of compound 22b (200 mg, 1.85 mmol), allyl bromide (7 μL, 0.09 mmol) and potassium carbonate (10 mg, 0.07 mmol) in anhydrous DMF (1 mL) was stirred at 0° C. for 3 days. The mixture was concentrated under reduced pressure, and extracted with $CH_2Cl_2$ and $H_2O$. The organic phase was dried over $MgSO_4$, filtered, and purified by flash chromatography on a silica gel column with elution of EtOAc/hexane (1:6 to 1:3) to give compound 23a (3 mg, 7% yield). $C_{31}H_{28}N_6O_6$; pale yellow solid; mp=83-85° C.; TLC (EtOAc/hexane=1:3)$R_f$=0.1; $^1H$ NMR (400 MHz, $CDCl_3$) δ 8.19 (2H, d, J=8.8 Hz), 7.46-7.50 (1H, m), 7.40-7.44 (3H, m), 7.26-7.30 (3H, m), 7.07-7.14 (2H, m), 6.89 (2H, d, J=8.8 Hz), 5.84-5.93 (1H, m), 5.30-5.31 (2H, m), 5.10-5.12 (1H, m), 4.95-4.99 (1H, m), 4.05 (2H, q, J=6.8 Hz), 3.79 (3H, s), 1.40 (3H, t, J=6.8 Hz); $^{13}C$ NMR (100 MHz, $CDCl_3$) δ 160.9, 156.5, 155.5, 153.4, 153.0, 152.7, 151.9, 151.0, 133.3, 132.4, 130.8, 129.9, 129.7 (2×), 129.4, 129.2 (2×), 126.4, 120.9 (3×), 120.8, 118.7, 116.2, 114.2 (2×), 112.4, 63.5, 55.9, 45.2, 14.8; ESI-HRMS calcd for $C_{31}H_{29}N_6O_6$: 581.2149, found: m/z 581.2172 $[M+H]^+$.

187

2-(4-Ethoxyphenyl)-9-(2-methoxyphenyl)-6-(5-methyl-1,2,4-oxadiazol-3-yl)purin-8-one (24a)

188

2-Allyl-3-[7-allyl-2-(4-ethoxyphenyl)-9-(2-methoxyphenyl)-8-oxopurin-6-yl]-1,2,4-oxadiazol-5-one (25a)

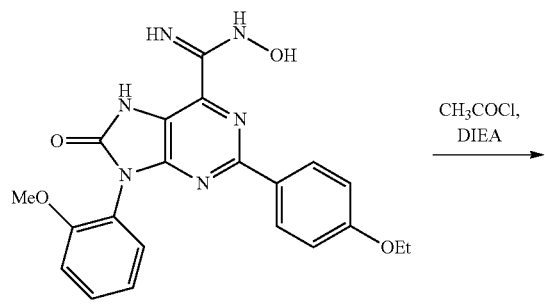

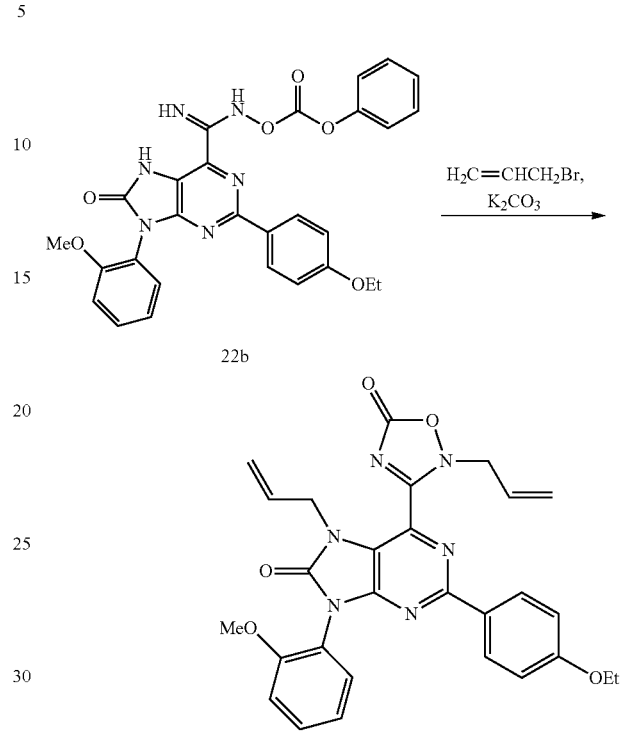

A mixture of compound 14a' (40 mg, 0.095 mmol), acetyl chloride (13.6 μL, 0.19 mmol) and DIEA (48 μL, 0.28 mmol) in CH$_3$CN (4 mL) was stirred in a sealed tube at 120° C. by microwave irradiation for 40 min. After cooling to room temperature, the mixture was extracted with CH$_2$Cl$_2$ and H$_2$O. The organic phase was dried over MgSO$_4$, filtered, and purified by flash chromatography on a silica gel column with elution of EtOAc/hexane (1:3) to give compound 24a (17 mg, 39% yield). The purity of compound 24a was 95.3% as shown by HPLC on a Platisil Silica column (Dikma, 4.6×250 mm, 5 Lm particle size), t$_R$=11.4 min (EtOAc/hexane=2:1) at a flow rate of 1.0 mL/min. C$_{23}$H$_{20}$N$_6$O$_4$; pale yellow solid; mp 291-293° C.; TLC (EtOAc/hexane=1:1) R$_f$=0.2; IR ν$_{max}$ (neat) 3403, 2920, 1734, 1631, 1601 1513, 1471, 1388, 1300, 1262, 1247, 1163, 1118, 1045, 886, 760 cm$^{-1}$; $^1$H NMR (400 MHz, CDCl$_3$) δ 8.85 (1H, br), 8.33 (2H, d, J=8.8 Hz), 7.48-7.52 (1H, m), 7.44-7.46 (1H, m), 7.11-7.15 (2H, m), 6.88 (2H, d, J=8.8 Hz), 4.05 (2H, q, J=7.2 Hz), 3.80 (3H, s), 2.75 (3H, s), 1.40 (3H, J=7.2 Hz); $^{13}$C NMR (100 MHz, CDCl$_3$) δ 177.7, 166.5, 160.9, 158.6, 155.5, 152.8, 152.2, 131.0, 129.8, 129.7 (3×), 129.4, 121.0, 120.3, 118.2, 114.1 (2×), 112.5, 63.4, 56.0, 14.8, 12.6; ESI-HRMS calcd for C$_{23}$H$_{21}$N$_6$O$_4$: 445.1624, found: m/z 445.1605 [M+H]$^+$.

A mixture of compound 22b (200 mg, 1.85 mmol), allyl bromide (7 μL, 0.09 mmol) and potassium carbonate (10 mg, 0.07 mmol) in anhydrous DMF (1 mL) was stirred at 0° C. for 3 days. The mixture was concentrated under reduced pressure, and extracted with CH$_2$Cl$_2$ and H$_2$O. The organic phase was dried over MgSO$_4$, filtered, and purified by flash chromatography on a silica gel column with elution of EtOAc/hexane (1:6 to 1:3) to give compound 25a (21 mg, 54% yield). C$_{28}$H$_{26}$N$_6$O$_5$; pale yellow solid; mp=88-90 OC; TLC (EtOAc/hexane=1:3)R$_f$=0.1; $^1$H NMR (400 MHz, CDCl$_3$) δ 8.18 (2H, d, J=8.8 Hz), 7.50-7.54 (1H, m), 7.44 (1H, dd, J=7.6, 1.6 Hz), 7.11-7.16 (2H, m), 6.89 (2H, d, J=8.8 Hz), 5.66-5.77 (2H, m), 5.06-5.14 (3H, m), 4.85-4.91 (3H, m), 4.61-4.65 (2H, m), 4.05 (2H, q, J=6.8 Hz), 3.79 (3H, s), 1.41 (3H, t, J=6.8 Hz); $^{13}$C NMR (100 MHz, CDCl$_3$) δ 161.2, 158.7, 157.4, 155.4, 153.7, 152.5, 152.3, 132.2, 131.1, 130.3, 129.7, 129.3 (2×), 128.9, 126.3, 121.0, 120.3, 120.0, 119.7, 117.3, 114.4 (2×), 112.5, 63.6, 56.0, 45.4, 44.3, 14.7.

8-(Acetylthio)-2-(4-ethoxyphenyl)-9-phenylpurine-6-carboxamide (26a)

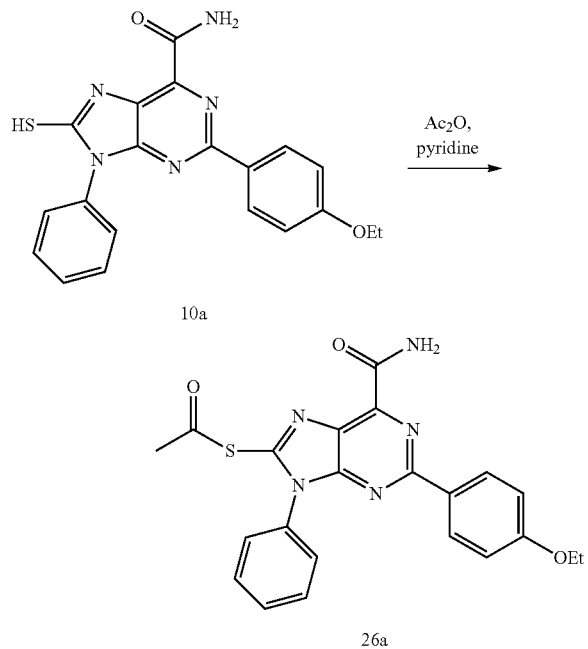

A mixture of compound 10a (100 mg, 0.26 mmol), potassium carbonate (40 mg, 0.29 mmol) and acetic anhydride (0.16 mL, 1.7 mmol) in dry pyridine (5 mL) was stirred at 60° C. for 45 h. The mixture was concentrated under reduced pressure, and purified by flash chromatography on a silica gel column with elution of MeOH/CH$_2$Cl$_2$ (1:50) to give compound 26a (27 mg, 24% yield). C$_{22}$H$_{19}$N$_5$O$_3$S; yellow solid; $^1$H NMR (400 MHz, DMSO-d$_6$) δ 8.28 (2H, d, J=8.0 Hz), 7.56-7.67 (5H, m), 7.01 (2H, d, J=8.0 Hz), 4.03 (2H, q, J=6.8 Hz), 1.34 (3H, t, J=6.8 Hz); $^{13}$C NMR (100 MHz, DMSO-d$_6$) δ174.1, 171.2, 162.6, 160.7, 156.4, 155.7, 133.6, 133.0, 129.9, 129.6 (2×), 129.2, 129.1 (2×), 128.6 (2×), 123.6, 114.4 (2×), 63.3, 25.6, 14.6; ESI-HRMS calcd for C$_{22}$H$_{18}$N$_5$O$_3$S: 432.1130, found: m/z 432.1148 [M–H]$^-$.

2-(4-Ethoxyphenyl)-8-mercapto-9-phenylpurine-6-carboxnitrile (27a)

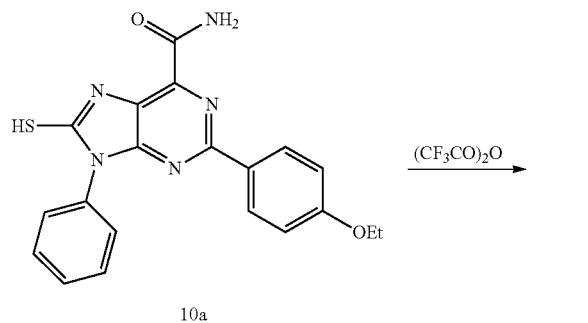

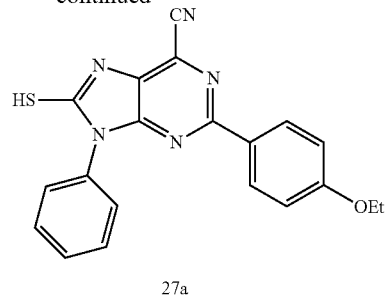

A mixture of amide compound 10a (200 mg, 0.51 mmol) and trifluoroacetic anhydride (0.20 mL, 1.4 mmol) in pyridine (8 mL) was stirred at room temperature for 3 h. The mixture was quenched with H$_2$O, and concentrated under reduced pressure. The residue was extracted with H$_2$O and CH$_2$Cl$_2$. The organic phase was dried over MgSO$_4$, filtered, concentrated under reduced pressure, and purified by flash chromatography on a silica gel column (hexane/EtOAc=1:1) to give compound 27a (160 mg, 84% yield). C$_{20}$H$_{15}$N$_5$OS; yellow solid; mp=278.5-280.0 OC; $^1$H NMR (400 MHz, DMSO-d$_6$) δ 8.08 (2H, d, J=8.4 Hz), 7.67-7.58 (5H, m), 7.00 (2H, d, J=8.4 Hz), 4.06 (2H, q, J=7.2 Hz), 1.33 (3H, t, J=7.2 Hz); $^{13}$C NMR (100 MHz, DMSO-d$_6$) δ 173.8, 160.8, 157.6, 154.9, 133.0, 129.2 (2×), 129.0 (3×), 128.2, 128.1, 115.4, 114.5 (3×), 114.1 (2×), 63.2, 14.4; ESI-HRMS (negative mode) calcd for C$_{20}$H$_{14}$N$_5$OS: 372.0919, found: m/z 372.0922 [M–H]$^-$.

8-(Benzyloxycarbonylthio)-2-(4-ethoxyphenyl)-9-phenylpurine-6-carboxnitrile (28a)

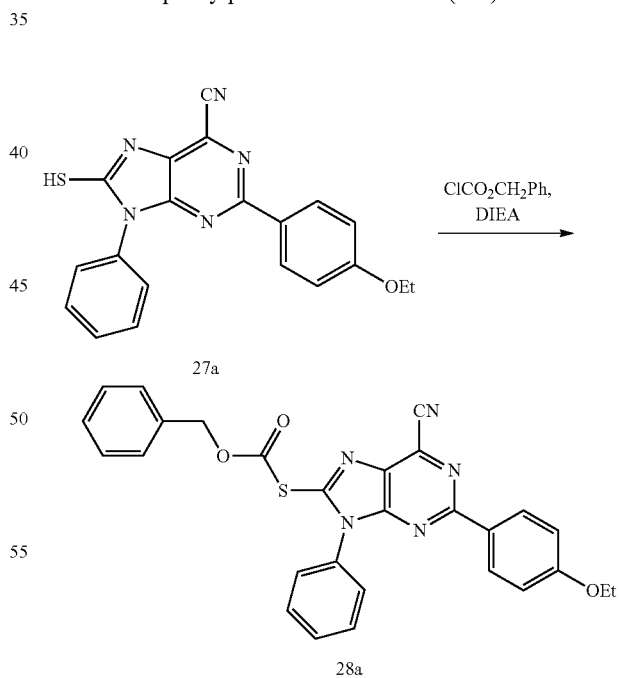

To a suspension of compound 27a (83 mg, 0.22 mmol) and benzyl chloroformate (0.15 mL, 1.05 mmol) in anhydrous CH$_2$Cl$_2$ (6 mL) was added DIEA (0.20 mL, 1.2 mmol). The mixture was stirred at 0° C. for 3 h under an atmosphere of argon. The mixture was then concentrated under reduced pressure, and purified by flash chromatography on a silica gel column (hexane/EtOAc=10:1) to give compound 28a (44 mg, 39% yield). $C_{28}H_{21}N_5O_3S$; yellow solid; mp=179.2-180.4° C.; $^1$H NMR (400 MHz, DMSO-$d_6$) δ 8.19 (2H, d, J=8.8 Hz), 7.61-7.57 (5H, m), 7.45-7.43 (2H, m), 7.40-7.38 (2H, m), 6.88 (2H, d, J=8.8 Hz), 5.69 (2H, br s), 4.05 (2H, q, J=7.2 Hz), 1.41 (3H, t, J=7.2 Hz); ESI-HRMS (positive mode) calcd for $C_{28}H_{22}N_5O_3S$: 508.1443, found: m/z 508.1456 [M+H]$^+$.

2-(4-Ethoxyphenyl)-8-mercapto-9-phenylpurine-6-carboxylic acid (29a)

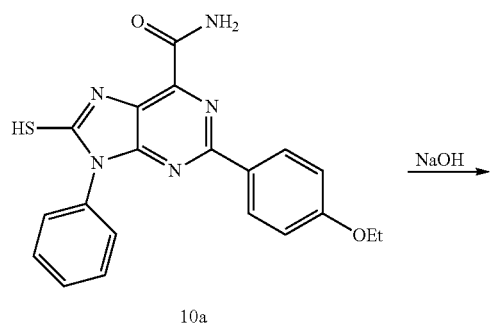

10a

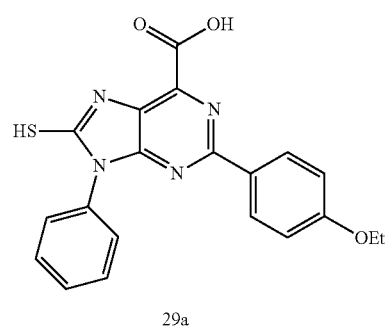

29a

A mixture of amide compound 10a (100 mg, 0.26 mmol) in MeOH (10 mL) and 10 M NaOH$_{(aq)}$ (10 mL) was heated at 100° C. under reflux for 4 h. The orange precipitate was collected by filtration, and washed successively with water, ice-cold MeOH and Et$_2$O. The collected solids were dried in the air, suspended in acetone, and 1 M HCl$_{(aq)}$ was added dropwise until the solids completely dissolved. After removal of acetone under reduced pressure, the solids were collected by filtration, washed with water, and dried in vacuum to give the acid compound 29a (35 mg, 59%). $C_{20}H_{16}N_4O_3S$; yellow solid; mp=320° C. (decomposed); $^1$H NMR (500 MHz, DMSO-$d_6$) δ 8.16 (2H, d, J=8.9 Hz), 7.60 (5H, qd, J=14.5, 7.4 Hz), 7.00 (2H, d, J=9.0 Hz), 4.07 (2H, q, J=6.9 Hz), 1.34 (3H, t, J=7.0 Hz); $^{13}$C NMR (126 MHz, DMSO-$d_6$) δ 173.5, 164.5, 160.5, 156.9, 155.3, 133.6, 133.3, 129.1 (2×), 129.1, 129.0 (2×), 129.0, 128.6 (2×), 122.4, 114.4 (2×), 63.2, 14.6. ESI-HRMS calculated for $C_{20}H_{17}N_4O_3S$: 393.1016, found: m/z 393.1029 [M+H]$^+$.

2-(4-Ethoxyphenyl)-8-mercapto-9-phenylpurine-6-(N-hydroxy)carboximidamide (30a)

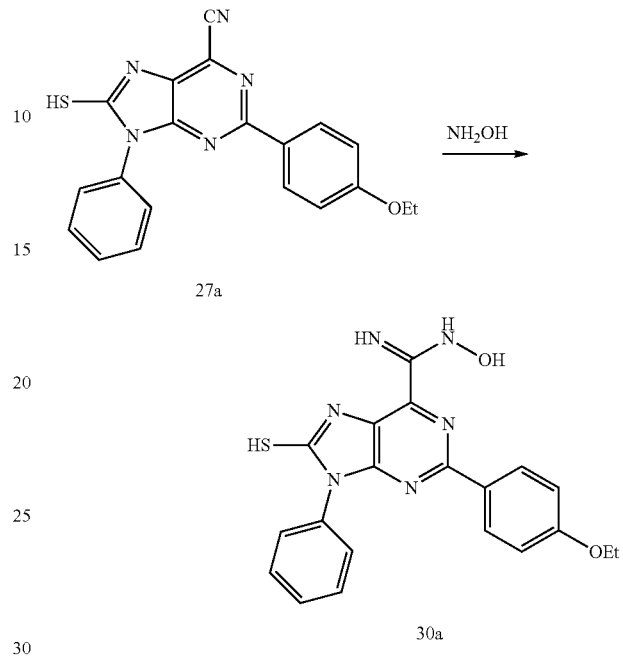

A mixture of nitrile compound 27a (40 mg, 0.11 mmol), hydroxylamine hydrochloride (30 mg, 0.43 mmol) and sodium acetate (60 mg, 0.43 mmol) in THF (4 mL) and MeOH (4 mL) was stirred at 70° C. for 1 h. The mixture was concentrated under reduced pressure, and washed successively with cold MeOH and H$_2$O. The residue was purified by flash chromatography on a silica gel column (hexane/EtOAc=1:1) to give compound 30a (39 mg, 90% yield). $C_{20}H_{18}N_6O_2S$; white solid; mp=207.5-208.7° C.; $^1$H NMR (400 MHz, DMSO-$d_6$) δ 10.30 (1H, br s), 8.30 (2H, m), 7.63-7.56 (5H, m), 6.97 (2H, d, J=9.2 Hz), 6.32 (2H, br s), 4.07 (2H, q, J=7.6 Hz), 1.33 (3H, t, J=7.6 Hz); $^{13}$C NMR (125 MHz, DMSO-$d_6$) δ 171.8, 160.4, 157.0, 153.0, 149.1, 136.4, 133.6, 129.3 (2×), 128.8 (3×), 128.3 (3×), 117.7, 114.2 (2×), 63.1, 14.4; ESI-HRMS (negative mode) calcd for $C_{20}H_{17}N_6O_2S$: 405.1134, found: m/z 405.1157 [M−H]$^-$.

8-Chloro-2-(4-ethoxyphenyl)-9-(2-methoxyphenyl)purine-6-carbonitrile (31a)

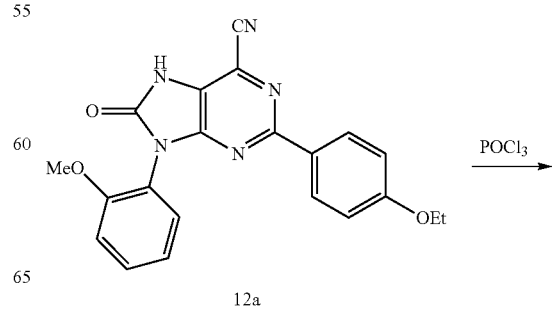

12a

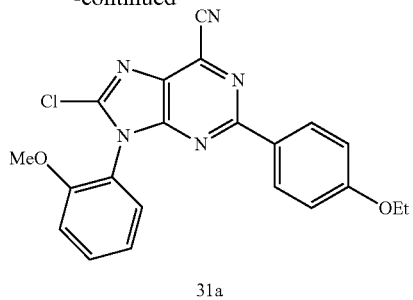

31a

A mixture of compound 12a (1 g, 2.6 mmol) in POCl₃ (40 mL) was stirred at 100° C. for 72 h. The solution was concentrated under reduced pressure, and purified by flash chromatography on a silica gel column with elution of EtOAc/hexane (1:4) to give compound 31a (83 mg, 8% yield). $C_{21}H_{16}ClN_5O_2$; pale yellow solid; mp 215-217° C.; TLC (EtOAc/hexane=1:4) $R_f$=0.5; IR $v_{max}$ (neat) 3449, 1639, 1517, 1467, 1365, 1262, 1171, 1042, 1015, 802, 756 cm⁻¹; ¹H NMR (400 MHz, CDCl₃) δ 8.30 (2H, d, J=8.8 Hz), 7.58-7.62 (1H, m), 7.38 (1H, dd, J=6.4, 1.6 Hz), 7.14-7.21 (2H, m), 6.90 (2H, d, J=8.8 Hz), 4.07 (2H, q, J=7.2 Hz), 3.77 (3H, s), 1.41 (3H, t, J=7.2 Hz); ¹³C NMR (100 MHz, CDCl₃) δ 161.6, 161.5, 155.3, 155.0, 148.2, 132.2 (2×), 130.1 (2×), 129.4, 129.3, 128.5, 121.1, 120.3, 114.3 (2×), 113.7, 112.4, 63.5, 55.8, 14.7; ESI-HRMS calcd for $C_{21}H_{17}ClN_5O_2$: 406.1071, found: m/z 403.1058 [M+H]⁺. Anal. Cacld for ($C_{21}H_{16}ClN_5O_2 \cdot \frac{1}{4}$ H₂O): C, 61.47; H, 4.05; N, 17.07. Found: C, 61.33; H, 3.93; N, 16.78.

9-Cyclohexyl-8-cyclohexylamino-2-(4-ethoxyphenyl)purine-6-carboxamide (32a)

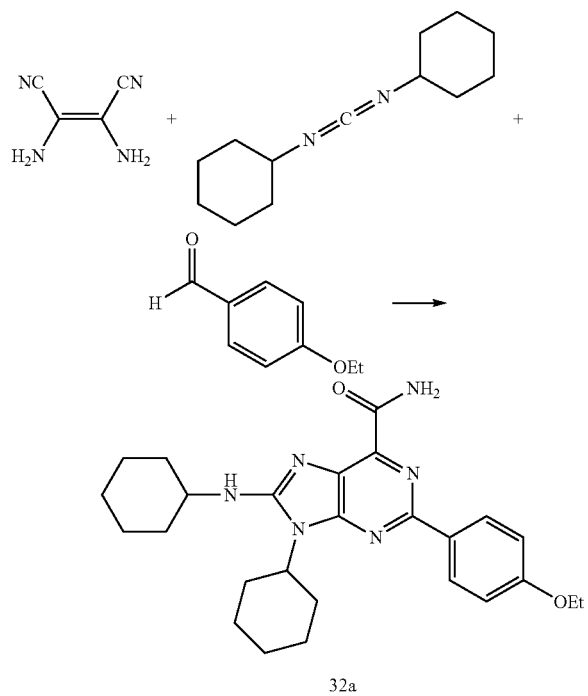

32a

A mixture of N,N'-dicyclohexylcarbodiimide (100 mg, 0.485 mmol), diaminomaleonitrile (210 mg, 1.94 mmol) and trimethylamine (0.03 mL, 0.24 mmol) in anhydrous THF (4 mL) was stirred at 65° C. for 52 h. The mixture was concentrated under reduced pressure to give a crude guanidine compound. A mixture of the above-prepared guanidine compound, 4-ethoxybenzaldehyde (0.13 mL, 0.93 mmol) and triethylamine (0.13 mL, 0.93 mmol) in MeOH (4 mL) was stirred at room temperature for 36 h. The mixture was concentrated under reduced pressure, and purified by flash chromatography on a silica gel column with elution of EtOAc/hexane (1:1) to give a small amount of compound 32a.

$C_{26}H_{34}N_6O_2$; pale yellow solid; TLC (EtOAc/hexane=1:1) $R_f$=0.1; ¹H NMR (400 MHz, CDCl₃) δ 8.78 (1H, br), 8.43 (2H, d, J=8.8 Hz), 6.95 (2H, d, J=9.2 Hz), 5.92 (1H, br), 4.06-4.17 (3H, m), 2.44-2.47 (1H, m), 2.15-2.18 (1H, m), 1.98-2.02 (3H, m), 1.91-1.94 (5H, m), 1.77-1.84 (3H, m), 1.67-1.70 (3H, m), 1.41-1.48 (6H, m), 1.12-1.34 (3H, m); ESI-HRMS calcd for $C_{26}H_{35}N_6O_2$: 463.2821, found: m/z 463.2813 [M+H]⁺.

8-Amino-2-(4-ethoxyphenyl)-9-(2-methoxyphenyl)purine-6-carbonitrile (33a)

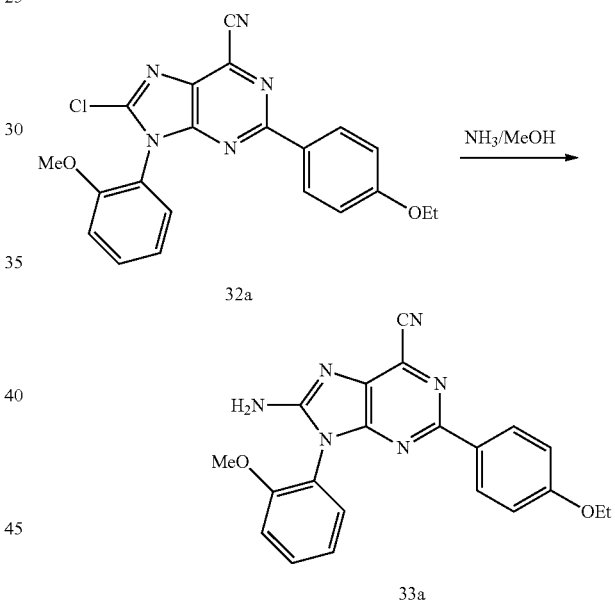

Compound 32a (30 mg, 0.074 mmol) in 7 M NH₃/MeOH (3 mL) was stirred at room temperature for 24 h. The mixture was concentrated under reduced pressure, and purified by flash chromatography on a silica gel column with elution of EtOAc/hexane (1:1) to give compound 33a (24 mg, 84% yield). The purity of compound 33a was 96.1% as shown by HPLC on a Platisil Silica column (Dikma, 4.6× 250 mm, 5 μm particle size), $t_R$=7.2 min (EtOAc/hexane=17:3) at a flow rate of 1.0 mL/min. $C_{21}H_{18}N_6O_2$; white solid; mp 297-299° C.; TLC (EtOAc/hexane=1:1) $R_f$=0.2; IR $v_{max}$ (neat) 3422, 2966, 2855, 2228, 1680, 1540, 1498, 1467, 1391, 1255, 1167, 1049 cm⁻¹; ¹H NMR (400 MHz, DMSO-d₆) δ 8.04 (2H, d, J=8.8 Hz), 7.71 (2H, br), 7.61 (1H, t, J=7.6 Hz), 7.50 (1H, d, J=7.2 Hz), 7.33 (1H, d, J=8.4 Hz), 7.19 (1H, t, J=7.6 Hz), 6.96 (2H, d, J=8.8 Hz), 4.04 (2H, q, J=7.2 Hz), 3.77 (3H, s), 1.32 (3H, d, J=6.8 Hz); ¹³C NMR (100 MHz, DMSO-d₆) δ 160.0, 158.8, 156.4, 155.3, 154.0, 137.1, 131.6, 130.0, 129.3, 128.6 (2×), 121.1, 119.8, 117.6, 115.8, 114.4 (2×), 113.2, 63.2, 55.9, 14.6; ESI-HRMS calcd for C$_{21}$H$_{17}$N$_6$O$_2$: 385.1413, found: m/z 385.1412 [M−H]$^-$.

2-(4-Ethoxyphenyl)-9-(2-methoxyphenyl)-8-morpholinopurine-6-carbonitrile (33b)

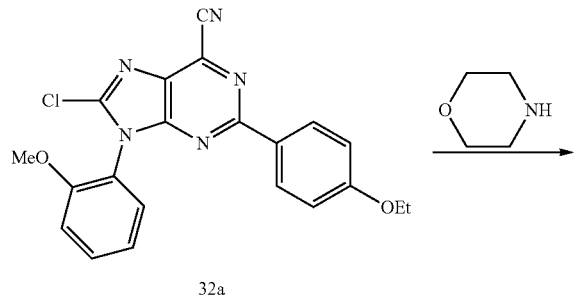

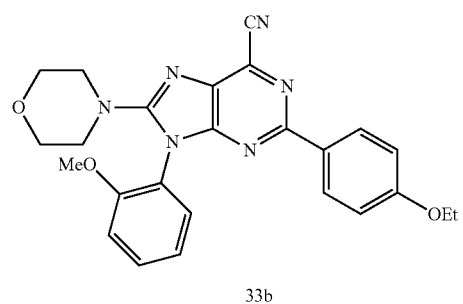

Compound 32a (10 mg, 0.025 mmol) in morpholine (1 mL) was stirred at 80° C. for 22 h. The mixture was concentrated under reduced pressure, and washed successively with H$_2$O, Et$_2$O, THF and CH$_3$CN. The residual solids were further purified by flash chromatography on a silica gel column with elution of EtOAc/hexane (1:1) to give compound 33b (9 mg, 80% yield). The purity of compound 25b was 95.3% as shown by HPLC on a Platisil Silica column (Dikma, 4.6×250 mm, 5 m particle size), t$_R$=14.7 min (EtOAc/hexane=1:1) at a flow rate of 1.0 mL/min. C$_{25}$H$_{24}$N$_6$O$_3$; pale yellow solid; mp 273-275° C.; TLC (EtOAc/hexane=1:1) R$_f$=0.4; IR ν$_{max}$ (neat) 2977, 2924, 2848, 2236, 1616, 1544, 1502, 1441, 1391,1171, 1121, 1023, 916, 844, 737 cm$^{-1}$; $^1$H NMR (400 MHz, CDCl$_3$) δ 8.18-8.21 (2H, m), 7.51-7.55 (1H, m), 7.41 (1H, dd, J=7.6, 1.6 Hz), 7.16 (1H, t, J=7.2 Hz), 7.10 (1H, d, J=8.4 Hz), 6.86 (2H, dd, J=7.2, 1.6 Hz), 4.04 (2H, q, J=7.2 Hz), 3.79 (3H, s), 3.63-3.66 (4H, m), 3.48-3.50 (4H, m), 1.40 (3H, J=6.8 Hz); $^{13}$C NMR (100 MHz, CDCl$_3$) δ 160.7, 158.1, 157.3, 156.5, 154.9, 134.7, 131.5, 129.8, 129.3 (2×), 129.1, 123.4, 122.4, 121.4, 115.3, 114.2 (2×), 112.5, 66.2, 63.5, 56.0, 47.6, 14.8; ESI-HRMS calcd for C$_{25}$H$_{25}$N$_6$O$_3$: 457.1988, found: m/z 457.1975 [M+H]$^+$.

Tert-butyl (6-cyano-2-(4-ethoxyphenyl)-9-(2-methoxyphenyl)purin-8-yl)carbamate (34a)

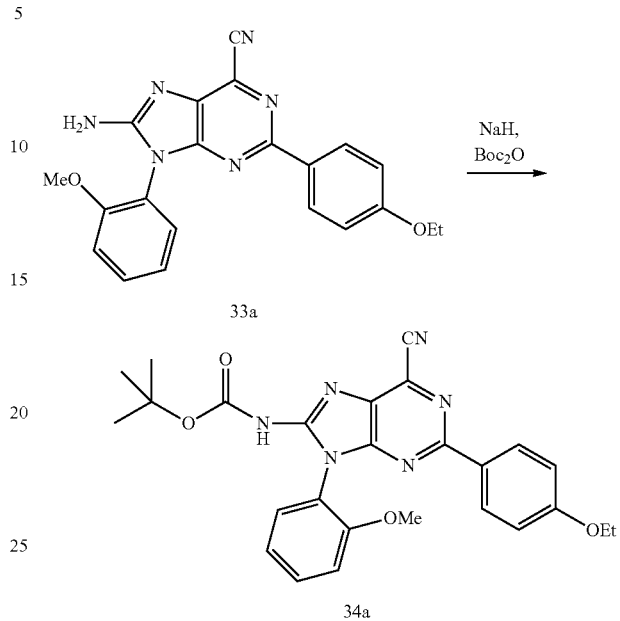

A mixture of compound 33a (20 mg, 0.052 mmol), NaH (4 mg, 0.1 mmol) and Boc anhydride (12 µL, 0.052 mmol) in anhydrous THF (2 mL) was stirred at room temperature for 19 h. The mixture was concentrated under reduced pressure, and extracted with CH$_2$Cl$_2$ and H$_2$O. The organic phase was dried over MgSO$_4$, filtered, and purified by flash chromatography on a silica gel column with elution of EtOAc/hexane (1:4 to 1:2) to give compound 34a (13 mg, 53% yield). C$_{26}$H$_{26}$N$_6$O$_4$; white solid; mp=260-262 OC (decomposed); TLC (EtOAc/hexane=1:1) R$_f$=0.5; $^1$H NMR (400 MHz, CDCl$_3$) δ 8.27 (2H, d, J=8.8 Hz), 7.59-7.63 (1H, m), 7.43 (1H, d, J=7.6 Hz), 7.18-7.24 (2H, m), 6.88 (2H, d, J=8.8 Hz), 4.05 (2H, q, J=6.8 Hz), 3.81 (3H, s), 1.50 (9H, s), 1.40 (3H, t, J=6.8 Hz); $^{13}$C NMR (100 MHz, CDCl$_3$) δ 161.2, 158.6, 154.6 (2×), 149.5, 149.2, 133.3, 132.2, 129.8 (2×), 129.7, 129.2, 127.2, 121.8, 119.6, 114.4, 114.3 (2×), 113.0, 83.8, 63.5, 56.2, 28.0 (3×), 14.8; ESI-HRMS calcd for C$_{26}$H$_{27}$N$_6$O$_4$: 487.2094, found: m/z 487.2137 [M+H]$^+$.

N-Acetyl-N-[6-cyano-2-(4-ethoxyphenyl)-9-(2-methoxyphenyl)purin-8-yl]acetamide (35a)

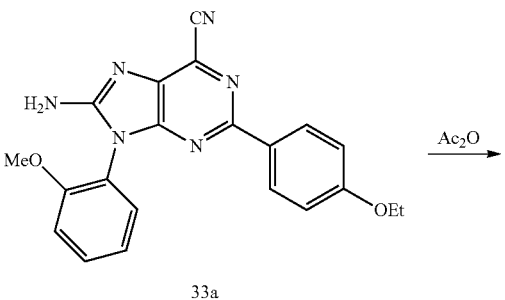

-continued

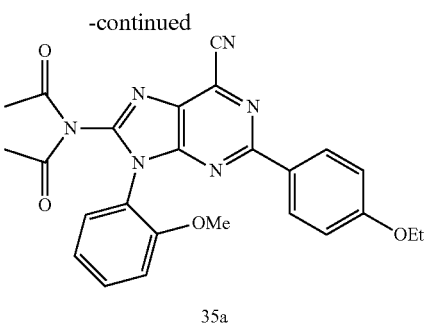

35a

A mixture of compound 33a (8 mg, 0.021 mmol) and acetic anhydride (1 mL) was stirred at 80° C. for 26 h. The mixture was concentrated under reduced pressure, and purified by flash chromatography on a silica gel column with elution of EtOAc/hexane (1:4 to 1:2) to give compound 35a (6 mg, 62% yield). $C_{25}H_{22}N_6O_4$; white solid; mp=210-212° C.; TLC (EtOAc/hexane=1:1) $R_f$=0.7; $^1$H NMR (400 MHz, CDCl$_3$) δ 8.32 (2H, d, J=8.8 Hz), 7.53-7.58 (1H, m), 7.32 (1H, dd, J=8.0, 1.2 Hz), 7.11-7.23 (2H, m), 6.90 (2H, d, J=9.2 Hz), 4.07 (2H, q, J=6.8 Hz), 3.79 (3H, s), 2.32 (6H, s), 1.42 (3H, t, J=6.8 Hz); $^{13}$C NMR (100 MHz, CDCl$_3$) δ 171.4 (2×), 161.7, 160.9, 154.8, 154.2, 150.0, 132.1, 131.4, 131.3, 130.3 (2×), 129.8, 128.7, 121.6, 119.9, 114.4 (2×), 113.8, 12.3, 63.6, 55.7, 25.7 (2×), 14.7; ESI-HRMS calcd for $C_{25}H_{23}N_6O_4$: 471.1781, found: m/z 471.1819 [M+H]$^+$.

8-Amino-2-(4-ethoxyphenyl)-9-(2-methoxyphenyl) purine-6-(N-hydroxy)carboximidamide (36a)

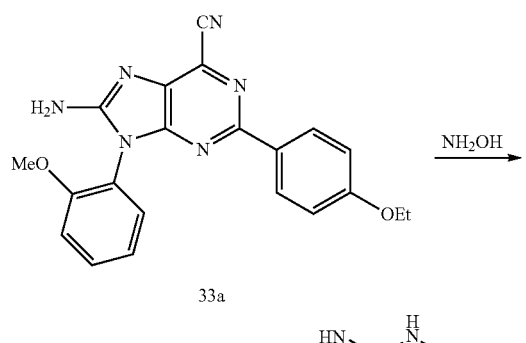

A mixture of compound 33a (10 mg, 0.026 mmol), hydroxylamine hydrochloride (7 mg, 0.10 mmol) and sodium acetate trihydrate (14 mg, 0.1 mmol) in THF (0.8 mL) and MeOH (0.8 mL) was stirred at room temperature for 4 h. The solution was concentrated under reduced pressure, and washed successively with H$_2$O, Et$_2$O and acetone to give compound 36a (2 mg, 20% yield).

$C_{21}H_{21}N_7O_3$; white solid; mp 245-247° C.; TLC (CH$_2$Cl$_2$/MeOH=9:1) $R_f$=0.1; IR $v_{max}$ (neat) 3479, 3380, 2981, 2932, 1646, 1517, 1384, 1243, 1167, 1049, 745 cm$^{-1}$; $^1$H NMR (400 MHz, CD$_3$OD) δ 8.24 (2H, d, J=8.8 Hz), 7.61 (1H, td, J=8.8, 2.0 Hz), 7.45 (1H, dd, J=8.0, 2.0 Hz), 7.30 (1H, d, J=8.0 Hz), 7.21 (1H, t, J=8.0 Hz), 6.90 (2H, d, J=8.8 Hz), 4.60 (2H, br) 4.07 (2H, q, J=6.8 Hz), 3.81 (3H, s), 1.39 (3H, t, J=6.8 Hz); ESI-HRMS calcd for $C_{21}H_{22}N_7O_3$: 420.1784, found: m/z 420.1794 [M+H]$^+$.

Assay of Inhibitory Effects of Exemplary Compounds Against Lung Cancer Cells

The inhibitory effect of the exemplary compounds against lung cancer cells was evaluated. The cytotoxic activity of test compounds in different human NSCLC cells was examined by performing a MTT assay. Table 1 shows that compound 5a inhibits the proliferation of several lung cancer cell lines, and in particular, shows inhibitory activity toward the gefitinib (Iressa)-resistant lung cancer cell line (PC/gef) with a low IC$_{50}$ of 0.253 μM. Compound 5a is relatively nontoxic to NBE normal cells with IC$_{50}$ of 21.7 μM (FIG. 1A).

TABLE 1

Inhibitory activity (IC$_{50}$) of compound 5a in different lung cancer cell lines.

| Cell line[a] | IC$_{50}$ (μM)[b] |
| --- | --- |
| H1975 | 0.243 ± 0.031 |
| PC9 | 0.333 ± 0.004 |
| PC9/gef | 0.253 ± 0.003 |
| CL1-0 | 0.242 ± 0.011 |
| CL1-5 | 0.281 ± 0.001 |
| A549 | 0.225 ± 0.018 |
| NBE | 21.663 ± 1.550 |

[a]H1975, PC9, PC9/gef (gefitinib (IRESSA)-resistant), CL1-0, CL1-5 and A549 are lung cancer lines, whereas NBE is a normal bronchial epithelial cell line.
[b]Data are expressed as mean values derived from three independent experiments.

Assay of Inhibitory Effects of Exemplary Compounds Against H1975 Lung Cancer Cell The inhibitory effect of the exemplary compounds against H1975 lung cancer cell was evaluated. The cytotoxic activity of test compounds was examined by performing an MTT assay. Table 2 shows the IC$_{50}$ values of some representative compounds against the growth of H1975 lung cancer cells.

TABLE 2

Inhibitory activity (IC$_{50}$) against the growth of H1975 lung cancer cells.

| Compound | IC$_{50}$ (μM)[a] |
| --- | --- |
| 5a | 0.30 ± 0.03 |
| 5b | 5.80 ± 0.13 |
| 5c | 4.66 ± 0.05 |
| 5e | 0.19 ± 0.02 |
| 5f | 4.73 ± 0.16 |
| 5j | 0.35 ± 0.01 |
| 5n | 0.6 |
| 5o | 10.5 ± 0.31 |
| 6e | 7.91 ± 0.18 |
| 8a | 0.49 ± 0.1 |
| 8b | 10.5 ± 0.25 |
| 8c | 0.39 ± 0.01 |
| 8d | 15.5 ± 1.96 |
| 8f | 26.3 ± 0.31 |
| 12f | 25.8 |
| 14f | 2.8 |
| 10a | 0.44 ± 0.01 |
| 10b | 0.24 ± 0.04 |
| 11b | 6.37 ± 0.51 |

TABLE 2-continued

Inhibitory activity ($IC_{50}$) against the growth of H1975 lung cancer cells.

| Compound | $IC_{50}$ (μM)[a] |
|---|---|
| 11f | 2.1 |
| 11g | 3.94 ± 0.06 |
| 11d | 1.8 |
| 26a | 41.6 ± 11.6 |

[a]Data are mean values derived from three independent experiments.

Assay of Inhibitory Effects of Exemplary Compounds Against MDA-MB231 Breast Cancer Cell and H1975 Lung Cancer Cell The inhibitory effect of the exemplary compounds against MDA-MB231 breast cancer cell and H1975 lung cancer cell was evaluated. The cytotoxic activity of test compounds was examined by performing a MTT assay. Table 3 shows the $IC_{50}$ values of some representative compounds against the growth of MDA-MB231 breast cancer cells and H1975 lung cancer cells.

TABLE 3

Inhibitory activity ($IC_{50}$) against the growth of MDA-MB231 breast cancer cells and H1975 lung cancer cells.

| | $IC_{50}$ (μM) | |
|---|---|---|
| Compound | MDA-MB231[a] | H1975[a] |
| 5a | 13.5 ± 10.1 | 0.3 |
| 5k | 26 | 7 |
| 5m | 25 ± 1 | 30.0 ± 13.2 |
| 5n | — | 0.6 |
| 5o | — | 10.5 ± 0.31 |
| 12a | 15.7 ± 0.1 | 6.4 ± 2.2 |
| 12b | 3.9 | 9.8 |
| 12d | 2.6 | 6.2 |
| 12e | 3.5 | 4.1 |
| 12f | — | 25.8 |
| 13a | 11.6 | 79 |
| 14a' | 4.2 ± 2.1 | 1.1 ± 0.3 |
| 14c | 13.6 | 11.2 |
| 14f | — | 2.8 |
| 15a | 6.2 | — |
| 17b | 22 | 13 |
| 17c | 48.6 | 34 |
| 17d | 16.9 ± 11.5 | 25.1 ± 0.4 |
| 19a | 1.9 | 0.4 |
| 19b | 2.8 | 0.3 |
| 20a | 65.3 | 60.9 |
| 20b | 47.2 | 6.9 |
| 21a | 87 | 30 |
| 21b | 56 | 42 |
| 22a | 3.9 | 3.1 |
| 22b | 3.9 | 3.1 |
| 23a | 48.1 | 51.1 |
| 24a | 64 | 17 |
| 26a | — | 41.6 ± 11.6 |
| 29a | 91 | 43.6 |
| 31a | 1.6 | 0.7 |
| 33b | — | 74 |
| 34a | 48.1 | 37.7 |
| 35a | 11.9 | 14.7 |
| 36a | 15.4 | 11.9 |

[a]MDA-MB231 is a triple-negative breast cancer cell line, while H1975 is a lung cancer cell line.

In Vitro Antitumor Activity of the Exemplified Compound 5a

To further investigate the long-term antitumor effect of compound 5a, the colony formation assay was conducted to determine whether compound 5a (GRC0321) would interfere with the ability of single cells to form a growing colony (FIG. 1B). H1975 cells were treated with the indicated concentrations of compound 5a for 14 days. The colonies were fixed and stained with crystal violet and counted. Data are expressed as the mean±SEM of three determinations. The results indicated that a 14-day treatment of H1975 cells with compound 5a inhibited the colony formation of the H1975 cells (FIG. 1B). These data suggested that compound 5a can inhibit NSCLC cell growth in vitro.

In Vivo Antitumor Activity of the Exemplified Compound 5a

The in vivo antitumor efficacy of compound 5a was evaluated in ectopic H1975 tumor xenograft models (FIG. 1C). H1975 cells were injected subcutaneously into the right flank region of nude mice. Three days after the injection, athymic nude mice that bear established subcutaneous H1975 tumors were treated intraperitoneally with compound 5a twice a week at 2 mg/kg versus a vehicle control (DMSO, n=8 for each group). Representative tumor images and H&E-stained sections of tumors taken from mice treated for 28 days with either vehicle or compound 5a are shown. The tumor size was measured with a caliper every time before compound delivery. FIG. 1C showed that compound 5a at this dosage markedly reduced the H1975 tumor size to 930.4±324.8 $mm^3$ ($P<0.01$) compared with 1699.3±413.3 $mm^3$ of the vehicle-treated group on day 28 of treatment. The body weight of the test mice and the biochemical markers of the liver and kidney functions, including GOT, GPT, BUN and Cre, were not significantly affected after a 28-day treatment, which indicates that compound 5a was well tolerated at the dosage of 2 mg/kg. This data demonstrates that compound 5a inhibits NSCLC cell growth in vivo.

Both the in vitro and in vivo data show that compound 5a could be a novel agent for anti-cancer therapy to provide additional options for NSCLC patients.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated by reference herein for the purposes or subject matter referenced herein.

If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Beelen, K.; Zwart, W.; Linn, S. C. Can predictive biomarkers in breast cancer guide adjuvant endocrine therapy? *Nat. Rev. Clin. Oncol.* 2012, 9, 529-541.
2. Booth, B. L.; Dias, A. M.; Proenc, M. F.; Zaki, E. A. The reactions of diaminomaleonitrile with isocyanates and either aldehydes or ketones revisited. *J. Org. Chem.* 2001, 66, 8436-8441.
3. *Fieser and Fieser's Reagents for Organic Synthesis*, Vol. 1-28, Wiley: New Jersey.
4. Greene, T. W.; Wuts, P. G. M. *Protective Groups in Organic Synthesis*, 3$^{rd}$ ed., Wiley: New Jersey, 1999.
5. Higashino, T.; Yoshida, S.; Hayashi, E. Reaction of 9-phenyl-9H-purine-6-carbonitrile with nucleophilic reagents. *Chem. Pharm. Bull.* 1982, 30, 4521-4525.
6. Holliday D. L.; Speirs, V. Choosing the right cell line for breast cancer research. *Breast Cancer Res.* 2011, 13, 215.
7. Larock, R. C. *Comprehensive Organic Transformations*, VCH Pub.: New York, 1989.
8. Mortensen, D. S.; Mederos, M. M. D.; Sapienza, J. J.; Albers, R. J.; Clareen, S. S.; Schwarz, K. L.; Parnes, J. S.; Riggs, J. R.; Papa, P. W.; Hegde, S. G.; McKenna, J. M. Methods of treatment using heteroaryl compounds and compositions thereof. U.S. Pat. No. 8,383,634B2, Feb. 26, 2013.
9. Paquette, L. A.; Crich, D.; Fuchs, P.; Molander, G. A. (Eds.) *Encyclopedia of Reagents for Organic Synthesis*, Wiley: New Jersey, 2009.
10. Subik, K.; Lee, J.-F.; Baxter, L.; Strzepek, T.; Costello, D.; Crowley, P.; Xing, L.; Hung, M.-C.; Bonfiglio, T.; Hicks, D. G.; Tang, P. The expression patterns ofER, PR, HER2, CK5/6, EGFR, Ki-67 and AR by immunohistochemical analysis in breast cancer cell lines. *Breast Cancer. Basic Clin. Res.* 2010, 4, 35-41.
11. Ullrich, A.; Coussens, L.; Hayflick, J. S.; Dull, T. J.; Gray, A.; Tam, A. W.; Lee, J.; Yarden, Y.; Libermann, T. A.; Schlessinger, J.; Downward, J.; Mayes, E. L. V.; Whittle, N.; Waterfield, M. D.; Seeburg, P. H. Human epidermal growth factor receptor cDNA sequence and aberrant expression of the amplified gene in A431 epidermoid carcinoma cells. *Nature* 1984, 309, 418-425.
12. Veale, D.; Ashcroft, T.; Marsh, C.; Gibson, G. J.; Harris, A. L. Epidermal growth factor receptors in non-small cell lung cancer. *Brit. J. Cancer* 1987, 55, 513-516.
13. Weichselbaum, R. R.; Dunphy, E. J.; Beckett, M. A.; Tybor, A. G.; Moran, W. J.; Goldman, M. E.; Vokes, E. E.; Panje, W. R. Epidermal growth factor receptor gene amplification and expression in head and neck cancer cell lines. *Head Neck* 1989, 11, 437-442.
14. Wheeler, D. L.; Dunn, E. F.; Harari, P. M. Understanding resistance to EGFR inhibitors-impact on future treatment strategies. *Nat. Rev. Clin. Oncol.* 2010, 7, 493-507.

What is claimed is:

1. A compound of Formula (I'):

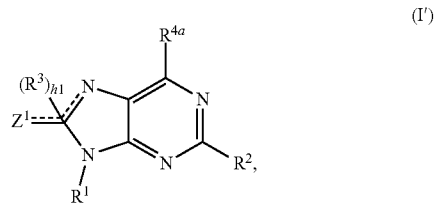

or a pharmaceutically acceptable salt thereof,
wherein:
$Z^1$ is independently Cl, N, O, or S, as valency permits;
h1 is 0, 1, or 2;
$R^1$ is

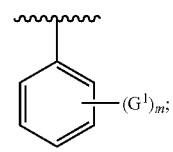

in which $G^1$ is independently halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —SR$^A$, —NHR$^B$, —N(R$^B$)$_2$, —C(=O)R$^A$, —C(=O)OR$^A$, —OC(=O)R$^A$, —C(=O)NHR$^B$, —C(=O)N(R$^B$)$_2$, —NR$^B$C(=O)R$^A$, —OC(=O)N(R$^B$)$_2$, —NR$^B$C(=O)OR$^A$, —NR$^B$C(=O)N(R$^B$)$_2$, —S(=O)R$^A$, —OS(=O)$_2$R$^A$, —SO$_2$R$^A$, —NR$^B$SO$_2$R$^A$, or —SO$_2$N(R$^B$)$_2$; and m is 1, 2, 3, 4 or 5;
wherein when $Z^1$ is S, $G^1$ is hydrogen;

R² is

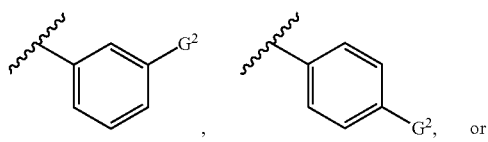
,

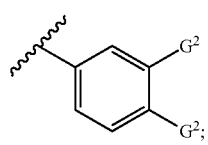
;

in which each instance of G² is independently halogen, —CN, —NO₂, —N₃, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —SR$^A$, —NHR$^B$, —N(R$^B$)₂, —C(=O)R$^A$, —C(=O)OR$^A$, —OC(=O)R$^A$, —C(=O)NHR$^B$, —C(=O)N(R$^B$)₂, —NR$^B$C(=O)R$^A$, —OC(=O)N(R$^B$)₂, NR$^B$C(=O)OR$^A$, NR$^B$C(=O)N(R$^B$)₂, —S(=O)R$^A$, —OS(=O)₂R$^A$, —SO₂R$^A$, —NR$^B$SO₂R$^A$, or —SO₂N(R$^B$)₂;

R³ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^A$, —SR$^A$, —NHR$^B$, —N(R$^B$)₂, —C(=O)R$^A$, —C(=O)OR$^A$, —C(=O)NHR$^B$, —C(=O)N(R$^B$)₂, —SO₂R$^A$, or two instances of R³ are taken together with Z¹ to form optionally substituted heterocyclyl;

R$^{4a}$ is —C(=NH)NH(OR$^A$), —C(=N(OR$^A$)NH₂, —C(=NH)NHN(R$^B$)₂, —C(=NHN(R$^B$)₂)NH₂, or —C(=NH)N(R$^B$)₂;

wherein

R$^A$ is hydrogen or optionally substituted C₁₋₆ alkyl; and each instance of R$^B$ is independently hydrogen, optionally substituted C₁₋₆ alkyl, optionally substituted aryl.

2. The compound of claim 1, wherein the compound is the formula:

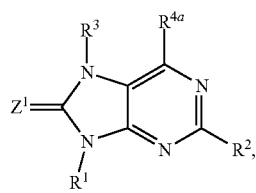
(IA')

wherein:
Z¹, R¹, R², R³ and R$^{4a}$ are defined therein.

3. The compound of claim 2, wherein the compound is of Formula (IA'-2):

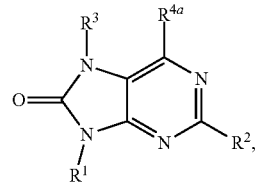
(IA'-2)

wherein:
R¹, R², R³ and R$^{4a}$ are defined therein.

4. The compound of claim 1, wherein the compound is of the formula:

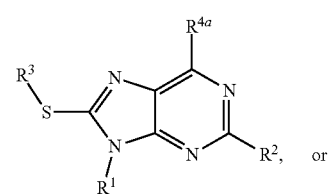
(IB'-3)
or

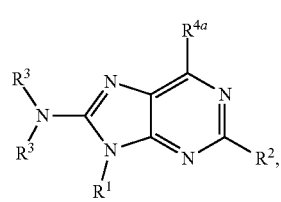
(IB'-4)

wherein R¹, R², R³, and R$^{4a}$ are defined therein.

5. The compound of claim 1, wherein the compound is of the formula:

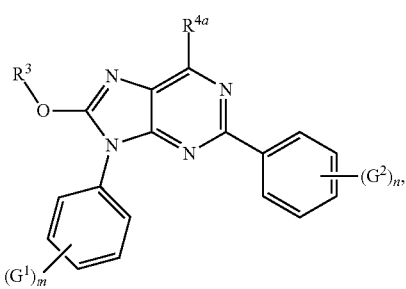
(I'-b1)

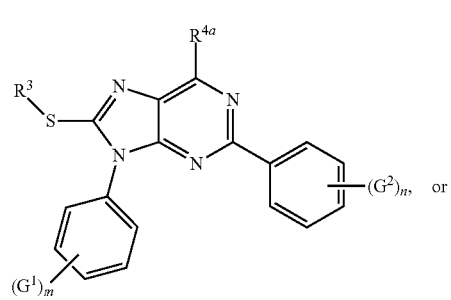
(I'-b2)
or

-continued

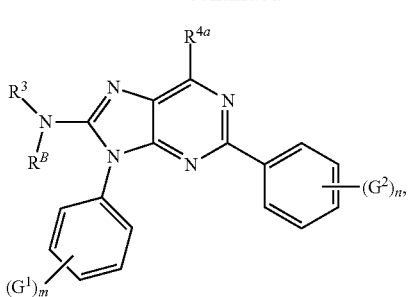
(I'-b3)

wherein:
R³, R⁴ᵃ, G¹, G², m, and n are defined therein.

6. The compound of claim 1, wherein R¹ is:

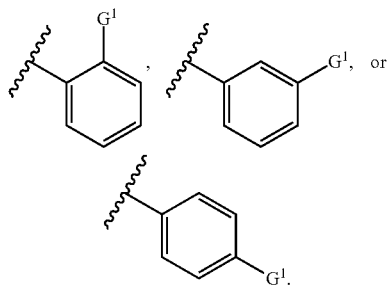

7. The compound of claim 5, wherein $R^B$ is of the formula: —(CH₂)$_q$G, wherein:
q is 2, 3, 4, 5, 6, 7, 8, 9, 10, 11, or 12;
G is hydrogen, optionally substituted alkyl, —N₃, or —N(R$^{a1}$)₂; and
$R^{a1}$ is hydrogen or optionally substituted alkyl.

8. The compound of claim 1, wherein R² is:

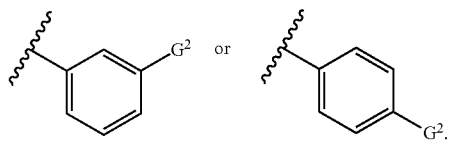

9. The compound of claim 1, wherein R² is:

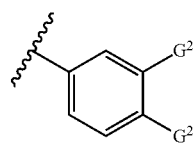

10. The compound of claim 8, wherein R² is:

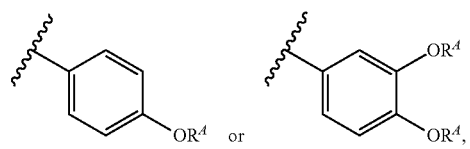

in which $R^A$ is hydrogen or optionally substituted C$_{1-6}$ alkyl.

11. The compound of claim 1, wherein at least one instance of R³ is of the formula: —(CH₂)$_p$C(=O)OR$^A$, in which:
p is 0, 1, or 2; and
$R^A$ is hydrogen or optionally substituted C$_{1-6}$ alkyl.

12. The compound of claim 1, wherein the two instances of R³, taken together with Z¹, form optionally substituted heterocyclyl, in which Z¹ is N.

13. The compound of claim 1, wherein the compound is of the formula:

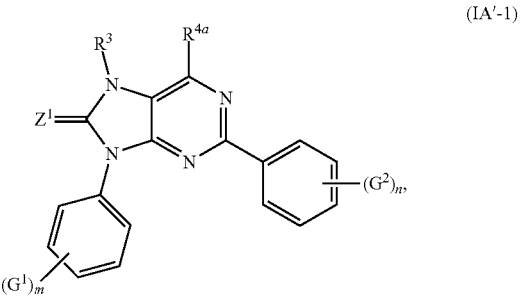
(IA'-1)

wherein Z¹, R³, R⁴ᵃ, G¹, G², m, and n are defined therein.

14. The compound of claim 1, wherein the compound is of the formula:

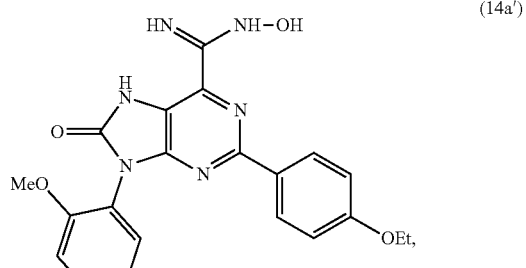
(14a')

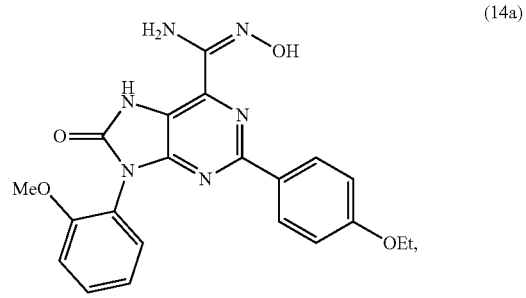
(14a)

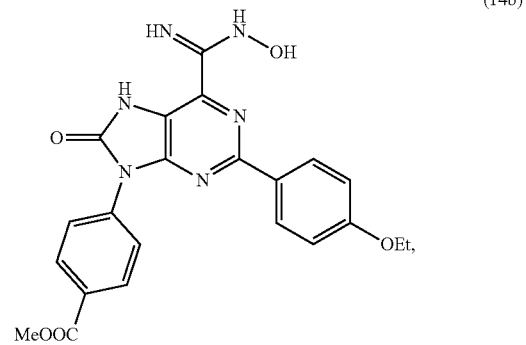
(14b)

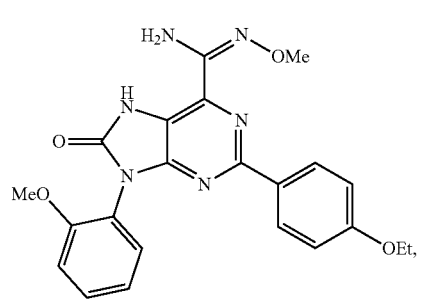
(14h')
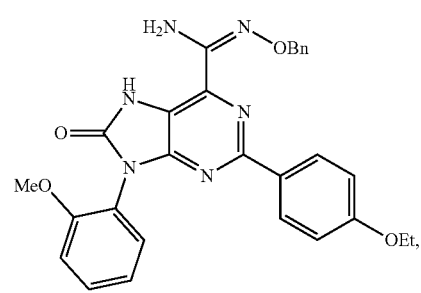
(14i')
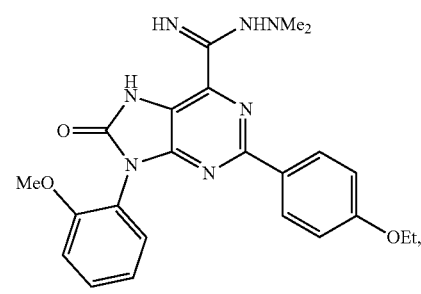
(14j)
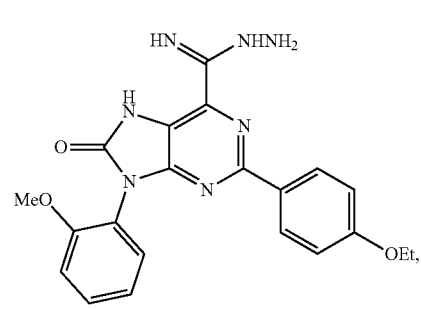
(14k)
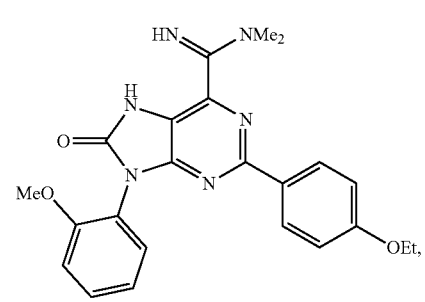
(14l)
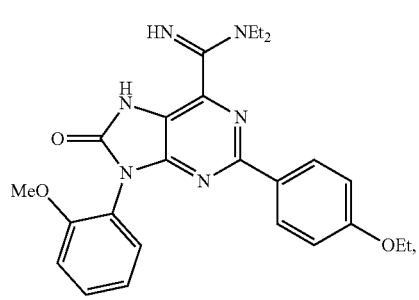
(14m)
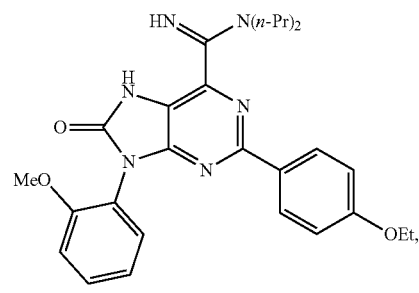
(14n)
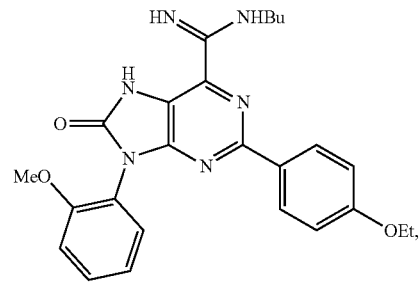
(14o)
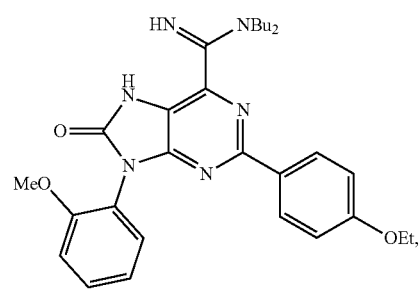
(14p)
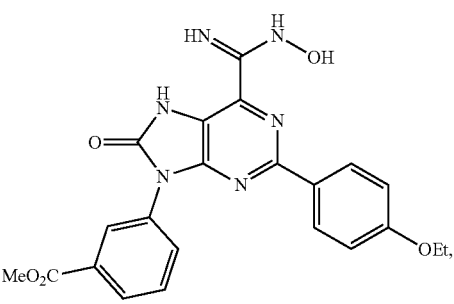
(14c)

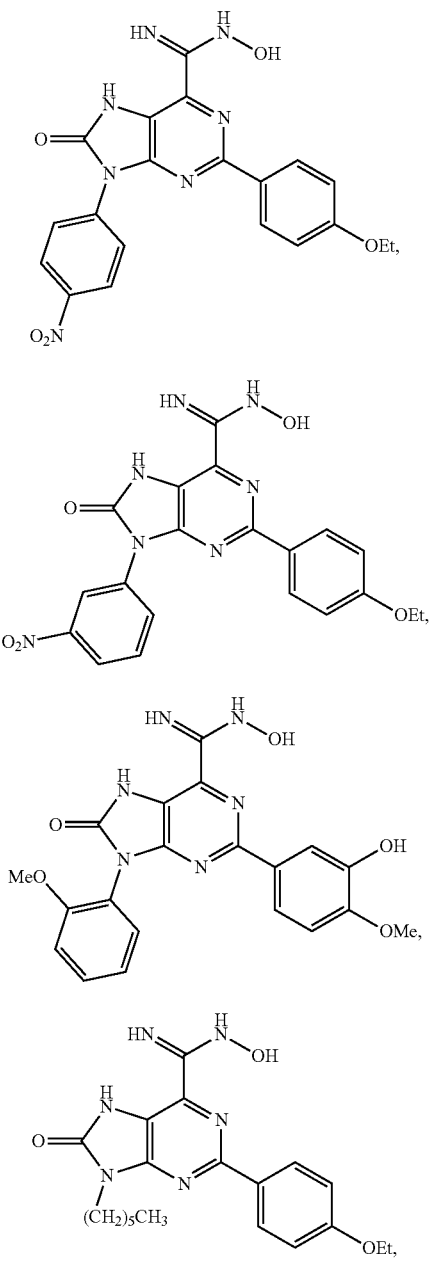
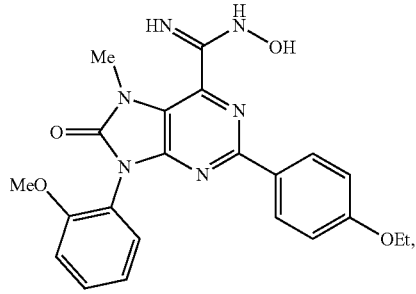
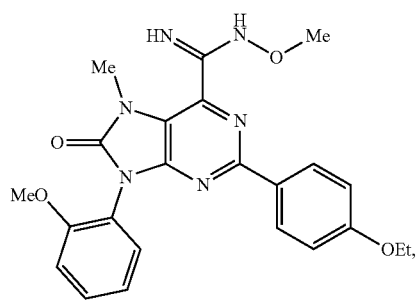
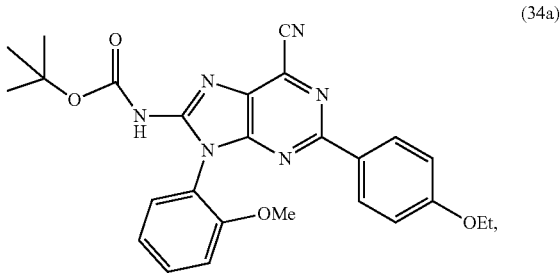
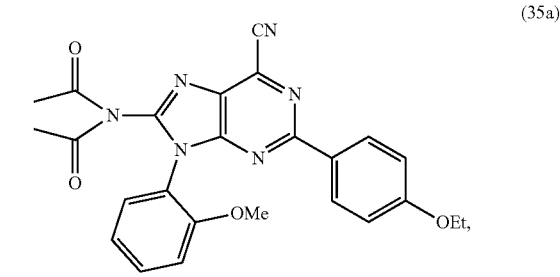
or a pharmaceutically acceptable salt thereof.
15. A pharmaceutical composition, comprising a compound of claim 1 and a pharmaceutically acceptable carrier.
16. A method for treating a proliferative disease, comprising administering to a subject in need thereof an effective amount of the compound of claim 1.
17. A compound, wherein the compound is of the formula:
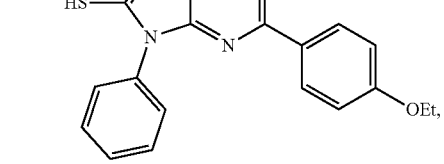

211
-continued
(10b)
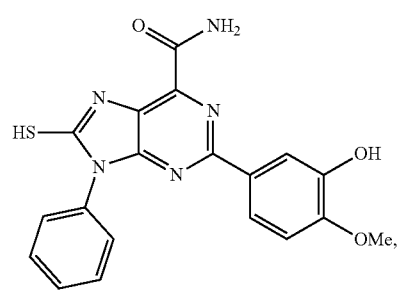
(10d)
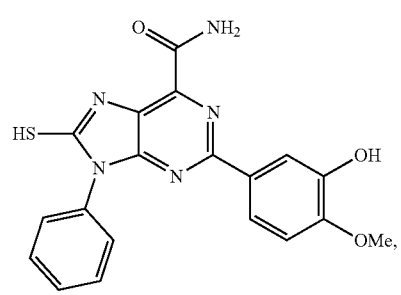
(11a)
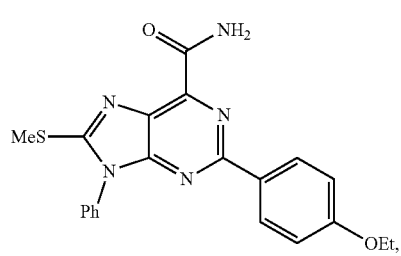
(11b)
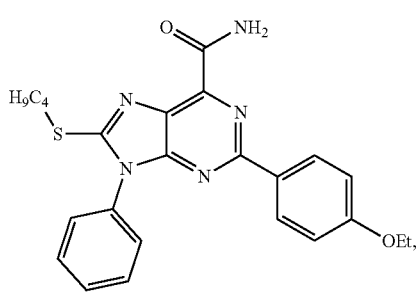
(11c)
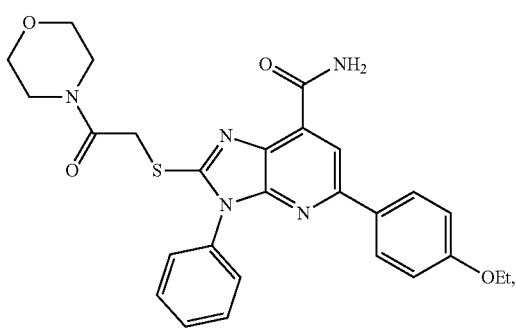
212
-continued
(11d)
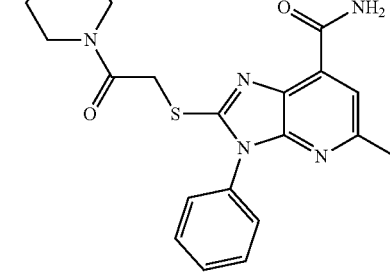
(11e)
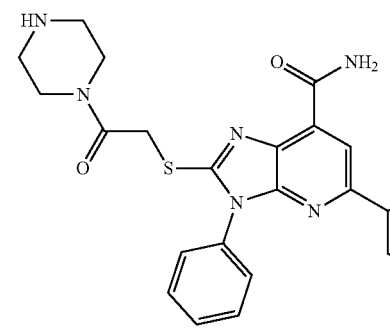
(11f)
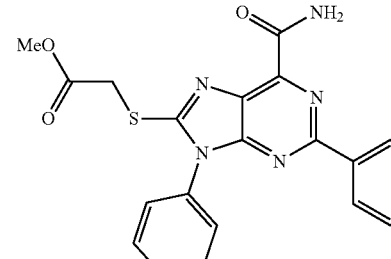
(11g)
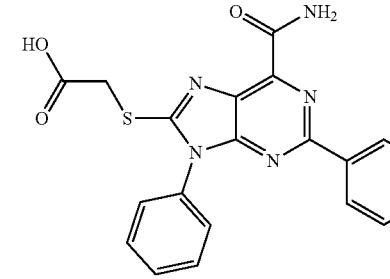
(11l)
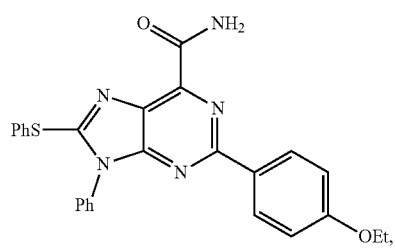

-continued
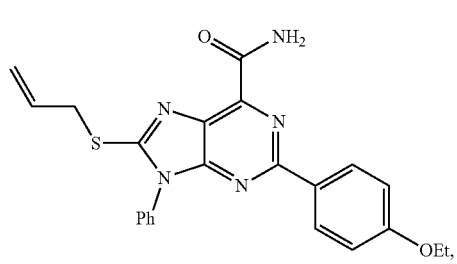
(11m)
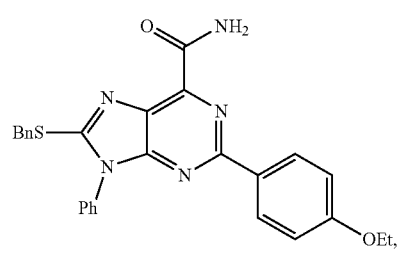
(11n)
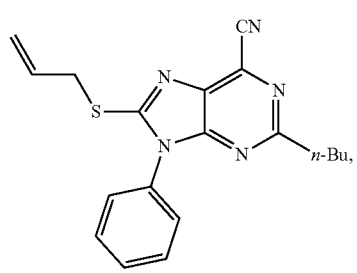
(28k)
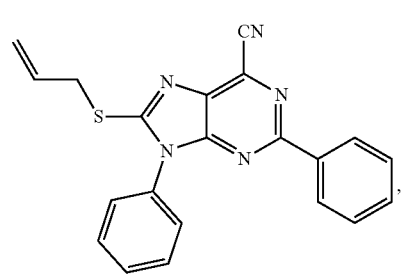
(28l)
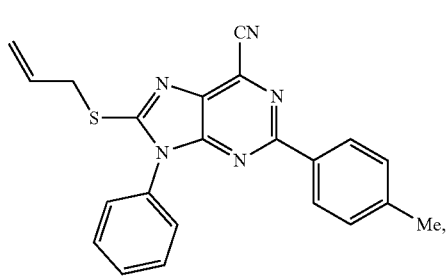
(28m)
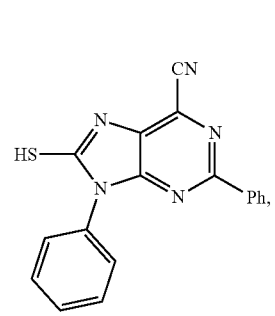
(27f)
-continued
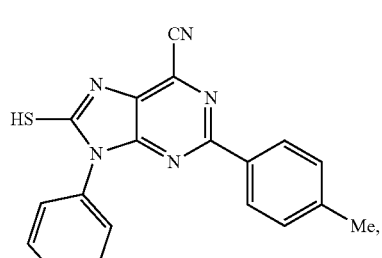
(27g)
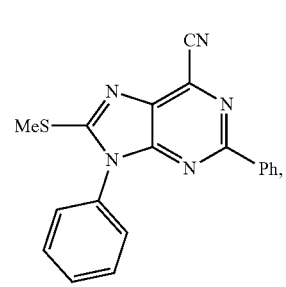
(28f)
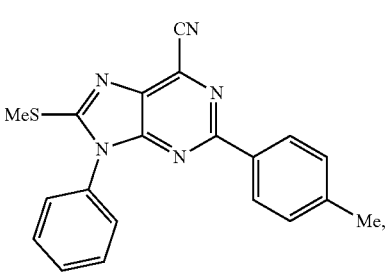
(28g)
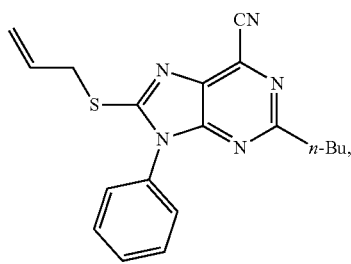
(28h)
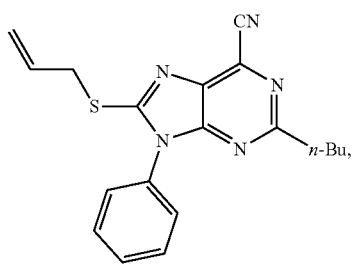
(28k)
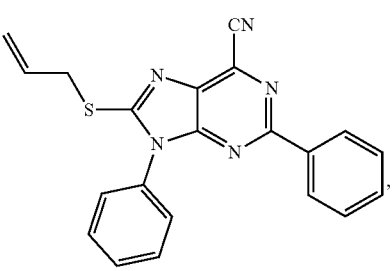
(28l)

-continued
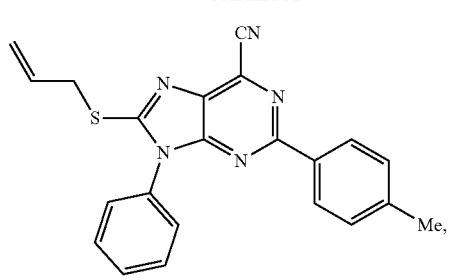
(28m)
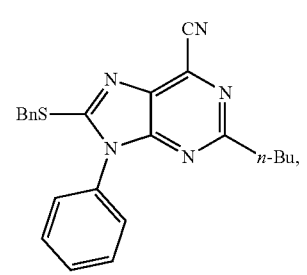
(28q)
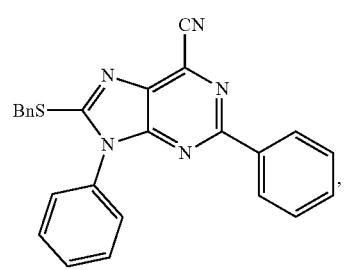
(28r)
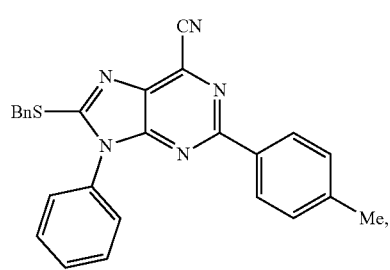
(28s)
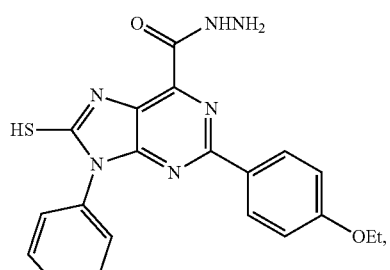
(30b)
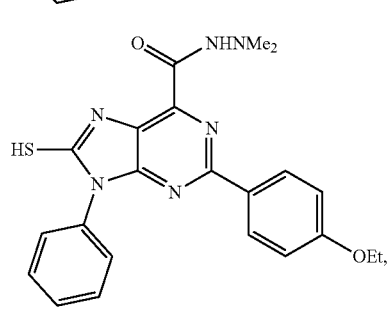
(30c)
-continued
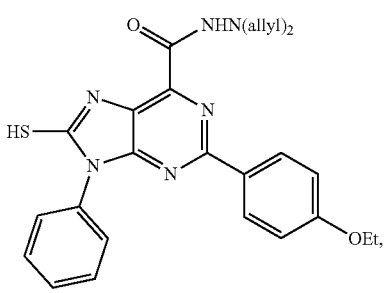
(30d)
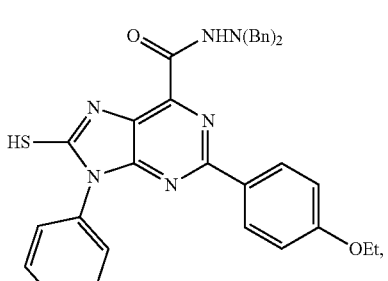
(30e)
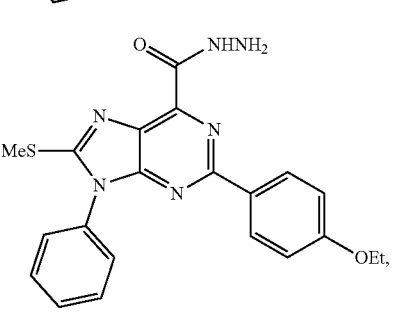
(30f)
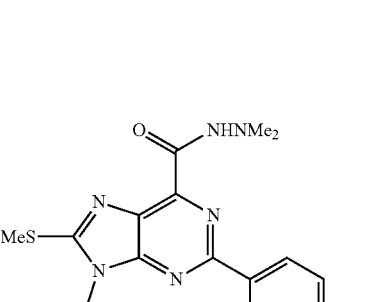
(30g)
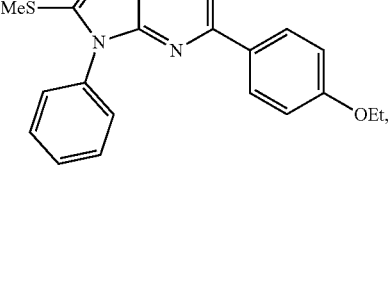
(30h)

-continued
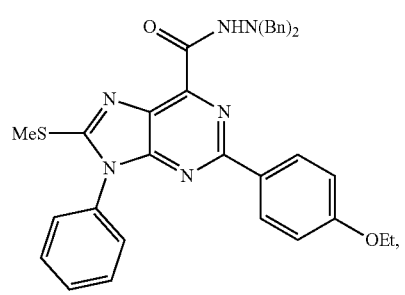 (30i)
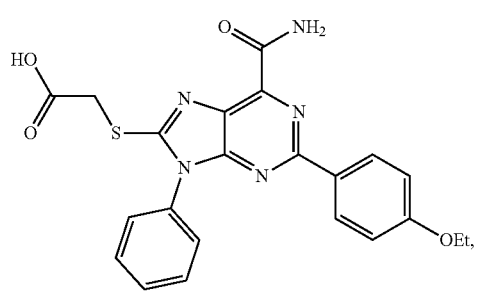 (11g)
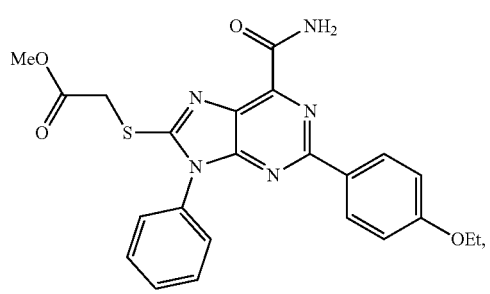 (11f)
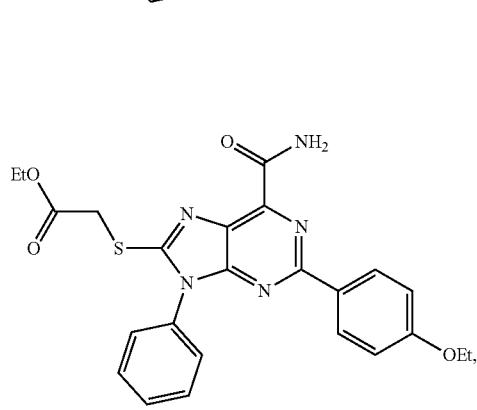 (11s)
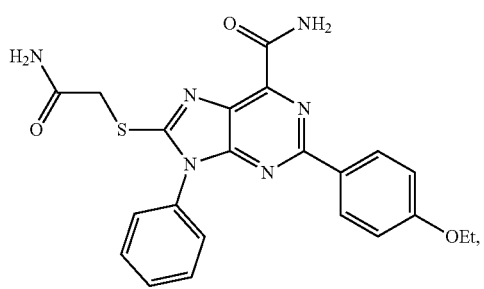 (11t)
-continued
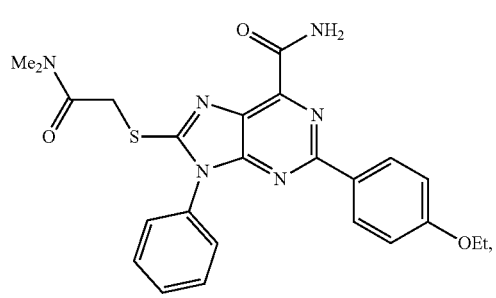 (11u)
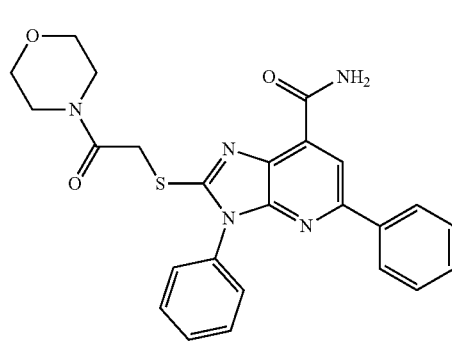 (11c)
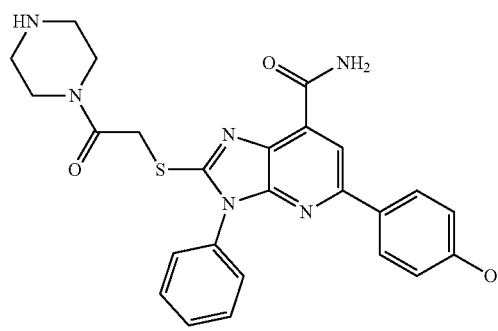 (11e)
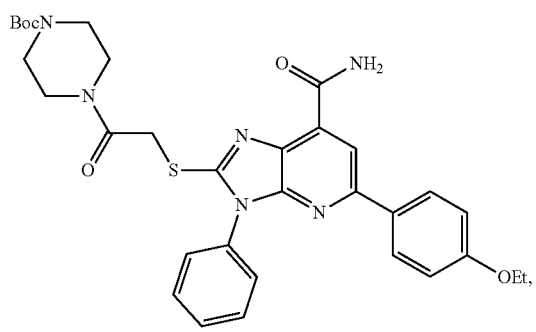 (11d)
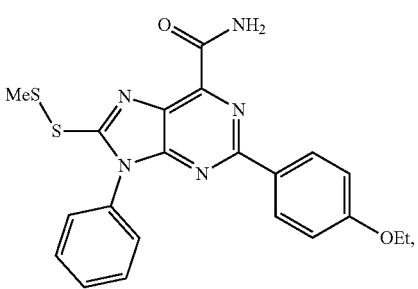 (26d)

-continued
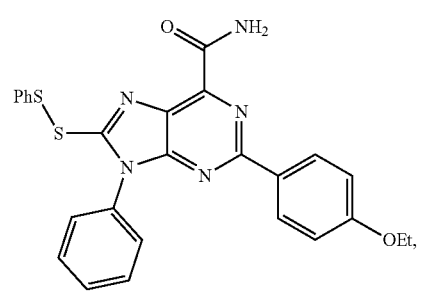
(26e)
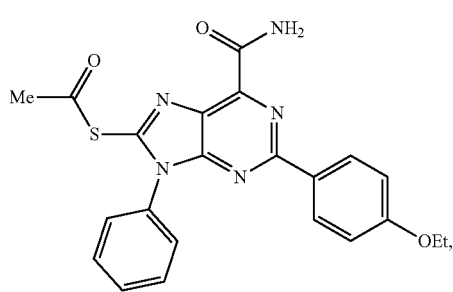
(26a)
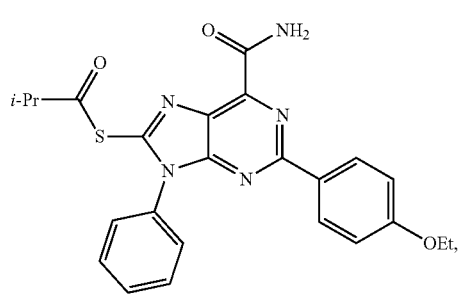
(26b)
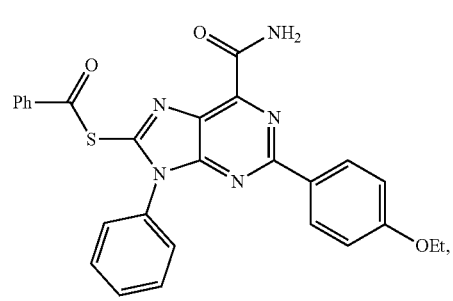
(26c)
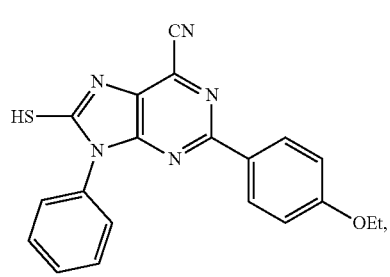
(27a)
-continued
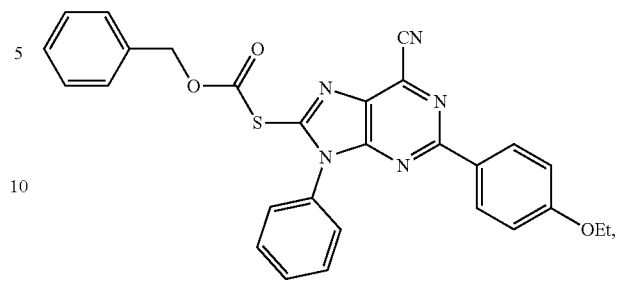
(28a)
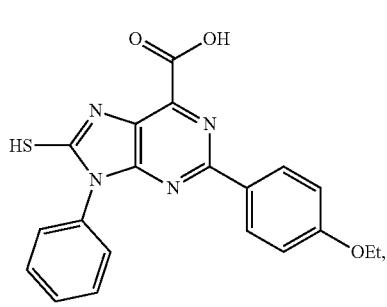
(29a)
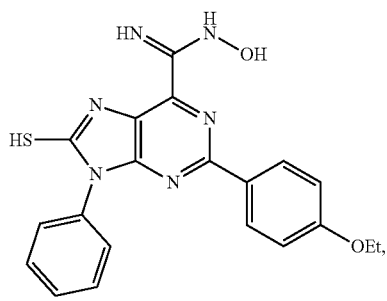
(30a)
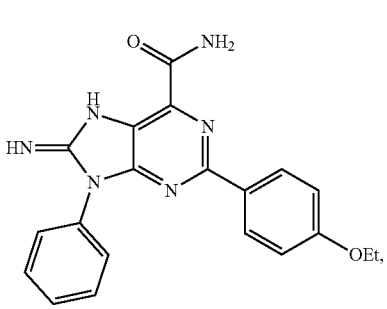
(32b′)
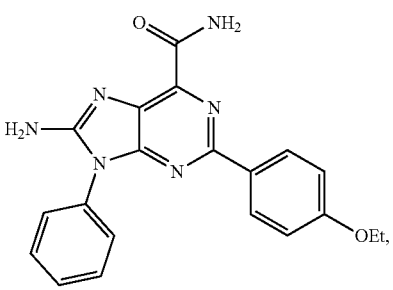
(32b)

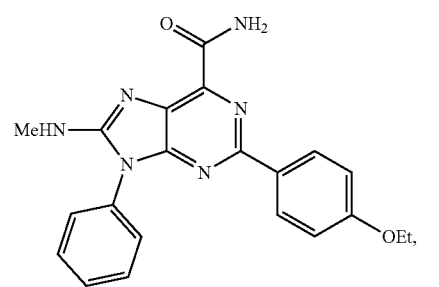 (32c)
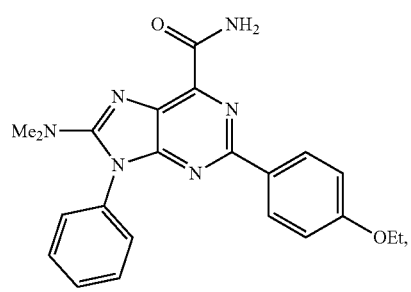 (32d)
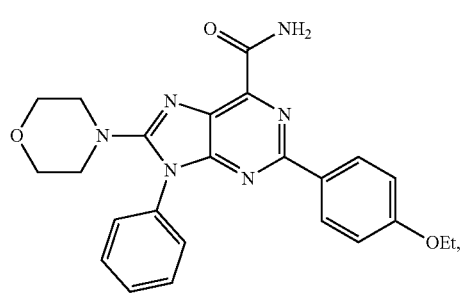 (32e)
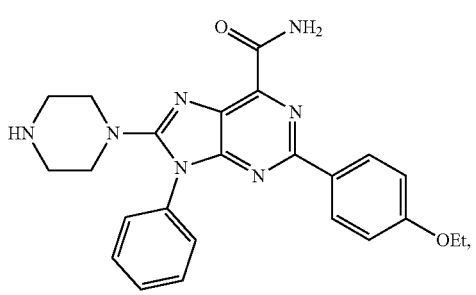 (32f)
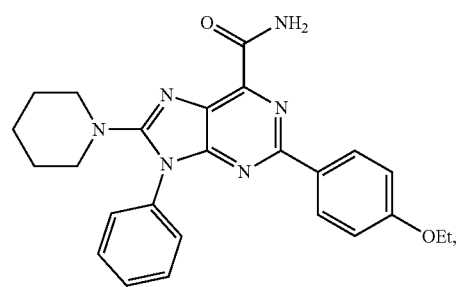 (32g)
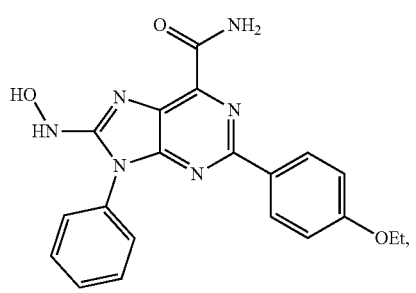 (32h)
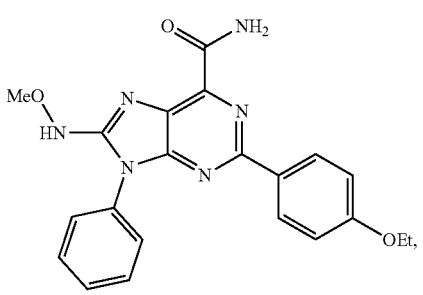 (32i)
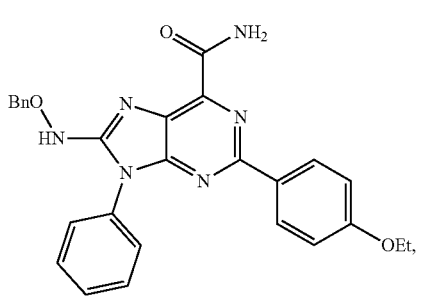 (32j)
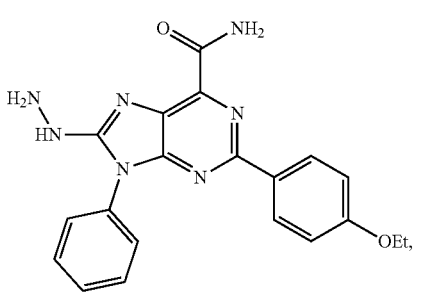 (32k)
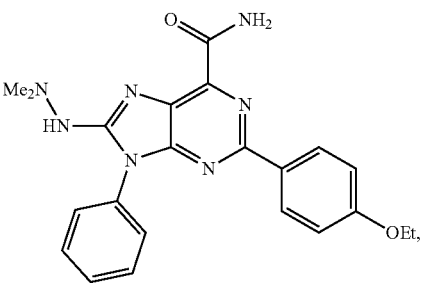 (32l)

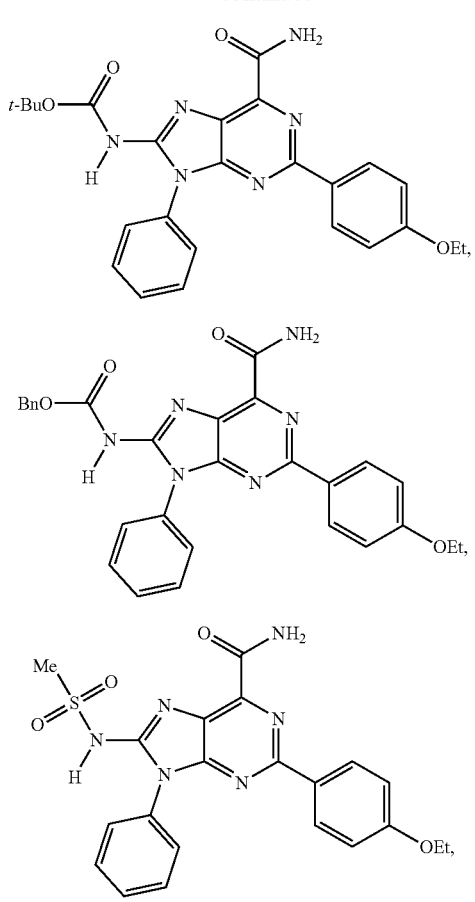
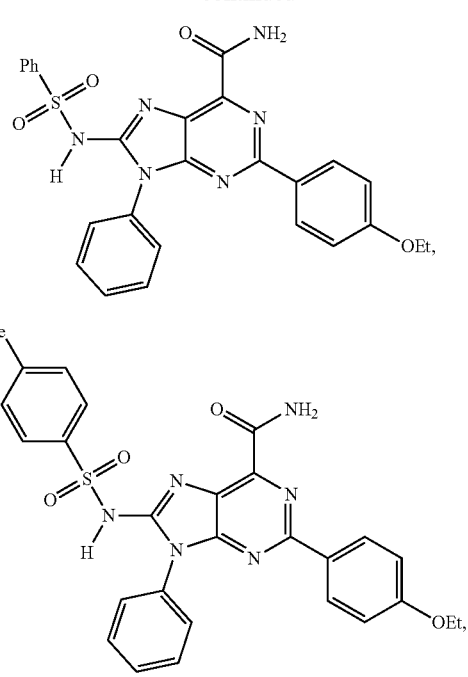
or a pharmaceutically acceptable salt thereof.
18. A pharmaceutical composition, comprising a compound of claim 17 and a pharmaceutically acceptable carrier.
19. A method for treating a proliferative disease, comprising administering to a subject in need thereof an effective amount of the compound of claim 17.
* * * * *